(12) United States Patent
Condon et al.

(10) Patent No.: US 8,399,683 B2
(45) Date of Patent: Mar. 19, 2013

(54) IAP INHIBITORS

(75) Inventors: Stephen M. Condon, Glenmoore, PA (US); Matthew G. Laporte, Honeybrook, PA (US)

(73) Assignee: TetraLogic Pharmaceuticals, Malvern, PA (US)

(*) Notice: Subject to any disclaimer, the term of this patent is extended or adjusted under 35 U.S.C. 154(b) by 2 days.

(21) Appl. No.: 13/063,219

(22) PCT Filed: Sep. 16, 2009

(86) PCT No.: PCT/US2009/057070
§ 371 (c)(1),
(2), (4) Date: Jun. 13, 2011

(87) PCT Pub. No.: WO2010/033531
PCT Pub. Date: Mar. 25, 2010

(65) Prior Publication Data
US 2011/0237517 A1    Sep. 29, 2011

Related U.S. Application Data

(60) Provisional application No. 61/097,762, filed on Sep. 17, 2008.

(51) Int. Cl.
*C07D 211/32* (2006.01)
*C07D 411/14* (2006.01)
*C07D 487/02* (2006.01)
*C07D 239/02* (2006.01)
*A61K 31/445* (2006.01)
*A61K 31/44* (2006.01)
*A61K 31/425* (2006.01)
*A61K 31/505* (2006.01)

(52) U.S. Cl. ............ 548/453; 548/276.7; 546/199; 546/202; 544/323; 514/326; 514/338; 514/421; 514/365; 514/275

(58) Field of Classification Search ............... None
See application file for complete search history.

(56) References Cited

U.S. PATENT DOCUMENTS

2012/0094917 A1* 4/2012 Condon et al. ............ 514/18.7
2012/0135990 A1* 5/2012 Condon et al. ............ 514/234.5

FOREIGN PATENT DOCUMENTS

WO   2005094818 A1   10/2005
WO   2005097791 A1   10/2005

OTHER PUBLICATIONS

Supplementary European Search Report dated Feb. 6, 2012 in EP Application No. 09815077.
International Search Report for PCT/US09/57070 dated Oct. 24, 2009.

* cited by examiner

*Primary Examiner* — Kamal Saeed
*Assistant Examiner* — Nyeemah A Grazier
(74) *Attorney, Agent, or Firm* — Banner & Witcoff, Ltd.

(57) ABSTRACT

The present invention describes compounds, processes for their preparation, pharmaceutical compositions containing them, and their use in therapy.

34 Claims, No Drawings

IAP INHIBITORS

BACKGROUND OF THE INVENTION

1. Field of the Invention

The present invention describes compounds that are inhibitors of IAPs (inhibitors of apoptosis proteins), processes for their preparation, pharmaceutical compositions containing them, and their use in therapy. The compounds of the present invention are useful in the treatment of cancer, autoimmune diseases and other disorders.

2. Description of Related Art

Apoptosis (programmed cell death) plays a central role in the development and homeostasis of all multi-cellular organisms. Apoptosis can be initiated within a cell from an external factor such as a chemokine (an extrinsic pathway) or via an intracellular event such a DNA damage (an intrinsic pathway). Alterations in apoptotic pathways have been implicated in many types of human pathologies, including developmental disorders, cancer, autoimmune diseases, as well as neurodegenerative disorders. One mode of action of chemotherapeutic drugs is cell death via apoptosis.

Apoptosis is conserved across species and executed primarily by activated caspases, a family of cysteine proteases with aspartate specificity in their substrates. These cysteine containing aspartate specific proteases ("caspases") are produced in cells as catalytically inactive zymogens and are proteolytically processed to become active proteases during apoptosis. Once activated, effector caspases are responsible for proteolytic cleavage of a broad spectrum of cellular targets that ultimately lead to cell death. In normal surviving cells that have not received an apoptotic stimulus, most caspases remain inactive. If caspases are aberrantly activated, their proteolytic activity can be inhibited by a family of evolutionarily conserved proteins called IAPs (inhibitors of apoptosis proteins).

The IAP family of proteins suppresses apoptosis by preventing the activation of procaspases and inhibiting the enzymatic activity of mature caspases. Several distinct mammalian IAPs including XIAP, c-IAP1, c-IAP2, ML-IAP, NAIP (neuronal apoptosis inhibiting protein), Bruce, and survivin, have been identified, and they all exhibit anti-apoptotic activity in cell culture. IAPs were originally discovered in baculovirus by their functional ability to substitute for P35 protein, an anti-apoptotic gene. IAPs have been described in organisms ranging from Drosophila to human, and are known to be overexpressed in many human cancers. Generally speaking, IAPs comprise one to three Baculovirus IAP repeat (BIR) domains, and most of them also possess a carboxyl-terminal RING finger motif. The BIR domain itself is a zinc binding domain of about 70 residues comprising 4 alpha-helices and 3 beta strands, with cysteine and histidine residues that coordinate the zinc ion. It is the BIR domain that is believed to cause the anti-apoptotic effect by inhibiting the caspases and thus inhibiting apoptosis. XIAP is expressed ubiquitously in most adult and fetal tissues. Overexpression of XIAP in tumor cells has been demonstrated to confer protection against a variety of pro-apoptotic stimuli and promotes resistance to chemotherapy. Consistent with this, a strong correlation between XIAP protein levels and survival has been demonstrated for patients with acute myelogenous leukemia. Down-regulation of XIAP expression by antisense oligonucleotides has been shown to sensitize tumor cells to death induced by a wide range of pro-apoptotic agents, both in vitro and in vivo In normal cells signaled to undergo apoptosis, however, the IAP-mediated inhibitory effect must be removed, a process at least in part performed by a mitochondrial protein named Smac (second mitochondrial activator of caspases). Smac (or, DIABLO), is synthesized as a precursor molecule of 239 amino acids; the N-terminal 55 residues serve as the mitochondria targeting sequence that is removed after import. The mature form of Smac contains 184 amino acids and behaves as an oligomer in solution. Smac and various fragments thereof have been proposed for use as targets for identification of therapeutic agents.

Smac is synthesized in the cytoplasm with an N-terminal mitochondrial targeting sequence that is proteolytically removed during maturation to the mature polypeptide and is then targeted to the inter-membrane space of mitochondria. At the time of apoptosis induction, Smac is released from mitochondria into the cytosol, together with cytochrome c, where it binds to IAPs, and enables caspase activation, therein eliminating the inhibitory effect of IAPs on apoptosis. Whereas cytochrome c induces multimerization of Apaf-1 to activate procaspase-9 and -3, Smac eliminates the inhibitory effect of multiple IAPs. Smac interacts with essentially all IAPs that have been examined to date including XIAP, c-IAP1, c-IAP2, ML-IAP, and survivin. Thus, Smac appears to be a master regulator of apoptosis in mammals.

It has been shown that Smac promotes not only the proteolytic activation of procaspases, but also the enzymatic activity of mature caspase, both of which depend upon its ability to interact physically with IAPs. X-ray crystallography has shown that the first four amino acids (AVPI) of mature Smac bind to a portion of IAPs. This N-terminal sequence is essential for binding IAPs and blocking their anti-apoptotic effects.

Currently, there are drug discovery efforts aimed at identifying compounds that interfere with the role played by IAPs in disease states where a defect in apoptosis is implicated, such as in cancers and autoimmune diseases. Indeed, a number of IAP inhibitors that mimic the interactions of the Smac tetrapeptide are now known and possess pro-apoptotic activity in vitro and in vivo. Some IAP inhibitors demonstrate potent single-agent anti-tumor activity in vitro and in vivo, but unfortunately present an elevated risk of unwanted effects when administered in vivo (e.g., reduced cardiac output and elevated intestinal epithelial apoptosis). Thus, the art continues to look for additional compounds that may function as IAP inhibitors.

SUMMARY OF THE INVENTION

The present invention provides IAP inhibitors and therapeutic methods of using these inhibitors to modulate apoptosis.

In one embodiment, which can be practiced either separately, or in combination with the other embodiments disclosed below, the present invention provides compounds of Formula (I):

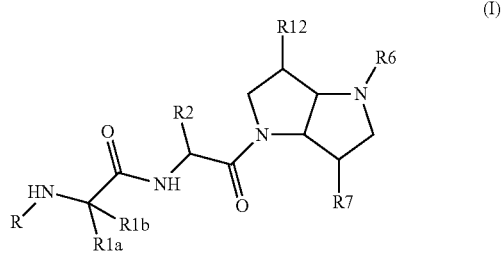

or pharmaceutically acceptable salts thereof, wherein:

R is selected from H, alkyl, substituted alkyl, alkenyl, substituted alkenyl, cycloalkyl, substituted cycloalkyl, aryl, substituted aryl, heteroaryl, or substituted heteroaryl;

R1a and R1b are each independently selected from H, alkyl, or substituted alkyl;

R2 is selected from H, alkyl, substituted alkyl, cycloalkyl, heterocycloalkyl, aryl, or heteroaryl;

R6 is selected from H, alkyl, substituted alkyl, alkylsulfonyl, arylsulfonyl, cycloalkyl, substituted cycloalkyl, heterocycloalkyl, substituted heterocycloalkyl, aryl, substituted aryl, heteroaryl, or substituted heteroaryl; or R6 has the following formula (IA)

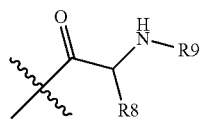

(IA)

wherein R8 is selected from H, alkyl, substituted alkyl, cycloalkyl, heterocycloalkyl, aryl, or heteroaryl;

and R9 is selected from H, alkyl, substituted alkyl, cycloalkyl, substituted cycloalkyl, aryl, substituted aryl, heterocycloalkyl, substituted heterocycloalkyl, heteroaryl, or substituted heteroaryl; or R9 has the following formula (IB);

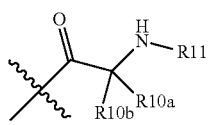

(IB)

where R10a and R10b are independently selected from H, alkyl, or substituted alkyl;

and R11 is selected from H, alkyl, substituted alkyl, alkenyl, substituted alkenyl, cycloalkyl, substituted cycloalkyl, aryl, substituted aryl, heteroaryl, or substituted heteroaryl;

R7 is selected from H, or a 3-indolyl of the formula (IC):

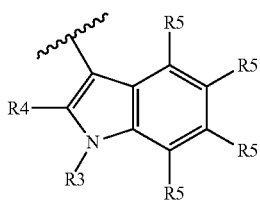

(IC)

where R3 is selected from H, alkyl, or substituted alkyl;

R4 is selected from H, halogen, alkyl, or substituted alkyl; and each R5 is independently selected from H, halogen, alkyl, or substituted alkyl; and R12 is selected from H or hydroxy.

In another embodiment, which can be practiced either separately, or in combination with the other embodiments disclosed above and below, the various substituents of Formula (I) are defined as follows:

R is selected from H, alkyl, substituted alkyl, alkenyl, substituted alkenyl, aryl, substituted aryl, cycloalkyl, substituted cycloalkyl, heteroaryl, or substituted heteroaryl; wherein the substitutents are selected from the group consisting of halogen, hydroxy, oxo, mercapto, carboxyl, alkyl, cycloalkyl, aryl, alkoxy, amino, heteroaryl, and nitro;

R1a and R1b are each independently selected from H, alkyl, or substituted alkyl, wherein the substitutents are selected from the group consisting of halogen, hydroxy, oxo, mercapto, carboxyl, cycloalkyl, aryl, alkoxy, amino, heteroaryl, and nitro;

R2 is alkyl, cycloalkyl, aryl, heterocycloalkyl, heteroaryl, or substituted alkyl, wherein the substituents are selected from the group consisting of halogen, hydroxy, oxo, alkoxy, cycloalkyl, aryl, heterocycloalkyl and heteroaryl;

R6 is selected from H; alkylsulfonyl; arylsulfonyl; alkyl; substituted alkyl, wherein the substituents are selected from the group consisting of halogen, hydroxy, oxo, mercapto, carboxyl, alkoxy, amino, nitro, cycloalkyl, aryl, heteroaryl optionally substituted with lower alkyl or halogen, alkylsulfonyl and arylsulfonyl; cycloalkyl; substituted cycloalkyl, wherein the substituents are selected from the group consisting of halogen, hydroxy, oxo, mercapto, carboxyl, alkyl, cycloalkyl, aryl, alkoxy, amino, heteroaryl, and nitro; aryl; substituted aryl, wherein the substituents are selected from the group consisting of alkyl, halogen, hydroxy, mercapto, carboxyl, cycloalkyl, aryl, alkoxy, amino, heteroaryl, nitro, alkylsulfonyl and arylsulfonyl; heterocycloalkyl; substituted heterocycloalkyl, wherein the substituents are selected from the group consisting of halogen, hydroxy, oxo, mercapto, carboxyl, alkyl, cycloalkyl, aryl, alkoxy, amino, heteroaryl, and nitro; heteroaryl; or substituted heteroaryl, wherein the substituents are selected from the group consisting of halogen, hydroxy, mercapto, carboxyl, alkyl, cycloalkyl, aryl, alkoxy, amino, heteroaryl, and nitro; or R6 has the following formula (IA):

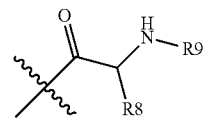

(IA)

where R8 is alkyl, cycloalkyl, aryl, heterocycloalkyl, heteroaryl, or substituted alkyl, wherein the substituents are selected from the group consisting of halogen, hydroxy, oxo, alkoxy, cycloalkyl, aryl, heterocycloalkyl and heteroaryl and R9 is selected from H, alkyl, substituted alkyl, aryl, substituted aryl, cycloalkyl, substituted cycloalkyl, heteroaryl, or substituted heteroaryl; wherein the substitutents are selected from the group consisting of halogen, hydroxy, oxo, mercapto, carboxyl, alkyl, cycloalkyl, aryl, alkoxy, amino, heteroaryl, and nitro; or, R9 has the following formula (IB):

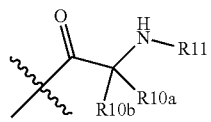

(IB)

where R10a and R10b are independently selected from H, alkyl, or substituted alkyl, wherein the substitutents are selected from the group consisting of halogen, hydroxy, oxo, mercapto, carboxyl, alkyl, cycloalkyl, aryl, alkoxy, amino, heteroaryl, and nitro; and R11 is selected from H, alkyl, substituted alkyl, aryl, substituted aryl, cycloalkyl, substituted cycloalkyl, heteroaryl, or substituted heteroaryl; wherein the substitutents are selected from the group consisting of halogen, hydroxy, oxo, mercapto, carboxyl, alkyl, cycloalkyl, aryl, alkoxy, amino, heteroaryl, and nitro;
R7 is selected from H, or a 3-indolyl of the formula (IC):

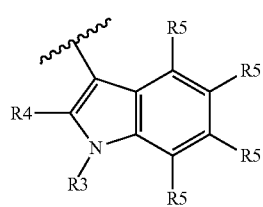

(IC)

where R3 is selected from H, alkyl, or substituted alkyl, where the substituents are selected from the group consisting of halogen, hydroxy, mercapto, carboxyl, alkyl, cycloalkyl, aryl, alkoxy, amino, heteroaryl, and nitro;

R4 is selected from H, halogen, alkyl, or substituted alkyl, where the substituents are selected from the group consisting of halogen, hydroxy, mercapto, carboxyl, alkyl, cycloalkyl, aryl, alkoxy, amino, heteroaryl, and nitro; and each R5 is independently selected from H, halogen, alkyl, or substituted alkyl, where the substituents are selected from the group consisting of halogen, hydroxy, mercapto, carboxyl, alkyl, cycloalkyl, aryl, alkoxy, amino, heteroaryl, and nitro; and R12 is selected from H or hydroxy.

In another embodiment, which can be practiced either separately, or in combination with the other embodiments disclosed above and below, the various substituents of Formula (I) are defined as follows:

R is selected from H, alkyl, substituted alkyl, alkenyl, or substituted alkenyl; wherein the substitutents are selected from the group consisting of halogen, hydroxy, oxo, mercapto, carboxyl, alkyl, cyclopropyl, alkoxy, amino, and nitro;

R1a and R1b are each independently selected from H, alkyl, or substituted alkyl, wherein the substitutents are selected from the group consisting of halogen, hydroxy, oxo, mercapto, carboxyl, alkyl, cyclopropyl, alkoxy, amino, and nitro.

R2 is alkyl, cycloalkyl, aryl, heterocycloalkyl, heteroaryl, or substituted alkyl, wherein the substituents are selected from the group consisting of halogen, hydroxy, oxo, alkoxy, cycloalkyl, aryl, heterocycloalkyl and heteroaryl;

R6 is selected from H; alkylsulfonyl; arylsulfonyl; alkyl; substituted alkyl, wherein the substituents are selected from the group consisting of halogen, hydroxy, oxo, mercapto, carboxyl, alkoxy, amino, nitro, cycloalkyl, aryl, heteroaryl optionally substituted with lower alkyl or halogen, alkylsulfonyl and arylsulfonyl; cycloalkyl; substituted cycloalkyl, wherein the substituents are selected from the group consisting of halogen, hydroxy, oxo, mercapto, carboxyl, alkyl, cycloalkyl, aryl, alkoxy, amino, heteroaryl, and nitro; aryl; substituted aryl, wherein the substituents are selected from the group consisting of alkyl, halogen, hydroxy, mercapto, carboxyl, cycloalkyl, aryl, alkoxy, amino, heteroaryl, nitro, alkylsulfonyl and arylsulfonyl; heterocycloalkyl; substituted heterocycloalkyl, wherein the substituents are selected from the group consisting of halogen, hydroxy, oxo, mercapto, carboxyl, alkyl, cycloalkyl, aryl, alkoxy, amino, heteroaryl, and nitro; heteroaryl; or substituted heteroaryl, wherein the substituents are selected from the group consisting of halogen, hydroxy, mercapto, carboxyl, alkyl, cycloalkyl, aryl, alkoxy, amino, heteroaryl, and nitro; or R6 has the following formula (IA):

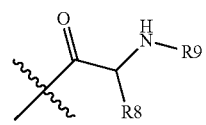

(IA)

where R8 is alkyl, cycloalkyl, aryl, heterocycloalkyl, heteroaryl, or substituted alkyl, wherein the substituents are selected from the group consisting of halogen, hydroxy, oxo, alkoxy, cycloalkyl, aryl, heterocycloalkyl and heteroaryl and R9 is selected from H, alkyl, substituted alkyl, aryl, substituted aryl, cycloalkyl, substituted cycloalkyl, heteroaryl, or substituted heteroaryl; wherein the substitutents are selected from the group consisting of halogen, hydroxy, oxo, mercapto, carboxyl, alkyl, cycloalkyl, aryl, alkoxy, amino, heteroaryl, and nitro; or, R9 has the following formula (IB):

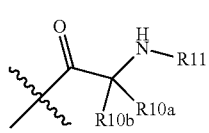

(IB)

where R10a and R10b are independently selected from H, alkyl, or substituted alkyl, wherein the substitutents are selected from the group consisting of halogen, hydroxy, oxo, mercapto, carboxyl, alkyl, cycloalkyl, aryl, alkoxy, amino, heteroaryl, and nitro; and R11 is selected from H, alkyl, substituted alkyl, aryl, substituted aryl, cycloalkyl, substituted cycloalkyl, heteroaryl, or substituted heteroaryl; wherein the substitutents are selected from the group consisting of halogen, hydroxy, oxo, mercapto, carboxyl, alkyl, cycloalkyl, aryl, alkoxy, amino, heteroaryl, and nitro;

R7 is selected from H, or a 3-indolyl of the formula (IC):

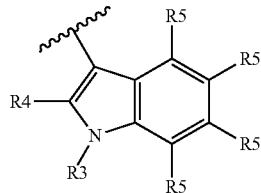

(IC)

where R3 is selected from H, alkyl, or substituted alkyl, where the substituents are selected from the group consisting of halogen, hydroxy, mercapto, carboxyl, alkyl, cycloalkyl, aryl, alkoxy, amino, heteroaryl, and nitro;

R4 is selected from H, halogen, alkyl, or substituted alkyl, where the substituents are selected from the group consisting of halogen, hydroxy, mercapto, carboxyl, alkyl, cycloalkyl, aryl, alkoxy, amino, heteroaryl, and nitro; and each R5 is independently selected from H, halogen, alkyl, or substituted alkyl, where the substituents are selected from the group consisting of halogen, hydroxy, mercapto, carboxyl, alkyl, cycloalkyl, aryl, alkoxy, amino, heteroaryl, and nitro; and R12 is selected from H or hydroxy.

In one embodiment, which can be practiced either separately, or in combination with the other embodiments disclosed above and below, the compounds of Formula (I), or their pharmaceutically acceptable salts, have the absolute configuration of formula (I-S) as follows:

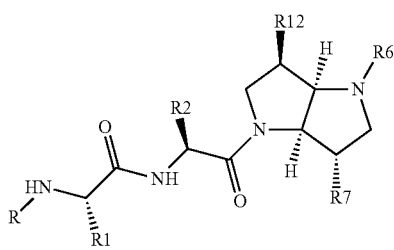

(I-S)

wherein:

R is selected from H, alkyl, substituted alkyl, alkenyl, substituted alkenyl, cycloalkyl, substituted cycloalkyl, aryl, substituted aryl, heteroaryl, or substituted heteroaryl;

R1 is selected from alkyl, or substituted alkyl;

R2 is selected from alkyl, substituted alkyl, cycloalkyl, heterocycloalkyl, aryl, or heteroaryl;

R6 is selected from H, alkylsulfonyl, arylsulfonyl, alkyl, substituted alkyl, cycloalkyl, substituted cycloalkyl, heterocycloalkyl, substituted heterocycloalkyl, aryl, substituted aryl, heteroaryl, or substituted heteroaryl; or R6 has the following formula (IA*):

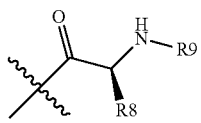

(IA*)

where R8 is selected from H, alkyl, substituted alkyl, cycloalkyl, heterocycloalkyl, aryl, or heteroaryl;

and R9 is selected from H, alkyl, substituted alkyl, cycloalkyl, substituted cycloalkyl, aryl, substituted aryl, heterocycloalkyl, substituted heterocycloalkyl, heteroaryl, or substituted heteroaryl; or R9 has the following formula (IB*):

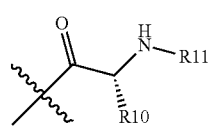

(IB*)

where R10 is selected from alkyl, or substituted alkyl;

and R11 is selected from H, alkyl, substituted alkyl, alkenyl, substituted alkenyl, cycloalkyl, substituted cycloalkyl, aryl, substituted aryl, heteroaryl, or substituted heteroaryl;

R7 is selected from H, or a 3-indolyl of the formula (IC):

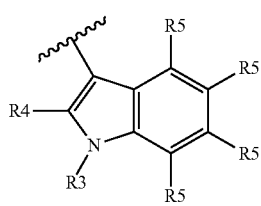

(IC)

where R3 is selected from H, alkyl, or substituted alkyl;

R4 is selected from H, halogen, alkyl, or substituted alkyl; and each R5 is independently selected from H, halogen, alkyl, or substituted alkyl; and R12 is selected from H or hydroxy.

In another embodiment, which can be practiced either separately, or in combination with the other embodiments disclosed above and below, the compounds and pharmaceutically acceptable salts of Formula (I) have the absolute configuration of formula (I-R) as follows (with the various substituents having the same definitions presented above in connection with formula (I-S):

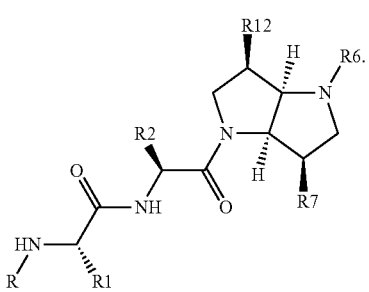

(I-R)

In another embodiment, which can be practiced either separately, or in combination with the other embodiments disclosed above and below, the various substituents of Formula (I-S) and (I-R) are defined as follows:

R is selected from H, alkyl, substituted alkyl, alkenyl, substituted alkenyl, aryl, substituted aryl, cycloalkyl, substituted cycloalkyl, heteroaryl, or substituted heteroaryl; wherein the substitutents are selected from the group consisting of halogen, hydroxy, oxo, mercapto, carboxyl, alkyl, cycloalkyl, aryl, alkoxy, amino, heteroaryl, and nitro;

R1 is alkyl, or substituted alkyl, wherein the substitutents are selected from the group consisting of halogen, hydroxy, oxo, mercapto, carboxyl, alkyl, cycloalkyl, aryl, alkoxy, amino, heteroaryl, and nitro;

R2 is alkyl, cycloalkyl, aryl, heterocycloalkyl, heteroaryl, or substituted alkyl, wherein the substituents are selected from the group consisting of halogen, hydroxy, oxo, alkoxy, cycloalkyl, aryl, heterocycloalkyl and heteroaryl;

R6 is selected from H; alkylsulfonyl; arylsulfonyl; alkyl; substituted alkyl, wherein the substituents are selected from the group consisting of halogen, hydroxy, oxo, mercapto, carboxyl, alkoxy, amino, nitro, cycloalkyl, aryl, heteroaryl optionally substituted with lower alkyl or halogen, alkylsulfonyl and arylsulfonyl; cycloalkyl; substituted cycloalkyl, wherein the substituents are selected from the group consisting of halogen, hydroxy, oxo, mercapto, carboxyl, alkyl, cycloalkyl, aryl, alkoxy, amino, heteroaryl, and nitro; aryl; substituted aryl, wherein the substituents are selected from the group consisting of alkyl, halogen, hydroxy, mercapto, carboxyl, cycloalkyl, aryl, alkoxy, amino, heteroaryl, nitro, alkylsulfonyl and arylsulfonyl; heterocycloalkyl; substituted heterocycloalkyl, wherein the substituents are selected from the group consisting of halogen, hydroxy, oxo, mercapto, carboxyl, alkyl, cycloalkyl, aryl, alkoxy, amino, heteroaryl, and nitro; heteroaryl; or substituted heteroaryl, wherein the substituents are selected from the group consisting of halogen, hydroxy, mercapto, carboxyl, alkyl, cycloalkyl, aryl, alkoxy, amino, heteroaryl, and nitro; or R6 has the following formula (IA*):

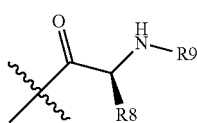

(IA*)

where R8 is alkyl, cycloalkyl, aryl, heterocycloalkyl, heteroaryl, or substituted alkyl, wherein the substituents are selected from the group consisting of halogen, hydroxy, oxo, alkoxy, cycloalkyl, aryl, heterocycloalkyl and heteroaryl;

and R9 is selected from H, alkyl, substituted alkyl, aryl, substituted aryl, cycloalkyl, substituted cycloalkyl, heteroaryl, or substituted heteroaryl; wherein the substitutents are selected from the group consisting of halogen, hydroxy, oxo, mercapto, carboxyl, alkyl, cycloalkyl, aryl, alkoxy, amino, heteroaryl, and nitro; or, R9 has the following formula (IB*):

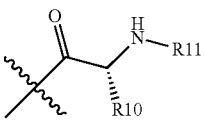

(IB*)

where R10 is selected from alkyl, or substituted alkyl, wherein the substitutents are selected from the group consisting of halogen, hydroxy, oxo, mercapto, carboxyl, alkyl, cycloalkyl, aryl, alkoxy, amino, heteroaryl, and nitro; and R11 is selected from H, alkyl, substituted alkyl, aryl, substituted aryl, cycloalkyl, substituted cycloalkyl, heteroaryl, or substituted heteroaryl; wherein the substitutents are selected from the group consisting of halogen, hydroxy, oxo, mercapto, carboxyl, alkyl, cycloalkyl, aryl, alkoxy, amino, heteroaryl, and nitro;

R7 is selected from H, or a 3-indolyl of the formula (IC):

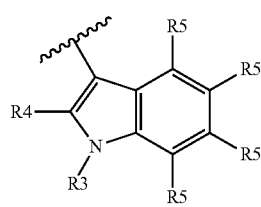

(IC)

where R3 is selected from H, alkyl, or substituted alkyl, where the substituents are selected from the group consisting of halogen, hydroxy, mercapto, carboxyl, alkyl, cycloalkyl, aryl, alkoxy, amino, heteroaryl, and nitro;

R4 is selected from H, halogen, alkyl, or substituted alkyl, where the substituents are selected from the group consisting of halogen, hydroxy, mercapto, carboxyl, alkyl, cycloalkyl, aryl, alkoxy, amino, heteroaryl, and nitro; and each R5 is independently selected from H, halogen, alkyl, or substituted alkyl, where the substituents are selected from the group consisting of halogen, hydroxy, mercapto, carboxyl, alkyl, cycloalkyl, aryl, alkoxy, amino, heteroaryl, and nitro; and R12 is selected from H, or hydroxy.

In another embodiment, which can be practiced either separately, or in combination with the other embodiments disclosed above and below, the various substituents of Formula (I-S) and (I-R) are defined as follows:

R is selected from H, alkyl, substituted alkyl, alkenyl, or substituted alkenyl; wherein the substitutents are selected from the group consisting of halogen, hydroxy, oxo, mercapto, carboxyl, alkyl, cyclopropyl, alkoxy, amino, and nitro;

R1 is selected from H, alkyl, or substituted alkyl, wherein the substitutents are selected from the group consisting of halogen, hydroxy, oxo, mercapto, carboxyl, alkyl, cyclopropyl, alkoxy, amino, and nitro.

R2 is alkyl, cycloalkyl, aryl, heterocycloalkyl, heteroaryl, or substituted alkyl, wherein the substituents are selected from the group consisting of halogen, hydroxy, oxo, alkoxy, cycloalkyl, aryl, heterocycloalkyl and heteroaryl;

R6 is selected from H; alkylsulfonyl; arylsulfonyl; alkyl; substituted alkyl, wherein the substituents are selected from the group consisting of halogen, hydroxy, oxo, mercapto, carboxyl, alkoxy, amino, nitro, cycloalkyl, aryl, heteroaryl optionally substituted with lower alkyl or halogen, alkylsulfonyl and arylsulfonyl; cycloalkyl; substituted cycloalkyl, wherein the substituents are selected from the group consisting of halogen, hydroxy, oxo, mercapto, carboxyl, alkyl, cycloalkyl, aryl, alkoxy, amino, heteroaryl, and nitro; aryl; substituted aryl, wherein the substituents are selected from the group consisting of alkyl, halogen, hydroxy, mercapto, carboxyl, cycloalkyl, aryl, alkoxy, amino, heteroaryl, nitro, alkylsulfonyl and arylsulfonyl; heterocycloalkyl; substituted heterocycloalkyl, wherein the substituents are selected from the group consisting of halogen, hydroxy, oxo, mercapto, carboxyl, alkyl, cycloalkyl, aryl, alkoxy, amino, heteroaryl, and nitro; heteroaryl; or substituted heteroaryl, wherein the substituents are selected from the group consisting of halogen, hydroxy, mercapto, carboxyl, alkyl, cycloalkyl, aryl, alkoxy, amino, heteroaryl, and nitro; or R6 has the following formula (IA*):

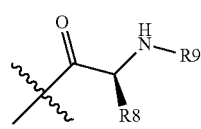

(IA*)

where R8 is alkyl, cycloalkyl, aryl, heterocycloalkyl, heteroaryl, or substituted alkyl, wherein the substituents are selected from the group consisting of halogen, hydroxy, oxo, alkoxy, cycloalkyl, aryl, heterocycloalkyl and heteroaryl;

and R9 is selected from H, alkyl, substituted alkyl, aryl, substituted aryl, cycloalkyl, substituted cycloalkyl, heteroaryl, or substituted heteroaryl; wherein the substitutents are selected from the group consisting of halogen, hydroxy, oxo, mercapto, carboxyl, alkyl, cycloalkyl, aryl, alkoxy, amino, heteroaryl, and nitro; or, R9 has the following formula (IB*):

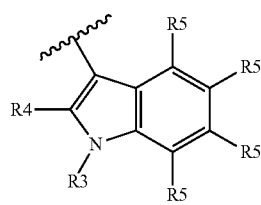
(IB*)

where R10 is selected from alkyl, or substituted alkyl, wherein the substitutents are selected from the group consisting of halogen, hydroxy, oxo, mercapto, carboxyl, alkyl, cycloalkyl, aryl, alkoxy, amino, heteroaryl, and nitro; and R11 is selected from H, alkyl, substituted alkyl, aryl, substituted aryl, cycloalkyl, substituted cycloalkyl, heteroaryl, or substituted heteroaryl; wherein the substitutents are selected from the group consisting of halogen, hydroxy, oxo, mercapto, carboxyl, alkyl, cycloalkyl, aryl, alkoxy, amino, heteroaryl, and nitro;

R7 is selected from H, or a 3-indolyl of the formula (IC):

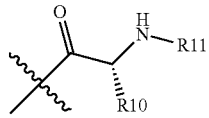
(IC)

where R3 is selected from H, alkyl, or substituted alkyl, where the substituents are selected from the group consisting of halogen, hydroxy, mercapto, carboxyl, alkyl, cycloalkyl, aryl, alkoxy, amino, heteroaryl, and nitro;

R4 is selected from H, halogen, alkyl, or substituted alkyl, where the substituents are selected from the group consisting of halogen, hydroxy, mercapto, carboxyl, alkyl, cycloalkyl, aryl, alkoxy, amino, heteroaryl, and nitro; and each R5 is independently selected from H, halogen, alkyl, or substituted alkyl, where the substituents are selected from the group consisting of halogen, hydroxy, mercapto, carboxyl, alkyl, cycloalkyl, aryl, alkoxy, amino, heteroaryl, and nitro; and R12 is selected from H, or hydroxy.

In other embodiments, which can be practiced either separately, or in combination with the other embodiments disclosed above and below, the present invention provides compounds of Formula (I), or pharmaceutically acceptable salts thereof, wherein:

R is selected from H, or lower alkyl;

R1a and R1b are each independently selected from H, or lower alkyl;

R2 is selected from H; lower alkyl; cycloalkyl; or substituted lower alkyl wherein the substituents are selected from the group consisting of hydroxy, and alkoxy;

R6 is selected from H; lower alkylsulfonyl; alkyl; substituted alkyl, wherein the alkyl substituents are selected from the group consisting of hydroxy, oxo, halogen, alkoxy, cycloalkyl, aryl, and heteroaryl optionally substituted with lower alkyl or halogen; cycloalkyl; or heteroaryl optionally substituted with lower alkyl or halogen; or R6 has the following formula (IA):

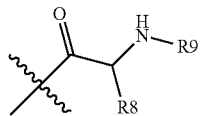
(IA)

where R8 is selected from H, lower alkyl, cycloalkyl, or substituted lower alkyl wherein the substituents are selected from the group consisting of hydroxy, and alkoxy; and R9 is selected from H, or lower alkyl; or R9 has the following formula (IB):

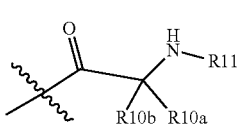
(IB)

where R10a and R10b are independently selected from H, or lower alkyl;

and R11 is selected from H, or lower alkyl;

R7 is selected from H, or a 3-indolyl of the formula (IC):

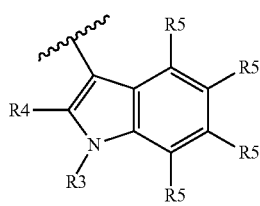
(IC)

where R3 is selected from H, or benzyl

R4 is selected from H, or halogen and each R5 is independently selected from H, or halogen; and R12 is H, or hydroxy.

In other embodiments, which can be practiced either separately, or in combination with the other embodiments disclosed above and below, the present invention provides compounds of Formula (I-S), or (I-R), or pharmaceutically acceptable salts thereof, wherein:

R is selected from H, or lower alkyl;

R1 is lower alkyl;

R2 is selected from lower alkyl; cycloalkyl; or substituted lower alkyl, wherein the substituents are selected from the group consisting of hydroxy, and alkoxy;

R6 is selected from H; lower alkylsulfonyl; alkyl; substituted alkyl, wherein the alkyl substituents are selected from the group consisting of hydroxy, oxo, halogen, alkoxy, cycloalkyl, aryl, and heteroaryl optionally substituted with lower alkyl or halogen; cycloalkyl; or heteroaryl optionally substituted with lower alkyl or halogen; or R6 has the following formula (IA*):

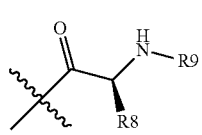
(IA*)

wherein R8 is selected from lower alkyl, cycloalkyl, or substituted lower alkyl, wherein the substituents are selected from the group consisting of hydroxy, and alkoxy; and R9 is selected from H, or lower alkyl; or R9 has the following formula (IB*):

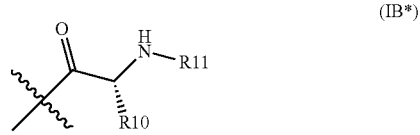

where R10 is lower alkyl; and
R11 is selected from H, or lower alkyl;
R7 is selected from H, or a 3-indolyl of the formula (IC):

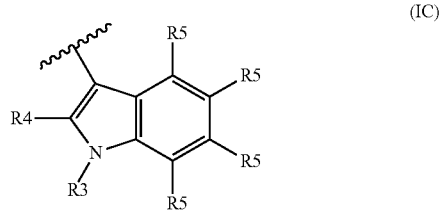

where R3 is selected from H, or aralkyl;
R4 is selected from H, or halogen and
each R5 is independently selected from H, or halogen; and
R12 is H, or hydroxy.

In another embodiment, which can be practiced either separately, or in combination with the other embodiments disclosed above and below, the present invention provides compounds of Formula (II):

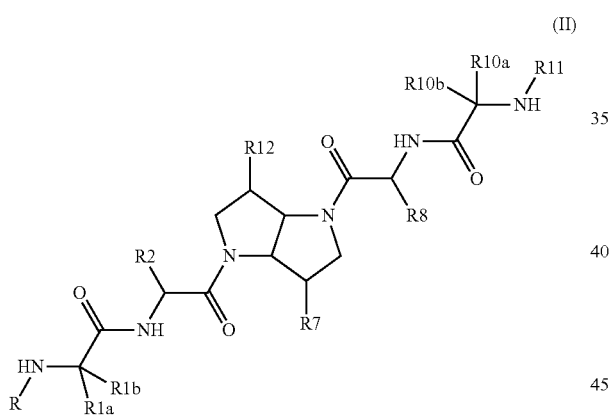

or pharmaceutically acceptable salts thereof, wherein:
R and R11 are independently selected from H, alkyl, substituted alkyl, alkenyl, substituted alkenyl, cycloalkyl, substituted cycloalkyl, aryl, substituted aryl, heteroaryl, or substituted heteroaryl;
R1a, R1b, R10a and R10b are independently selected from H, alkyl, or substituted alkyl;
R2 and R8 are independently selected from H, alkyl, substituted alkyl, cycloalkyl, heterocycloalkyl, aryl, or heteroaryl;
R7 is selected from H, or a 3-indolyl of the formula (IIC):

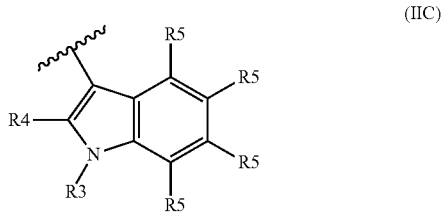

where R3 is selected from H, alkyl, or substituted alkyl;
R4 is selected from H, halogen, alkyl, or substituted alkyl; and
each R5 is independently selected from H, halogen, alkyl, or substituted alkyl; and
R12 is selected from H, or hydroxy, In another embodiment, which can be practiced either separately, or in combination with the other embodiments disclosed above and below, the various substituents of Formula (II) are defined as follows:
R and R11 are independently selected from H, alkyl, substituted alkyl, alkenyl, substituted alkenyl, aryl, substituted aryl, cycloalkyl, substituted cycloalkyl, heteroaryl, or substituted heteroaryl; wherein the substitutents are selected from the group consisting of halogen, hydroxy, oxo, mercapto, carboxyl, alkyl, cycloalkyl, aryl, alkoxy, amino, heteroaryl, and nitro;
R1a, R1b, R10a and R10b are independently selected from H, alkyl, or substituted alkyl, wherein the substitutents are selected from the group consisting of halogen, hydroxy, oxo, mercapto, carboxyl, alkyl, cycloalkyl, aryl, alkoxy, amino, heteroaryl, and nitro;
R2 and R8 are independently selected from alkyl, cycloalkyl, aryl, heterocycloalkyl, heteroaryl, or substituted alkyl, wherein the substituents are selected from the group consisting of halogen, hydroxy, oxo, alkoxy, cycloalkyl, aryl, heterocycloalkyl and heteroaryl;
R7 is selected from H, or a 3-indolyl of the formula (IIC):

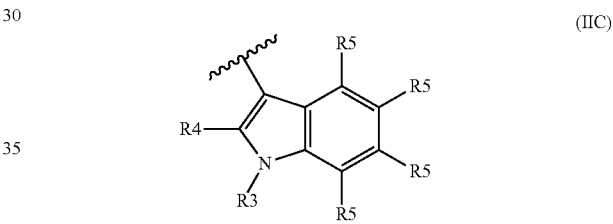

where R3 is selected from H, alkyl, or substituted alkyl, where the substituents are selected from the group consisting of halogen, hydroxy, mercapto, carboxyl, alkyl, cycloalkyl, aryl, alkoxy, amino, heteroaryl, and nitro;
R4 is selected from H, halogen, alkyl, or substituted alkyl, where the substituents are selected from the group consisting of halogen, hydroxy, mercapto, carboxyl, alkyl, cycloalkyl, aryl, alkoxy, amino, heteroaryl, and nitro; and
each R5 is independently selected from H, halogen, alkyl, or substituted alkyl, where the substituents are selected from the group consisting of halogen, hydroxy, mercapto, carboxyl, alkyl, cycloalkyl, aryl, alkoxy, amino, heteroaryl, and nitro; and
R12 is selected from H, or hydroxy.

In another embodiment, which can be practiced either separately, or in combination with the other embodiments disclosed above and below, the various substituents of Formula (II) are defined as follows:
R and R11 are independently selected from H, alkyl, substituted alkyl, alkenyl, or substituted alkenyl; wherein the substitutents are selected from the group consisting of halogen, hydroxy, oxo, mercapto, carboxyl, alkyl, cyclopropyl, alkoxy, amino, and nitro;
R1a, R1b, R10a and R10b are independently selected from H, alkyl, or substituted alkyl, wherein the substitutents are selected from the group consisting of halogen, hydroxy, oxo, mercapto, carboxyl, alkyl, cyclopropyl, alkoxy, amino, and nitro;

R2 and R8 are independently selected from alkyl, cycloalkyl, aryl, heterocycloalkyl, heteroaryl, or substituted alkyl, wherein the substituents are selected from the group consisting of halogen, hydroxy, oxo, alkoxy, cycloalkyl, aryl, heterocycloalkyl and heteroaryl;

R7 is selected from H, or a 3-indolyl of the formula (IIC):

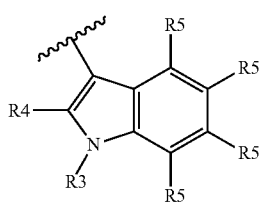

(IIC)

where R3 is selected from H, alkyl, or substituted alkyl, where the substituents are selected from the group consisting of halogen, hydroxy, mercapto, carboxyl, alkyl, cycloalkyl, aryl, alkoxy, amino, heteroaryl, and nitro;

R4 is selected from H, halogen, alkyl, or substituted alkyl, where the substituents are selected from the group consisting of halogen, hydroxy, mercapto, carboxyl, alkyl, cycloalkyl, aryl, alkoxy, amino, heteroaryl, and nitro; and each R5 is independently selected from H, halogen, alkyl, or substituted alkyl, where the substituents are selected from the group consisting of halogen, hydroxy, mercapto, carboxyl, alkyl, cycloalkyl, aryl, alkoxy, amino, heteroaryl, and nitro; and R12 is selected from H, or hydroxy.

In another embodiment, which can be practiced either separately, or in combination with the other embodiments disclosed above and below, the compounds of Formula (II), or their pharmaceutically acceptable salts, have the absolute configuration of formula (II-S) as follows:

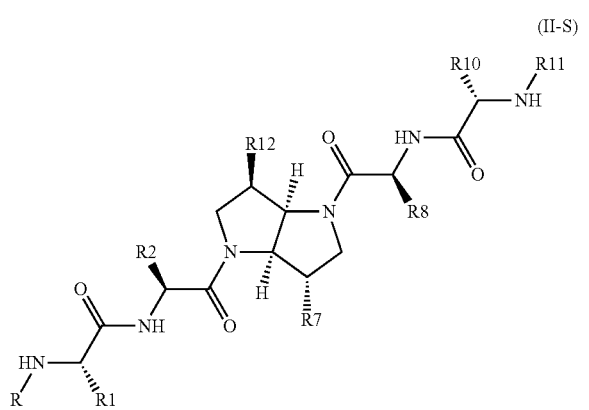

(II-S)

wherein:

R and R11 are independently selected from H, alkyl, substituted alkyl, alkenyl, substituted alkenyl, cycloalkyl, substituted cycloalkyl, aryl, substituted aryl, heteroaryl, or substituted heteroaryl;

R1 and R10 are independently selected from alkyl, or substituted alkyl;

R2 and R8 are independently selected from alkyl, substituted alkyl, cycloalkyl, heterocycloalkyl, aryl, or heteroaryl;

R7 is selected from H, or a 3-indolyl of the formula (IIC):

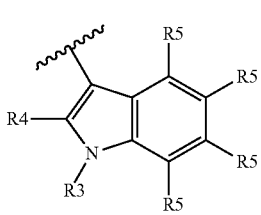

(IIC)

where R3 is selected from H, alkyl, or substituted alkyl;

R4 is selected from H, halogen, alkyl, or substituted alkyl; and each R5 is independently selected from H, halogen, alkyl, or substituted alkyl; and R12 is selected from H, or hydroxy.

In another embodiment, which can be practiced either separately, or in combination with the other embodiments disclosed above and below, the compounds of Formula (II), or their pharmaceutically acceptable salts, have the absolute configuration of formula (II-R) as follows (with the various substituents having the same definitions presented above with respect to formula (II-S)):

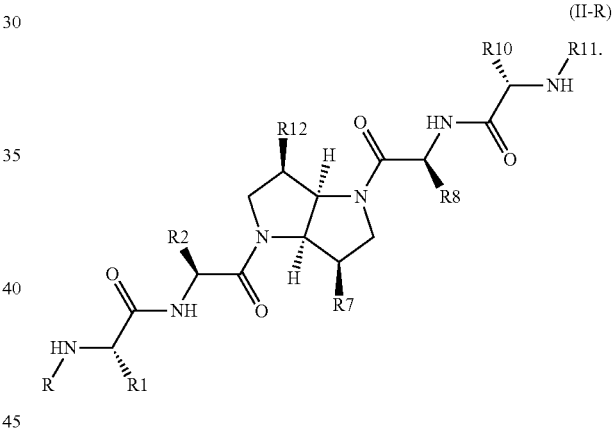

(II-R)

In another embodiment, which can be practiced either separately, or in combination with the other embodiments disclosed above and below, the various substituents of Formula (II-S) and (II-R) are defined as follows:

R and R11 are independently selected from H, alkyl, substituted alkyl, alkenyl, substituted alkenyl, aryl, substituted aryl, cycloalkyl, substituted cycloalkyl, heteroaryl, or substituted heteroaryl; wherein the substitutents are selected from the group consisting of halogen, hydroxy, oxo, mercapto, carboxyl, alkyl, cycloalkyl, aryl, alkoxy, amino, heteroaryl, and nitro;

R1 and R10 are independently selected from alkyl, or substituted alkyl, wherein the substitutents are selected from the group consisting of halogen, hydroxy, oxo, mercapto, carboxyl, alkyl, cycloalkyl, aryl, alkoxy, amino, heteroaryl, and nitro;

R2 and R8 are independently selected from alkyl, cycloalkyl, aryl, heterocycloalkyl, heteroaryl, or substituted alkyl, wherein the substituents are selected from the group consisting of halogen, hydroxy, oxo, alkoxy, cycloalkyl, aryl, heterocycloalkyl and heteroaryl;

R7 is selected from H, or a 3-indolyl of the formula (IIC):

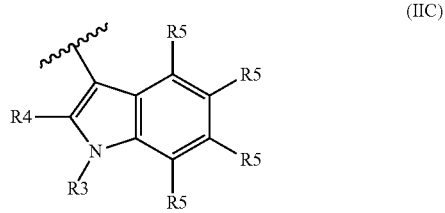

where R3 is selected from H, alkyl, or substituted alkyl, where the substituents are selected from the group consisting of halogen, hydroxy, mercapto, carboxyl, alkyl, cycloalkyl, aryl, alkoxy, amino, heteroaryl, and nitro;
R4 is selected from H, halogen, alkyl, or substituted alkyl, where the substituents are selected from the group consisting of halogen, hydroxy, mercapto, carboxyl, alkyl, cycloalkyl, aryl, alkoxy, amino, heteroaryl, and nitro; and
each R5 is independently selected from H, halogen, alkyl, or substituted alkyl, where the substituents are selected from the group consisting of halogen, hydroxy, mercapto, carboxyl, alkyl, cycloalkyl, aryl, alkoxy, amino, heteroaryl, and nitro; and
R12 is selected from H, or hydroxy.

In another embodiment, which can be practiced either separately, or in combination with the other embodiments disclosed above and below, the various substituents of Formula (II-S) and (II-R) are defined as follows:
R and R11 are independently selected from H, alkyl, substituted alkyl, alkenyl, or substituted alkenyl; wherein the substitutents are selected from the group consisting of halogen, hydroxy, oxo, mercapto, carboxyl, alkyl, cyclopropyl, alkoxy, amino, and nitro;
R1 and R10 are independently selected from alkyl, or substituted alkyl, wherein the substitutents are selected from the group consisting of halogen, hydroxy, oxo, mercapto, carboxyl, alkyl, cyclopropyl, alkoxy, amino, and nitro;
R2 and R8 are independently selected from alkyl, cycloalkyl, aryl, heterocycloalkyl, heteroaryl, or substituted alkyl, wherein the substituents are selected from the group consisting of halogen, hydroxy, oxo, alkoxy, cycloalkyl, aryl, heterocycloalkyl and heteroaryl;
R7 is selected from H, or a 3-indolyl of the formula (IIC):

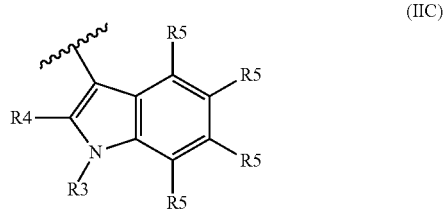

where R3 is selected from H, alkyl, or substituted alkyl, where the substituents are selected from the group consisting of halogen, hydroxy, mercapto, carboxyl, alkyl, cycloalkyl, awl, alkoxy, amino, heteroaryl, and nitro;
R4 is selected from H, halogen, alkyl, or substituted alkyl, where the substituents are selected from the group consisting of halogen, hydroxy, mercapto, carboxyl, alkyl, cycloalkyl, aryl, alkoxy, amino, heteroaryl, and nitro; and each R5 is independently selected from H, halogen, alkyl, or substituted alkyl, where the substituents are selected from the group consisting of halogen, hydroxy, mercapto, carboxyl, alkyl, cycloalkyl, aryl, alkoxy, amino, heteroaryl, and nitro; and
R12 is selected from H, or hydroxy.

In other embodiments, which can be practiced either separately, or in combination with the other embodiments disclosed above and below, the present invention provides compounds of Formula (II), or pharmaceutically acceptable salts thereof, wherein:
R and R11 are independently selected from H, or lower alkyl;
R1a, R1b, R10a and R10b are independently selected from H, or lower alkyl;
R2 and R8 are independently selected from H, lower alkyl, cycloalkyl, or substituted lower alkyl, wherein the substituents are selected from the group consisting of hydroxy, and alkoxy;
R7 is selected from H, or a 3-indolyl of the formula (IIC):

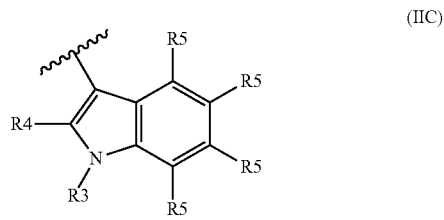

where R3 is selected from H, or aralkyl;
R4 is selected from H, or halogen and
each R5 is independently selected from H, or halogen; and
R12 is H, or hydroxy.

In other embodiments, which can be practiced either separately, or in combination with the other embodiments disclosed above and below, the present invention provides compounds of Formula (II-S), or (II-R), or pharmaceutically acceptable salts thereof, wherein:
R and R11 are independently selected from H, or lower alkyl;
R1 and R10 are independently selected from lower alkyl;
R2 and R8 are independently selected from lower alkyl; cycloalkyl; or substituted lower alkyl, wherein the substituents are selected from the group consisting of hydroxy, and alkoxy;
R7 is selected from H, or a 3-indolyl of the formula (IIC):

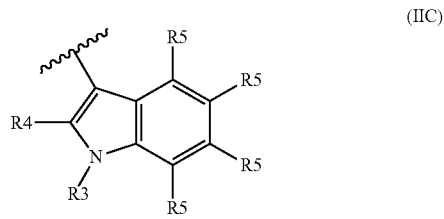

where R3 is selected from H, or aralkyl;
R4 is selected from H, or halogen and
each R5 is independently selected from H, or halogen; and
R12 is H, or hydroxy.

In another embodiment, which can be practiced either separately, or in combination with the other embodiments disclosed above and below, the present invention provides compounds of Formula (III):

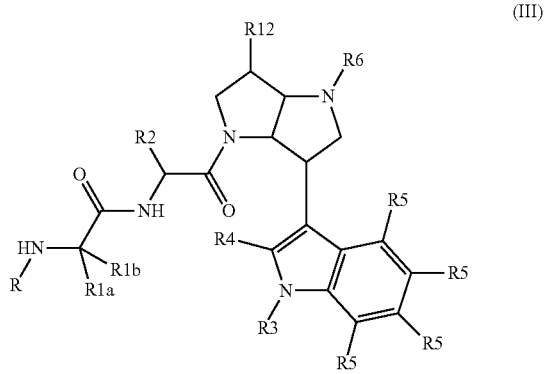

or pharmaceutically acceptable salts thereof, wherein:

R is selected from H, alkyl, substituted alkyl, alkenyl, substituted alkenyl, cycloalkyl, substituted cycloalkyl, aryl, substituted aryl, heteroaryl, or substituted heteroaryl;

R1a and R1b are each independently selected from H, alkyl, or substituted alkyl;

R2 is selected from H, alkyl, substituted alkyl, cycloalkyl, heterocycloalkyl, aryl, or heteroaryl;

R6 is selected from H, alkylsulfonyl, arylsulfonyl, alkyl, substituted alkyl, cycloalkyl, substituted cycloalkyl, heterocycloalkyl, substituted heterocycloalkyl, aryl, substituted aryl, heteroaryl, or substituted heteroaryl; or R6 has the following formula (IIIA):

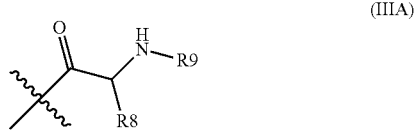

where R8 is selected from H, alkyl, substituted alkyl, cycloalkyl, heterocycloalkyl, aryl, or heteroaryl;

and R9 is selected from H, alkyl, substituted alkyl, cycloalkyl, substituted cycloalkyl, aryl, substituted aryl, heterocycloalkyl, substituted heterocycloalkyl, heteroaryl, or substituted heteroaryl; or R9 has the following formula (IIIB):

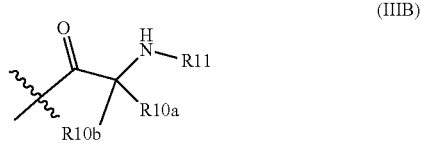

where R10a and R10b are independently selected from H, alkyl, or substituted alkyl;

and R11 is selected from H, alkyl, substituted alkyl, alkenyl, substituted alkenyl, cycloalkyl, substituted cycloalkyl, aryl, substituted aryl, heteroaryl, or substituted heteroaryl;

R3 is selected from H, alkyl, or substituted alkyl;

R4 is selected from H, halogen, alkyl, or substituted alkyl; and each R5 is independently selected from H, halogen, alkyl, or substituted alkyl; and R12 is selected from H, or hydroxy.

In another embodiment, which can be practiced either separately, or in combination with the other embodiments disclosed above and below, the various substituents of Formula (III) are defined as follows:

R is selected from H, alkyl, substituted alkyl, alkenyl, substituted alkenyl, aryl, substituted aryl, cycloalkyl, substituted cycloalkyl, heteroaryl, or substituted heteroaryl;

wherein the substitutents are selected from the group consisting of halogen, hydroxy, oxo, mercapto, carboxyl, alkyl, cycloalkyl, aryl, alkoxy, amino, heteroaryl, and nitro;

R1a and R1b are each independently selected from H, alkyl, or substituted alkyl, wherein the substitutents are selected from the group consisting of halogen, hydroxy, oxo, mercapto, carboxyl, alkyl, cycloalkyl, aryl, alkoxy, amino, heteroaryl, and nitro;

R2 is selected from H, alkyl, cycloalkyl, aryl, heterocycloalkyl, heteroaryl, or substituted alkyl, wherein the substituents are selected from the group consisting of halogen, hydroxy, oxo, alkoxy, cycloalkyl, aryl, heterocycloalkyl and heteroaryl;

R6 is selected from H; alkylsulfonyl; arylsulfonyl; alkyl; substituted alkyl, wherein the substituents are selected from the group consisting of halogen, hydroxy, oxo, mercapto, carboxyl, alkoxy, amino, nitro, cycloalkyl, aryl, heteroaryl optionally substituted with lower alkyl or halogen, alkylsulfonyl and arylsulfonyl; cycloalkyl; substituted cycloalkyl, wherein the substituents are selected from the group consisting of halogen, hydroxy, oxo, mercapto, carboxyl, alkyl, cycloalkyl, aryl, alkoxy, amino, heteroaryl, and nitro; aryl; substituted aryl, wherein the substituents are selected from the group consisting of alkyl, halogen, hydroxy, mercapto, carboxyl, cycloalkyl, aryl, alkoxy, amino, heteroaryl, nitro, alkylsulfonyl and arylsulfonyl; heterocycloalkyl; substituted heterocycloalkyl, wherein the substituents are selected from the group consisting of halogen, hydroxy, oxo, mercapto, carboxyl, alkyl, cycloalkyl, aryl, alkoxy, amino, heteroaryl, and nitro; heteroaryl; or substituted heteroaryl, wherein the substituents are selected from the group consisting of halogen, hydroxy, mercapto, carboxyl, alkyl, cycloalkyl, aryl, alkoxy, amino, heteroaryl, and nitro; or R6 has the following formula (IIIA):

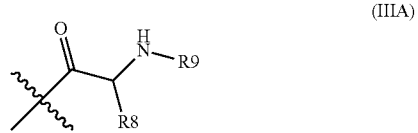

where R8 is selected from alkyl, cycloalkyl, aryl, heterocycloalkyl, heteroaryl, or substituted alkyl, wherein the substituents are selected from the group consisting of halogen, hydroxy, oxo, alkoxy, cycloalkyl, aryl, heterocycloalkyl and heteroaryl;

and R9 is selected from H, alkyl, substituted alkyl, aryl, substituted aryl, cycloalkyl, substituted cycloalkyl, heteroaryl, or substituted heteroaryl; wherein the substitutents are selected from the group consisting of halogen, hydroxy, oxo, mercapto, carboxyl, alkyl, cycloalkyl, aryl, alkoxy, amino, heteroaryl, and nitro; or, R9 has the following formula (IIIB):

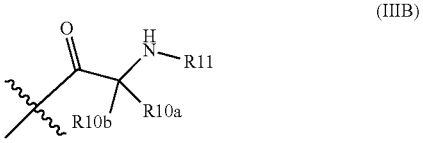

where R10a and R10b are independently selected from H, alkyl, or substituted alkyl, wherein the substitutents are selected from the group consisting of halogen, hydroxy, oxo, mercapto, carboxyl, alkyl, cycloalkyl, aryl, alkoxy, amino, heteroaryl, and nitro; and R11 is selected from H, alkyl, substituted alkyl, aryl, substituted aryl, cycloalkyl, substituted cycloalkyl, heteroaryl, or substituted heteroaryl; wherein the substitutents are selected from the group consisting of halogen, hydroxy, oxo, mercapto, carboxyl, alkyl, cycloalkyl, aryl, alkoxy, amino, heteroaryl, and nitro;

R3 is selected from H, alkyl, or substituted alkyl, where the substituents are selected from the group consisting of halogen, hydroxy, mercapto, carboxyl, alkyl, cycloalkyl, aryl, alkoxy, amino, heteroaryl, and nitro;

R4 is selected from H, halogen, alkyl, or substituted alkyl, where the substituents are selected from the group consisting of halogen, hydroxy, mercapto, carboxyl, alkyl, cycloalkyl, aryl, alkoxy, amino, heteroaryl, and nitro; and each R5 is independently selected from H, halogen, alkyl, or substituted alkyl, where the substituents are selected from the group consisting of halogen, hydroxy, mercapto, carboxyl, alkyl, cycloalkyl, aryl, alkoxy, amino, heteroaryl, and nitro; and R12 is selected from H, or hydroxy.

In another embodiment, which can be practiced either separately, or in combination with the other embodiments disclosed above and below, the various substituents of Formula (III) are defined as follows:

R is selected from H, alkyl, substituted alkyl, alkenyl, or substituted alkenyl; wherein the substitutents are selected from the group consisting of halogen, hydroxy, oxo, mercapto, carboxyl, alkyl, cyclopropyl, alkoxy, amino, and nitro;

R1a and R1b are each independently selected from H, alkyl, or substituted alkyl, wherein the substitutents are selected from the group consisting of halogen, hydroxy, oxo, mercapto, carboxyl, alkyl, cyclopropyl, alkoxy, amino, and nitro;

R2 is selected from H, alkyl, cycloalkyl, aryl, heterocycloalkyl, heteroaryl, or substituted alkyl, wherein the substituents are selected from the group consisting of halogen, hydroxy, oxo, alkoxy, cycloalkyl, aryl, heterocycloalkyl and heteroaryl;

R6 is selected from H; alkylsulfonyl; arylsulfonyl; alkyl; substituted alkyl, wherein the substituents are selected from the group consisting of halogen, hydroxy, oxo, mercapto, carboxyl, alkoxy, amino, nitro, cycloalkyl, aryl, heteroaryl optionally substituted with lower alkyl or halogen, alkylsulfonyl and arylsulfonyl; cycloalkyl; substituted cycloalkyl, wherein the substituents are selected from the group consisting of halogen, hydroxy, oxo, mercapto, carboxyl, alkyl, cycloalkyl, aryl, alkoxy, amino, heteroaryl, and nitro; aryl; substituted aryl, wherein the substituents are selected from the group consisting of alkyl, halogen, hydroxy, mercapto, carboxyl, cycloalkyl, aryl, alkoxy, amino, heteroaryl, nitro, alkylsulfonyl and arylsulfonyl; heterocycloalkyl; substituted heterocycloalkyl, wherein the substituents are selected from the group consisting of halogen, hydroxy, oxo, mercapto, carboxyl, alkyl, cycloalkyl, aryl, alkoxy, amino, heteroaryl, and nitro; heteroaryl; or substituted heteroaryl, wherein the substituents are selected from the group consisting of halogen, hydroxy, mercapto, carboxyl, alkyl, cycloalkyl, aryl, alkoxy, amino, heteroaryl, and nitro; or R6 has the following formula (IIIA):

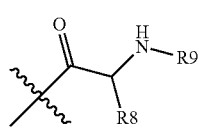

(IIIA)

where R8 is selected from alkyl, cycloalkyl, aryl, heterocycloalkyl, heteroaryl, or substituted alkyl, wherein the substituents are selected from the group consisting of halogen, hydroxy, oxo, alkoxy, cycloalkyl, aryl, heterocycloalkyl and heteroaryl;

and R9 is selected from H, alkyl, substituted alkyl, aryl, substituted aryl, cycloalkyl, substituted cycloalkyl, heteroaryl, or substituted heteroaryl; wherein the substitutents are selected from the group consisting of halogen, hydroxy, oxo, mercapto, carboxyl, alkyl, cycloalkyl, aryl, alkoxy, amino, heteroaryl, and nitro; or, R9 has the following formula (IIIB):

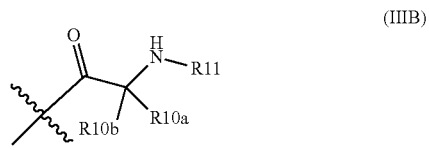

(IIIB)

where R10a and R10b are independently selected from H, alkyl, or substituted alkyl, wherein the substitutents are selected from the group consisting of halogen, hydroxy, oxo, mercapto, carboxyl, alkyl, cycloalkyl, aryl, alkoxy, amino, heteroaryl, and nitro; and R11 is selected from H, alkyl, substituted alkyl, aryl, substituted aryl, cycloalkyl, substituted cycloalkyl, heteroaryl, or substituted heteroaryl; wherein the substitutents are selected from the group consisting of halogen, hydroxy, oxo, mercapto, carboxyl, alkyl, cycloalkyl, aryl, alkoxy, amino, heteroaryl, and nitro;

R3 is selected from H, alkyl, or substituted alkyl, where the substituents are selected from the group consisting of halogen, hydroxy, mercapto, carboxyl, alkyl, cycloalkyl, aryl, alkoxy, amino, heteroaryl, and nitro;

R4 is selected from H, halogen, alkyl, or substituted alkyl, where the substituents are selected from the group consisting of halogen, hydroxy, mercapto, carboxyl, alkyl, cycloalkyl, aryl, alkoxy, amino, heteroaryl, and nitro; and each R5 is independently selected from H, halogen, alkyl, or substituted alkyl, where the substituents are selected from the group consisting of halogen, hydroxy, mercapto, carboxyl, alkyl, cycloalkyl, aryl, alkoxy, amino, heteroaryl, and nitro; and R12 is selected from H, or hydroxy.

In another embodiment, which can be practiced either separately, or in combination with the other embodiments disclosed above and below, the compounds of Formula (III), or their pharmaceutically acceptable salts, have the absolute configuration of formula (III-S) as follows:

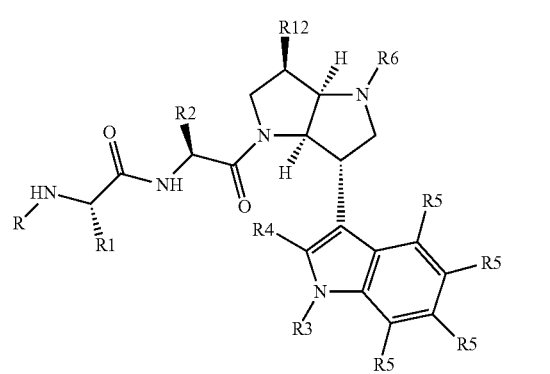

(III-S)

wherein

R is selected from H, alkyl, substituted alkyl, alkenyl, substituted alkenyl, cycloalkyl, substituted cycloalkyl, aryl, substituted aryl, heteroaryl, or substituted heteroaryl;

R1 is selected from alkyl, or substituted alkyl;

R2 is selected from alkyl, substituted alkyl, cycloalkyl, heterocycloalkyl, aryl, or heteroaryl;

R6 is selected from H, alkylsulfonyl, arylsulfonyl, alkyl, substituted alkyl, cycloalkyl, substituted cycloalkyl, heterocycloalkyl, substituted heterocycloalkyl, aryl, substituted aryl, heteroaryl, or substituted heteroaryl; or R6 has the following formula (IIIA*):

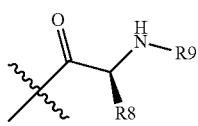

where R8 is selected from H, alkyl, substituted alkyl, cycloalkyl, heterocycloalkyl, aryl, or heteroaryl;

and R9 is selected from H, alkyl, substituted alkyl, cycloalkyl, substituted cycloalkyl, aryl, substituted aryl, heterocycloalkyl, substituted heterocycloalkyl, heteroaryl, or substituted heteroaryl; or R9 has the following formula (IIIB*):

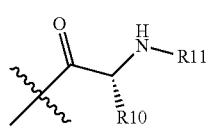

where R10 is selected from alkyl, or substituted alkyl;

and R11 is selected from H, alkyl, substituted alkyl, alkenyl, substituted alkenyl, cycloalkyl, substituted cycloalkyl, aryl, substituted aryl, heteroaryl, or substituted heteroaryl;

R3 is selected from H, alkyl, or substituted alkyl:

R4 is selected from H, halogen, alkyl, or substituted alkyl; and each R5 is independently selected from H, halogen, alkyl, or substituted alkyl; and R12 is selected from H or hydroxy.

In another embodiment, which can be practiced either separately, or in combination with the other embodiments disclosed above and below, the compounds of Formula (III), or their pharmaceutically acceptable salts, have the absolute configuration of formula (III-R) as follows (with the various substituents having the same definition presented above with respect to formula (III-S)):

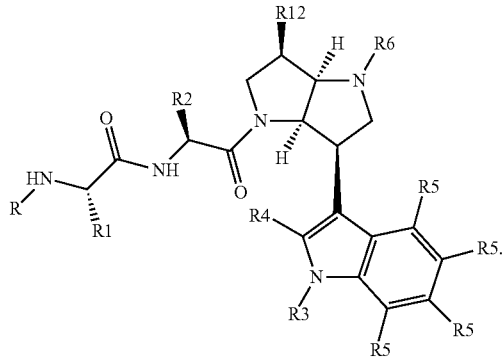

In another embodiment, which can be practiced either separately, or in combination with the other embodiments disclosed above and below, the various substituents of Formula (III-S) and (III-R) are defined as follows:

R is selected from H, alkyl, substituted alkyl, alkenyl, substituted alkenyl, aryl, substituted aryl, cycloalkyl, substituted cycloalkyl, heteroaryl, or substituted heteroaryl; wherein the substitutents are selected from the group consisting of halogen, hydroxy, oxo, mercapto, carboxyl, alkyl, cycloalkyl, aryl, alkoxy, amino, heteroaryl, and nitro;

R1 is selected from alkyl, or substituted alkyl, wherein the substitutents are selected from the group consisting of halogen, hydroxy, oxo, mercapto, carboxyl, alkyl, cycloalkyl, aryl, alkoxy, amino, heteroaryl, and nitro;

R2 is selected from alkyl, cycloalkyl, aryl, heterocycloalkyl, heteroaryl, or substituted alkyl, wherein the substituents are selected from the group consisting of halogen, hydroxy, oxo, alkoxy, cycloalkyl, aryl, heterocycloalkyl and heteroaryl;

R6 is selected from H; alkylsulfonyl; arylsulfonyl; alkyl; substituted alkyl, wherein the substituents are selected from the group consisting of halogen, hydroxy, oxo, mercapto, carboxyl, alkoxy, amino, nitro, cycloalkyl, aryl, heteroaryl optionally substituted with lower alkyl or halogen, alkylsulfonyl and arylsulfonyl; cycloalkyl; substituted cycloalkyl, wherein the substituents are selected from the group consisting of halogen, hydroxy, oxo, mercapto, carboxyl, alkyl, cycloalkyl, aryl, alkoxy, amino, heteroaryl, and nitro; aryl; substituted aryl, wherein the substituents are selected from the group consisting of alkyl, halogen, hydroxy, mercapto, carboxyl, cycloalkyl, aryl, alkoxy, amino, heteroaryl, nitro, alkylsulfonyl and arylsulfonyl; heterocycloalkyl; substituted heterocycloalkyl, wherein the substituents are selected from the group consisting of halogen, hydroxy, oxo, mercapto, carboxyl, alkyl, cycloalkyl, aryl, alkoxy, amino, heteroaryl, and nitro; heteroaryl; or substituted heteroaryl, wherein the substitutents are selected from the group consisting of halogen, hydroxy, mercapto, carboxyl, alkyl, cycloalkyl, aryl, alkoxy, amino, heteroaryl, and nitro; or R6 has the following formula (IIIA*):

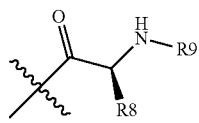

where R8 is selected from alkyl, cycloalkyl, aryl, heterocycloalkyl, heteroaryl, or substituted alkyl, wherein the substituents are selected from the group consisting of halogen, hydroxy, oxo, alkoxy, cycloalkyl, aryl, heterocycloalkyl and heteroaryl;

and R9 is selected from H, alkyl, substituted alkyl, aryl, substituted aryl, cycloalkyl, substituted cycloalkyl, heteroaryl, or substituted heteroaryl; wherein the substitutents are selected from the group consisting of halogen, hydroxy, oxo, mercapto, carboxyl, alkyl, cycloalkyl, aryl, alkoxy, amino, heteroaryl, and nitro; or, R9 has the following formula (IIIB*):

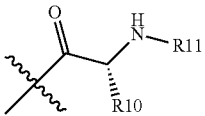

where R10 is selected from alkyl, or substituted alkyl, wherein the substitutents are selected from the group consisting of halogen, hydroxy, oxo, mercapto, carboxyl, alkyl, cycloalkyl, aryl, alkoxy, amino, heteroaryl, and nitro; and R11 is selected from H, alkyl, substituted alkyl, aryl, substituted aryl, cycloalkyl, substituted cycloalkyl, heteroaryl, or substituted heteroaryl; wherein the substitutents are selected from the group consisting of halogen, hydroxy, oxo, mercapto, carboxyl, alkyl, cycloalkyl, aryl, alkoxy, amino, heteroaryl, and nitro;

R3 is selected from H, alkyl, or substituted alkyl, where the substituents are selected from the group consisting of halogen, hydroxy, mercapto, carboxyl, alkyl, cycloalkyl, aryl, alkoxy, amino, heteroaryl, and nitro;

R4 is selected from H, halogen, alkyl, or substituted alkyl, where the substituents are selected from the group consisting of halogen, hydroxy, mercapto, carboxyl, alkyl, cycloalkyl, aryl, alkoxy, amino, heteroaryl, and nitro; and each R5 is independently selected from H, halogen, alkyl, or substituted alkyl, where the substituents are selected from the group consisting of halogen, hydroxy, mercapto, carboxyl, alkyl, cycloalkyl, aryl, alkoxy, amino, heteroaryl, and nitro; and R12 is selected from H, or hydroxy.

In another embodiment, which can be practiced either separately, or in combination with the other embodiments disclosed above and below, the various substituents of Formula (III-S) and (III-R) are defined as follows:

R is selected from H, alkyl, substituted alkyl, alkenyl, or substituted alkenyl; wherein the substitutents are selected from the group consisting of halogen, hydroxy, oxo, mercapto, carboxyl, alkyl, cyclopropyl, alkoxy, amino, and nitro;

R1 is selected from alkyl, or substituted alkyl, wherein the substitutents are selected from the group consisting of halogen, hydroxy, oxo, mercapto, carboxyl, alkyl, cyclopropyl, alkoxy, amino, and nitro;

R2 is selected from alkyl, cycloalkyl, aryl, heterocycloalkyl, heteroaryl, or substituted alkyl, wherein the substituents are selected from the group consisting of halogen, hydroxy, oxo, alkoxy, cycloalkyl, aryl, heterocycloalkyl and heteroaryl;

R6 is selected from H; alkylsulfonyl; arylsulfonyl; alkyl; substituted alkyl, wherein the substituents are selected from the group consisting of halogen, hydroxy, oxo, mercapto, carboxyl, alkoxy, amino, nitro, cycloalkyl, aryl, heteroaryl optionally substituted with lower alkyl or halogen, alkylsulfonyl and arylsulfonyl; cycloalkyl; substituted cycloalkyl, wherein the substituents are selected from the group consisting of halogen, hydroxy, oxo, mercapto, carboxyl, alkyl, cycloalkyl, aryl, alkoxy, amino, heteroaryl, and nitro; aryl; substituted aryl, wherein the substituents are selected from the group consisting of alkyl, halogen, hydroxy, oxo, mercapto, carboxyl, cycloalkyl, aryl, alkoxy, amino, heteroaryl, nitro, alkylsulfonyl and arylsulfonyl; heterocycloalkyl; substituted heterocycloalkyl, wherein the substituents are selected from the group consisting of halogen, hydroxy, oxo, mercapto, carboxyl, alkyl, cycloalkyl, aryl, alkoxy, amino, heteroaryl, and nitro; heteroaryl; or substituted heteroaryl, wherein the substituents are selected from the group consisting of halogen, hydroxy, mercapto, carboxyl, alkyl, cycloalkyl, aryl, alkoxy, amino, heteroaryl, and nitro; or R6 has the following formula (IIIA*):

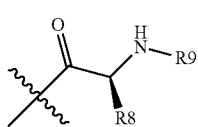

(IIIA*)

where R8 is selected from alkyl, cycloalkyl, aryl, heterocycloalkyl, heteroaryl, or substituted alkyl, wherein the substituents are selected from the group consisting of halogen, hydroxy, oxo, alkoxy, cycloalkyl, aryl, heterocycloalkyl and heteroaryl;

and R9 is selected from H, alkyl, substituted alkyl, aryl, substituted aryl, cycloalkyl, substituted cycloalkyl, heteroaryl, or substituted heteroaryl; wherein the substitutents are selected from the group consisting of halogen, hydroxy, oxo, mercapto, carboxyl, alkyl, cycloalkyl, aryl, alkoxy, amino, heteroaryl, and nitro; or, R9 has the following formula (IIIB*):

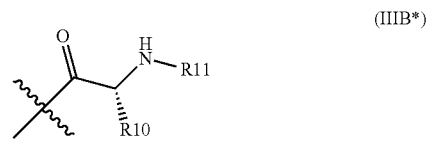

(IIIB*)

where R10 is selected from alkyl, or substituted alkyl, wherein the substitutents are selected from the group consisting of halogen, hydroxy, oxo, mercapto, carboxyl, alkyl, cycloalkyl, aryl, alkoxy, amino, heteroaryl, and nitro; and R11 is selected from H, alkyl, substituted alkyl, aryl, substituted aryl, cycloalkyl, substituted cycloalkyl, heteroaryl, or substituted heteroaryl; wherein the substitutents are selected from the group consisting of halogen, hydroxy, oxo, mercapto, carboxyl, alkyl, cycloalkyl, aryl, alkoxy, amino, heteroaryl, and nitro;

R3 is selected from H, alkyl, or substituted alkyl, where the substituents are selected from the group consisting of halogen, hydroxy, mercapto, carboxyl, alkyl, cycloalkyl, aryl, alkoxy, amino, heteroaryl, and nitro;

R4 is selected from H, halogen, alkyl, or substituted alkyl, where the substituents are selected from the group consisting of halogen, hydroxy, mercapto, carboxyl, alkyl, cycloalkyl, aryl, alkoxy, amino, heteroaryl, and nitro; and each R5 is independently selected from H, halogen, alkyl, or substituted alkyl, where the substituents are selected from the group consisting of halogen, hydroxy, mercapto, carboxyl, alkyl, cycloalkyl, aryl, alkoxy, amino, heteroaryl, and nitro; and R12 is selected from H, or hydroxy.

In other embodiments, which can be practiced either separately, or in combination with the other embodiments disclosed above and below, the present invention provides compounds of Formula (III), or pharmaceutically acceptable salts thereof, wherein:

R is selected from H, or lower alkyl;

R1a and R1b are each independently selected from H, or lower alkyl;

R2 is selected from H, lower alkyl, cycloalkyl, or substituted lower alkyl wherein the substituents are selected from the group consisting of hydroxy, and alkoxy;

R6 is selected from H; lower alkylsulfonyl; lower alkyl; substituted lower alkyl, wherein the alkyl substituents are selected from the group consisting of hydroxy, oxo, halogen, alkoxy, cycloalkyl, aryl, and heteroaryl optionally substituted with lower alkyl or halogen; cycloalkyl; or heteroaryl optionally substituted with lower alkyl or halogen; or R6 has the following formula (IIIA):

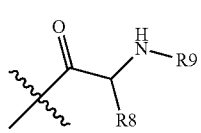

(IIIA)

where R8 is selected from H; lower alkyl; cycloalkyl, or substituted lower alkyl wherein the substituents are selected from the group consisting of hydroxy, and alkoxy; and R9 is selected from H, or lower alkyl; or R9 has the following formula (IIIB):

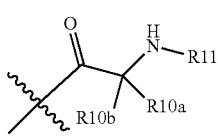

(IIIB)

where R10a and R10b are independently selected from H, or lower alkyl;
and R11 is selected from H, or lower alkyl;
R3 is selected from H, or aralkyl;
R4 is selected from H, or halogen; and
each R5 is independently selected from H, or halogen; and
R12 is H, or hydroxy.

In other embodiments, which can be practiced either separately, or in combination with the other embodiments disclosed above and below, the present invention provides compounds of Formula (III-S), or (III-R), or pharmaceutically acceptable salts thereof, wherein:
R is selected from H, or lower alkyl;
R1 is lower alkyl;
R2 is selected from lower alkyl; cycloalkyl; or substituted lower alkyl, wherein the substituents are selected from the group consisting of hydroxy, and alkoxy;
R6 is selected from H; lower alkylsulfonyl; alkyl; substituted alkyl, wherein the alkyl substituents are selected from the group consisting of hydroxy, oxo, halogen, alkoxy, cycloalkyl, aryl, and heteroaryl optionally substituted with lower alkyl or halogen; cycloalkyl; or heteroaryl optionally substituted with lower alkyl or halogen; or R6 has the following formula (IIIA*)

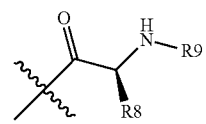

(IIIA*)

wherein R8 is selected from lower alkyl; cycloalkyl; or substituted lower alkyl wherein the substituents are selected from the group consisting of hydroxy, and alkoxy; and
R9 is selected from H, or lower alkyl; or R9 has the following formula (IIIB*);

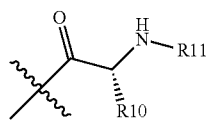

(IIIB*)

where R10 is lower alkyl; and
R11 is selected from H, or lower alkyl;
R3 is selected from H, or aralkyl;
R4 is selected from H, or halogen and
each R5 is independently selected from H, or halogen; and
R12 is H, or hydroxy.

In still other embodiments, which can be practiced either separately, or in combination with the other embodiments disclosed above and below, the substituents on the 3-indolyl of the following formula:

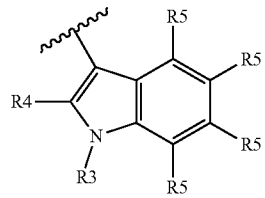

are defined as follows:
R3 is selected from H, lower alkyl, or substituted lower alkyl, where the substituents are selected from the group consisting of halogen, hydroxy, mercapto, carboxyl, alkyl, cycloalkyl, aryl, alkoxy, amino, heteroaryl, and nitro;
R4 is selected from H, halogen, lower alkyl, or substituted lower alkyl, where the substituents are selected from the group consisting of halogen, hydroxy, mercapto, carboxyl, alkyl, cycloalkyl, aryl, alkoxy, amino, heteroaryl, and nitro; and
each R5 is independently selected from H, halogen, lower alkyl, or substituted lower alkyl, where the substituents are selected from the group consisting of halogen, hydroxy, mercapto, carboxyl, alkyl, cycloalkyl, aryl, alkoxy, amino, heteroaryl, and nitro.

In all of the embodiments identified above, the pharmaceutically acceptable salts of the compounds embraced by the formulae are also included in each of the embodiments.

For simplicity and illustrative purposes, the principles of the invention are described by referring mainly to specific illustrative embodiments thereof. In addition, in the following description, numerous specific details are set forth in order to provide a thorough understanding of the invention. It will be apparent however, to one of ordinary skill in the art, that the invention may be practiced without limitation to these specific details. In other instances, well known methods and structures have not been described in detail so as not to unnecessarily obscure the invention.

DEFINITIONS

"Alkyl" (monovalent) and "alkylene" (divalent) when alone or as part of another term (e.g., alkoxy) mean branched or unbranched, saturated aliphatic hydrocarbon group, having up to 12 carbon atoms unless otherwise specified. Examples of particular alkyl groups include, but are not limited to, methyl, ethyl, n-propyl, isopropyl, n-butyl, iso-butyl, sec-butyl, tert-butyl, n-pentyl, 2-methylbutyl, 2,2-dimethylpropyl, n-hexyl, 2-methylpentyl, 2,2-dimethylbutyl, n-heptyl, 3-heptyl, 2-methylhexyl, and the like. The term, "lower," when used to modify alkyl, alkenyl, etc., means 1 to 4 carbon atoms, branched or linear so that, e.g., the terms "lower alkyl", "$C_1$-$C_4$ alkyl" and "alkyl of 1 to 4 carbon atoms" are synonymous and used interchangeably to mean methyl, ethyl, 1-propyl, isopropyl, cyclopropyl, 1-butyl, sec-butyl or t-butyl. Examples of alkylene groups include, but are not limited to, methylene, ethylene, n-propylene, n-butylene and 2-methyl-butylene.

The term substituted alkyl refers to alkyl moieties having substituents replacing one or more hydrogens on one or more (often no more than four) carbon atoms of the hydrocarbon backbone. Such substituents are independently selected from the group consisting of: a halogen (e.g., I, Br, Cl, or F), hydroxy, amino, cyano, mercapto, alkoxy (such as a $C_1$-$C_6$ alkoxy, e.g., methoxy or ethoxy to yield an alkoxyalkyl), aryloxy (such as phenoxy to yield an aryloxyalkyl), nitro, oxo (e.g., carbonyl), carboxyl (which is the combination of an oxo and hydroxy substituent on a single carbon atom), carbamoyl (an aminocarbonyl such as $NH_2C(O)$—), cycloalkyl (e.g., a cycloalkylalkyl), aryl (resulting for example in aralkyls such as benzyl or phenylethyl), heterocyclylalkyl (e.g., heterocycloalkylalkyl), heteroaryl (e.g., heteroarylalkyl), alkylsulfonyl (including lower alkylsulfonyl such as methylsulfonyl), arylsulfonyl (such as phenylsulfonyl), and —$OCF_3$ (which is a halogen substituted alkoxy). The invention further contemplates that several of these alkyl substituents, including specifically alkoxy, cycloalkyl, aryl, heterocyclyalkyl and heteroaryl, are optionally further substituted as defined in connection with each of their respective definitions provided below. In addition, certain alkyl substituent moieties result from a combination of such substitutions on a single carbon atom. For example, an ester moiety, e.g., an alkoxycarbonyl such as tert-butoxycarbonyl or Boc is a substituted alkyl that results from the substitution on a methyl group (—$CH_3$) of both an oxo (=O) and an unsubstituted alkoxy, e.g., a tert-butoxy (—$(CH_3)_3C$—O—), replacing the three hydrogens. Similarly, an amide moiety, e.g., an alkylaminocarbonyl such as dimethylaminocarbonyl is a substituted alkyl that results from the substitution on a methyl group (—$CH_3$) of both an oxo (=O) and a di-unsubstitutedalkylamino, e.g., dimethylamino (—N—$(CH_3)_2$), replacing the three hydrogens. Exemplary substituted alkyl groups include cyanomethyl, nitromethyl, hydroxyalkyls such as hydroxymethyl, trityloxymethyl, propionyloxymethyl, aminoalkyls such as aminomethyl, carboxylalkyls such as carboxymethyl, carboxyethyl, carboxypropyl, 2,3-dichloropentyl, 3-hydroxy-5-carboxyhexyl, acetyl (e.g., an alkanoyl, where in the case of acetyl the two hydrogen atoms on the —$CH_2$ portion of an ethyl group are replaced by an oxo (=O)), 2-aminopropyl, pentachlorobutyl, trifluoromethyl, methoxyethyl, 3-hydroxypentyl, 4-chlorobutyl, 1,2-dimethyl-propyl, pentafluoroethyl, alkyloxycarbonylmethyl, allyloxycarbonylaminomethyl, carbamoyloxymethyl, methoxymethyl, ethoxymethyl, t-butoxymethyl, acetoxymethyl, chloromethyl, bromomethyl, iodomethyl, trifluoromethyl, 6-hydroxyhexyl, 2,4-dichloro (n-butyl), 2-amino (iso-propyl), and 2-carbamoyloxyethyl. Particular substituted alkyls are substituted methyl groups. Examples of substituted methyl group include groups such as hydroxymethyl, protected hydroxymethyl (e.g., tetrahydropyranyl-oxymethyl), acetoxymethyl, carbamoyloxymethyl, trifluoromethyl, chloromethyl, carboxymethyl, carboxyl (where the three hydrogen atoms on the methyl are replaced, two of the hydrogens are replaced by an oxo (=O) and the other hydrogen is replaced by a hydroxy (—OH)), tert-butoxycarbonyl (where the three hydrogen atoms on the methyl are replaced, two of the hydrogens are replaced by an oxo (=O) and the other hydrogen is replaced by a tert-butoxy (—O—$C(CH_3)_3$), bromomethyl and iodomethyl.

The term substituted alkylene refers to alkylene moieties having substituents replacing one or more hydrogens on one or more (often no more than four) carbon atoms of the hydrocarbon backbone where the alkylene is similarly substituted with groups as set forth above for alkyl.

Alkoxy is —O-alkyl. A substituted alkoxy is —O-substituted alkyl, where the alkoxy is similarly substituted with groups as set forth above for alkyl. One substituted alkoxy is acetoxy where two of the hydrogens in ethoxy (e.g., —O—$CH_2$—$CH_3$) are replaced by an oxo, (=O) to yield —O—C(O)—$CH_3$ another is an aralkoxy where one of the hydrogens in the alkoxy is replaced by an aryl, such as benzyloxy.

"Alkenyl" (monovalent) and "alkenylene" (divalent) when alone or as part of another term mean an unsaturated hydrocarbon group containing at least one carbon-carbon double bond, typically 1 or 2 carbon-carbon double bonds, which may be linear or branched and which have at least 2 and up to 12 carbon atoms unless otherwise specified. Representative alkenyl groups include, by way of example, vinyl, allyl, isopropenyl, but-2-enyl, n-pent-2-enyl, and n-hex-2-enyl.

The terms substituted alkenyl and substituted alkenylene refer to alkenyl and alkenylene moieties having substituents replacing one or more hydrogens on one or more (often no more than four) carbon atoms of the hydrocarbon backbone. Such substituents are independently selected from the group consisting of: halo (e.g., I, Br, Cl, F), hydroxy, amino, cyano, alkoxy (such as $C_1$-$C_6$ alkoxy), aryloxy (such as phenoxy), nitro, mercapto, carboxyl, oxo, carbamoyl, cycloalkyl, aryl, heterocyclyl, heteroaryl, alkylsulfonyl, arylsulfonyl and —$OCF_3$.

"Alkynyl" means a monovalent unsaturated hydrocarbon group containing at least one carbon-carbon triple bond, typically 1 carbon-carbon triple bond, which may be linear or branched and which have at least 2 and up to 12 carbon atoms unless otherwise specified. Representative alkynyl groups include, by way of example, ethynyl, propargyl, and but-2-ynyl.

"Cycloalkyl" when alone or as part of another term means a saturated or partially unsaturated cyclic aliphatic hydrocarbon group (carbocycle group), having up to 12 carbon atoms unless otherwise specified and includes cyclic and polycyclic, including fused cycloalkyl.

The term substituted cycloalkyl refers to cycloalkyl moieties having substituents replacing one or more hydrogens on one or more (often no more than four) carbon atoms of the hydrocarbon backbone. Such substituents are independently selected from the group consisting of: halo (e.g., I, Br, Cl, F), hydroxy, amino, cyano, alkoxy (such as $C_1$-$C_6$ alkoxy), substituted alkoxy, aryloxy (such as phenoxy), nitro, mercapto, carboxyl, oxo, carbamoyl, alkyl, substituted alkyls such as trifluoromethyl, aryl, substituted aryls, heterocyclyl, heteroaryl, alkylsulfonyl, arylsulfonyl and —$OCF_3$. Examples of cycloalkyls include cyclopropy, cyclobutyl, cyclopentyl, cyclohexyl, tetrahydronaphthyl and indanyl.

"Amino" denotes primary (i.e., —$NH_2$), secondary (i.e., —NHR) and tertiary (i.e., —NRR) amines, where the R groups can be a variety of moieties, usually an alkyl, a substituted alkyl, an aryl, or a substituted aryl and especially a lower alkyl. Particular secondary and tertiary aminos are alkylaminos, dialkylaminos, arylaminos, diarylaminos, aralkylaminos and diaralkylaminos. Particular secondary and tertiary amines are methylamino, ethylamino, propylamino, isopropylamino, phenylamino, benzylamino dimethylamino, diethylamino, dipropylamino and disopropylamino.

"Aryl" when used alone or as part of another term means an aromatic carbocyclic group whether or not fused having the number of carbon atoms designated, or if no number is designated, from 6 up to 14 carbon atoms. Particular aryl groups include phenyl, naphthyl, biphenyl, phenanthrenyl, naphthacenyl, and the like (see e.g. Lang's Handbook of Chemistry (Dean, J. A., ed) 13$^{th}$ ed. Table 7-2 [1985]). Phenyl groups are generally preferred.

The term substituted aryl refers to aryl moieties having substituents replacing one or more hydrogens on one or more (usually no more than six) carbon atoms of the aromatic hydrocarbon core. Such substituents are independently selected from the group consisting of: halo (e.g., I, Br, Cl, F), hydroxy, amino, cyano, alkoxy (such as $C_1$-$C_6$ alkoxy), substituted alkoxy, aryloxy (such as phenoxy), nitro, mercapto, carboxyl, carbamoyl, alkyl, substituted alkyl (such as trifluoromethyl), aryl, —$OCF_3$, alkylsulfonyl (including lower alkylsulfonyl), arylsulfonyl, heterocyclyl and heteroaryl. Examples of such substituted phenyls include but are not limited to a mono- or di(halo) phenyl group such as 2-chlorophenyl, 2-bromophenyl, 4-chlorophenyl, 2,6-dichlorophenyl, 2,5-dichlorophenyl, 3,4-dichlorophenyl, 3-chlorophenyl, 3-bromophenyl, 4-bromophenyl, 3,4-dibromophenyl, 3-chloro-4-fluorophenyl, 2-fluorophenyl; a mono- or di(hydroxy)phenyl group such as 4-hydroxyphenyl, 3-hydroxyphenyl, 2,4-dihydroxyphenyl, the protected-hydroxy derivatives thereof; a nitrophenyl group such as 3- or 4-nitrophenyl; a cyanophenyl group, for example, 4-cyanophenyl; a mono- or di(lower alkyl)phenyl group such as 4-methylphenyl, 2,4-dimethylphenyl, 2-methylphenyl, 4-(iso-propyl)phenyl, 4-ethylphenyl, 3-(n-propyl)phenyl; a mono or di(alkoxy) phenyl group, for example, 3,4-dimethoxyphenyl, 3-methoxy-4-benzyloxyphenyl, 3-methoxy-4-(1-chloromethyl)benzyloxy-phenyl, 3-ethoxyphenyl, 4-(isopropoxy) phenyl, 4-(t-butoxy)phenyl, 3-ethoxy-4-methoxyphenyl; 3- or 4-trifluoromethylphenyl; a mono- or dicarboxyphenyl or (protected carboxy)phenyl group such 4-carboxyphenyl; a mono- or di(hydroxymethyl)phenyl or (protected hydroxymethyl)phenyl such as 3-(protected hydroxymethyl)phenyl or 3,4-di(hydroxymethyl)phenyl; a mono- or di(aminomethyl) phenyl or (protected aminomethyl)phenyl such as 2-(aminomethyl)phenyl or 2,4-(protected aminomethyl)phenyl; or a mono- or di(N-(methylsulfonylamino)) phenyl such as 3-(N-methylsulfonylamino) phenyl. Also, the substituents, such as in a disubstituted phenyl groups, can be the same or different, for example, 3-methyl-4-hydroxyphenyl, 3-chloro-4-hydroxyphenyl, 2-methoxy-4-bromophenyl, 4-ethyl-2-hydroxyphenyl, 3-hydroxy-4-nitrophenyl, 2-hydroxy-4-chlorophenyl, as well as for trisubstituted phenyl groups where the substituents are different, as for example 3-methoxy-4-benzyloxy-6-methyl sulfonylamino, 3-methoxy-4-benzyloxy-6-phenyl sulfonylamino, and tetrasubstituted phenyl groups where the substituents are different such as 3-methoxy-4-benzyloxy-5-methyl-6-phenyl sulfonylamino. Particular substituted phenyl groups are 2-chlorophenyl, 2-aminophenyl, 2-bromophenyl, 3-methoxyphenyl, 3-ethoxy-phenyl, 4-benzyloxyphenyl, 4-methoxyphenyl, 3-ethoxy-4-benzyloxyphenyl, 3,4-diethoxyphenyl, 3-methoxy-4-benzyloxyphenyl, 3-methoxy-4-(1-chloromethyl)benzyloxy-phenyl, 3-methoxy-4-(1-chloromethyl)benzyloxy-6-methyl sulfonyl aminophenyl groups. Fused aryl rings may also be substituted with the substituents specified herein, for example with 1, 2 or 3 substituents, in the same manner as substituted alkyl groups.

Aryloxy is —O-aryl. A substituted aryloxy is —O-substituted aryl.

"Heterocyclic group", "heterocyclic", "heterocycle", "heterocyclyl", "heterocycloalkyl" or "heterocyclo" alone and when used as a moiety in a complex group, are used interchangeably and refer to any mono-, bi-, or tricyclic, saturated or unsaturated, non-aromatic hetero-atom-containing ring system having the number of atoms designated, or if no number is specifically designated then from 5 to about 14 atoms, where the ring atoms are carbon and at least one heteroatom and usually not more than four heteroatoms (i.e., nitrogen, sulfur or oxygen). Included in the definition are any bicyclic groups where any of the above heterocyclic rings are fused to an aromatic ring (i.e., an aryl (e.g., benzene) or a heteroaryl ring). In a particular embodiment the group incorporates 1 to 4 heteroatoms. Typically, a 5-membered ring has 0 to 1 double bonds and a 6- or 7-membered ring has 0 to 2 double bonds and the nitrogen or sulfur heteroatoms may optionally be oxidized (e.g. SO, $SO_2$), and any nitrogen heteroatom may optionally be quaternized. Particular unsubstituted non-aromatic heterocycles include morpholinyl (morpholino), pyrrolidinyl, oxiranyl, indolinyl, isoindolinyl, tetrahydroquinolinyl, tetrahydroisoquinolinyl, oxetanyl, tetrahydrofuranyl, 2,3-dihydrofuranyl, 2H-pyranyl, tetrahydropyranyl, aziridinyl, azetidinyl, 1-methyl-2-pyrrolyl, piperazinyl and piperidinyl.

The term substituted heterocyclo refers to heterocyclo moieties having substituents replacing one or more hydrogens on one or more (usually no more than six) atoms of the heterocyclo backbone. Such substituents are independently selected from the group consisting of: halo (e.g., I, Br, Cl, F), hydroxy, amino, cyano, alkoxy (such as $C_1$-$C_6$ alkoxy), substituted alkoxy, aryloxy (such as phenoxy), nitro, carboxyl, oxo, carbamoyl, alkyl, substituted alkyl (such as trifluoromethyl), —$OCF_3$, aryl, substituted aryl, alkylsulfonyl (including lower alkylsulfonyl), and arylsulfonyl.

"Heteroaryl" alone and when used as a moiety in a complex group refers to any mono-, bi-, or tricyclic aromatic ring system having the number of atoms designated, or if no number is specifically designated then at least one ring is a 5-, 6- or 7-membered ring and the total number of atoms is from 5 to about 14 and containing from one to four heteroatoms selected from the group consisting of nitrogen, oxygen, and sulfur (Lang's Handbook of Chemistry, supra). Included in the definition are any bicyclic groups where any of the above heteroaryl rings are fused to a benzene ring. The following ring systems are examples of the heteroaryl groups denoted by the term "heteroaryl": thienyl (alternatively called thiophenyl), furyl, imidazolyl, pyrazolyl, thiazolyl, isothiazolyl, oxazolyl, isoxazolyl, triazolyl, thiadiazolyl, oxadiazolyl, tetrazolyl, thiatriazolyl, oxatriazolyl, pyridyl, pyrimidyl, pyrazinyl, pyridazinyl, thiazinyl, oxazinyl, triazinyl, thiadiazinyl, oxadiazinyl, dithiazinyl, dioxazinyl, oxathiazinyl, tetrazinyl, thiatriazinyl, oxatriazinyl, dithiadiazinyl, imidazolinyl, dihydropyrimidyl, tetrahydropyrimidyl, tetrazolo[1,5-b]pyridazinyl and purinyl, as well as benzo-fused derivatives, for example benzoxazolyl, benzofuryl, benzothienyl, benzothiazolyl, benzothiadiazolyl, benzotriazolyl, benzoimidazolyl and indolyl.

The term substituted heteroaryl refers to heteroaryl moieties having substituents replacing one or more hydrogens on one or more (usually no more than six) atoms of the heteroaryl backbone. Such substituents are independently selected from the group consisting of: halo (e.g., I, Br, Cl, F), hydroxy, amino, cyano, alkoxy (such as $C_1$-$C_6$ alkoxy), aryloxy (such as phenoxy), nitro, mercapto, carboxyl, carbamoyl, alkyl, substituted alkyl (such as trifluoromethyl), —$OCF_3$, aryl, substituted aryl, alkylsulfonyl (including lower alkylsulfonyl), and arylsulfonyl. Particular "heteroaryls" include; 1H-pyrrolo[2,3-b]pyridine, 1,3-thiazol-2-yl, 4-(carboxymethyl)-5-methyl-1,3-thiazol-2-yl, 1,2,4-thiadiazol-5-yl, 3-methyl-1,2,4-thiadiazol-5-yl, 1,3,4-triazol-5-yl, 2-methyl-1,3,4-triazol-5-yl, 2-hydroxy-1,3,4-triazol-5-yl, 2-carboxy-4-methyl-1,3,4-triazol-5-yl, 1,3-oxazol-2-yl, 1,3,4-oxadiazol-5-yl, 2-methyl-1,3,4-oxadiazol-5-yl, 2-(hydroxymethyl)-1,3,4-oxadiazol-5-yl, 1,2,4-oxadiazol-5-yl, 1,3,4-thiadiazol-5-yl, 2-thiol-1,3,4-thiadiazol-5-yl, 2-(methylthio)-1,3,4-thiadiazol-5-yl, 2-amino-1,3,4-thiadiazol-5-yl, 1H-tetrazol-5-yl, 1-methyl-1H-tetrazol-5-yl, 1-(1-(dimethylamino) eth-2-yl)-1H-tetrazol-5-yl, 1-(carboxymethyl)-1H-tetrazol-5-yl, 1-(methylsulfonic acid)-1H-tetrazol-5-yl, 2-methyl-1H-tetrazol-5-yl, 1,2,3-triazol-5-yl, 1-methyl-1,2,3-triazol-5-yl, 2-methyl-1,2,3-triazol-5-yl, 4-methyl-1,2,3-triazol-5-yl, pyrid-2-yl N-oxide, 6-methoxy-2-(n-oxide)-pyridaz-3-yl, 6-hydroxypyridaz-3-yl, 1-methylpyrid-2-yl, 1-methylpyrid-4-yl, 2-hydroxypyrimid-4-yl, 1,4,5,6-tetrahydro-5,6-dioxo-4-methyl-as-triazin-3-yl, 1,4,5,6-tetrahydro-4-(formylmethyl)-5,6-dioxo-as-triazin-3-yl, 2,5-dihydro-5-oxo-6-hydroxy-astriazin-3-yl, 2,5-dihydro-5-oxo-6-hydroxy-as-triazin-3-yl, 2,5-dihydro-5-oxo-6-hydroxy-2-methyl-astriazin-3-yl, 2,5-dihydro-5-oxo-6-hydroxy-2-methyl-as-triazin-3-yl, 2,5-dihydro-5-oxo-6-methoxy-2-methyl-as-triazin-3-yl, 2,5-dihydro-5-oxo-as-triazin-3-yl, 2,5-dihydro-5-oxo-2-methyl-as-triazin-3-yl, 2,5-dihydro-5-oxo-2,6-dimethyl-as-triazin-3-yl, tetrazolo[1,5-b]pyridazin-6-yl and 8-aminotetrazolo[1,5-b]-pyridazin-6-yl. An alternative group of "heteroaryl" includes: 4-(carboxymethyl)-5-methyl-1,3-thiazol-2-yl, 1,3,4-triazol-5-yl, 2-methyl-1,3,4-triazol-5-yl, 1H-tetrazol-5-yl, 1-methyl-1H-tetrazol-5-yl, 1-(1-(dimethylamino) eth-2-yl)-1H-tetrazol-5-yl, 1-(carboxymethyl)-1H-tetrazol-5-yl, 1-(methylsulfonic acid)-1H-tetrazol-5-yl, 1,2,3-triazol-5-yl, 1,4,5,6-tetrahydro-5,6-dioxo-4-methyl-as-triazin-3-yl, 1,4,5,6-tetrahydro-4-(2-formylmethyl)-5,6-dioxo-as-triazin-3-yl, 2,5-dihydro-5-oxo-6-hydroxy-2-methyl-as-triazin-3-yl, 2,5-dihydro-5-oxo-6-hydroxy-2-methyl-as-triazin-3-yl, tetrazolo[1,5-b]pyridazin-6-yl, and 8-aminotetrazolo[1,5-b]pyridazin-6-yl.

"IAP Inhibitor" or "IAP antagonist" means a compound (1) which interferes with the physiological function of an IAP protein, including the binding of IAP proteins to caspase proteins, for example by reducing or preventing the binding of IAP proteins to caspase proteins, or (2) which reduces or prevents the inhibition of apoptosis by an IAP protein, or (3) which binds to an IAP BIR domain in a manner similar to the binding of the amino terminal portion of Smac, or (4) has any two, or all three of the preceding functions.

As used herein, the terms "pharmaceutically acceptable", "physiologically tolerable" and grammatical variations thereof, as they refer to compositions, excipients, carriers, diluents and reagents, are used interchangeably and represent that the materials can be administered to a subject or patient.

"Pharmaceutically acceptable salts" include both acid and base addition salts.

"Pharmaceutically acceptable acid addition salt" refers to those non-toxic salts which retain the biological effectiveness and essential properties of the associated free bases and which are not biologically or otherwise undesirable, and are formed with inorganic acids and with organic acids. The acid addition salts of the basic compounds are prepared by contacting the free base form of the compound with a sufficient amount of the desired acid to produce the salt in the conventional manner. The free base form may be regenerated by contacting the salt form with a base and isolating the free base in the conventional manner. The free base forms generally differ from their respective salt forms somewhat in certain physical properties such as solubility in polar solvents.

"Pharmaceutically acceptable base addition salts" refer to those non-toxic salts which retain the biological effectiveness and essential properties of the associated free acids and which are not biologically or otherwise undesirable and are formed with metals or amines, such as alkali and alkaline earth metal hydroxides, or with organic amines. The base addition salts of acidic compounds are prepared by contacting the free acid form with a sufficient amount of the desired base to produce the salt in the conventional manner. The free acid form may be regenerated by contacting the salt form with an acid and isolating the free acid in a conventional manner. The free acid forms usually differ from their respective salt forms somewhat in certain physical properties such as solubility in polar solvents.

The terms "treating", "treat" or "treatment" and the like include preventative (e.g., prophylactic) and palliative treatment.

As used herein "subject" or "patient" refers to an animal or mammal including, but not limited to, human, dog, cat, horse, cow, pig, sheep, goat, chicken, monkey, rabbit, rat, and mouse.

As used herein, the term "therapeutic" refers to the amelioration of, the prevention of, an improvement of, or a delay in the onset of one or more symptoms of an unwanted condition or disease of a patient. Embodiments of the present invention are directed to therapeutic treatments by promoting apoptosis, and thus cell death.

The terms "therapeutically effective amount" or "effective amount", as used herein, means an amount of a compound, or a pharmaceutically acceptable salt thereof, often as part of a pharmaceutical composition, sufficient to inhibit, halt, ameliorate, attenuate, delay the onset of, or cause an improvement in one or more symptoms of the disease being treated when administered alone or in conjunction with another pharmaceutical agent for treatment in a particular subject or subject population. For example in a human or other mammal, a therapeutically effective amount can be determined experimentally in a laboratory or clinical setting, or may be the amount required by the guidelines of the United States Food and Drug Administration, or equivalent foreign agency, for the particular disease and subject being treated.

The term "excipient" means any pharmaceutically acceptable additive, carrier, diluent, adjuvant, or other ingredient, other than the active pharmaceutical ingredient (API), which is typically included for formulation and/or administration to a patient.

DETAILED DESCRIPTION OF THE INVENTION

It has been demonstrated in accordance with the present invention that the IAP-binding compounds of the present invention are capable of potentiating apoptosis of cells.

Compounds of the present invention can be used in their free base or free acid forms or in the form of their pharmaceutically-acceptable salts. In the practice of the present invention, compounds of the present invention in their free base or free acid forms generally will have a molecular weight of 1000 or below, most often a molecular weight of 800 or below and often a molecular weight of 600 or below.

The following preparations and schemes are illustrative of synthesis of compounds of the present invention. Abbreviations which are used throughout these schemes and in the application generally, are identified in the following table:

| ABBREVIATION | MEANING |
|---|---|
| ACN | Acetonitrile |
| Ac₂O | Acetic anhydride |
| Cbz and Z | Benzyloxycarbonyl |
| Boc and/or boc | tert-butyloxycarbonyl |
| THF | Tetrahydrofuran |
| DCM | Dichloromethane |
| DDQ | 2,3-dichloro-5,6-dicyano-1,4-benzoquinone |
| mCPBA | 3-chloroperbenzoic acid |
| Cbz—Cl | Benzyloxycarbonyl chloride |
| Hex | Hexanes |
| HPLC | high performance liquid chromatography |

-continued

| ABBREVIATION | MEANING |
|---|---|
| TLC | thin layer chromatography |
| EtOAc | ethyl acetate |
| Ph | Phenyl |
| HATU | 2-(7-Aza-1H-benzotriazole-1-y1)-1,1,3,3-tetramethyluronium hexafluorophosphate |
| Me | Methyl* |
| iPr | Iso-propyl |
| cPr | Cyclopropyl |
| (2R-EtOMe) and/or R—MeCHOMe | Me⟋⟍OMe (with wavy bond) |
| TBAF | tetrabutyl ammonium fluoride |
| OMs | Methanesulfonyloxy |
| TBDMSCl | tert-butyl-dimethyl-silyl chloride |
| Ph₃P | Triphenylphosphine |
| n-Bu | Normal butyl |
| Swern[O] | Swern Oxidation |
| TBA-Cl | Tetra-n-butyl ammonium chloride |
| NP-HPLC | Normal phase-high performance liquid chromatography |
| EDCI | N-3-(dimethylaminopropyl)-N'-ethylcarbodiimide hydrochloride 1-Ethyl-3-(3-Dimethylaminopropyl)carbodiimide-HCl |
| TES | Triethylsilane |
| MeNO₂ | Nitromethane |
| EtOH | Ethanol |
| DCE | Dichloroethane |
| NaHMDS | Sodium hexamethyldisilazide or sodium bis(trimethylsilyl)amide |
| Boc-Chg-OH | [structure: Boc-NH-CH(cyclohexyl)-COOH] |
| Boc-N(Me)Ala-OH | [structure: Boc-N(Me)-CH(Me)-COOH] |
| Boc-Abu-OH | [structure: Boc-NH-CH(Et)-COOH] |
| Boc-Ser-OH | [structure: Boc-NH-CH(CH₂OH)-COOH] |
| Boc-Ser(Me)—OH | [structure: Boc-NH-CH(CH₂OMe)-COOH] |

-continued

| ABBREVIATION | MEANING |
|---|---|
| Boc-Thr(tBu)-OH | [structure: Boc-NH-CH(CH(OtBu)Me)-COOH] |
| Boc-Thr(Me)—OH | [structure: Boc-NH-CH(CH(OMe)Me)-COOH] |
| h | hour |
| NMP | N-methylpyrrolidinone |
| PhCOCl | Benzoyl chloride |
| DIAD | diisopropyl azo dicarboxylate |
| DIBAL | Diisobutylaluminium hydride |
| DMAP | 4-dimethylamino pyridine |
| DMF | Dimethylformamide |
| DMSO | dimethyl sulfoxide |
| TFA | trifluoroacetic acid |
| TFAA | trifluoroactic anhydride |
| HOAc or AcOH | acetic acid |
| DIPEA | Diisopropylethylamine |
| NMM | N-methylmorpholine |
| NCS | N-chlorosuccinimide |
| TEA (Et₃N) | Triethylamine |
| MsCl | Methane-sulfonylchloride |
| Et | Ethyl |
| tBu or tert-Bu | tert-butyl |
| cHex | Cyclohexyl |
| (2R—EtOH) and/or R—MeCHOH | Me⟋⟍OH (with wavy bond) |
| MsCl | Methanesulfonyl chloride |
| OTs | —O—SO₂—Ph—Me |
| OTBS | tert-butyl-dimethyl-silanyloxy |
| Ac | Acetyl (—C(=O)—Me) |
| DMA | Dimethylamine |
| HWE | Honer-Wadsworth-Emmons reaction |
| DMS | Dimethylsulfide |
| Meldrum's Acid | 2,2-dimethyl-1,3-dioxane-4,6-dione |
| Imid. | Imidazole |
| RT | Room temperature |
| MeOH | Methanol |
| NaOAc | Sodium acetate |
| ClCO₂Me | Ethyl chloroformate |
| TBSCl | tert-butyl-dimethyl-silanyl chloride |
| Cbz—N(Me)Ala-OH | [structure: Cbz-N(Me)-CH(Me)-COOH] |

| ABBREVIATION | MEANING |
|---|---|
| Boc-Tle-OH | (structure) |
| Boc-Val-OH | (structure) |
| Cbz-Ser(tBu)-OH | (structure) |
| Cbz-Thr(tBu)-OH | (structure) |
| Boc-Thr-OH | (structure) |
| PSI | Pounds per Square Inch (Gauge) |

*As is a commonly accepted convention, depending on the context, which will be apparent to those skilled in the art, a vacant terminal bond may be used to indicate either a methyl group, or the point of attachment to another structure for a radical.

Abbreviations for NMR data reported in the following examples are as follows: s=singlet, d=doublet, t=triplet, q=quartet, m=multiplet, dd=doublet of doublets, ddd=doublet of doublet of doublets, dt=doublet of triplets, app=apparent, br=broad, δ indicates the chemical shift; J and $J_{CF}$ indicate NMR coupling constants measured in Hertz.

The binding affinities of compounds of the present invention to XIAP BIR-3 or to cIAP-1 BIR-3 (as reported below) were determined substantially as described by Nikolovska-Coleska, Z. et. al. (Analytical Biochemistry (2004), vol. 332: 261-273 and incorporated herein by reference) using as the fluorogenic substrate: the fluorescently labeled peptide AbuRPF-K(5-Fam)-NH$_2$. The binding affinities of the compounds are reported as a $K_D$ value (μM). Briefly, various concentrations of test peptides were mixed with 5 nM of the fluorescently labeled peptide (i.e., a mutated N-terminal Smac peptide—AbuRPF-K(5-Fam)-NH$_2$) and 40 nM of the respective IAP BIR3 for 15 min at RT in 100 mL of 0.1M Potassium Phosphate buffer, pH 7.5 containing 100 mg/ml bovine g-globulin. Following incubation, the polarization values (mP) were measured on a Victor2V (available from PerkinElmer Life Sciences) using a 485 nm excitation filter and a 520 nm emission filter. The reported $K_D$ values are supplied as ranges (A=<0.1 μM, B=0.1 μM to 1 μM, C>1 μM to 10 μM, D=>10 μM).

Compounds of the invention also were tested for their ability to inhibit the growth of an ovarian cancer cell line, SK-OV-3. A known assay previously used for measuring cell growth (as described in Hansen, M. B., Nielsen, S. E., and Berg, K. (1989) *J. Immunol. Methods* 119, 203-210 and incorporated herein by reference in its entirety) was used. Briefly, SK-OV-3 cells are seeded in 96-well plates in McCoy's medium containing 10% fetal bovine serum albumin (5,000 per well) and incubated overnight at 37° C. The next day, test compounds are added at various concentrations (0.003-10 μM) and the plates are incubated at 37° C. for an additional 72 hrs. This incubation time was considered to be optimal for measuring inhibitory effects of the different compounds tested. 50 microliters of 5 mg/mL MTT reagent is added to each well and the plates are incubated at 37° C. for another three (3) hours. At the end of the three (3) hour incubation period, 50 microliters of DMSO is added to each well to dissolve cells and the optical density (OD) of the wells is measured with a microplate reader (Victor$^2$ 1420, Wallac, Finland) at 535 nm. Cell survival (CS) was calculated using the following equation:

CS=(OD treated well/mean OD control wells)×100%.

The CC$_{50}$ (reported in the following tables), is defined as the drug concentration that results in 50% cell survival (CS), and is derived by calculating the point where the dose-response curve crosses the 50% CS point using GraphPad Prism. The reported CC$_{50}$ values are supplied as ranges (A=<0.1 μM, B=0.1 μM to 1 μM, C=>1 μM to 10 μM, D=>10 μM).

Scheme A1

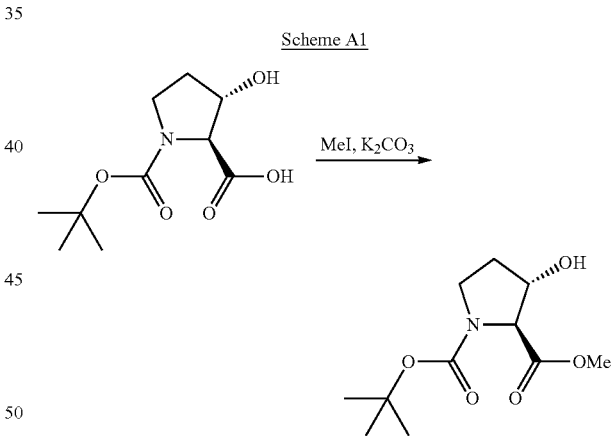

A solution containing 3-hydroxy-pyrrolidine-1,2-dicarboxylic acid 1-tert-butyl ester (16 g, 71 mmol. See: Hodges, J. A.; Raines, R. T. *J. Am. Chem. Soc.* 2005, 45, 15923) in DMF (100 mL) was cooled to 0° C. To this solution was added K$_2$CO$_3$ (16 g, 116 mmol) followed by iodomethane (5.4 mL, 87 mmol). The reaction mixture was slowly warmed to ambient temperature over 1 h at which time it became a yellow heterogeneous solution. This mixture was heated at 90° C. for 1 h and then cooled to ambient temperature. The solution was diluted with brine, extracted with diethyl ether, dried over anhydrous Na$_2$SO$_4$, filtered, and concentrated to afford 14.8 g (87%) of 3-hydroxypyrrolidine-1,2-dicarboxylic acid 1-tert-butyl ester 2-methyl ester as a yellow oil (See: Demange, L.; Cluzeau, J.; Menez, A.; Dugave, C. *Tetrahedron Lett.* 2001, 42, 651).

Scheme B1

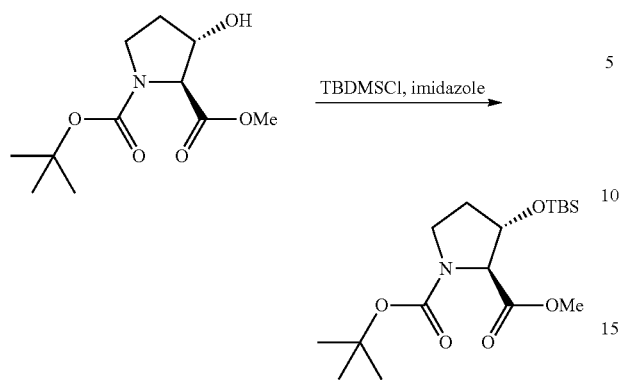

A solution containing 3-hydroxypyrrolidine-1,2-dicarboxylic acid 1-tert-butyl ester 2-methyl ester (14.8 g, 60 mmol) in DCM (150 mL) was cooled to 0° C. To this solution was added imidazole (5.4 g, 79 mmol) followed by t-butyldimethylsilyl-chloride (10 g, 66 mmol) in two portions. The reaction mixture was warmed to ambient temperature over 1 h. After 5 h, the solution was diluted with 1M HCl and extracted twice with DCM. The combined organic extracts were dried over anhydrous $Na_2SO_4$, filtered, and concentrated to afford 21.2 g (99%) of 3-(tert-Butyldimethylsilanyloxy)pyrrolidine-1,2-dicarboxylic acid 1-tert-butyl ester 2-methyl ester as a yellow oil. $^1$H NMR ($CDCl_3$, 300 MHz): δ4.38-4.34 (m, 1H), 4.18 (br s, rotomers, 0.5H), 4.04 (app d, J=2.1 Hz, rotomers, 0.5H), 3.74 (s, 3H), 3.62-3.50 (m, 2H), 2.04-1.96 (m, 1H), 1.85-1.78 (m, 1H), 1.46 (s, minor rotomer), 1.41 (s, 9H), 0.92 (s, minor rotomer), 0.86 (s, 9H), 0.11 (s, 6H), 0.09 (s, minor rotomer) ppm.

Scheme C1

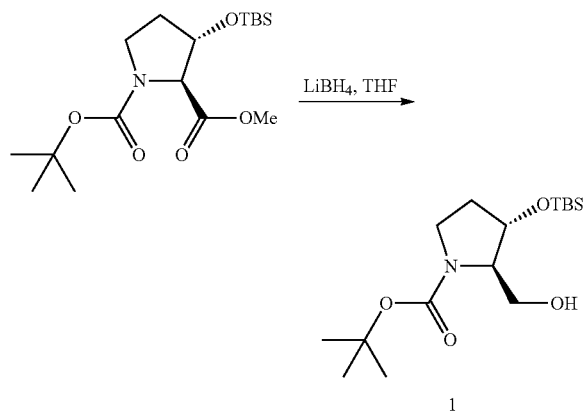

A solution containing 3-(tert-Butyldimethylsilanyloxy)pyrrolidine-1,2-dicarboxylic acid 1-tert-butyl ester 2-methyl ester (12 g, 33 mmol) in THF (50 mL) was cooled to 0° C. $LiBH_4$ in THF (2M, 20 mL) was added in a dropwise fashion. After 1 h, the solution was warmed to ambient temperature. After 2 h, the solution was diluted with MeOH, then $H_2O$, and concentrated. The residue was extracted with EtOAc, washed with 1M HCl, saturated aqueous $NaHCO_3$, brine, dried over anhydrous $Na_2SO_4$, filtered, and concentrated to afford 9.5 g (87%) of 3-(tert-Butyldimethylsilanyloxy)-2-hydroxymethylpyrrolidine-1-carboxylic acid tert-butyl ester (1) as a colorless oil (See: Herdeis, C.; Hubmann, H. P.; Lotter, H. *Tetrahedron: Asymmetry*, 1994, 5, 119).

Example 1

N-{1S-Cyclohexyl-2-[(3aR,6aR)-6R-(1H-indol-3-yl-1)-hexahydro-pyrrolo[3,2-b]pyrrol-1-yl]-2-oxo-ethyl}-2S-methylamino-propionamide (16)

Scheme I

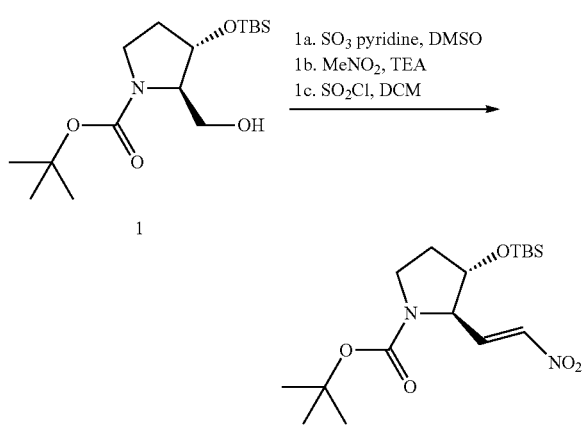

3S-(tert-Butyl-dimethyl-silanyloxy)-2R-(2-nitro-vinyl)-pyrrolidine-1-carboxylic acid tert-butyl ester (2)

To a stirred solution containing alcohol 1 (5.7 g, 17.2 mmol) in DCM (60 mL) was added at ambient temperature $Et_3N$ (14 mL, 103 mmol) and DMSO (50 mL). The reaction mixture was cooled to 0° C. and a solution of $SO_3$·pyridine (11.0 g, 69 mmol) in DMSO (50 mL) was added in a dropwise fashion. After 1 h, the reaction was warmed to ambient temperature. After 1 h, the reaction mixture was poured onto a 30% citric acid/ice mixture. The aqueous layer was extracted with DCM (3×250 mL) and the combined organic extracts were washed with brine (400 mL), dried over anhydrous $Na_2SO_4$, filtered, and concentrated to afford 5.6 g (99%) of crude N-Boc-(3S-OTBS)-2R-prolinal as a yellow-colored oil.

To a stirred solution containing crude N-Boc-(3S-OTBS)-2R-prolinal (5.6 g, 17 mmol) in nitromethane (30 mL) was added $Et_3N$ (1.5 mL). After 12 h, the reaction mixture was concentrated in vacuo to afford 6.6 g (99%) of the intermediate carbinol as a yellow-colored oil.

To a solution containing crude carbinol (6.6 g, 17 mmol) at −78° C. in DCM (30 mL) was added thionyl chloride (2.60 g, 21.9 mmol) in $CH_2Cl_2$ (15 mL). After 1 h, TEA (6.96 mL, 68.8 mmol) was added and, after an additional 1 h at −78° C., the reaction mixture was quenched with MeOH (15 mL), $H_2O$ (20 mL), and saturated aqueous $NaHCO_3$ (20 mL) followed by warming to 0° C. After 1 h, the reaction mixture was concentrated in vacuo and extracted with EtOAc (3×200 mL). The combined organic extracts were washed with brine (300 mL), dried over anhydrous $Na_2SO_4$, filtered, and concentrated to afford 6.1 g (98%) of 2 as an orange-colored oil. $^1$H NMR ($CDCl_3$, 300 MHz) δ7.04 (dd, J=13.2, 6.5 Hz, 1H), 6.91 (d, J=13.2 Hz, 1H), 4.08 (m, 1H), 3.54 (m, 2H), 3.37 (m, 1H), 1.80 (m, 2H), 1.35 (d, J=13.2 Hz, 6H), 0.80 (s, 9H), 0.00 (s, 9H) ppm. Mass spectrum, m/z calcd for $C_{12}H_{24}NO_3Si$ [M+H]+ 272.53. found 272.84.

Scheme II

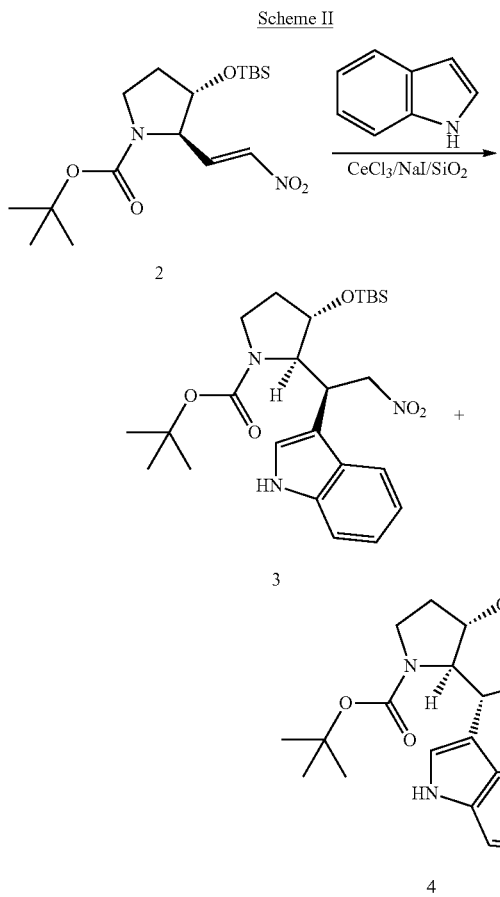

3S-(tert-Butyl-dimethyl-silanyloxy)-2R-[1S-(1H-indol-3-yl)-2-nitro-ethyl]-pyrrolidine-1-carboxylic acid tert-butyl ester (3) and 3S-(tert-Butyl-dimethyl-silanyloxy)-2R-[1R-(1H-indol-3-yl)-2-nitro-ethyl]-pyrrolidine-1-carboxylic acid tert-butyl ester (4)

To solid $CeCl_3 \cdot 7H_2O/NaI/SiO_2$ (1.84 g; prepared as described in Bartoli, G.; et al. *J. Org. Chem.* 2005, 70, 1941) was added vinylnitro species 2 (1.2 g, 3.2 mmol) and indole (377 mg, 3.2 mmol) in ACN (8 mL). After 30 min at ambient temperature, the reaction mixture was concentrated to dryness using a rotary evaporator. After 16 h, the solid residue was suspended in diethyl ether and the mixture was filtered through a pad of diatomaceous earth (Celite®). The dark filtrate was concentrated to dryness and the crude products were purified by silica gel HPLC (10-100% EtOAc/hexanes) to afford 0.23 g (19%) of recovered 2, 0.59 g (38%) of isomer 3, and 0.40 g (25%) of isomer 4 [TLC analysis, $SiO_2$, 4:1 hexanes/EtOAc; $R_f(2)$=0.6; $R_f(3)$=0.48; $R_f(4)$=0.45]. 3: $^1H$ NMR ($CDCl_3$, 300 MHz), mixture of carbamate rotamers: δ9.25 (br s, 0.5H), 9.18 (br s, 0.5H), 8.23 (d, J=7.9 Hz, 0.5H), 8.16 (d, J=7.9 Hz, 0.5H), 7.86 (m, 1H), 7.83-7.56 (m, 2H), 7.55 (s, 1H), 5.47 (m, 1H), 5.28 (m, 1H), 4.78 (m, 1H), 4.48 (s, 1H), 4.09 (m, 1H), 3.84 (app t, J=9.6 Hz, 1H), 2.65 (m, 1H), 2.29 (m, 1H), 2.01 (s, 9H), 1.16 (s, 9H), 0.09 (s, 3H), 0.03 (s, 3H) ppm. Mass spectrum, m/z [389.9] (M−Boc)+. 4: $^1H$ NMR ($CDCl_3$, 300 MHz), mixture of carbamate rotamers: δ9.05 (br s, 0.5H), 8.98 (br s, 0.5H), 8.05 (d, J=6.7 Hz, 1H), 7.73 (m, 1H), 7.57 (m, 2H), 7.37 (s, 0.5H), 7.36 (s, 0.5H), 5.42 (m, 0.5H), 5.23 (m, 1H), 5.08 (m, 0.5H), 4.57 (m, 2H), 3.99 (m, 0.5H), 3.83 (m, 0.5H), 3.54 (m, 0.5H), 3.40 (m, 0.5H), 2.15 (m, 1H), 2.00 (s, 4.5H), 1.93 (s, 4.5H), 1.52 (m, 1H), 1.20 (s, 4.5H), 1.14 (s, 4.5H), 0.34 (s, 3H), 0.25 (s, 1.5H), 0.19 (s, 1.5H) ppm. Mass spectrum, m/z [389.9] (M−Boc)+.

Scheme III

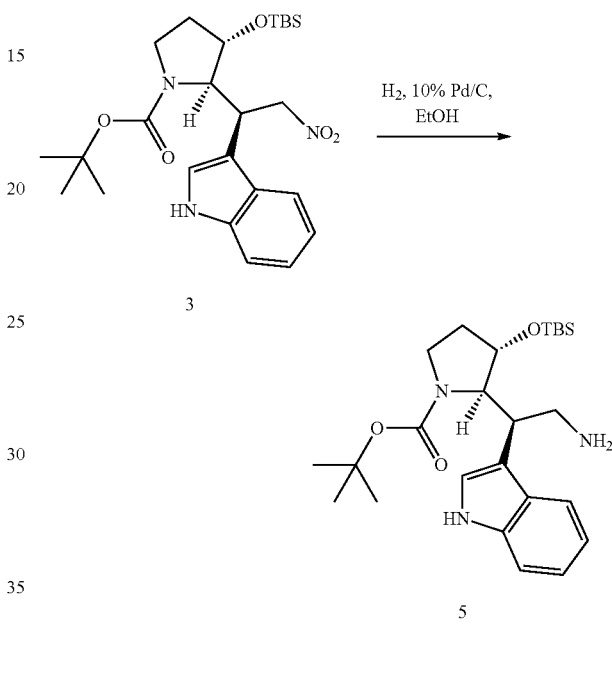

2R-[2-Amino-1S-(1H-indol-3-yl)-ethyl]-3S-(tert-butyl-dimethyl-silanyloxy)-pyrrolidine-1-carboxylic acid tert-butyl ester (5)

A Parr bottle was charged with 3 (0.59 g, 1.20 mmol) and 10% Pd/C (~0.1 g) in absolute EtOH (20 mL). After 2 h at 55 PSI $H_2$ pressure (379.2 KPa), LC/MS analysis indicated no significant consumption of 3. An additional portion of 10% Pd/C was added (~0.1 g) and the reduction was continued for ~5 h at which point LC/MS analysis revealed only unreacted 3. Glacial HOAc (1 mL) and additional catalyst (0.1 g) was added and the reaction mixture was placed on a Parr apparatus at 55 PSI $H_2$ (379.2 KPa). After 16 h, the reaction was ~50% complete by LC/MS analysis therefore an additional portion of catalyst (0.1 g) was added and the reaction was continued for ~10 h. Upon complete consumption of 3, the reaction mixture was filtered through diatomaceous earth (Celite®) and the solids were washed with MeOH. The filtrate was concentrated and the residue was dissolved in EtOAc, washed successively with saturated aqueous $NaHCO_3$, and brine, dried over anhydrous $Na_2SO_4$, filtered, and concentrated to afford 0.38 g (69%) of crude 5 which was used without further purification. 5: $^1H$ NMR ($CDCl_3$, 300 MHz), mixture of carbamate rotamers: δ0.25 (br s, 1H), 8.04 (m, 1H), 7.80 (m, 1H), 7.49 (m, 1H), 7.46 (m, 2H), 4.38 (br s, 2H), 4.15 (m, 1H), 3.98 (m, 1H), 3.82-2.99 (m, 4H), 1.96 (s, 9H), 1.16 (s, 9H), 0.13 (s, 3H), 0.04 (s, 3H) ppm. Mass spectrum, m/z [460.0] (M)+.

Scheme IV

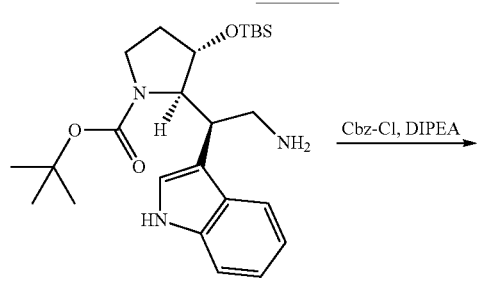

5

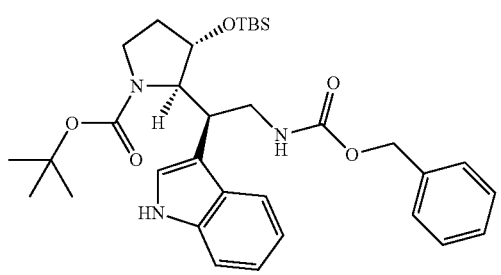

6

2R-[2-Benzyloxycarbonylamino-1R-(1H-indol-3-yl)-ethyl]-3S-(tert-butyl-dimethyl-silanyloxy)-pyrrolidine-1-carboxylic acid tert-butyl ester (6)

To a solution of DCM (10 mL) containing crude 5 (0.38 g, 0.82 mmol) at 0° C. was added DIPEA (0.16 g, 1.23 mmol) followed by Cbz-Cl (0.16 g, 0.90 mmol). After 3 h, the reaction mixture was diluted with DCM, washed successively with 1N HCl, and brine, dried over anhydrous Na$_2$SO$_4$, filtered, and concentrated to afford crude 6 which was purified by flash silica gel chromatography (9:1 hexanes/EtOAc to 2:1 hexanes/EtOAc) to afford 0.41 g (83%) of 6. $^1$H NMR (CDCl$_3$, 300 MHz) δ9.00 (br s, 1H), 8.04 (m, 1H), 7.71 (m, 7H), 7.58 (m, 1H), 7.49 (m, 1H), 7.35 (s, 1H), 6.13 (m, 1H), 5.42 (app s, 2H), 5.10 (m, 1H), 4.33 (m, 1H), 4.27-3.81 (m, 2H), 3.75 (app t, J=9.6 Hz, 1H), 3.34 (m, 1H), 2.33 (m, 1H), 1.26 (m, 1H), 1.94 (s, 9H), 1.12 (s, 9H), 0.07 (s, 6H) ppm. Mass spectrum, m/z [594.1] (M)+.

Scheme V

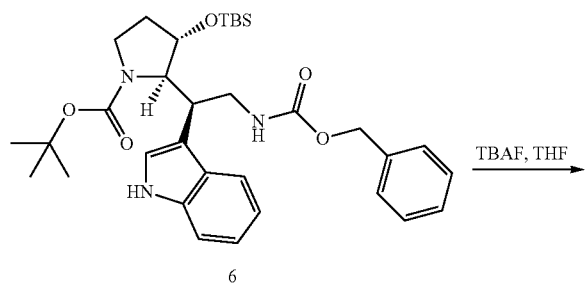

6

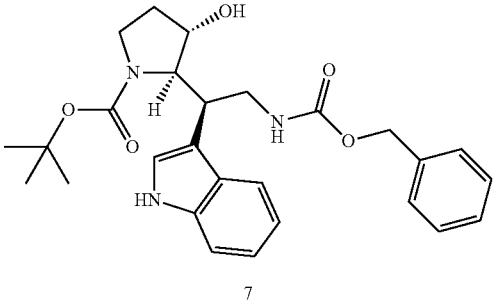

7

2R-[2-Benzyloxycarbonylamino-1R-(1H-indol-3-yl)-ethyl]-3S-hydroxy-pyrrolidine-1-carboxylic acid tert-butyl ester (7)

At 0° C., TBAF (1M/THF, 0.76 mL, 0.76 mmol) was added to a solution containing 6 (0.41 g, 0.69 mmol) in anhydrous THF (10 mL). After 1 h, another portion of 1M TBAF/THF (0.7 mL) was added and the reaction mixture was allowed to warm to ambient temperature. After 16 h, the opaque reaction mixture was diluted with EtOAc, washed successively with 1N HCl, and brine, dried over anhydrous Na$_2$SO$_4$, filtered, and concentrated to afford crude 7 which was purified by flash silica gel chromatography (1:2 hexanes/EtOAc) to afford 0.27 g (81%) of 7. $^1$H NMR (CDCl$_3$, 300 MHz), mixture of carbamate rotamers, selected resonances: δ8.71 (br s, 1H), 7.53 (d, J=7.9 Hz, 1H), 7.27 (m, 7H), 7.13 (m, 1H), 7.05 (m, 1H), 6.89 (s, 1H), 5.69 (m, 1H), 5.00 (app s, 2H), 1.50 (s, 9H) ppm.

Scheme VI

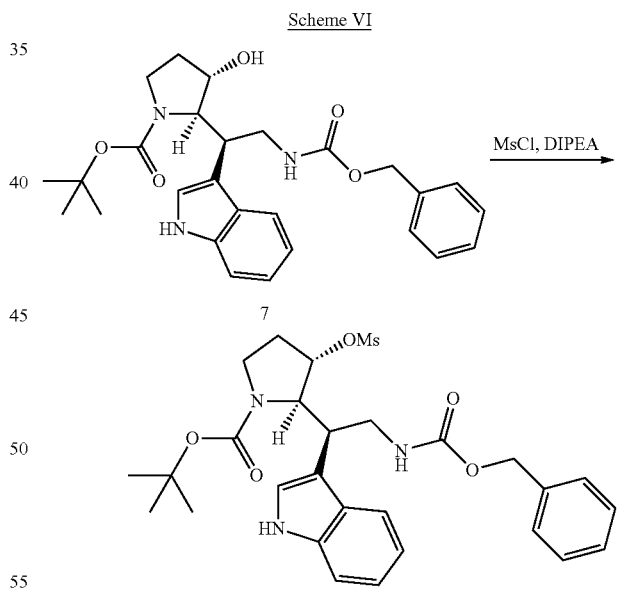

2R-[2-Benzyloxycarbonylamino-1R-(1H-indol-3-yl)-ethyl]-3S-methanesulfonyloxy-pyrrolidine-1-carboxylic acid tert-butyl ester (8)

At 0° C., MsCl (82 mg, 0.71 mmol) was added to a solution containing 7 (0.23 g, 0.47 mmol), DIPEA (185 mg, 1.43 mmol), and DMAP (5 mg, cat.) in DCM (10 mL). After 15 min, the reaction mixture was diluted with EtOAc, washed successively with 1N HCl, water, and brine, dried over anhydrous Na$_2$SO$_4$, filtered, and concentrated to afford crude 8 which was purified by silica gel HPLC (60-100% EtOAc/hexanes) to afford 0.19 g (71%) of 8. $^1$H NMR (CDCl$_3$, 300 MHz), mixture of carbamate rotamers: δ8.82 (br s, 1H), 7.60 (d, J=7.6 Hz, 1H), 7.29 (m, 7H), 7.15 (m, 1H), 7.07 (m, 1H), 6.92 (s, 1H), 5.62 (m, 1H), 5.08 (m, 1H), 4.98 (s, 2H), 4.73 (m, 1H), 4.56 (d, J=9.6 Hz, 1H), 3.80 (m, 1H), 3.56 (m, 2H), 3.32 (m, 1H), 3.14 (m, 1H), 2.44 (s, 3H), 1.90 (m, 1H), 1.53 (s, 9H) ppm.

Scheme VII

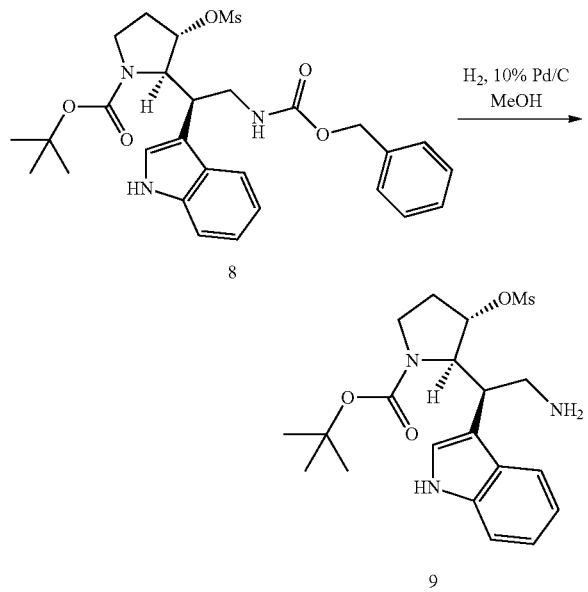

2R-[2-Amino-1R-(1H-indol-3-yl)-ethyl]-3S-methanesulfonyloxy-pyrrolidine-1-carboxylic acid tert-butyl ester (9)

A solution containing 8 (0.19 g, 0.34 mmol) and 10% Pd/C (0.1 g) in MeOH (20 mL) was placed in a Parr apparatus and pressurized to 55 PSI H$_2$ (379.2 KPa). After 3 h, the catalyst was removed by filtration through diatomaceous earth (Celite®) and the clarified filtrate was concentrated to afford 0.13 g of 9 which was used without further purification. $^1$H NMR (CDCl$_3$/d$_4$-MeOH, 300 MHz) δ10.17 (br s, 1H), 7.55 (app d, J=6.1 Hz, 1H), 7.38 (m, 2H), 7.11-6.98 (m, 2H), 4.77-3.07 (m, 5H), 2.48 (s, 3H), 2.28-1.90 (m, 6H), 1.51 (s, 9H) ppm.

Scheme VIII

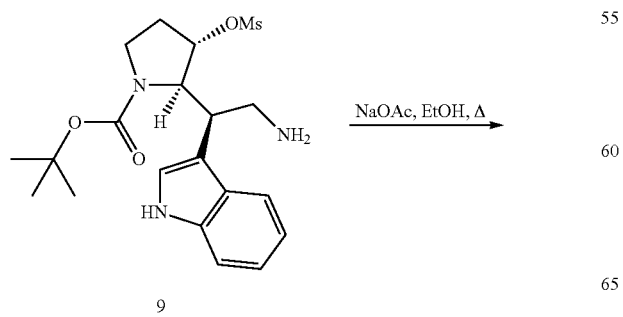

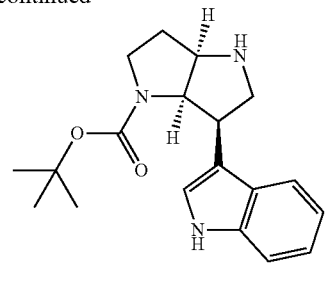

(3aR,6aR)-6R-(1H-Indol-3-yl)-hexahydro-pyrrolo[3,2-b]pyrrole-1-carboxylic acid tert-butyl ester (10)

A solution containing crude 9 (0.13 g, 0.30 mmol) and NaOAc (50 mg, 0.61 mmol) in anhydrous EtOH (10 mL) was warmed to gentle reflux. After 30 min, the reaction mixture was concentrated in vacuo and the residue was dissolved in EtOAc, washed successively with water and brine, dried over anhydrous Na$_2$SO$_4$, filtered, and concentrated to afford 98 mg of crude 10 which was used without further purification. $^1$H NMR (CDCl$_3$, 300 MHz) δ8.85 (br s, 1H), 7.62 (d, J=7.3 Hz, 1H), 7.34 (app d, J=8.1 Hz, 1H), 7.13 (m, 2H), 6.91 (s, 1H), 4.49 (m, 1H), 4.21 (m, 1H), 3.89 (m, 1H), 3.59 (m, 1H), 3.28 (m, 2H), 2.92 (app t, J=10.5 Hz, 1H), 2.38 (m, 1H), 2.08 (m, 1H), 1.89 (m, 1H), 0.70 (s, 9H) ppm. Mass spectrum, m/z [327.8] (M)+.

Scheme IX

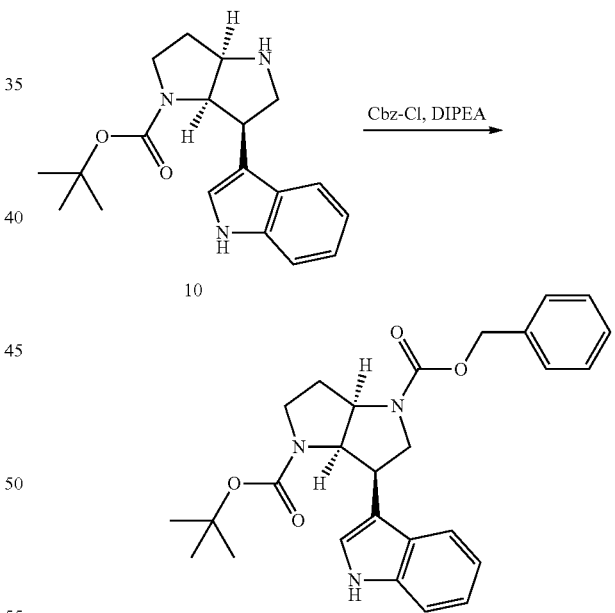

(3aR,6aR)-3R-(1H-Indol-3-yl)-hexahydro-pyrrolo[3,2-b]pyrrole-1,4-dicarboxylic acid 1-benzyl ester 4-tert-butyl ester (11)

To a solution containing crude 10 (98 mg, 0.29 mmol) in DCM (5 mL) at 0° C. was added Cbz-Cl (61 mg, 0.35 mmol). After 4 h, the reaction mixture was diluted with EtOAc, washed successively with 1N HCl and brine, dried over anhydrous Na$_2$SO$_4$, filtered, and concentrated to afford 0.16 g (>100%) of crude 11 which was used without further purification. ¹H NMR (CDCl₃, 300 MHz) δ8.61 (br s, 1H), 7.58 (d, J=7.3 Hz, 1H), 7.36 (m, 5H), 7.35 (m, 1H), 7.18-7.11 (m, 2H), 6.96 (s, 1H), 5.21-5.13 (m, 2H), 4.57 (m, 1H), 4.02 (m, 2H), 3.76 (m, 1H), 3.39 (t, J=11 Hz, 1H), 3.18 (m, 1H), 1.42 (m, 2H), 0.65 (s, 9H) ppm. Mass spectrum, m/z [461.9] (M)+.

Scheme X

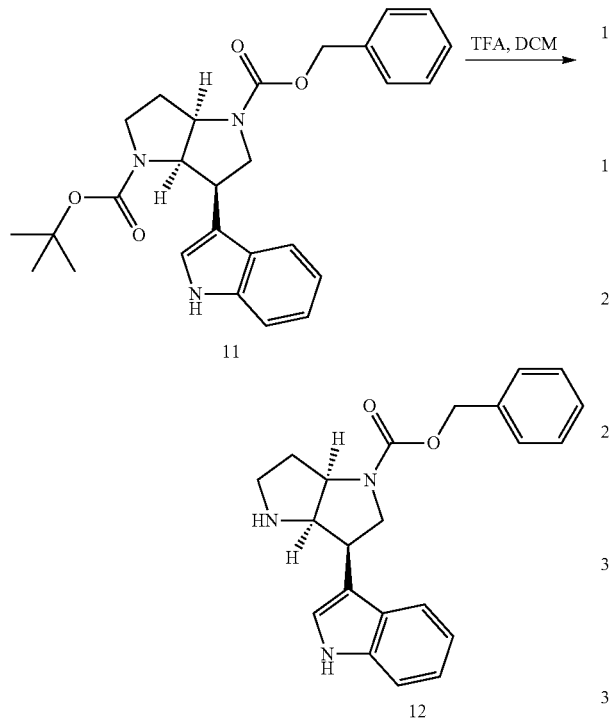

(3aR,6aR)-3R-(1H-Indol-3-yl)-hexahydro-pyrrolo[3,2-b]pyrrole-1-carboxylic acid benzyl ester (12)

At 0° C., TFA (3 mL) was added to a solution containing crude 11 (0.16 g) in DCM (10 mL). After 2 h, the reaction mixture was concentrated in vacuo. The crude residue was diluted with EtOAc, washed successively with aqueous NaHCO₃ and brine, dried over anhydrous Na₂SO₄, filtered, and concentrated to afford 0.14 g of crude 12 which was used without further purification. Mass spectrum, m/z [361.8] (M)+.

Scheme XI

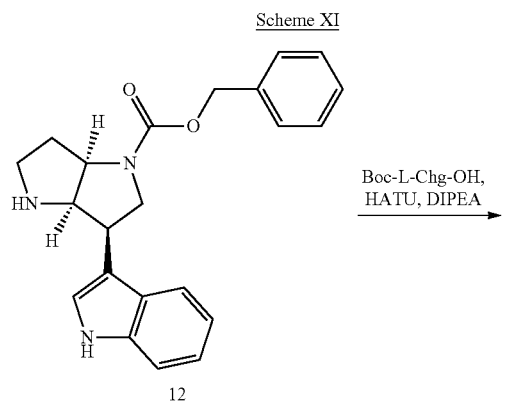

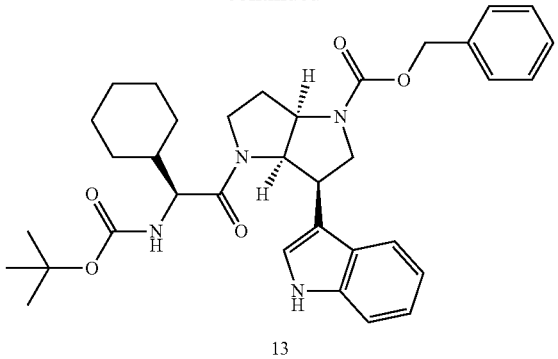

(3aR,6aR)-4-(2-tert-Butoxycarbonylamino-2S-cyclohexyl-acetyl)-3R-(1H-indol-3-yl)-hexahydro-pyrrolo[3,2-b]pyrrole-1-carboxylic acid benzyl ester (13)

To a solution containing crude 12 (0.14 g, 0.38 mmol), Boc-L-Chg-OH (109 mg, 0.42 mmol), and HATU (176 mg, 0.46 mmol) in anhydrous NMP (5 mL) was added DIPEA (65 mg, 0.50 mmol) at 0° C. The reaction mixture was slowly warmed to ambient temperature. After 16 h, the reaction mixture was diluted with diethyl ether and washed successively with 1N HCl, water (5×), aqueous NaHCO₃, water (2×), and brine, dried over anhydrous Na₂SO₄, filtered, and concentrated. The crude product was purified by flash silica gel chromatography (3:1 hexanes/EtOAc to 1:1 hexanes/EtOAc) to afford 116 mg (57%, 5 steps) of 13. ¹H NMR (CDCl₃, 300 MHz) δ8.15 (br s, 1H), 7.70 (app d, J=6.4 Hz, 1H), 7.38 (m, 5H), 7.26 (m, 1H), 7.15 (m, 2H), 6.90 (s, 1H), 5.20 (m, 2H), 5.07 (d, J=9.0 Hz, 1H), 4.64 (m, 2H), 4.20-3.83 (m, 2H), 3.64 (app t, J=10.2 Hz, 1H), 3.23 (m, 1H), 2.40-1.38 (m, 7H), 1.33 (s, 9H), 1.28-0.90 (m, 8H) ppm. Mass spectrum, m/z [601.1] (M)+.

Scheme XII

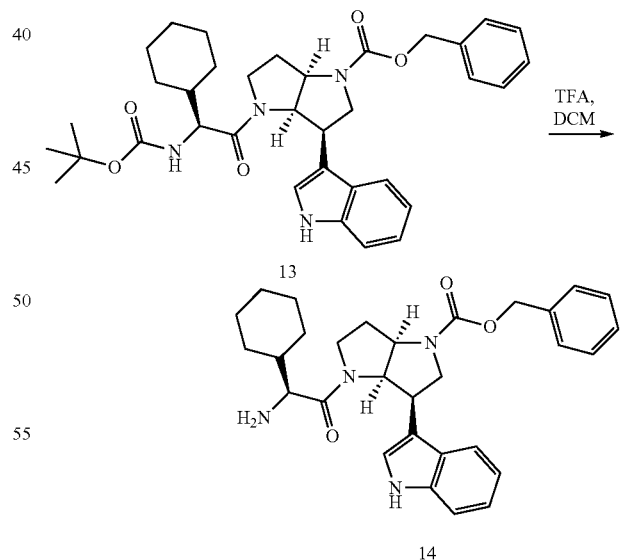

(3aR,6aR)-4-(2-Amino-2S-cyclohexyl-acetyl)-3R-(1H-indol-3-yl)-hexahydro-pyrrolo[3,2-b]pyrrole-1-carboxylic acid benzyl ester (14)

At 0° C., TFA (2 mL) was added to a solution containing 13 (116 mg, 0.19 mmol) in DCM (10 mL). After 1 h, the reaction mixture was diluted with EtOAc, washed successively with aqueous NaHCO$_3$ (2×) and brine, dried over anhydrous Na$_2$SO$_4$, filtered, and concentrated to afford 95 mg of crude 14 which was used without further purification. $^1$H NMR (CDCl$_3$, 300 MHz): crude, ~1:1 mixture of amide/carbamate rotamers δ9.71 (br s, indole NH), 9.57 (br s, indole NH), 7.53 (app d, J=7.6 Hz, 1H), 7.39-7.09 (m, 8H), 6.97 (s, 1H), 5.21-5.15 (m, 2H), 4.87 (m, 1H), 4.68 (m, 2H), 4.25-3.67 (m, 5H), 3.48 (app t, J=11 Hz, 1H), 3.22 (m, 1H), 2.48-0.90 (m, 13H) ppm. Mass spectrum, m/z [501.0] (M)+.

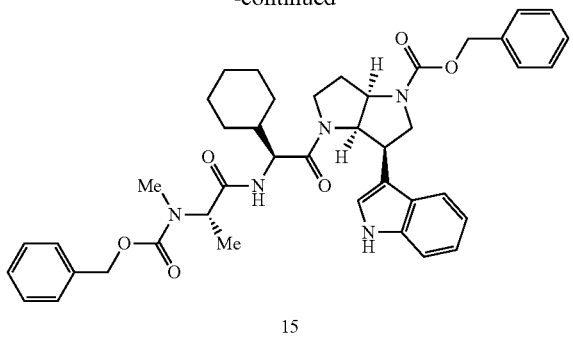

15

(3aR,6aR)-4-{2-[2S-(Benzyloxycarbonyl-methyl-amino)-propionylamino]-2S-cyclohexyl-acetyl}-3R-(1H-indol-3-yl)-hexahydro-pyrrolo[3,2-b]pyrrole-1-carboxylic acid benzyl ester (15)

To a solution containing crude 14 (95 mg, 0.18 mmol), Cbz-L-N(Me)Ala-OH (50 mg, 0.21 mmol), and HATU (87 mg, 0.23 mmol) in anhydrous NMP (5 mL) was added DIPEA (32 mg, 0.25 mmol) at 0° C. The reaction mixture was slowly warmed to ambient temperature. After 16 h, the reaction mixture was diluted with diethyl ether and washed successively with 1N HCl, water (5×), aqueous NaHCO$_3$, water (2×), and brine, dried over anhydrous Na$_2$SO$_4$, filtered, and concentrated to afford 140 mg (quant.) of crude 15 which was used without further purification. Mass spectrum, m/z [720.1] (M)+.

Scheme XIII

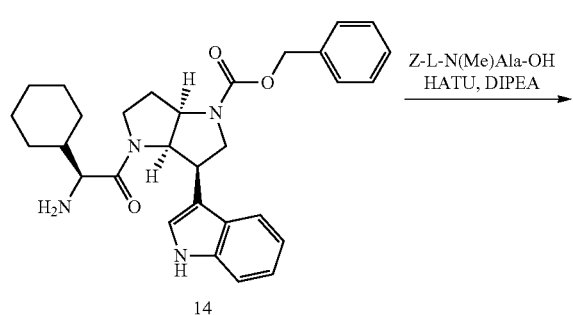

14

Scheme XIV

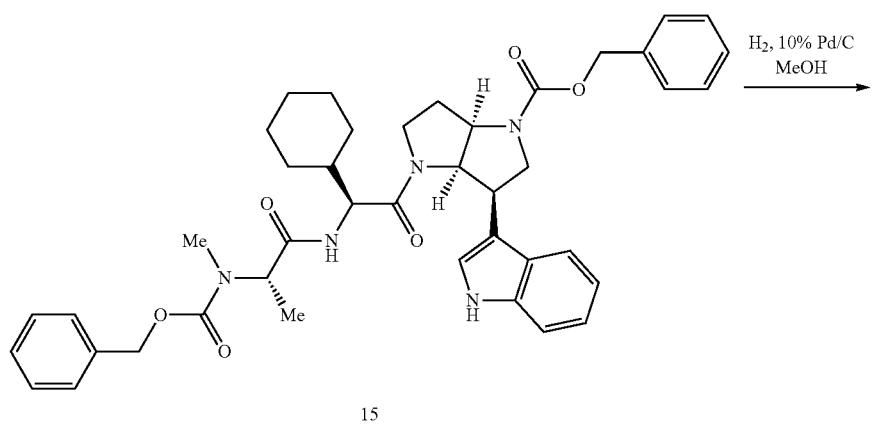

15

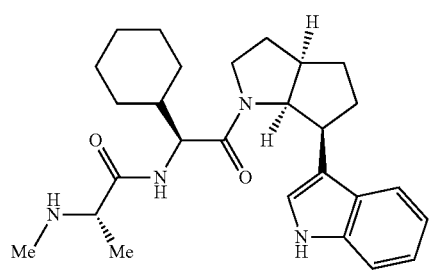

16

N-{1S-Cyclohexyl-2-[(3aR,6aR)-6R-(1H-indol-3-yl)-hexahydro-pyrrolo[3,2-b]pyrrol-1-yl]-2-oxo-ethyl}-2S-methylamino-propionamide (16)

A solution containing crude 15 (0.14 g) and 10% Pd/C (0.1 g) in MeOH (20 mL) was placed in a Parr apparatus and pressurized to 55 PSI $H_2$ (379.2 KPa). After 2 h, the catalyst was removed by filtration through diatomaceous earth (Celite®) and the clarified filtrate was concentrated in vacuo. The crude product was purified by reverse-phase HPLC (2" Dynamax C18 column; Flow: 40 mL/min; Method: 10-40% ACN/water containing 0.1% v/v HOAc over 30 min). The product-containing fractions were pooled, diluted with water, frozen, and lyophilized to dryness to afford 35.6 mg (41%, 3 steps) of 16 as a white solid (acetate salt). NMR ($CDCl_3/d_4$-MeOH, 300 MHz): δ9.41 (br s, 1H), 7.68 (d, J=7.5 Hz, 1H), 7.47 (d, J=7.8 Hz, 1H), 7.31 (app d, J=8.7 Hz, 1H), 7.16 (s, 1H), 7.11 (app dd, J=7.8, 8.7 Hz, 2H), 5.28 (app t, J=7.5 Hz, 1H), 4.38 (m, 1H), 4.29 (app d, J=5.7 Hz, 1H), 4.14-3.93 (m, 4H), 3.62-3.38 (m, 4H), 3.34 (br s, MeOH/AcOH/water), 2.42 (s, 3H), 1.49 (m, 3H), 1.31 (d, J=6.6 Hz, 3H), 1.08 (m, 2H), 0.88 (m, 3H), 0.57 (m, 1H), 0.48 (m, 1H) ppm. $^{13}C$ NMR ($CDCl_3/d_4$-MeOH, 75 MHz): δ171.5, 169.9, 136.1, 127.6, 122.2, 122.1, 119.4, 119.3, 111.3, 109.9, 62.7, 61.2, 58.5, 55.1, 50.3, 47.6, 40.2, 40.0, 32.9, 30.5, 29.4, 26.8, 25.9, 25.9, 17.7 ppm. Mass spectrum, m/z [452.0] (M)+.

Example 2

N-{1S-Cyclohexyl-2-[(3aR,6aR)-6S-(1H-indol-3-yl)-hexahydro-pyrrolo[3,2-b]pyrrol-1-yl]-2-oxo-ethyl}-2S-methylamino-propionamide (26)

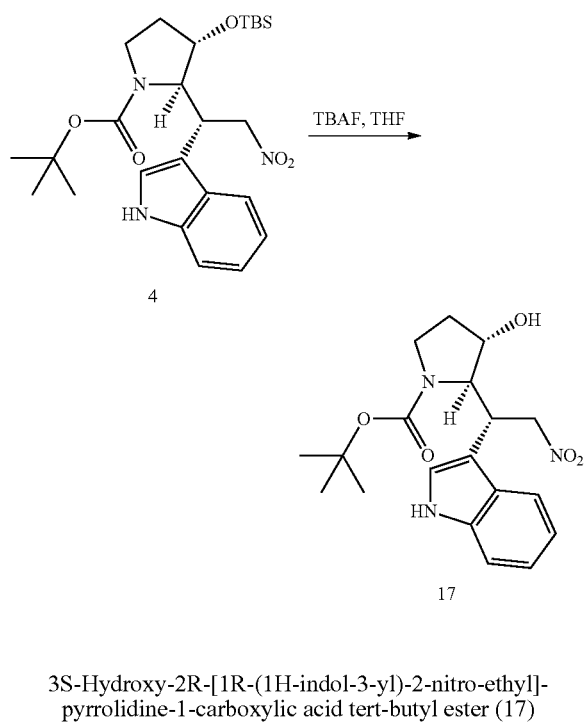

3S-Hydroxy-2R-[1R-(1H-indol-3-yl)-2-nitro-ethyl]-pyrrolidine-1-carboxylic acid tert-butyl ester (17)

At 0° C., TBAF (1M/THF, 1.63 mL, 1.63 mmol) was added to a solution containing 4 (0.40 g, 0.81 mmol) in anhydrous THF (15 mL). After 16 h, the reaction mixture was diluted with EtOAc, washed successively with 1N HCl (2×), and brine, dried over anhydrous $Na_2SO_4$, filtered, and concentrated to afford crude 17 which was purified by flash silica gel chromatography (1:1 hexanes/EtOAc to 1:2 hexanes/EtOAc) to afford 0.25 g (82%) of 17 as a waxy solid. $^1H$ NMR ($CDCl_3$, 300 MHz) δ8.29 (br s, 1H), 7.65 (d, J=7.6 Hz, 1H), 7.36 (d, J=7.6 Hz, 1H), 7.21-7.12 (m, 2H), 7.04 (s, 1H), 5.00-4.47 (m, 2H), 4.35 (app t, J=6.7 Hz, 1H), 4.24 (m, 2H), 3.62-3.35 (m, 1H), 3.09-2.99 (m, 1H), 1.83 (m, 1H), 1.52 (s, 9H), 1.15 (m, 1H) ppm. Mass spectrum, m/z [275.7] (M–Boc)+.

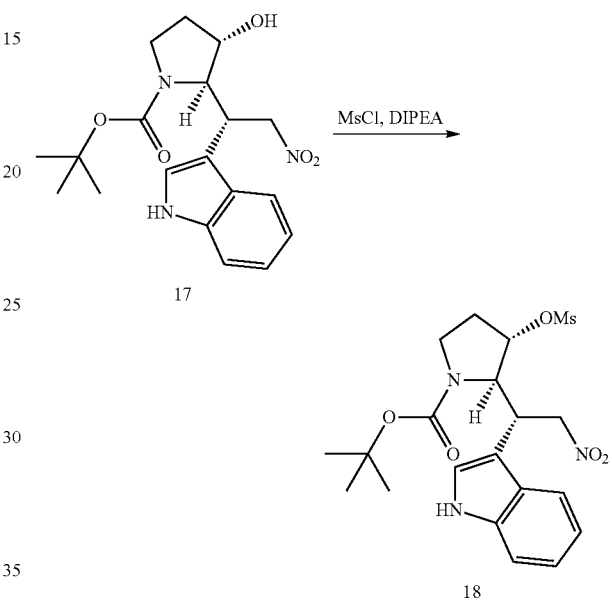

2R-[1R-(1H-Indol-3-yl)-2-nitro-ethyl]-3S-methane-sulfonyloxy-pyrrolidine-1-carboxylic acid tert-butyl ester (18)

At 0° C., MsCl (114 mg, 0.99 mmol) was added to a solution containing 17 (0.25 g, 0.66 mmol), DIPEA (258 mg, 1.99 mmol), and DMAP (8 mg, 0.06 mmol) in DCM (20 mL). After 1 h, the reaction mixture was diluted with DCM, washed successively with 1N HCl, and brine, dried over anhydrous $Na_2SO_4$, filtered, and concentrated to afford crude 18 which was purified by silica gel HPLC (40-100% EtOAc/hexanes) to afford 0.21 g (70%) of 18. Mass spectrum, m/z [353.7] (M–Boc)+.

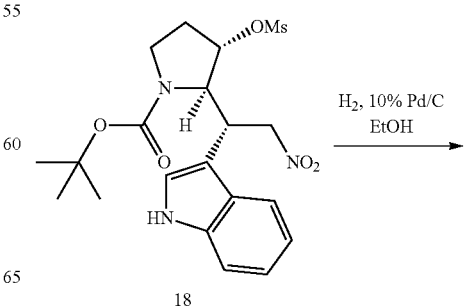

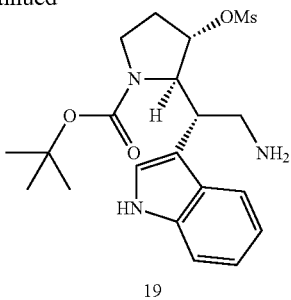

2R-[2-Amino-1S-(1H-indol-3-yl)-ethyl]-3S-methanesulfonyloxy-pyrrolidine-1-carboxylic acid tert-butyl ester (19)

A solution containing 18 (0.21 g, 0.46 mmol) and 10% Pd/C (0.1 g) in anhydrous EtOH (20 mL) was placed in a Parr apparatus and pressurized to 55 PSI $H_2$ (379.2 KPa). After 16 h, the catalyst was removed by filtration through diatomaceous earth (Celite®) and the clarified filtrate was concentrated to afford 0.22 g of 19 which was used without further purification. $^1$H NMR (CDCl$_3$, 300 MHz), selected resonances: δ9.55 (br s, 1H), 7.36 (m, 2H), 7.21-7.01 (m, 3H), 4.96 (m, 1H), 4.42 (m, 1H), 1.51 (s, 9H) ppm. Mass spectrum, m/z [423.9] (M)+.

Scheme XVIII

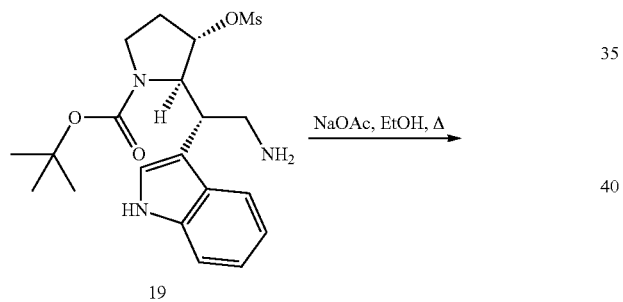

(3aR,6aR)-6S-(1H-Indol-3-yl)-hexahydro-pyrrolo[3,2-b]pyrrole-1-carboxylic acid tert-butyl ester (20)

A solution containing crude 19 (0.22 g, 0.51 mmol) and NaOAc (85 mg, 1.03 mmol) in anhydrous EtOH (10 mL) was warmed to gentle reflux. After 3 h, the reaction mixture was concentrated in vacuo and the residue was dissolved in EtOAc, washed successively with aqueous NaHCO$_3$, and brine, dried over anhydrous Na$_2$SO$_4$, filtered, and concentrated to afford 150 mg of crude 20 which was used without further purification. Mass spectrum, m/z [327.8] (M)+.

Scheme XIX

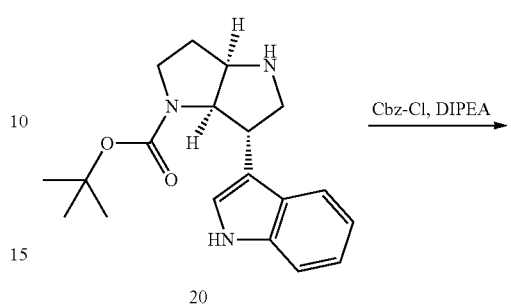

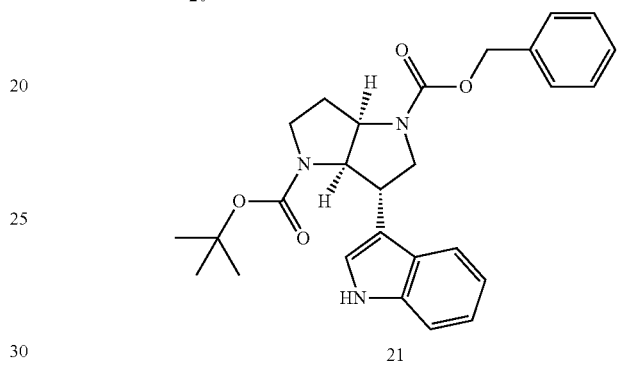

(3aR,6aR)-3S-(1H-Indol-3-yl)-hexahydro-pyrrolo[3,2-b]pyrrole-1,4-dicarboxylic acid 1-benzyl ester 4-tert-butyl ester (21)

To a solution containing crude 20 (150 mg, 0.45 mmol) in DCM (10 mL) at 0° C. was added Cbz-Cl (94 mg, 0.54 mmol). After 2 h, the reaction mixture was diluted with DCM, washed successively with 1N HCl, water, and brine, dried over anhydrous Na$_2$SO$_4$, filtered, and concentrated. The crude product was purified by silica gel HPLC (10-100% EtOAc/hexanes) to afford 170 mg (81%) of 21. $^1$H NMR (CDCl$_3$, 300 MHz), mixture of carbamate rotamers: δ8.24 (br s, 0.5H), 8.14 (br s, 0.5H), 7.33 (m, 7H), 7.16 (m, 2H), 6.83-6.67 (m, 1H), 5.19 (m, 2H), 4.49-4.22 (m, 2H), 4.00 (m, 1H), 3.83 (br s, 1H), 3.65 (m, 1H), 3.28 (m, 1H), 2.35-2.13 (m, 1H), 1.87 (m, 1H), 1.52 (s, 9H) ppm.

Scheme XX

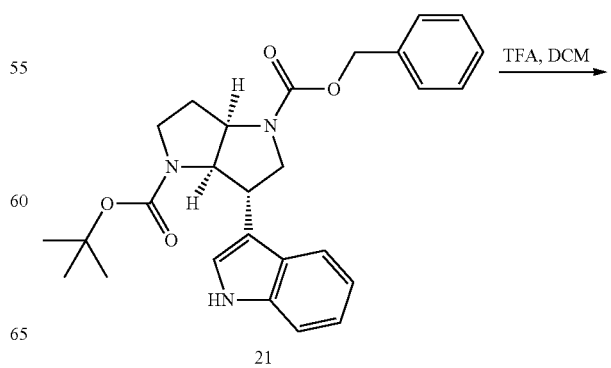

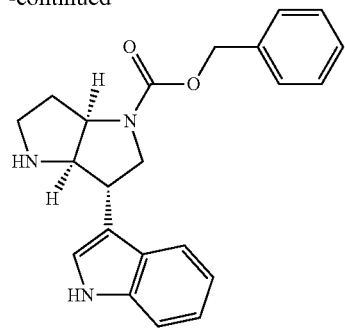

22

(3aR,6aR)-3S-(1H-Indol-3-yl)-hexahydro-pyrrolo[3,2-b]pyrrole-1-carboxylic acid benzyl ester (22)

At 0° C., TFA (2 mL) was added to a solution containing 21 (0.17 g, 0.36 mmol) in DCM (10 mL). After 2 h, the reaction mixture was concentrated in vacuo. The crude residue was diluted with EtOAc, washed successively with aqueous NaHCO₃, and brine, dried over anhydrous Na₂SO₄, filtered, and concentrated to afford 83 mg of crude 22 which was used without further purification. Mass spectrum, m/z [361.8] (M)+.

Scheme XXI

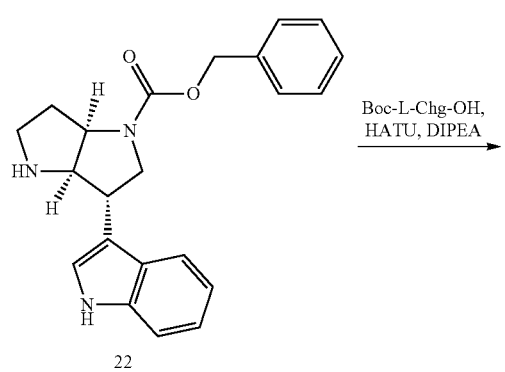

(3aR,6aR)-4-(2-tert-Butoxycarbonylamino-2S-cyclohexyl-acetyl)-3S-(1H-indol-3-yl)-hexahydro-pyrrolo[3,2-b]pyrrole-1-carboxylic acid benzyl ester (23)

To a solution containing crude 22 (83 mg, 0.23 mmol), Boc-L-Chg-OH (65 mg, 0.25 mmol), and HATU (105 mg, 0.27 mmol) in anhydrous NMP (5 mL) was added DIPEA (38 mg, 0.29 mmol) at 0° C. The reaction mixture was slowly warmed to ambient temperature. After 16 h, the reaction mixture was diluted with diethyl ether and washed successively with 1N HCl, water (5×), aqueous NaHCO₃, water (2×), and brine, dried over anhydrous Na₂SO₄, filtered, and concentrated. The crude product was purified by silica gel HPLC (10-100% EtOAc/hexanes) to afford 130 mg (59%, 2 steps) of 23. ¹H NMR (CDCl₃, 300 MHz), mixture of carbamate rotamers: δ8.25 (app d, J=8.2 Hz, 1H), 8.17 (br s, 1H), 7.40 (m, 1H), 7.34 (m, 5H), 7.19 (m, 2H), 6.79 (s, 0.5H), 6.65 (s, 0.5H), 5.38 (app t, J=8.2 Hz, 1H), 5.21 (m, 2H), 4.68 (d, J=4.6 Hz, 0.5H), 4.62 (d, J=4.9 Hz, 0.5H), 4.34 (m, 2H), 4.15-3.96 (m, 3H), 3.49 (m, 2H), 2.43 (m, 0.5H), 2.25 (m, 0.5H), 1.91-1.74 (m, 7H), 1.43 (s, 9H), 1.28-1.09 (m, 4H) ppm. Mass spectrum, m/z [601.1] (M)+.

Scheme XXII

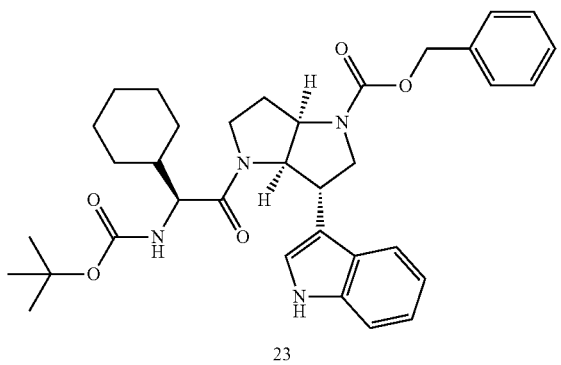

(3aR,6aR)-4-(2-Amino-2S-cyclohexyl-acetyl)-3S-(1H-indol-3-yl)-hexahydro-pyrrolo[3,2-b]pyrrole-1-carboxylic acid benzyl ester (24)

At 0° C., TFA (2 mL) was added to a solution containing 23 (130 mg, 0.21 mmol) in DCM (10 mL). After 1 h, the reaction mixture was diluted with EtOAc, washed successively with aqueous NaHCO₃ (2×), and brine, dried over anhydrous Na₂SO₄, filtered, and concentrated to afford 105 mg of crude 24 which was used without further purification. Mass spectrum, m/z [501.0] (M)+.

Scheme XXIII

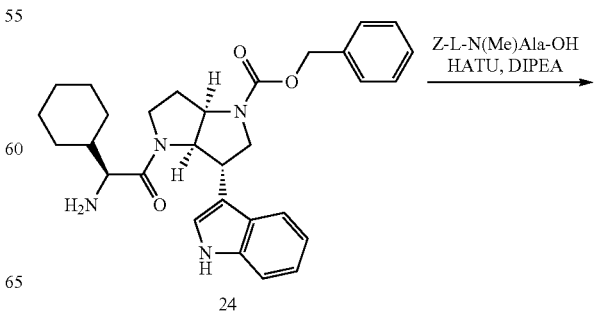

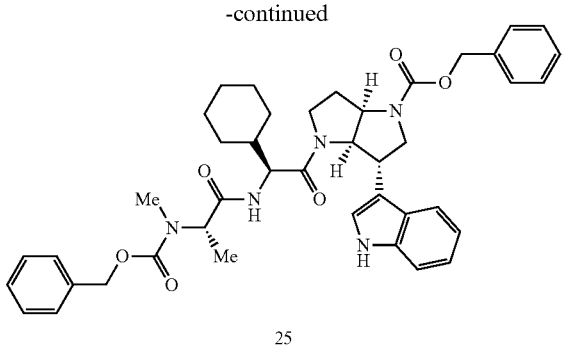

25

(3aR,6aR)-4-{2-[2S-(Benzyloxycarbonyl-methyl-amino)-propionylamino]-2S-cyclohexyl-acetyl}-3S-(1H-indol-3-yl)-hexahydro-pyrrolo[3,2-b]pyrrole-1-carboxylic acid benzyl ester (25)

To a solution containing crude 24 (105 mg, 0.21 mmol), Cbz-L-N(Me)Ala-OH (55 mg, 0.23 mmol), and HATU (96 mg, 0.25 mmol) in anhydrous NMP (5 mL) was added DIPEA (35 mg, 0.27 mmol) at 0° C. The reaction mixture was slowly warmed to ambient temperature. After 16 h, the reaction mixture was diluted with diethyl ether and washed successively with 1N HCl, water (5×), aqueous NaHCO₃, water (2×), and brine, dried over anhydrous Na₂SO₄, filtered, and concentrated to afford crude 25 which was used without further purification. Mass spectrum, m/z [720.0] (M)+.

N-{1S-Cyclohexyl-2-[(3aR,6aR)-6S-(1H-indol-3-yl]-hexahydro-pyrrolo[3,2-b]pyrrol-1-yl-2-oxo-ethyl}-2S-methylamino-propionamide (26)

A solution containing crude 25 from the previous reaction (0.21 mmol) and 10% Pd/C (0.1 g) in MeOH (20 mL) was placed in a Parr apparatus and pressurized to 55 PSI H₂ (379.2 KPa). After 2 h, the catalyst was removed by filtration through diatomaceous earth (Celite®) and the clarified filtrate was concentrated in vacuo. The crude product was purified by reverse-phase HPLC (2" Dynamax C18 column; Flow: 40 mL/min; Method: 10-40% ACN/water containing 0.1% v/v HOAc over 30 min). The product-containing fractions were pooled, diluted with water, frozen, and lyophilized to dryness to afford 42.5 mg (43%, 3 steps) of 26 as a white solid (acetate salt). $^1$H NMR (CDCl₃/d₄-MeOH, 300 MHz): δ9.66 (br s, 1H), 8.25 (d, J=8.4 Hz, 1H), 7.93 (d, J=7.6 Hz, 1H), 7.37 (app d, J=8.2 Hz, 1H), 7.36 (s, 1H), 7.26-7.05 (m, 2H), 4.83 (app d, J=5.2 Hz, 1H), 4.50 (app d, J=7.6 Hz, 1H), 4.31-4.19 (m, 1H), 4.05 (app d, J=4.9 Hz, 1H), 3.78 (m, 1H), 3.73-3.48 (m, 2H), 3.39 (br s, MeOH/AcOH/water), 2.44 (m, 1H), 2.38 (s, 3H), 2.12 (m, 1H), 1.77-1.53 (m, 7H), 1.40 (d, J=6.7 Hz, 3H), 1.31-1.00 (m, 4H) ppm. $^{13}$C NMR (CDCl₃, 75 MHz) δ171.5, 171.0, 136.7, 126.3, 122.5, 121.6, 119.6, 119.3, 112.6, 111.7, 77.5, 68.7, 61.3, 58.3, 56.3, 50.9, 47.1, 41.8, 40.4, 32.7, 29.9, 29.6, 29.0, 26.1, 25.9, 17.6 ppm. Mass spectrum, m/z [452.0] (M)+.

Examples 89 and 90 were prepared from intermediates 3 and 4 following the procedures described by Schemes III through XXIV by Scheme XXIV

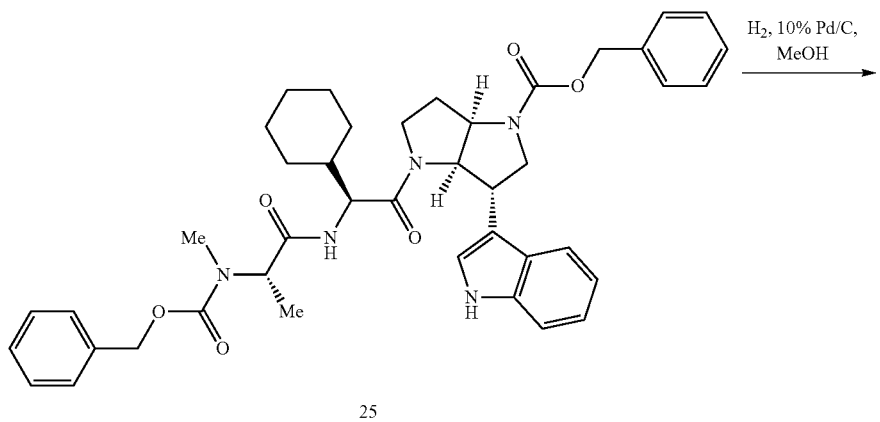

25

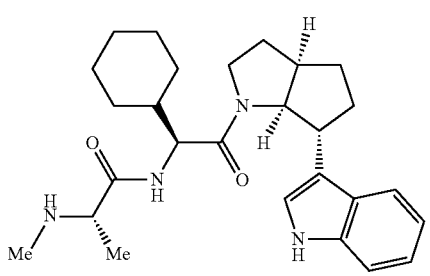

26 replacing Boc-Chg-OH with other amino acid reagents including Boc-Thr(Me)-OH.

Example 3

N-{1-[4-Cyclopentyl-6-(6-fluoro-1H-indol-3-yl)-hexahydro-pyrrolo[3,2-b]pyrrole-1-carbonyl]-2,2-dimethyl-propyl}-2-methylamino-propionamide (41)

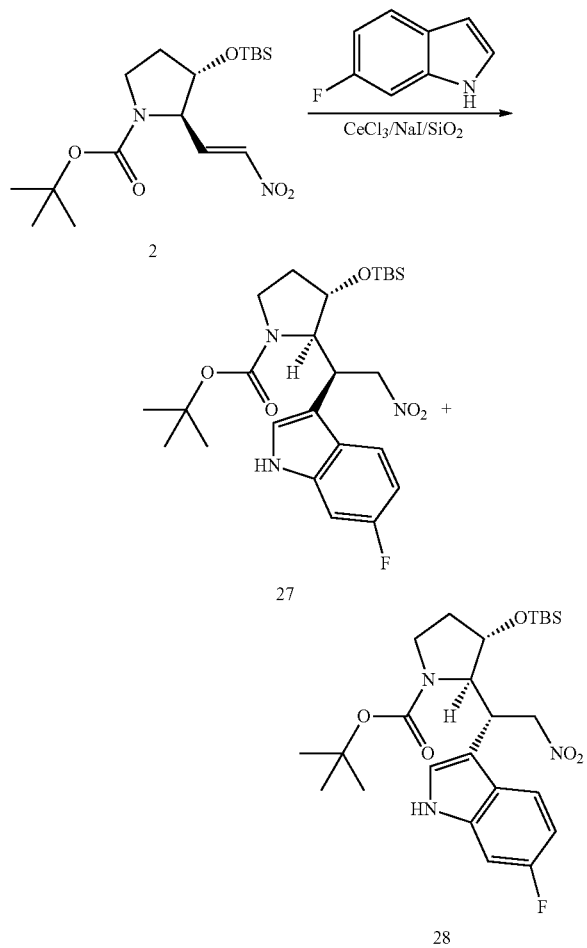

3S-(tert-Butyl-dimethyl-silanyloxy)-2R-[1S-(6-F-indol-3-yl)-2-nitro-ethyl]-pyrrolidine-1-carboxylic acid tert-butyl ester (27) and 3S-(tert-Butyl-dimethyl-silanyloxy)-2R-[1R-(6-F-indol-3-yl)-2-nitro-ethyl]-pyrrolidine-1-carboxylic acid tert-butyl ester (28)

(See: Bartoli, G.; et al. *J. Org. Chem.* 2005, 70, 1941) A 1 L round-bottomed flask was charged with CeCl$_3$.7H$_2$O (10.3 g, 27.7 mmol), NaI (4.2 g, 27.7 mmol), and reagent grade MeOH (200 mL). To the clear, water-white solution was added silica gel (Fisher Grade 60, 230-400 mesh, 45 g) and the white, heterogeneous mixture was concentrated in vacuo (rotovap bath temp: 40° C.). To the white, free-flowing CeCl$_2$/NaI/SiO$_2$ was added 2 (25.8 g, 69.2 mmol) and 6-F-indole (11.2 g, 83.1 mmol) in anhydrous ACN (160 mL) and the pale orange mixture was concentrated under high vacuum (bath temp: 40° C.). The orange-brown solid was allowed to stand at ambient temperature. After 16 h, the solid residue was poured atop a short column of silica gel and the products were eluted (20% EtOAc/hexanes to 40% EtOAc/hexanes). The diastereomers were separated by normal phase HPLC (2" Dynamax SiO$_2$; 10-50% EtOAc/hexanes over 30 min; Flow: 40 mL/min) to afford 12 g (34%) of isomer 27, and 10 g (28%) of isomer 28 together with some recovered 2 [TLC analysis, SiO$_2$, 4:1 hexanes/EtOAc; R$_f$(2)=0.6; R$_f$(27)=0.48; R$_f$(28)= 0.45].

Compound 27: $^1$H NMR (CDCl$_3$, 300 MHz), ~3:2 mixture of carbamate rotamers: δ8.86 (br s, 0.4H, minor rotamer), 8.83 (br s, 0.6H, major rotamer), 8.15 (dd, J=5.1, 8.7 Hz, 0.6H, major rotamer), 8.04 (dd, J=5.4, 9.0 Hz, 0.4H, minor rotamer), 7.55 (d, J=2.4 Hz, 0.6H, major rotamer), 7.53 (br s, 1H), 7.50 (d, J=2.1 Hz, 0.4H, minor rotamer), 7.40 (app t, J=8.7 Hz, 0.6H, major rotamer), 7.39 (app t, J=9.3 Hz, 0.4H, minor rotamer), 5.74-5.35 (m, 1H), 5.29-5.20 (m, 1H), 4.68 (app t, J=11.4 Hz, 1H), 4.43 (m, 1H), 4.24-3.95 (m, 2H), 3.82 (t, J=9.6 Hz, 1H), 2.61 (m, 1H), 2.28 (m, 1H), 2.08 (s, 3H, minor rotamer), 1.99 (s, 6H, major rotamer), 1.14 (s, 9H), 0.10 (s, 1H, minor rotamer), 0.09 (s, 2H, major rotamer), 0.01 (s, 2H, major rotamer), 0.00 (s, 1H, minor rotamer) ppm. $^{13}$C NMR (300 MHz, CDCl$_3$), ~3:2 mixture of carbamate rotamers: δ171.2, 161.3, 157.5 (d, J$_{CF}$=102.4 Hz), 157.1 (d, J$_{CF}$=164.2 Hz), 136.7 (d, J$_{CF}$=11.1 Hz), 136.5 (d, J$_{CF}$=12.3 Hz), 123.3 (d, J$_{CF}$=18.3 Hz), 122.3 (d, J$_{CF}$=18.9 Hz), 119.3 (d, J$_{CF}$=30.9 Hz), 111.3 (d, J$_{CF}$=37.2 Hz), 108.3 (d, J$_{CF}$=25.5 Hz), 98.1 (d, J$_{CF}$=23.1 Hz), 97.8 (d, J$_{CF}$=24.6 Hz), 80.8, 79.4, 74.2, 73.8, 68.9, 68.8, 60.3, 45.2, 44.9, 40.4, 39.9, 32.0, 31.1, 28.3, 28.2, 25.2, 20.7, 17.5, 13.9, −5.6, −5.7 ppm. Mass spectrum, m/z [408.2] (M−Boc)+.

Compound 28: $^1$H NMR (CDCl$_3$, 300 MHz), ~3:2 mixture of carbamate rotamers: δ9.03 (br s, 0.4H, minor rotamer), 8.92 (br s, 0.6H, major rotamer), 8.03 (m, 1H), 7.52-7.44 (m, 2H), 7.36 (app t, J=8.4 Hz, 1H), 5.42-5.19 (m, 2H), 4.79 (m, 1H), 4.63 (m, 2H), 4.07-3.86 (m, 1H), 3.63-3.46 (m, 1H), 2.06 (s, 3H, minor rotamer), 1.99 (s, 6H, major rotamer), 1.95 (m, 1H), 1.65 (m, 1H), 1.27 (s, 6H, major rotamer), 1.20 (s, 3H, minor rotamer), 0.38-0.25 (m, 6H) ppm. $^{13}$C NMR (300 MHz, CDCl$_3$), ~3:2 mixture of carbamate rotamers: δ171.4, 161.5, 157.3 (d, J$_{CF}$=151.9 Hz), 157.1 (d, J$_{CF}$=186.9 Hz), 136.2 (d, J$_{CF}$=12.3 Hz), 123.2, 122.5 (d, J$_{CF}$=24.9 Hz), 119.5 (d, J$_{CF}$=36.0), 110.8, 108.5 (d, J$_{CF}$=24.3 Hz), 97.8 (d, J$_{CF}$=28.9 Hz), 81.2, 79.9, 78.0, 75.1, 68.8, 60.4, 46.3, 38.8, 37.9, 33.2, 32.5, 28.4, 25.5, 25.4, 20.9, 17.7, 14.1, −5.1, −5.4 ppm. Mass spectrum, m/z [408.2] (M−Boc)+.

Scheme XXVI

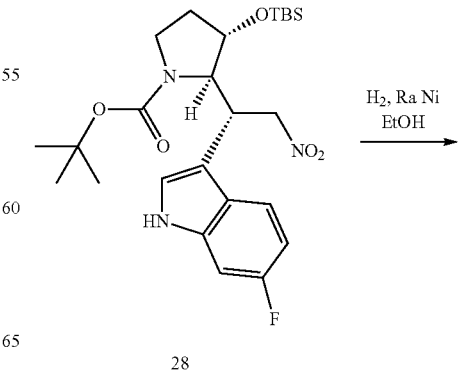

28

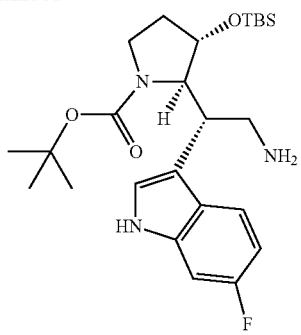

29

2R-[2-Amino-1S-(6-F-indol-3-yl)-ethyl]-3S-(tert-butyl-dimethyl-silanyloxy)-pyrrolidine-1-carboxylic acid tert-butyl ester (29)

A Parr bottle was charged with 28 (12 g, 23.7 mmol) and Raney Ni (20 mL, 2400 Ni slurry in H$_2$O) in EtOH (120 mL) and subjected to 50 PSI H$_2$ pressure (379.2 KPa). Rapid absorption of H$_2$ was observed and the reaction was twice recharged to 50 PSI H$_2$ (379.2 KPa). After 1.5 h, the reaction mixture was filtered through diatomaceous earth (Celite®) and the solids were washed with EtOH. The filtrate was concentrated and the residue was dissolved in EtOAc, washed with saturated NaHCO$_3$, brine, dried over anhydrous Na$_2$SO$_4$, filtered and concentrated to give 29 (10.7, 95%) as a yellow foam. $^1$H NMR (CDCl$_3$, 300 MHz), mixture of carbamate rotamers: δ9.30 (br s, 0.5H), 9.07 (br s, 0.5H), 7.86-7.75 (m, 1H), 7.24 (app t, J=6.6 Hz, 1H), 7.15 (s, 1H), 7.08 (ap t, J=9.0 Hz, 1H), 4.38-4.30 (m, 3H), 3.86-3.61 (m, 2H), 3.44-3.28 (m, 3H), 1.71 (s, 9H), 0.96 (s, 9H), 0.06 (s, 3H), 0.001 (s, 3H) ppm. $^{13}$C NMR (CDCl$_3$, 75 MHz), mixture of carbamate rotamers: δ166.5 & 163.4, 161.3 (J$_{CF}$=13.5 Hz), 141.7 (J$_{CF}$=12.1 Hz), 129.4, 127.6 & 127.3, 125.1 (J$_{CF}$=10.4 Hz) & 124.8 (J$_{CF}$=10.4 Hz), 119.1 & 118.5, 113.2 & 112.9, 102.8 (J$_{CF}$=17.6 Hz) & 102.5 (J$_{CF}$=16.6 Hz), 85.1 & 84.4, 80.4 & 80.1, 74.7 & 74.1, 51.4 & 51.1, 48.5, 38.5 & 37.7, 33.6 & 30.7, 22.9, 0.09 ppm. Mass spectrum, m/z [478.3] (M+H)+.

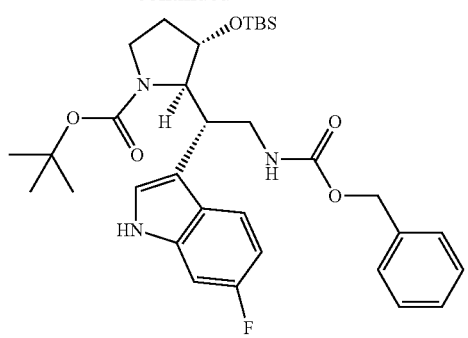

30

2R-[2-Benzyloxycarbonylamino-1S-(6-fluoro-1H-indol-3-yl)-ethyl]-3S-(tert-butyl-dimethyl-silanyloxy)-pyrrolidine-1-carboxylic acid tert-butyl ester (30)

To a solution of DCM (10 mL) containing crude 29 (10.7 g, 22.4 mmol) at 0° C. was added TEA (4.8 mL, 34.5 mmol) followed by Cbz-Cl (3.5 mL, 25 mmol). After 1 h, the reaction was warmed to room temperature. After 1.5 h, the reaction mixture was diluted with DCM, washed successively with 1N HCl and brine, dried over anhydrous Na$_2$SO$_4$, filtered, and concentrated to afford 30 (13.5 g, 98%). $^1$H NMR (CDCl$_3$, 300 MHz) δ8.73 (br s, 1H), 7.57 (app q, J=5.1 Hz, 1H), 7.48-7.32 (m, 5H), 7.10 (m, 1H), 6.91 (m, 1H), 6.45 (br s, 1H), 5.20 (s, 2H), 4.24-4.09 (m, 2H), 3.65-3.40 (m, 4H), 3.02 (app t, J=9.6 Hz, 1H), 1.57 (s, 9H), 0.87 (s, 9H), 0.00 (s, 6H) ppm. Mass spectrum, m/z [612.4] (M+H)+.

Scheme XXVIII

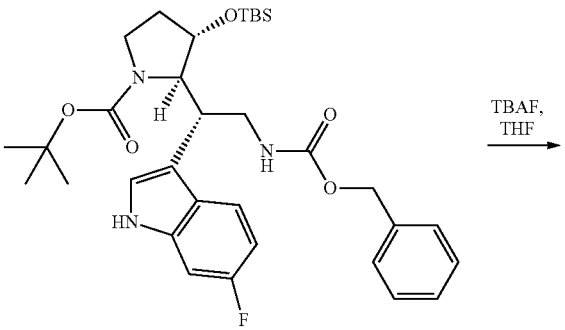

Scheme XXVII

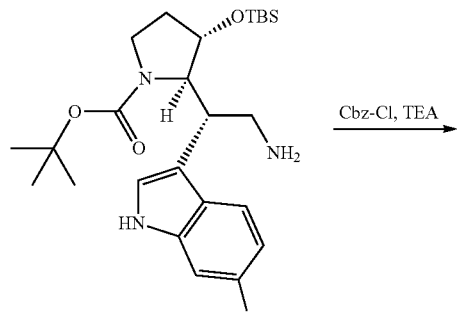

2R-[2-Benzyloxycarbonylamino-1S-(6-fluoro-1H-indol-3-yl)-ethyl]-3S-hydroxy-pyrrolidine-1-carboxylic acid tert-butyl ester (31)

A solution of 30 (13.5 g, 22.0 mmol) in THF (60 mL) was treated with TBAF (45 mL, 1M in THF, 45 mmol) at room temperature. After 5 h, the reaction mixture was warmed for 1 h at 45° C. and then diluted with EtOAc, washed successively with 1N HCl and brine, dried over anhydrous $Na_2SO_4$, filtered, and concentrated to afford crude 31 which was purified by flash silica gel chromatography (1:2 hexanes/EtOAc) to afford 10.1 g (93%) of 31 as light peach-colored foam. $^1$H NMR (CDCl$_3$, 300 MHz) δ8.88 (s, 1H), 7.40-7.31 (m, 5H), 6.94 (app d, J=9.6 Hz, 1H), 6.81-6.75 (m, 1H), 6.67 (s, 1H), 6.45 (m, 1H), 5.12 (app q, J=11.7 Hz, 2H), 4.18-4.03 (m, 2H), 3.51-3.34 (m, 4H), 2.92 (app t, J=9.9 Hz, 1H), 2.33 (br s, 1H), 1.48 (s, 9H), 0.91-0.86 (m, 1H) ppm. $^{13}$C NMR (CDCl$_3$, 75 MHz) δ158.5, 157.2, 157.0, 136.9, 136.5, 136.3, 128.7, 128.3, 123.7, 122.8, 120.6, 113.6, 108.7, 108.4, 98.0, 97.7, 80.1, 75.7, 67.3, 66.9, 46.5, 43.4, 41.1, 32.3, 28.7 ppm. Mass spectrum, m/z [498.2] (M+H)+.

Scheme XXIX

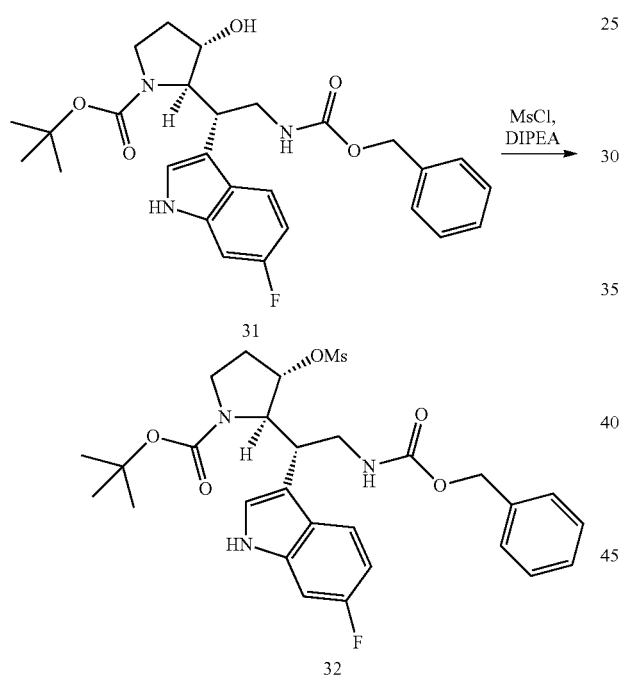

2R-[2-Benzyloxycarbonylamino-1S-(6-fluoro-1H-indol-3-yl)-ethyl]-3S-methanesulfonyloxy-pyrrolidine-1-carboxylic acid tert-butyl ester (32)

A solution of 31 (10.0 g, 20.1 mmol) in DCM (100 mL) was cooled to 0° C. A solution of MsCl (1.5 mL, 19.4 mmol) in DCM (3 mL) was added dropwise followed by the addition of DMAP (250 mg, 2.0 mmol). After 3 h at 0° C., the reaction mixture was diluted with DCM, washed successively with 1N HCl, water, and brine, dried over anhydrous $Na_2SO_4$, filtered, and concentrated to afford 32 (10.4 g, 90%) as a light peach colored foam. $^1$H NMR (CDCl$_3$, 300 MHz) δ 8.71 (s, 1H), 7.50 (app q, J=5.4 Hz, 1H), 7.38-7.32 (m, 5H), 7.00 (app d, J=8.4 Hz, 1H), 6.89-6.81 (m, 2H), 6.29 (br s, 1H), 5.14 (s, 2H), 4.92 (app d, J=3.9 Hz, 1H), 4.52 (s, 1H), 3.55-3.39 (m, 4H), 3.04 (app t, J=9.9 Hz, 1H), 2.79 (s, 3H), 1.82 (app q, J=7.5 Hz, 1H), 1.52 (s, 9H), 1.14 (m, 1H) ppm. Mass spectrum, m/z [576.3] (M+H)+.

Scheme XXX

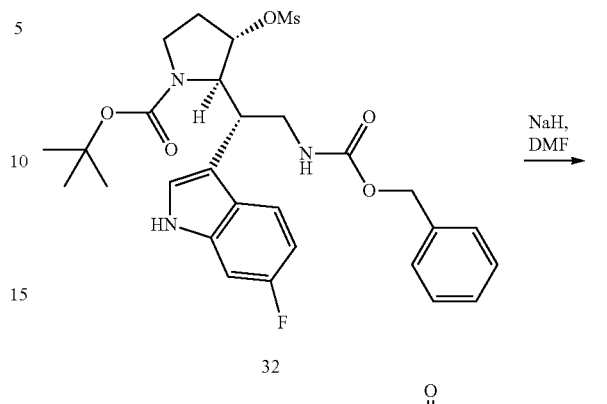

(3aR,6aR)-6S-(6-fluoro-1H-Indol-3-yl)-hexahydro-pyrrolo[3,2-b]pyrrole-1-carboxylic acid tert-butyl ester (33)

A solution of 32 (10.4 g, 18 mmol) in DMF (30 mL) was added to a suspension of NaH (1.9 g, 60%, 46 mmol) in DMF (100 mL) at 0° C. After 1 h, the reaction mixture was diluted with $H_2O$, extracted with diethyl ether, washed with brine, dried over anhydrous $Na_2SO_4$, filtered, and concentrated to give 33 (8.3 g, 97%) as a light tan colored solid. $^1$H NMR (CDCl$_3$, 300 MHz) mixture of carbamate rotamers: δ8.25 (br s, 0.5H), 8.16 (s, 0.5H), 8.04 (dd, J=8.4, 14.1 Hz, 0.5H), 7.95 (dd, J=7.8, 13.5 Hz, 0.5H), 7.71 (m, 0.5H), 7.64 (m, 0.5H), 7.34 (m, 4H), 6.99 (app t, J=13.2 Hz, 1H), 6.91-6.84 (m, 1H), 6.81-6.76 (m, 0.5H), 6.68-6.61 (m, 0.5H), 5.24-5.15 (m, 2H), 4.46-4.31 (m, 2H), 4.20-4.02 (m, 1H), 3.96 (m, 1H), 3.84-3.68 (m, 1H), 3.63 (app q, J=5.7 Hz, 1H), 3.25 (m, 1H), 2.31 (dd, J=6.0, 13.5 Hz, 0.5H), 2.14 (dd, J=5.7, 13.5 Hz, 0.5H), 1.94-1.84 (m, 1H), 1.52 (s, 7H), 1.31-1.26 (m, 2H), 0.91-0.83 (m, 2H) ppm.

Scheme XXXI

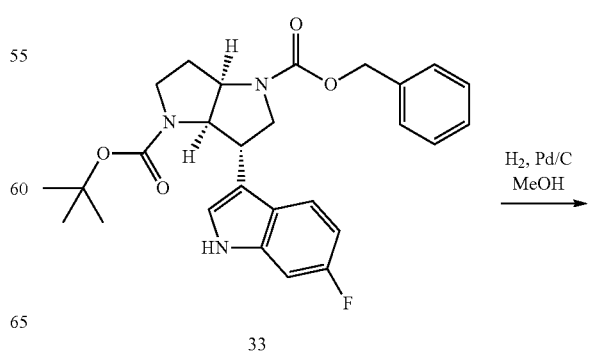

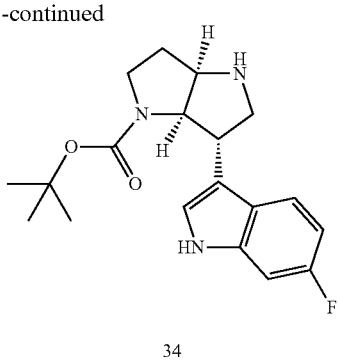

34

6-(6-Fluoro-1H-indol-3-yl)-hexahydro-pyrrolo[3,2-b]pyrrole-1-carboxylic acid tert-butyl ester (34)

A 500 mL Parr bottle was charged with 33 (6.84 g, 14.2 mmol) and 10% Pd-on-carbon (0.2 g) in reagent grade MeOH (100 mL). The mixture was pressurized to 55 PSI H$_2$ (379.2 KPa) then shaken for 5 h. The catalyst was removed by filtration through diatomaceous earth (Celite®) and the solids were washed with MeOH and EtOAc. The filtrate was concentrated in vacuo and the crude amine (34, 5.23 g) was used without further purification. $^1$H NMR (CDCl$_3$, 300 MHz) mixture of carbamate rotamers: δ8.31 (br s, 1H), 7.71 (br s, 0.5H). 7.56 (br s, 0.5H), 7.04-6.85 (m, 3H), 4.46-4.44 (m, 1H), 4.05 (m, 1H), 3.77 (m, 1H), 3.40 (m, 1H), 3.30-3.28 (m, 1H), 3.15-3.13 (m, 0.5H), 3.04-3.01 (m, 0.5H), 2.48 (br s, 1H), 1.91 (m, 2H), 1.26 (s, 3H), 1.19 (s, 9H) ppm. $^{13}$C NMR (CDCl$_3$, 75 MHz), mixture of carbamate rotamers: δ161.6 & 158.5, 154.6, 136.6, 123.5 & 121.2, 119.9, 116.8 & 116.3, 108.0 & 107.7, 97.8 & 97.5, 79.7 & 68.2, 63.4 & 62.1, 53.8 & 53.7, 52.9, 46.4 & 44.2, 45.5 & 44.2, 45.5 & 45.3, 32.9, 32.2 & 32.0, 29.9, 28.8 & 28.5 ppm. Mass spectrum, m/z [346.1] (M+H)+.

Scheme XXXII

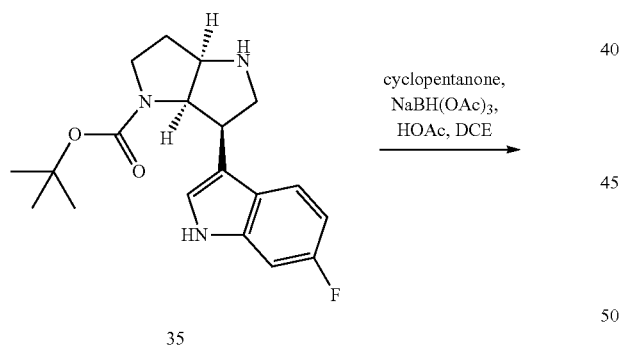

4-Cyclopentyl-6-(6-fluoro-1H-indol-3-yl)-hexahydro-pyrrolo[3,2-b]pyrrole-1-carboxylic acid tert-butyl ester (36)

To a solution containing crude 35 (prepared from 27 by the methods described in Schemes 26 through 31: 2.65 g, 7.67 mmol) in reagent grade dichloroethane (30 mL) was added cyclopentanone (0.71 g, 8.43 mmol), NaBH(OAc)$_3$ (2.27 g, 10.7 mmol), and glacial HOAc (0.46 g, 7.67 mmol). After 2 h, the reaction mixture was carefully quenched with saturated aqueous NaHCO$_3$ then partitioned with DCM. The layers were separated and the DCM layer was washed with brine, dried over anhydrous Na$_2$SO$_4$, filtered, and concentrated. The crude product was chromatographed on silica gel (40-100% EtOAc/hexanes) and the product-containing fractions were combined, concentrated, and then repurified by normal phase HPLC (2" Dynamax SiO$_2$, 40-100% EtOAc/hexanes over 30 min; Flow: 40 mL/min) to afford 2.0 g (63%) of 36. Mass spectrum, m/z [414.3] (M+H)+.

Scheme XXXIII

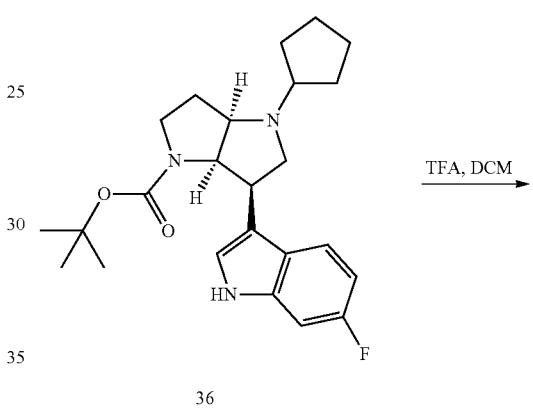

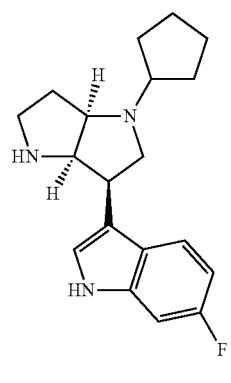

37

3-(1-Cyclopentyl-octahydro-pyrrolo[3,2-b]pyrrol-3-yl)-6-fluoro-1H-indole (37)

A solution containing 36 (2.0 g, 4.8 mmol) in DCM (20 mL) was cooled to 0° C. TFA (6 mL) was added and the pink reaction mixture was stirred at 0° C. After 1 h, the reaction mixture was warmed to ambient temperature then concentrated in vacuo. The residue was dissolved in EtOAc and the organic solution was washed successively with saturated aqueous NaHCO$_3$ and brine, dried over anhydrous Na$_2$SO$_4$, filtered, and concentrated to afford 1.4 g of 37 which was used without further purification. $^1$H NMR (CDCl$_3$, 300 MHz): δ8.50 (br s, 1H), 7.58 (dd, J=5.4, 8.4 Hz, 1H), 7.05-7.01 (m,

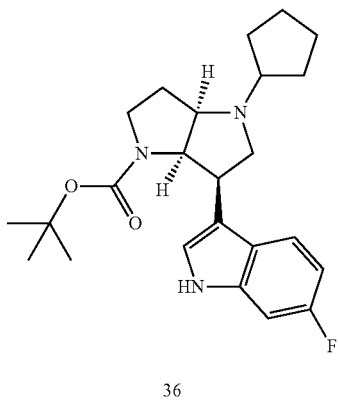

36

2H), 6.92-6.85 (m, 1H), 4.17-4.11 (m, 1H), 3.92 (app q, J=6.0 Hz, 1H), 3.74 (app q, J=6.6 Hz, 1H), 3.21-3.15 (m, 1H), 3.08-2.88 (m, 3H), 2.75-2.67 (m, 2H), 1.96-1.78 (m, 5H), 1.61 (m, 4H) ppm. Mass spectrum, m/z [314.2] (M+H)+.

Scheme XXXIV

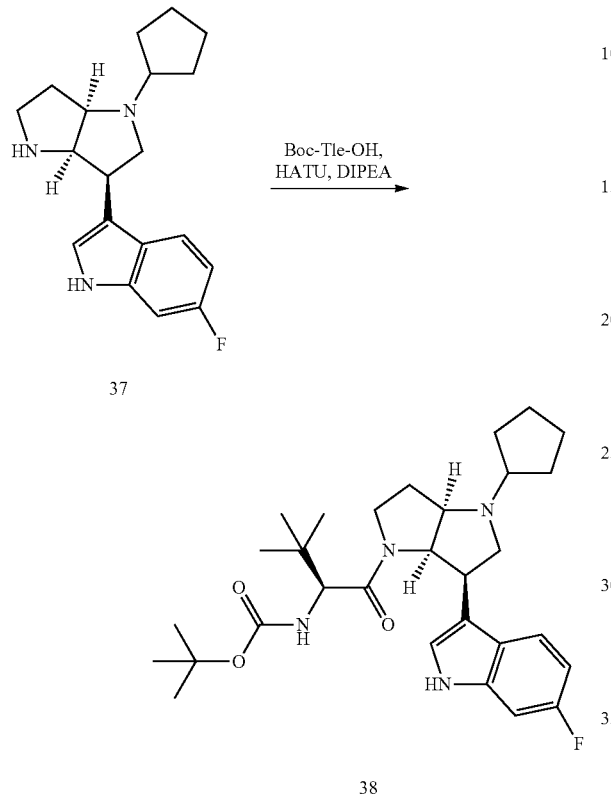

{1-[4-Cyclopentyl-6-(6-fluoro-1H-indol-3-yl)-hexahydro-pyrrolo[3,2-b]pyrrole-1-carbonyl]-2,2-dimethyl-propyl}-carbamic acid tert-butyl ester (38)

To a solution containing Boc-L-Tle-OH (160 mg, 0.7 mmol) in anhydrous NMP (4 mL) was cooled to 0° C. HATU (264 mg, 0.7 mmol) and DIPEA (148 mg, 0.7 mmol) were added followed by the addition of crude 37 (220 mg, 0.7 mmol) in anhydrous NMP (5 mL). The reaction mixture was slowly warmed to ambient temperature. After 4 h, the reaction mixture was diluted with EtOAc and washed successively with aqueous NaHCO3 and brine, dried over anhydrous Na2SO4, filtered, and concentrated. The crude product was purified by silica gel HPLC (2" Dynamax SiO2, 20-100% EtOAc/hexanes over 30 min; Flow: 40 mL/min) to afford 280 mg (66%, 2 steps) of 38. $^1$H NMR (CDCl3, 300 MHz): δ8.37 (s, 1H), 7.58 (dd, J=5.7, 8.4 Hz, 1H), 7.12 (s, 1H), 6.73 (dd, J=1.8, 9.6 Hz, 1H), 6.65-6.58 (m, 1H), 5.07 (d, J=9.3 Hz, 1H), 4.76 (app t, J=8.4 Hz, 1H), 3.76 (d, J=9.3 Hz, 1H), 3.69 (app t, J=7.2 Hz, 1H), 3.41 (app t, J=8.7 Hz, 1H), 3.09 (app t, J=6.9 Hz, 1H), 3.00-2.94 (m, 2H), 2.66-2.50 (m, 2H), 1.69-1.51 (m, 5H), 1.39 (m, 3H), 1.18 (s, 9H), 0.01 (s, 9H) ppm. Mass spectrum, m/z [527.4] (M+H)+.

Scheme XXXV

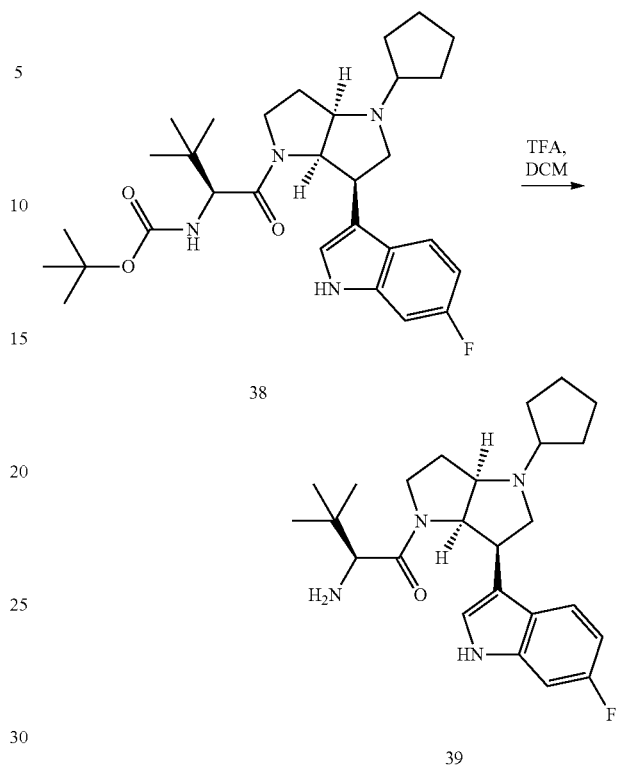

2-Amino-1-[4-cyclopentyl-6-(6-fluoro-1H-indol-3-yl)-hexahydro-pyrrolo[3,2-b]pyrrol-1-yl]-3,3-dimethyl-butan-1-one (39)

To a solution containing 38 (0.28 g, 0.53 mmol) in DCM (10 mL) was added TFA (3 mL) at ambient temperature. After 90 min, the reaction mixture was concentrated in vacuo. The residue was dissolved in EtOAc and the organic solution was washed successively with saturated aqueous NaHCO3 and brine, dried over anhydrous Na2SO4, filtered, and concentrated to afford 218 mg of 39 which was used without further purification. $^1$H NMR (CDCl3, 300 MHz), mixture of rotamers: δ9.31 (s, 0.5H), 8.24 (s, 0.5H), 7.86 (dd, J=5.4, 8.7 Hz, 0.5H), 7.54 (dd, J=5.4, 8.7 Hz, 0.5H), 7.28 (s, 1H), 7.00 (dd, J=2.4, 9.9 Hz, 0.5H), 6.96-9.6.91 (m, 1H), 6.86-6.79 (m, 0.5H), 4.98 (app t, J=8.1 Hz, 0.5H), 4.80 (app t, J=7.8 Hz, 0.5H), 4.16-4.09 (m, 0.5H), 3.94-3.81 (m, 1.5H), 3.54-3.45 (m, 1H), 3.29-3.06 (m, 2H), 2.90-2.70 (m, 2H), 2.26-2.21 (m, 0.5H), 2.12-2.05 (m, 0.5H), 1.90-1.68 (m, 4H), 1.60-1.50 (m, 4H), 1.16 (br s, 2H), 0.80 (s, 4.5H), 0.21 (s, 4.5H) ppm. Mass spectrum, m/z [427.3] (M+H)+.

Scheme XXXVI

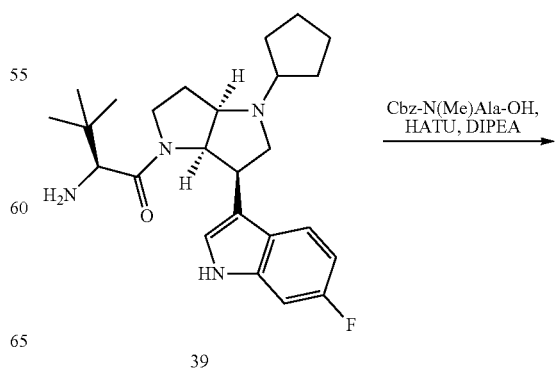

(1-{1-[4-Cyclopentyl-6-(6-fluoro-1H-indol-3-yl)-hexahydro-pyrrolo[3,2-b]pyrrole-1-carbonyl]-2,2-dimethyl-propylcarbamoyl}-ethyl)-methyl-carbamic acid benzyl ester (40)

To a solution containing Cbz-N(Me)Ala-OH (116 mg, 0.5 mmol) in anhydrous NMP (5 mL) was cooled to 0° C. HATU (191 mg, 0.5 mmol) and DIPEA (148 mg, 0.7 mmol) were added followed by the addition of crude 39 (218 mg, 0.5 mmol) in anhydrous NMP (5 mL). The reaction mixture was slowly warmed to ambient temperature. After 3 h, the reaction mixture was diluted with EtOAc and washed successively with aqueous $NaHCO_3$ and brine, dried over anhydrous $Na_2SO_4$, filtered, and concentrated to afford 300 mg of crude 40 as an amber-colored oil which was used without further purification. Mass spectrum, m/z [646.4] (M+H)+.

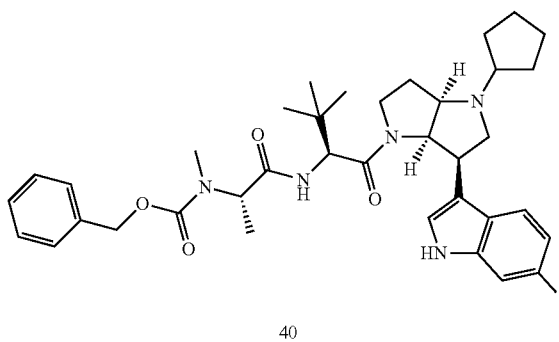

40

Scheme XXXVII

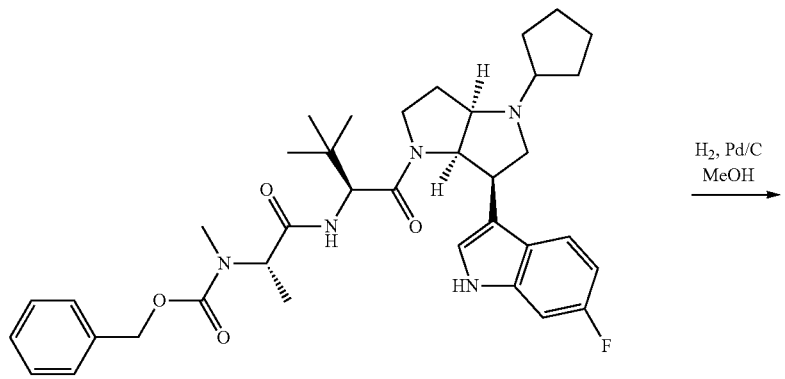

40

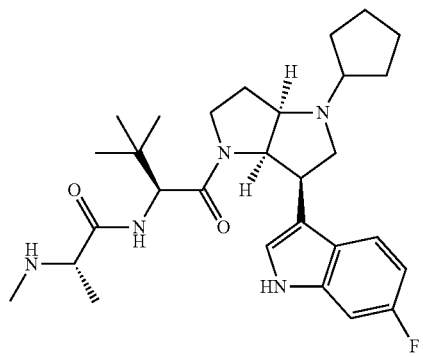

41

N-{1-[4-Cyclopentyl-6-(6-fluoro-1H-indol-3-yl)-hexahydro-pyrrolo[3,2-b]pyrrole-1-carbonyl]-2,2-dimethyl-propyl}-2-methylamino-propionamide (41)

A 500 mL Parr bottle was charged with crude 40 (300 mg, 0.5 mmol) and 10% Pd-on-carbon (50 mg) in reagent grade MeOH (20 mL). The mixture was pressurized to 50 PSI $H_2$ (379.2 KPa) then shaken for 30 min. The catalyst was removed by filtration through diatomaceous earth (Celite®) and the solids were washed with MeOH. The filtrate was concentrated in vacuo and the crude product was purified by RP-HPLC (2" C18 Dynamax, 5-40% ACN/water containing 0.1% HOAc over 30 min; Flow: 40 mL/min) to afford 121 mg (44%, 3 steps) of 41.2HOAc as a white solid. $^1$H NMR (300 MHz, d$_6$-DMSO), mixture of amide rotamers: δ10.7 (s, 1H), 7.81 (dd, J=5.4, 8.4 Hz, 0.2H), 7.64 (d, J=10.2 Hz, 0.2H), 7.58 (d, J=9.6 Hz, 0.8H), 7.49 (dd, J=3.0, 8.7 Hz, 0.8H), 7.16 (s, 0.8H), 6.99 (s, 0.2H), 6.87 (dd, J=2.1, 9.9 Hz, 1H), 6.63-6.57 (m, 1H), 4.85 (app t, J=8.4 Hz, 0.2H), 4.63 (app t, J=8.4 Hz, 0.8H), 4.02 (d, J=9.3 Hz, 1H), 3.62 (app t, J=6.9 Hz, 1H), 3.51-3.45 (m, 1H), 3.16 (app t, J=6.9 Hz, 0.8H), 2.96-2.91 (m, 1H), 2.75 (app q, J=6.9 Hz, 0.8H), 2.68-2.56 (m, 1H), 2.38-2.37 (m, 1H), 2.00 (s, 2H), 1.88 (s, 1H), 1.78 (s, 2H), 1.72-1.50 (m, 5H), 1.41 (m, 3H), 1.06 (d, J=7.2 Hz, 1H), 0.09 (d, J=9.6 Hz, 2H), 0.74 (s, 1H), 0.00 (s, 8H) ppm. $^{13}$C NMR (75 MHz, d$_6$-DMSO), mixture of amide rotamers: δ173.9, 168.7, 159.4 ($J_{CF}$=232.9 Hz), 136.2 & 136.1, 125.2, 123.9, 121.3 ($J_{CF}$=10.4 Hz), 116.1, 106.8 ($J_{CF}$=24.4 Hz), 97.2 ($J_{CF}$=25.0 Hz), 66.6, 65.8 & 65.4, 60.3 & 59.9, 55.7, 48.4, 37.7, 35.1 & 34.9, 32.9, 30.9 & 30.7, 27.1, 26.0, 24.1, 23.5, 21.8, 19.6 ppm. Mass spectrum, m/z [512.3] (M+H)+.

Examples 4-16 were prepared using intermediates 34 and 35 and by the procedures described in Schemes XXXI through XXXVII by substituting for Boc-Tle-OH with other amino acid reagents including Boc-Abu-OH, Boc-Val-OH, Boc-Chg-OH, Boc-Ser-OH, Cbz-Ser(tBu)-OH, Boc-Ser(Me)-OH, Cbz-Thr(tBu)-OH, Boc-Thr(tBu)-OH, Boc-Thr-OH, or Boc-Thr(Me)-OH.

Example 5

N-{1-[4-Cyclopentyl-6-(6-fluoro-1H-indol-3-yl)-hexahydro-pyrrolo[3,2-b]pyrrole-1-carbonyl]-propyl}-2-methylamino-propionamide $^1$H NMR (300 MHz, d$_6$-DMSO), mixture of amide rotamers: δ10.7 (s, 1H), 7.67-7.65 (dd, J=5.4, 9.0 Hz, 0.2H), 7.60 (d, J=8.4 Hz, 1H), 7.48 (dd, J=5.4, 8.7 Hz, 0.8H), 7.13 (s, 0.8H), 7.05 (s, 0.2H), 6.87 (dd, J=2.1, 10.2 Hz, 0.8H), 6.82 (dd, J=2.4, 10.2 Hz, 0.2H), 6.62-6.56 (m, 0.8H), 6.52-6.45 (m, 0.2H), 4.63 (app t, J=8.4 Hz, 1H), 4.52-4.44 (m, 0.2H), 3.96-3.89 (m, 0.8H), 3.65 (app t, J=6.9 Hz, 0.2H), 3.57 (app t, J=6.6 Hz, 0.8H), 3.38-3.32 (m, 1H), 3.19-3.15 (m, 1H), 2.92 (app d, J=8.1 Hz, 1H), 2.87-2.74 (m, 2H), 2.65-2.54 (m, 2H), 2.35 (s, 1H), 2.00 (s, 2H), 1.87 (s, 0.5H), 1.75 (s, 2.5H), 1.71-1.53 (m, 6H), 1.46-1.39 (m, 3H), 0.98 (d, J=6.9 Hz, 0.8H), 0.90 (d, J=6.6 Hz, 2.2H), 0.62 (app t, J=7.5 Hz, 0.2H), 0.25-0.15 (m, 1H), 0.02 (app t, J=7.2 Hz, 0.8 Hz) ppm. $^{13}$C NMR (75 MHz, d$_6$-DMSO), mixture of amide rotamers: δ173.8, 172.7, 159.3 ($J_{CF}$=232.9 Hz), 136.2 & 136.0, 125.2, 124.3, 121.1 ($J_{CF}$=10.0 Hz), 115.4, 106.7 ($J_{CF}$=24.2 Hz), 97.2 ($J_{CF}$=25.3 Hz), 66.4, 65.9 & 64.6, 60.0 & 59.3, 51.1, 47.1, 37.8, 34.7 & 34.4, 32.9, 31.2, 30.8 & 30.7, 26.7, 24.0, 23.5, 19.6 & 19.2, 10.1 ppm. Mass spectrum, m/z [484.2] (M+H)+.

Example 7

N-{1-[4-Cyclopentyl-6-(6-fluoro-1H-indol-3-yl)-hexahydro-pyrrolo[3,2-b]pyrrole-1-carbonyl]-2-methyl-propyl}-2-methylamino-propionamide $^1$H NMR (300 MHz, CDCl$_3$), mixture of amide rotamers: δ9.30 (br s, 0.2H), 8.26 (s, 0.8H), 7.79 (dd, J=5.7, 8.7 Hz, 1H), 7.50 (d, J=8.7 Hz, 1H), 7.31 (s, 0.8H), 7.14 (s, 0.2H), 6.94 (dd, J=2.1, 9.6 Hz, 1H), 6.85-6.77 (m, 2H), 4.97 (app t, J=8.4 Hz, 0.8H), 4.74 (app t, J=8.2 Hz, 0.2H), 4.64 (dd, J=4.5, 8.8 Hz, 0.2H), 4.32 (dd, J=4.8, 9.0 Hz, 0.8H), 3.93-3.87 (m, 0.8H), 3.8 (m, 0.2H), 3.67-3.59 (m, 1H), 3.41-3.36 (m, 1H), 3.23-3.17 (m, 3H), 2.98 (dd, J=6.9, 9.3 Hz, 0.2H), 2.86 (dd, J=6.9, 9.3 Hz, 0.8H), 2.79-2.75 (m, 1H), 2.36 (s, 2H), 2.32 (s, 1H), 2.19-2.12 (m, 0.2H), 2.04 (s, 3H), 1.95-1.90 (m, 2H), 1.81-1.72 (m, 3H), 1.59 (m, 3H), 1.27 (d, J=7.2 Hz, 3H), 1.06-0.99 (m, 1H), 0.94 (d, J=6.6 Hz, 0.8H), 0.77 (d, J=6.6 Hz, 0.2H), 0.26 (d, J=6.6 Hz, 3H), 0.06 (d, J=6.6 Hz, 3H) ppm. Mass spectrum, m/z [498.2] (M+H)+.

Example 9

N-{1-Cyclohexyl-2-[4-cyclopentyl-6-(6-fluoro-1H-indol-3-yl)-hexahydro-pyrrolo[3,2-b]pyrrol-1-yl]-2-oxo-ethyl}-2-methylamino-propionamide $^1$H NMR (CDCl$_3$/d$_4$-MeOH, 300 MHz), mixture of amide rotamers: δ7.51-7.47 (m, 1H), 7.31 (s, 1H), 7.22 (s, 1H), 7.12-6.99 (m, 2H), 6.85-6.79 (m, 1H), 5.19-4.94 (m, 1H), 4.78-4.73 (m, 0.5H), 4.56-4.54 (m, 0.5H), 4.03-3.98 (m, 2H), 3.74-3.63 (m, 1H), 3.48-3.26 (m, 3H), 3.09-2.91 (m, 5H), 2.84-2.76 (m, 1.5H), 2.61-2.55 (m, 0.5H), 2.32-2.29 (m, 3H), 2.10-1.56 (m, 14H), 1.34-0.60 (m, 7H) ppm. $^{13}$C NMR (CDCl$_3$, 75 MHz), mixture of amide rotamers: δ174.6 & 173.0, 169.9 & 169.7, 159.9 ($J_{CF}$=236.5 Hz), 137.5 & 136.5, 123.8 & 123.6, 122.4 & 122.2, 119. ($J_{CF}$=10.0 Hz) & 119.2 ($J_{CF}$=9.8 Hz), 115.5 & 113.6, 107.6 ($J_{CF}$=24.4 Hz), 98.4 ($J_{CF}$=25.6 Hz) & 97.7 ($J_{CF}$=25.9 Hz), 69.2 & 67.6, 67.2, 66.8, 66.7 & 66.5, 60.5, 59.7 & 59.5, 54.9 & 54.8, 45.9, 44.3 & 43.4, 42.7 & 41.8, 40.9, 34.4 & 34.1, 32.5 & 31.8, 30.3 & 29.9, 29.9 & 29.6, 28.4 & 27.5, 26.2 & 26.0, 23.9, 23.3 & 23.2, 19.1 & 18.8 ppm. Mass spectrum, m/z [538.4] (M+H)+.

Example 10

N-{2-[4-Cyclopentyl-6-(6-fluoro-1H-indol-3-yl)-hexahydro-pyrrolo[3,2-b]pyrrol-1-yl]-1-hydroxymethyl-2-oxo-ethyl}-2-methylamino-propionamide $^1$H NMR (300 MHz, CDCl$_3$), mixture of amide rotamers: δ8.69 (br s, 1H), 7.84 (d, J=7.8 Hz, 1H), 7.77 (dd, J=5.4, 9.0 Hz, 0.8 Hz), 7.65 (d, J=5.1, 9.0 Hz, 0.2H), 7.28 (br s, 1H), 6.99 (dd, J=2.4, 9.6 Hz, 1H), 6.83 (dt, J=1.8, 9.6 Hz, 1H), 5.95 (br s, 4H), 4.94 (t, J=8.1 Hz, 1H), 4.40 (m, 1H), 3.88 (m, 1H), 3.59 (m, 1H), 3.45-3.36 (m, 2H), 3.26 (m, 1H), 3.16-3.07 (m, 2H), 2.85 (dd, J=6.9, 9.6 Hz, 1H), 2.77 (m, 1H), 2.51 (m, 1H), 2.42 (s, 3H), 2.29 (m, 1H), 1.12 (m, 1H), 2.03 (s, 6H, HOAc), 1.96-1.50 (m, 8H), 1.30 (d, J=6.9 Hz, 3H) ppm. Mass spectrum, m/z [486] (M+H)+.

Example 12

N-{2-[4-Cyclopentyl-6-(6-fluoro-1H-indol-3-yl)-hexahydro-pyrrolo[3,2-b]pyrrol-1-yl]-1-methoxymethyl-2-oxo-ethyl}-2-methylamino-propionamide ¹H NMR (300 MHz, CDCl₃), ~3:2 mixture of amide rotamers: δ8.19 (br s, 1H), 7.77 (dd, J=5.4, 8.7 Hz, 0.6H), 7.65 (dd, J=5.4, 8.7 Hz, 0.4H), 7.45-7.37 (m, 1H), 7.26-6.75 (m, 3H), 5.04-4.92 (m, 1H), 4.66-4.51 (m, 1H), 3.86 (m, 0.6H), 3.58 (m, 0.4H), 3.45-2.87 (m, 4H), 2.89-2.62 (m, 3H), 2.38 (s, 3H), 2.07 (s, 3H), 1.95-1.72 (m, 6H), 1.62-1.58 (m, 6H), 1.28-1.16 (m, 3H) ppm. Mass spectrum, m/z [500] (M+H)+.

Example 14

N-{1-[4-Cyclopentyl-6-(6-fluoro-1H-indol-3-yl)-hexahydro-pyrrolo[3,2-b]pyrrole-1-carbonyl]-2-hydroxy-propyl}-2-methylamino-propionamide ¹H NMR (300 MHz, CDCl₃), mixture of amide rotamers: δ8.32 (br s, 1H), 7.86 (dd, J=8.7, 5.4 Hz, 1H), 7.58 (d, J=8.7 Hz, 1H), 7.31 (d, J=2.1 Hz, 1H), 7.01 (dd, J=1.8, 9.3 Hz, 1H), 6.86 (dt, J=1.8, 9.3 Hz, 1H), 4.92 (t, J=8.7 Hz, 1H), 4.55 (br s, 4H), 4.13 (dd, J=1.2, 9.3 Hz, 1H), 3.90 (m, 1H), 3.75 (m, 1H), 3.38 (m, 1H), 3.27-3.10 (m, 3H), 2.85 (dd, J=6.6, 9.6 Hz, 1H), 2.78 (m, 1H), 2.55 (m, 1H), 2.35 (s, 3H), 2.12 (m, 1H), 2.05 (s, 6H, HOAc), 1.94-1.58 (m, 9H), 1.27 (d, J=6.9 Hz, 3H), 0.68 (d, J=6.3 Hz, 3H) ppm. Mass spectrum, m/z [500] (M+H)+.

Example 16

N-{1-[4-Cyclopentyl-6-(6-fluoro-1H-indol-3-yl)-hexahydro-pyrrolo-[3,2-b]pyrrole-1-carbonyl]-2-methoxy-propyl}-2-methylamino-propionamide ¹H NMR (CDCl₃, 300 MHz), mixture of amide rotamers: δ8.78 (br s, 0.4H), 8.61 (br s, 0.6H), 7.72 (d, J=8.1 Hz, 1H), 7.55-7.50 (m, 2H), 7.25 (s, 0.6H), 7.06 (s, 0.4H), 7.00 (d, J=8.7 Hz, 0.4H), 6.92 (d, J=9.6 Hz, 0.6H), 6.85-6.79 (m, 1H), 5.10-5.06 (m, 0.6H), 4.93-4.88 (m, 0.4H), 4.84-4.79 (m, 0.6H), 4.31-4.29 (m, 0.4H), 4.07-4.01 (m, 0.4H), 3.95-3.89 (m, 0.6H), 3.75-3.59 (m, 2H), 3.48-3.39 (m, 2H), 3.28 (s, 2.4H), 3.07 (s, 0.6H), 3.04-2.97 (m, 0.4H), 2.82-2.76 (m, 1.6H), 2.56-2.50 (m, 1H), 2.3-2.25 (m, 3H), 2.10 (br s, 3H), 1.88-1.55 (m, 7H), 1.24-1.07 (m, 5H), 0.07 (m, 1H) ppm. ¹³C NMR (CDCl₃, 75 MHz), mixture of amide rotamers: δ175.0 & 173.6, 159.7 (J_{CF}=233.7 Hz), 137.1 & 136.5, 123.4, 122.7, 122.2, 119.7 (J_{CF}=10.0 Hz) & 119.4 (J_{CF}=10.3 Hz), 115.6 & 114.6, 107.8 (J_{CF}=20.4 Hz) & 107.5 (J_{CF}=20.4 Hz), 98.1 (J_{CF}=25.9 Hz) & 97.5 (J_{CF}=25.8 Hz), 68.7, 67.9, 66.6 & 66.2, 60.0 & 59.7, 56.9, 54.0 & 53.2, 46.0 & 44.1, 42.8 & 42.6, 34.9 & 34.7, 32.5 & 32.4, 31.9, 30.2, 23.8, 23.2 & 23.1, 19.4 & 19.2, 15.6 & 15.0 ppm. Mass spectrum, m/z [514.3] (M+H)+.

Examples 17-27, 97-98, and 100-107 were prepared using intermediate 34 and by the procedures described in Schemes XXXII through XXXVII by substituting for Boc-Tle-OH with other amino acid reagents including Boc-Chg-OH and by replacing cyclopentanone with other aldehydes including formaldehyde, acetaldehyde, benzaldehyde, acetone, cyclohexanone, N-Boc-piperidinone, N-Me-piperidinone, 5-methylthiazole-2-carboxaldehyde, pyridine-2-carboxaldehyde, pyridine-3-carboxaldehyde, pyridine-4-carboxaldehyde, and 1-methylimidazole-2-carboxaldehyde.

Example 17

N-{1-Cyclohexyl-2-[6-(6-fluoro-1H-indol-3-yl)-4-methyl-hexahydro-pyrrolo[3,2-b]pyrrol-1-yl]-2-oxo-ethyl}-2-methylamino-propionamide ¹H NMR (CDCl₃, 300 MHz), mixture of amide rotamers: δ8.82 (br s, 0.3H), 8.74 (br s, 0.7H), 7.56 (d, J=9.3 Hz, 0.7H), 7.51-7.47 (m, 0.3H), 7.42 (dd, J=5.7, 9.9 Hz, 0.7H), 7.22 (s, 0.3H), 7.06-7.04 (m, 1H), 6.84-6.77 (m, 2H), 4.86-4.82 (m, 0.7H), 4.79-4.75 (m, 0.3H), 4.66-4.60 (m, 0.7H), 4.36-4.31 (m, 0.3H), 4.12-4.04 (m, 1H), 3.75-3.66 (m, 1H), 3.46-3.21 (m, 2H), 3.15 (app t, J=5.1 Hz, 1H), 3.03-2.93 (m, 1H), 2.58 (br s, 3H), 2.48-2.35 (m, 4H), 2.23 (s, 3H), 2.05-1.98 (m, 2H), 1.95-1.67 (m, 7H), 1.25-0.99 (m, 8H) ppm. ¹³C NMR (CDCl₃, 75 MHz), mixture of amide rotamers: δ174.8 & 173.9, 169.8, 159.6 (J_{CF}=236.3 Hz) 136.5, 124.5 & 123.0, 122.0, 119.5 (J_{CF}=10.1 Hz) & 119.2, 116.1 & 114.1, 107.9 & 107.5 (J_{CF}=24.7 Hz), 98.3 (J_{CF}=25.6 Hz) & 97.5 (J_{CF}=25.9 Hz), 71.9 & 69.6, 68.3 & 67.6, 64.4 & 63.6, 60.1, 54.7 & 54.6, 45.9 & 45.3, 44.6 & 44.3, 41.3 & 41.0, 34.8, 30.0 & 29.9, 29.6, 28.3, 27.1 & 26.2, 26.0 & 25.9, 19.6 & 19.4 ppm. Mass spectrum, m/z [484.3] (M+H)+.

Example 18

N-{1-Cyclohexyl-2-[4-ethyl-6-(6-fluoro-1H-indol-3-yl)-hexahydro-pyrrolo[3,2-b]pyrrol-1-yl]-2-oxo-ethyl}-2-methylamino-propionamide ¹H NMR (CDCl₃, 300 MHz), mixture of amide rotamers: δ8.79 (br s, 0.3H), 8.69 (br s, 0.7H), 7.55 (d, J=9.6 Hz, 0.7H), 7.52-7.43 (m, 1.3H), 7.08 (d, J=1.8 Hz, 0.7H), 7.02 (dd, J=2.1, 9.6 Hz, 0.3H), 6.86-6.77 (m, 2H), 4.86-4.85 (m, 0.7H), 4.75-4.71 (m, 0.3H), 4.66-4.60 (m, 0.7H), 4.35-4.30 (m, 0.3H), 4.09-4.00 (m, 1H), 3.74-3.65 (m, 1H), 3.54-3.49 (m, 1H), 3.40-3.34 (m, 1H), 3.27 (app t, J=6.6 Hz, 1H), 3.03-2.96 (m, 1H), 2.93-2.80 (m, 1H), 2.48 (br s, 3H), 2.39-2.31 (m, 3H), 2.24 (s, 3H), 2.05-1.99 (m, 2H), 1.88-1.65 (m, 8H), 1.27-0.98 (m, 10H) ppm. ¹³C NMR (CDCl₃, 75 MHz), mixture of amide rotamers: δ174.8 & 173.9, 169.7, 159.6 (J_{CF}=236.5 Hz), 137.4 & 136.5, 124.2 & 123.1, 122.2 & 121.9, 119.5 (J_{CF}=10.0 Hz) & 119.3, 116.1 & 114.3, 107.9 & 107.4 (J_{CF}=24.7 Hz), 98.3 (J_{CF}=25.6 Hz) & 97.5 (J_{CF}=25.6 Hz), 70.3 & 67.9, 67.5 & 67.3, 60.9, 60.1, 54.6 & 54.5, 48.6 & 48.4, 45.8, 44.6 & 43.7, 41.4 & 41.1, 34.8, 30.4, 30.0 & 29.9, 28.8 & 28.3, 27.2 & 26.2, 26.0 & 25.9, 19.6 & 19.5, 13.6 ppm. Mass spectrum, m/z [498.3] (M+H)+.

Example 19

N-{1-Cyclohexyl-2-[6-(6-fluoro-1H-indol-3-yl)-4-isopropyl-hexahydro-pyrrolo[3,2-b]pyrrol-1-yl]-2-oxo-ethyl}-2-methylamino-propionamide ¹H NMR (CDCl₃, 300 MHz), mixture of amide rotamers: δ8.72 (br s, 0.3H), 8.58 (br s, 0.7H), 7.56 (d, J=9.3 Hz, 1H), 7.52-7.45 (m, 1H), 7.26 (s, 1H), 7.00 (dd, J=2.4, 9.9 Hz, 0.3H), 6.85-6.78 (m, 1.7H), 4.99-4.95 (m, 0.7H), 4.69-4.59 (m, 1H), 4.24-4.20 (m, 0.3H), 4.07-3.98 (m, 1H), 3.81-3.77 (m, 0.3H), 3.72-3.63 (m, 0.7H), 3.56-3.46 (m, 1H), 3.42-3.33 (m, 1H), 3.26-3.21 (m, 0.3H), 3.03-2.96 (m, 0.7H), 2.86-2.77 (m, 1H), 2.61-2.53 (m, 1H), 2.28 (s, 0.3H), 2.5 (br s, 2.7H), 2.05-1.99 (m, 1H), 1.72-1.60 (m, 7H), 1.26-1.05 (m, 12H) ppm. ¹³C NMR (CDCl₃, 75 MHz), mixture of amide rotamers: δ174.9 & 173.7, 169.6, 159.7 (J_{CF}=236.5 Hz), 137.1 & 136.4, 123.3 & 123.1, 122.6 & 122.0, 119.5 (J_{CF}=10.4 Hz) &

119.3, 116.0 & 114.6, 107.8 & 107.4 ($J_{CF}$=15.5 Hz), 98.1 ($J_{CF}$=25.9 Hz) & 97.4 ($J_{CF}$=25.9 Hz), 67.7 & 66.6, 66.3 & 64.0, 60.3 & 60.2, 56.7 & 55.8, 54.4 & 54.2, 51.6 & 51.5, 45.6 & 44.0, 43.1 & 42.6, 41.7 & 41.2, 34.9, 32.0, 30.1 & 29.8, 28.2 & 27.4, 26.1 & 25.9, 22.6, 19.7 & 19.6, 18.2 & 18.0 ppm. Mass spectrum, m/z [512.3] (M+H)+.

Example 20

N-{1-Cyclohexyl-2-[4-cyclohexyl-6-(6-fluoro-1H-indol-3-yl)-hexahydro-pyrrolo[3,2-b]pyrrol-1-yl]-2-oxo-ethyl}-2-methylamino-propionamide $^1$H NMR (CDCl$_3$, 300 MHz), mixture of amide rotamers: δ8.74 (br s, 0.3H), 8.44 (br s, 0.7H), 7.56-7.50 (m, 1.7H), 7.44-7.41 (m, 0.3H), 7.20 (s, 0.7H), 7.16 (s, 0.3H), 6.88-6.79 (m, 2H), 4.99-4.95 (m, 0.7H), 4.63-4.58 (m, 1H), 4.20-4.17 (m, 0.3H), 4.02-3.97 (m, 0.7H), 3.88-3.83 (m, 0.3H), 3.69-3.59 (m, 1.3H), 3.46-3.36 (m, 2H), 3.30-3.25 (m, 0.7H), 3.03-2.96 (m, 0.7H), 2.87-2.80 (m, 0.6H), 2.64-2.58 (m, 0.7H), 2.37 (br s, 3H), 2.28 (br s, 3H), 2.06-1.79 (m, 7H), 1.66 (br s, 5H), 1.35-0.92 (m, 12H) ppm. $^{13}$C NMR (CDCl$_3$, 75 MHz), mixture of amide rotamers: δ175.1 & 173.8, 169.9 & 169.8, 159.9 ($J_{CF}$=236.5) 137.4 & 136.6, 123.7 & 123.3, 122.9 & 122.2, 119.9 ($J_{CF}$=10.1 Hz) & 119.6 ($J_{CF}$=9.8 Hz), 116.3 & 114.8, 108.1 ($J_{CF}$=9.0 Hz) & 107.7 ($J_{CF}$=8.7 Hz), 98.4 ($J_{CF}$=25.6 Hz) & 97.7 ($J_{CF}$=25.9 Hz), 67.8 & 66.3, 64.0, 61.2, 60.4 & 60.2, 57.4 & 56.6, 54.7 & 54.5, 45.9, 44.2 & 43.0, 42.6 & 42.2, 41.4, 35.2 & 34.9, 33.3, 32.4, 30.2 & 29.9, 29.5 & 29.3, 28.5 & 27.6, 26.3, 26.2, 25.9, 25.6, 25.5, 19.8 ppm. Mass spectrum, m/z [552.4] (M+H)+.

Example 21

N-{1-Cyclohexyl-2-[6-(6-fluoro-1H-indol-3-yl)-4-piperidin-4-yl-hexahydro-pyrrolo[3,2-b]pyrrol-1-yl]-2-oxo-ethyl}-2-methylamino-propionamide $^1$H NMR (CDCl$_3$, 300 MHz), mixture of amide rotamers: δ9.10 (br s, 0.3H), 8.78 (br s, 0.7H), 7.64-7.61 (m, 0.7H), 7.55-7.51 (m, 1H), 7.49-7.44 (m, 0.3H), 7.16 (s, 1H), 7.03 (dd, J=2.1, 9.6 Hz, 0.3H), 6.90 (dd, J=2.1, 9.6 Hz, 0.7H), 6.86-6.77 (m, 1H), 4.95-4.90 (m, 0.7H), 4.68-4.64 (m, 0.3H), 4.61-4.56 (m, 0.7H), 4.20-4.16 (m, 0.3H), 4.07-3.85 (m, 6H), 3.66-3.56 (m, 2H), 3.43-3.23 (m, 4H), 3.05-2.98 (m, 1H), 2.86-2.56 (m, 4H), 2.29 (s, 3H), 2.03-1.79 (m, 6H), 1.70-1.62 (m, 6H), 1.30-0.86 (m, 5H) ppm. $^{13}$C NMR (CDCl$_3$, 75 MHz), mixture of amide rotamers: δ178.1, 174.9 & 173.8, 169.9 & 169.7, 159.8 ($J_{CF}$=236.5 Hz), 137.1 & 136.3, 123.4 & 123.2, 122.5 & 121.9, 119.6 ($J_{CF}$=10.3 Hz), 116.0 & 114.6, 107.7 ($J_{CF}$=24.2 Hz), 98.1 ($J_{CF}$=26.5 Hz) & 97.5 ($J_{CF}$=25.9 Hz), 67.5, 66.5, 65.7, 63.3, 60.1, 57.3 & 57.1, 56.6 & 56.0, 54.6 & 54.4, 45.9, 44.2, 43.6, 43.4, 42.6, 42.0 & 41.7, 41.1, 34.9 & 34.8, 31.4, 30.7, 29.9 & 29.7, 28.4, 27.7 & 27.5, 26.1 & 25.9, 23.7, 19.5 ppm. Mass spectrum, m/z [553.4] (M+H)+.

Example 22

N-{1-Cyclohexyl-2-[6-(6-fluoro-1H-indol-3-yl)-4-(1-methyl-piperidin-4-yl)-hexahydro-pyrrolo[3,2-b]pyrrol-1-yl]-2-oxo-ethyl}-2-methylamino-propionamide $^1$H NMR (CDCl$_3$, 300 MHz), mixture of amide rotamers: δ8.89 (br s, 0.3H), 8.67 (br s, 0.7H), 7.59-7.50 (m, 1.7H), 7.46-7.44 (m, 0.3H), 7.16 (s, 1H), 7.00 (dd, J=2.4, 10.2 Hz, 0.3H), 6.88-6.76 (m, 1.7H), 4.99-4.96 (m, 0.7H), 4.70-4.66 (m, 0.3H), 4.63-4.57 (m, 0.7H), 4.21-4.17 (m, 0.3H), 4.04-3.85 (m, 4H), 3.69-3.48 (m, 2H), 3.42-3.36 (m, 1.7H), 3.27-3.22 (m, 0.3H), 3.06-2.97 (m, 2.3H), 2.87-2.81 (m, 0.7H), 2.66-2.59 (m, 1H), 2.49-2.41 (m, 1H), 2.35 (s, 3H), 2.27 (s, 3H), 2.21-2.11 (m, 2H), 2.00 (s, 3H), 1.90-1.81 (m, 4H), 1.76-1.60 (m, 6H), 1.26-0.88 (m, 5H) ppm. $^{13}$C NMR (CDCl$_3$, 75 MHz), mixture of amide rotamers: δ175.9, 174.9 & 173.8, 169.8 & 169.7, 159.7 ($J_{CF}$=236.5 Hz), 137.2 & 136.4, 123.4 & 123.2, 122.5 & 121.9, 119.6 ($J_{CF}$=10.0 Hz) & 119.3, 116.0 & 114.7, 107.7 ($J_{CF}$=24.7 Hz), 98.2 ($J_{CF}$=25.3 Hz) & 97.4 ($J_{CF}$=25.9 Hz), 67.4, 66.3 & 66.0, 63.7, 60.2 & 60.0, 58.2 & 57.8, 57.2 & 56.3, 54.5, 54.3, 54.2, 54.0, 45.7, 45.1, 44.1, 42.8, 42.2 & 41.9, 41.2, 34.9 & 34.8, 31.9, 31.2 & 30.9, 29.9 & 29.7, 28.3, 28.2, 27.9 & 27.4, 26.1, 25.9, 22.3, 19.5 ppm. Mass spectrum, m/z [567.4] (M+H)+.

Example 23

N-{1-Cyclohexyl-2-[6-(6-fluoro-1H-indol-3-yl)-4-(5-methyl-thiazol-2-ylmethyl)-hexahydro-pyrrolo[3,2-b]pyrrol-1-yl]-2-oxo-ethyl}-2-methylamino-propionamide $^1$H NMR (CDCl$_3$, 300 MHz), mixture of amide rotamers: δ8.58 (br s, 1H), 7.59 (d, J=9.0 Hz, 1H), 7.52-7.47 (m, 1H), 7.08 (d, J=2.4 Hz, 0.7H), 7.01 (dd, J=2.1, 9.6 Hz, 0.3H), 6.87-6.77 (m, 3H), 4.81-4.74 (m, 1H), 4.66-4.61 (m, 0.7H), 4.42-4.38 (m, 0.3H), 4.23-4.16 (m, 1H), 4.11-4.05 (m, 1H), 3.99-3.95 (m, 1H), 3.90-3.38 (m, 0.3H), 3.81-3.72 (m, 0.7H), 3.64-3.37 (m, 3H), 3.04-2.94 (m, 1.3H), 2.69 (app t, J=9.0 Hz, 0.7H), 2.44-2.42 (m, 3H), 2.38 (s, 0.3H), 2.26 (s, 2.7H), 2.04-1.90 (m, 4H), 1.79-1.71 (m, 6H), 1.27-1.01 (m, 6H) ppm. $^{13}$C NMR (CDCl$_3$, 75 MHz), mixture of amide rotamers: δ174.9 & 174.2, 169.9 & 169.6, 159.7 ($J_{CF}$=236.8 Hz), 152.6 & 152.5, 136.5, 124.3 & 123.0, 121.9, 119.7 ($J_{CF}$=10.0 Hz) & 119.2 ($J_{CF}$=14.8 Hz), 116.2, 114.3 & 113.8, 107.8 ($J_{CF}$=24.7 Hz) & 107.6 ($J_{CF}$=24.4 Hz), 98.2 ($J_{CF}$=25.9 Hz) & 97.5 ($J_{CF}$=25.9 Hz), 69.8 & 68.1, 67.3 & 67.0, 61.3 & 60.8, 60.4 & 60.2, 54.6, 46.4, 44.8, 43.3, 41.2, 35.0, 30.0 & 29.9, 28.4, 26.0, 19.7 & 19.45, 17.1 ppm. Mass spectrum, m/z [581.4] (M+H)+.

Example 24

N-{1-Cyclohexyl-2-[6-(6-fluoro-1H-indol-3-yl)-4-pyridin-2-ylmethyl-hexahydro-pyrrolo[3,2-b]pyrrol-1-yl]-2-oxo-ethyl}-2-methylamino-propionamide $^1$H NMR (CDCl$_3$, 300 MHz), mixture of amide rotamers: δ8.58-8.53 (m, 2H), 7.71-7.64 (m, 1H), 7.59-7.50 (m, 1H), 7.48-7.41 (m, 1.6H), 7.25 (m, 0.4H), 7.22-7.15 (m, 1H), 7.08 (d, J=2.4 Hz, 0.6H), 7.02 (dd, J=2.4, 9.9 Hz, 0.4H), 6.87-6.75 (m, 2H), 4.86-4.83 (m, 0.6H), 4.77-4.73 (m, 0.4H), 4.66-4.61 (m, 0.6H), 4.33-4.39 (m, 0.4H), 4.17-4.02 (m, 2H), 3.84-3.69 (m, 2H), 3.57-3.53 (m, 1H), 3.45-3.36 (m, 1.6H), 3.28-3.22 (m, 0.4H), 3.03-2.92 (m, 1.6H), 2.75 (app t, J=9.9 Hz, 0.4H), 2.62-2.54 (m, 1H), 2.36 (s, 0.6H), 2.25 (s, 2.4H), 2.17 (s, 1.6H), 2.06 (s, 0.4H), 1.96-1.66 (m, 10H), 1.26-0.99 (m, 8H) ppm. $^{13}$C NMR (CDCl$_3$, 75 MHz), mixture of amide rotamers: δ174.9 & 174.2, 170.0 & 169.8, 159.7 ($J_{CF}$=236.5 Hz), 158.9, 149.2 & 149.1, 136.6 & 136.4, 123.1 & 122.9, 122.2 & 122.1, 121.9, 119.7 ($J_{CF}$=10.1 Hz) & 119.4, 116.3, 114.6, 107.9 & 107.5 ($J_{CF}$=24.5 Hz), 98.2 ($J_{CF}$=25.6 Hz) & 97.5 ($J_{CF}$=25.6 Hz), 70.2 & 67.8, 67.6 & 67.5, 61.5 & 60.9, 60.2 & 59.8, 54.6, 46.0 & 44.7, 43.5, 41.1, 34.9, 30.9 & 30.2, 30.0 & 29.8, 28.3 & 27.2, 26.1, 19.8 & 19.5 ppm. Mass spectrum, m/z [561.4] (M+H)+.

Example 25

N-{1-Cyclohexyl-2-[6-(6-fluoro-1H-indol-3-yl)-4-pyridin-3-ylmethyl-hexahydro-pyrrolo[3,2-b]pyrrol-1-yl]-2-oxo-ethyl}-2-methylamino-propionamide $^1$H NMR (CDCl$_3$, 300 MHz), mixture of amide rotamers: δ8.71 (br s, 1H), 8.59-8.49 (m, 2H), 7.68-7.47 (m, 2H), 7.42-7.38 (m, 0.7H), 7.29-7.21 (m, 1.3H), 7.03-6.99 (m, 1H), 6.84-6.74 (m, 2H), 4.89-4.85 (m, 0.7H), 4.80-4.76 (m, 0.3H), 4.66-4.60 (m, 0.7H), 4.41-4.36 (m, 0.3H), 4.13-4.02 (m, 2H), 3.78-3.69 (m, 1H), 3.61-3.52 (m, 0.3H), 3.48-3.41 (m, 1.7H), 3.36-3.24 (m, 2H), 3.03-2.90 (m, 1H), 2.62 (app t, J=8.7 Hz, 0.3H), 2.44 (app t, J=8.7 Hz, 0.7H), 2.36 (s, 0.3H), 2.24 (s, 2.7H), 2.14 (s, 3H), 2.05-1.99 (m, 1H), 1.94-1.62 (m, 5H), 1.26-0.99 (m, 9H) ppm. $^{13}$C NMR (CDCl$_3$, 75 MHz), mixture of amide rotamers: δ174.8 & 173.9, 170.0 & 169.8, 159.7 (J$_{CF}$=237.1 Hz), 150.1 & 149.9, 148.7 & 148.6, 136.6 & 136.4, 134.2 & 134.1, 123.4 & 122.9, 122.2 & 122.1, 121.9, 119.5 (J$_{CF}$=9.8 Hz) & 119.3, 116.2, 114.3, 107.9 & 107.6 (J$_{CF}$=24.4 Hz), 98.3 (J$_{CF}$=25.6 Hz) & 97.6 (J$_{CF}$=25.9 Hz), 70.2 & 67.7, 67.5 & 67.3, 61.2 & 60.7, 60.3 & 60.2, 55.6 & 55.4, 54.7, 45.9, 44.8, 43.6, 41.1, 34.9, 30.1 & 30.0, 29.8, 28.4 & 28.3, 27.2 & 26.2, 26.0 & 25.9, 19.6 & 19.5 ppm. Mass spectrum, m/z [561.4] (M+H)+.

Example 26

N-{1-Cyclohexyl-2-[6-(6-fluoro-1H-indol-3-yl)-4-pyridin-4-ylmethyl-hexahydro-pyrrolo[3,2-b]pyrrol-1-yl]-2-oxo-ethyl}-2-methylamino-propionamide $^1$H NMR (CDCl$_3$, 300 MHz), mixture of amide rotamers: δ8.65 (br s, 0.7H), 8.57-8.53 (m, 2.3H), 7.60-7.57 (m, 1H), 7.53-7.48 (m, 0.3H), 7.45-7.40 (m, 0.7H), 7.29-7.25 (m, 2H), 7.05-7.00 (m, 1H) 6.89-6.75 (m, 2H), 4.89-4.85 (m, 0.7H), 4.80-4.76 (m, 0.3H), 4.66-4.61 (m, 0.7H), 4.51-4.41 (m, 0.3H), 4.14-4.02 (m, 2H), 3.79-3.70 (m, 1H), 3.65-3.59 (m, 0.3H), 3.48-3.41 (m, 1.7H), 3.40-3.28 (m, 2H), 3.03-2.90 (m, 1H), 2.61 (app t, J=9.3 Hz, 0.3H), 2.45 (app t, J=9.3 Hz, 0.7H), 2.25 (s, 2H), 2.17 (s, 1H), 2.05-1.98 (m, 1H), 1.91-1.70 (m, 8H), 1.27-0.99 (m, 6H) ppm. $^{13}$C NMR (CDCl$_3$, 75 MHz), mixture of amide rotamers: δ174.9 & 174.3, 170.1 & 169.8, 159.7 (J$_{CF}$=236.8 Hz), 149.8, 148.1 & 148.0, 137.1 & 136.6, 137.2 & 136.6, 123.6 & 123.5, 122.9 & 121.9, 119.5 (J$_{CF}$=10.1 Hz), 116.1, 114.4, 107.9 & 107.6 (J$_{CF}$=24.4 Hz), 98.3 (J$_{CF}$=25.9 Hz) & 97.6 (J$_{CF}$=25.9 Hz), 70.4 & 67.7, 67.6 & 67.3, 61.2 & 60.9, 60.4 & 60.2, 57.2 & 57.0, 54.6, 45.9, 44.9, 43.7, 41.1, 35.1 & 35.0, 30.9 & 29.9, 28.4 & 28.1, 26.2 & 25.9, 19.8 & 19.5 ppm. Mass spectrum, m/z [561.4] (M+H)+.

Example 27

N-{1-Cyclohexyl-2-[6-(6-fluoro-1H-indol-3-yl)-4-(1-methyl-1H-imidazol-2-ylmethyl)-hexahydro-pyrrolo[3,2-b]pyrrol-1-yl]-2-oxo-ethyl}-2-methylamino-propionamide $^1$H NMR (CDCl$_3$, 300 MHz), mixture of amide rotamers: δ8.71 (br s, 1H), 7.59 (d, J=9.0 Hz, 0.6H), 7.54-7.46 (m, 1.4H), 7.43-7.40 (m, 1H), 7.20 (s, 0.4H), 7.06 (d, J=2.4 Hz, 0.6H), 7.02 (dd, J=2.1, 9.6 Hz, 0.4H), 6.90-6.76 (m, 3.6H), 4.90-4.86 (m, 0.6H), 4.82-4.79 (m, 0.4H), 4.63-4.58 (m, 0.6H), 4.38-4.34 (m, 0.4H), 4.11-4.04 (m, 1H), 3.91-3.85 (m, 1H), 3.71-3.67 (m, 3H), 3.65-3.36 (m, 5H), 3.16-3.10 (m, 0.4H), 3.03-2.90 (m, 0.6H), 2.62 (app t, J=10.2 Hz, 0.4H), 2.48-2.36 (m, 4.6H), 2.25 (s, 2H), 2.18 (s, 1H), 2.06 (br s, 0.6H), 1.88-1.56 (m, 6.4H), 1.26-0.97 (m, 8H) ppm. $^{13}$C NMR (CDCl$_3$, 75 MHz), mixture of amide rotamers: δ174.9 & 174.2, 170.0 & 169.8, 159.7 (J$_{CF}$=236.8 Hz), 137.3 & 136.5, 128.8, 124.5, 122, 121.9, 119.6 (J$_{CF}$=10.0 Hz) & 119.2 (J$_{CF}$=10.4 Hz), 116.0, 114.1, 107.8 (J$_{CF}$=24.7 Hz) & 107.6 (J$_{CF}$=24.4 Hz), 98.3 (J$_{CF}$=25.6 Hz) & 97.6 (J$_{CF}$=25.6 Hz), 70.4 & 67.7, 61.5 & 61.2, 60.3 & 60.2, 54.6, 47.4, 45.9, 44.7, 43.4, 41.1, 34.9, 31.6 & 30.9, 30.0, 28.4 & 28.3, 27.1, 26.0, 19.7 & 19.5 ppm. Mass spectrum, m/z [564.4] (M+H)+.

Example 28

N-{1-[6-(6-Fluoro-1H-indol-3-yl)-hexahydro-pyrrolo[3,2-b]pyrrole-1-carbonyl]-2-hydroxy-propyl}-2-methylamino-propionamide (47)

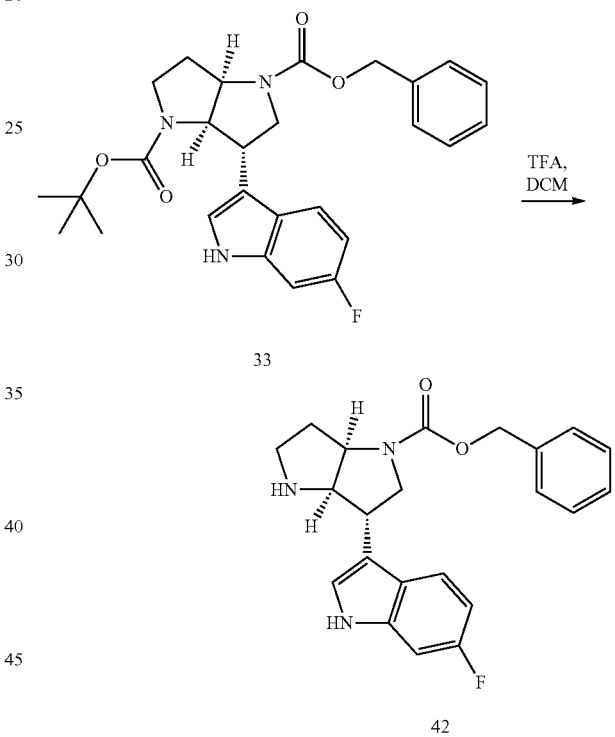

3-(6-Fluoro-1H-indol-3-yl)-hexahydro-pyrrolo[3,2-b]pyrrole-1-carboxylic acid benzyl ester (42)

To a solution containing 33 (312 mg, 0.65 mmol) in DCM (10 mL) was added TFA (3 mL) at ambient temperature. After 1 h, the reaction mixture was concentrated in vacuo. The residue was dissolved in EtOAc and the organic solution was washed successively with saturated aqueous NaHCO$_3$ and brine, dried over anhydrous Na$_2$SO$_4$, filtered, and concentrated to afford 252 mg of 42 as a light brown-colored foam which was used without further purification. $^1$H NMR (CDCl$_3$, 300 MHz) δ8.69 & 8.63 (2 br s, 1H), 7.47 (dd, J=5.1, 8.4 Hz, 1H), 7.36-7.26 (m, 5H), 6.99 (dd, J=1.5, 9.6 Hz, 1H), 6.89-6.74 (m, 2H), 5.19-5.13 (m, 2H), 4.39-4.35 (m, 1H), 3.94-3.76 (m, 3H), 3.45 (m, 1H), 3.08-3.02 (m, 2H), 2.01-2.00 (m, 2H), 2.42 (br s, 1H) ppm. Mass spectrum, m/z [380.1] (M+H)+.

Scheme XXXIX

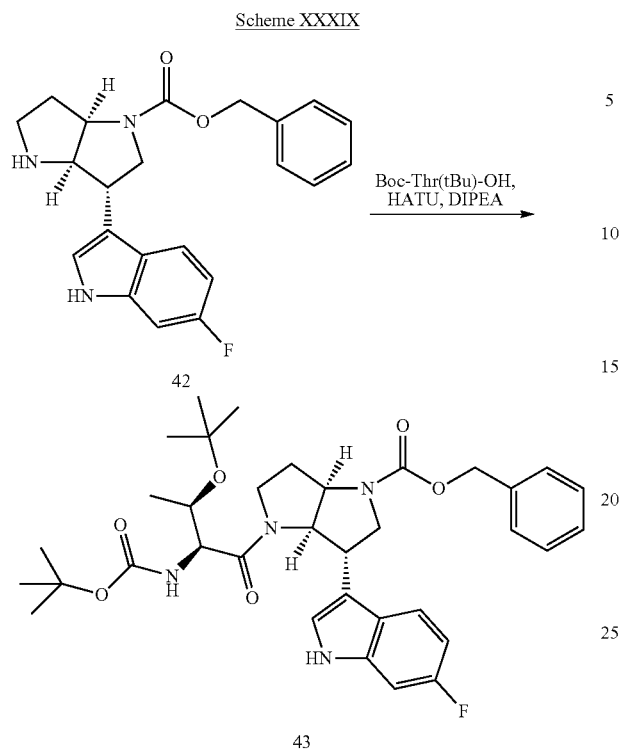

Scheme XL

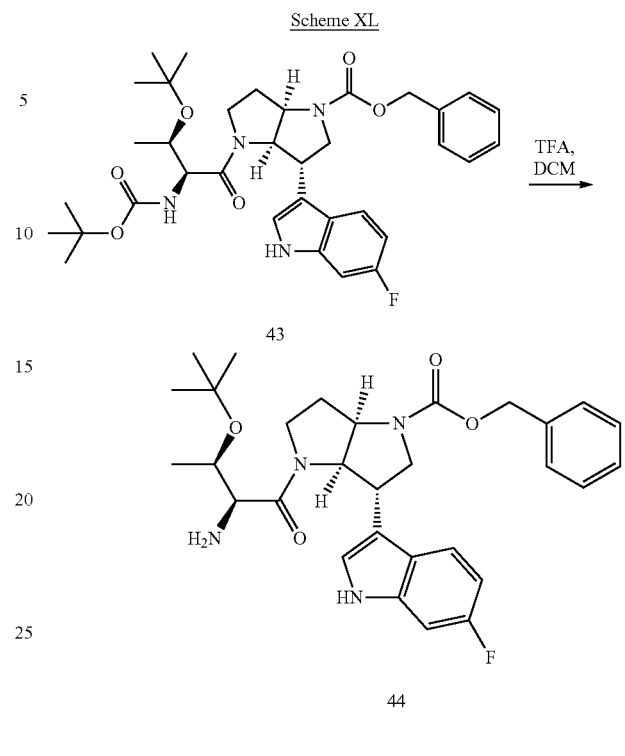

4-(3-tert-Butoxy-2-tert-butoxycarbonylamino-butyryl)-3-(6-fluoro-1H-indol-3-yl)-hexahydro-pyrrolo[3,2-b]pyrrole-1-carboxylic acid benzyl ester (43)

To a solution containing Boc-Thr(tBu)-OH (138 mg, 0.5 mmol) in anhydrous NMP (4 mL) was cooled to 0° C. HATU (190 mg, 0.5 mmol) and DIPEA (111 mg, 0.8 mmol) were added followed by the addition of crude 42 (195 mg, 0.5 mmol) in anhydrous NMP (5 mL). The reaction mixture was slowly warmed to ambient temperature. After 4 h, the reaction mixture was diluted with EtOAc and washed successively with 1M HCl, aqueous NaHCO₃, and brine, dried over anhydrous Na₂SO₄, filtered, and concentrated to afford 336 mg of crude 43 as an amber-colored foam which was used without further purification. Mass spectrum, m/z [637.3] (M+H)+.

4-(2-Amino-3-tert-butoxy-butyryl)-3-(6-fluoro-1H-indol-3-yl)-hexahydro-pyrrolo[3,2-b]pyrrole-1-carboxylic acid benzyl ester (44)

A solution containing crude 43 (340 mg, 0.53 mmol) in DCM (10 mL) was cooled to 0° C. TFA (3 mL) was added. After 2 h, the reaction mixture was quenched by the slow addition of cold, aqueous K₂CO₃. The reaction mixture was extracted with DCM and the resultant organic phase was washed successively with saturated aqueous NaHCO₃ and brine, dried over anhydrous Na₂SO₄, filtered, and concentrated to afford 283 mg of 44 as an amber-colored foam which was used without further purification. Mass spectrum, m/z [537.3] (M+H)+.

Scheme XLI

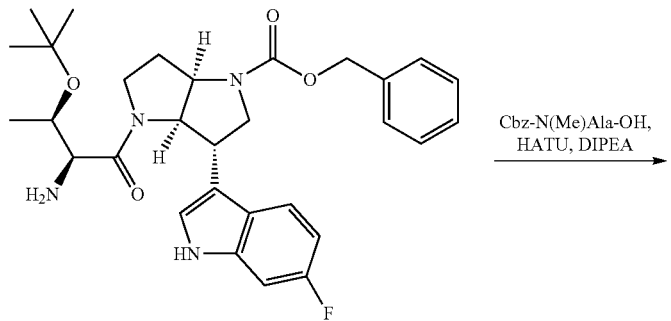

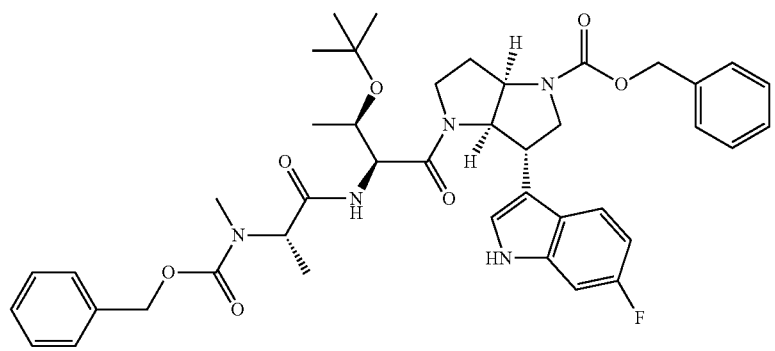

45

4-{2-[2-(Benzyloxycarbonyl-methyl-amino)-propionylamino]-3-tert-butoxy-butyryl}-3-(6-fluoro-1H-indol-3-yl)-hexahydro-pyrrolo[3,2-b]pyrrole-1-carboxylic acid benzyl ester (45)

To a solution containing Cbz-N(Me)Ala-OH (119 mg, 0.5 mmol) in anhydrous NMP (4 mL) was cooled to 0° C. HATU (189 mg, 0.5 mmol) and DIPEA (111 mg, 0.8 mmol) were added followed by the addition of crude 44 (280 mg, 0.5 mmol) in anhydrous NMP (4 mL). The reaction mixture was slowly warmed to ambient temperature. After 2 h, the reaction mixture was diluted with EtOAc and washed successively with 1M HCl, aqueous NaHCO₃, and brine, dried over anhydrous Na₂SO₄, filtered, and concentrated to afford 330 mg of crude 45 as an amber-colored oil which was used without further purification. Mass spectrum, m/z [756.4] (M+H)+.

Scheme XLII

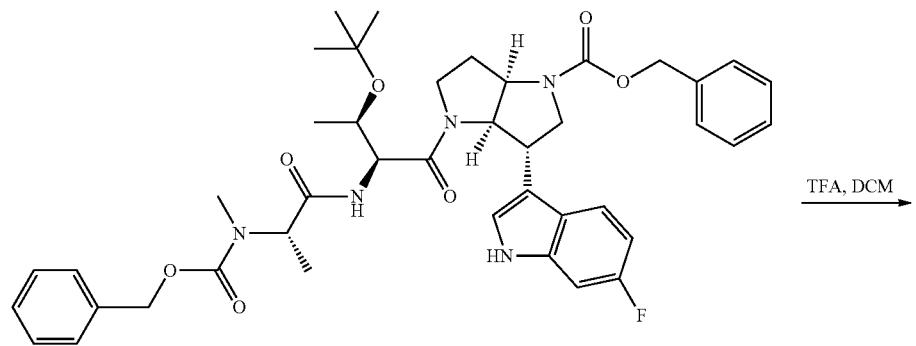

45

TFA, DCM

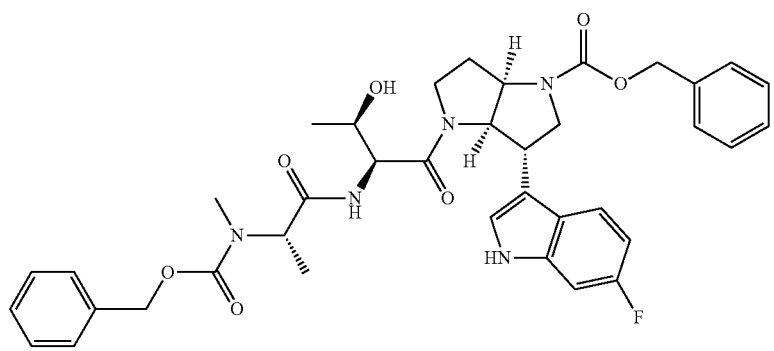

46

4-{2-[2-(Benzyloxycarbonyl-methyl-amino)-propionylamino]-3-hydroxy-butyryl}-3-(6-fluoro-1H-indol-3-yl)-hexahydro-pyrrolo[3,2-b]pyrrole-1-carboxylic acid benzyl ester (46)

A solution containing crude 45 (330 mg, 0.44 mmol) in DCM (10 mL) was treated with TFA (3 mL) at ambient temperature. After 2 h, the reaction mixture was concentrated in vacuo. The residue was dissolved in EtOAc and the resultant organic solution was washed successively with saturated aqueous NaHCO$_3$ and brine, dried over anhydrous Na$_2$SO$_4$, filtered, and concentrated to afford 300 mg of 46 as a pale brown-colored foam which was used without further purification. $^1$H NMR (CDCl$_3$, 300 MHz) mixture of rotamers: δ8.38 (s, 0.5H), 8.34 (s, 0.5H), 8.12 (dd, J=5.1, 8.7 Hz, 0.5H), 8.03 (dd, J=5.4, 8.4 Hz, 0.5H), 7.35-7.26 (m, 5H), 7.05-6.87 (m, 2H), 6.77 (s, 0.5H), 6.62 (s, 0.5H), 5.29-5.12 (m, 3H), 4.76-4.52 (m, 1.5H), 4.34-4.30 (m, 1H), 4.22-4.19 (m, 0.5H), 3.89 (app t, J=5.4 Hz, 1H), 3.57-3.42 (m, 2H), 2.82 (s, 3H), 2.45-2.39 (m, 0.5H), 2.27-2.21 (m, 0.5H), 1.90 (br s, 1H), 1.38 (d, J=7.5 Hz, 3H), 1.16 (d, J=6.3 Hz, 3H) ppm. Mass spectrum, m/z [700.3] (M+H)+.

89 mg (40%, 5 steps) of 47.2HOAc as a white solid. $^1$H NMR (300 MHz, CDCl$_3$/d$_4$-MeOH), mixture of rotamers: δ10.38 (br s, 1H), 8.35 (br s, 1H), 7.90 (dd, J=5.1, 8.7 Hz, 0.8H), 7.51 (dd, J=5.1, 8.7 Hz, 0.2H), 7.42 (s, 0.2H), 7.28 (s, 0.8H), 7.06 (dd, J=1.8, 9.6 Hz, 1H), 6.87-6.80 (m, 1H), 4.82 (d, J=5.4 Hz, 1H), 4.69 (d, J=4.8 Hz, 1H), 4.32-4.28 (m, 1H), 4.21-4.13 (m, 1H), 4.10-4.08 (m, 1H), 3.90-3.82 (m, 1H), 3.75 (app q, J=7.2 Hz, 1H), 3.63-3.50 (m, 2H), 3.37-3.35 (m, 0.2H), 3.56 (s, 3H), 2.49-2.42 (m, 1H), 2.23-2.14 (m, 1H), 2.03 (s, 3H), 1.48 (d, J=6.6 Hz, 2.4H), 1.38 (d, J=6.9 Hz, 0.6H), 1.26 (d, J=6.0 Hz, 2.4H), 0.83 (d, J=6.6 Hz, 0.4H) ppm. Mass spectrum, m/z [432.2] (M+H)+.

Examples 29-35, 87-88, 91-93, and 99 were prepared following the procedures described in Schemes XXXVIII through XLIII by substituting for Boc-Tle-OH with other amino acid reagents including Boc-Abu-OH, Boc-Val-OH, Boc-Chg-OH, Cbz-Ser(tBu)-OH, Boc-Ser-OH Boc-Ser(Me)-OH, Cbz-Thr(tBu)-OH, Boc-Thr(tBu)-OH, Boc-Thr-OH, or Boc-Thr(Me)-OH and Boc-N(Me)Ala-OH or by substituting for Cbz-N(Me)Ala-OH with Boc-Ala-OH or Cbz-Ala-OH.

Scheme XLIII

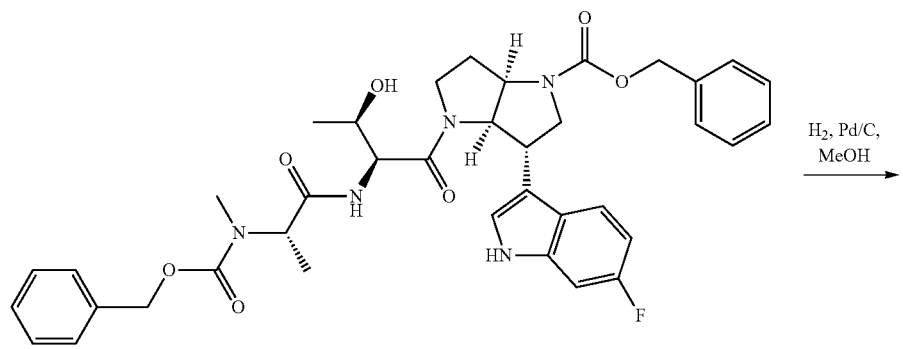

46

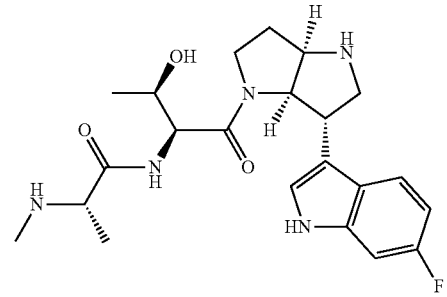

47

N-{1-[6-(6-Fluoro-1H-indol-3-yl)-hexahydro-pyrrolo[3,2-b]pyrrole-1-carbonyl]-2-hydroxy-propyl}-2-methylamino-propionamide (47)

A 500 mL Parr bottle was charged with crude 46 (300 mg, 0.46 mmol) and 10% Pd-on-carbon (50 mg) in reagent grade MeOH (30 mL). The mixture was pressurized to 50 PSI H$_2$ (344.7 KPa) then shaken for 2 h. The catalyst was removed by filtration through diatomaceous earth (Celite®) and the solids were washed with MeOH. The filtrate was concentrated in vacuo and the crude product was purified by RP-HPLC (Phenomenex Luna C18, 100×21.2 mm, 5-10% ACN/water containing 0.1% HOAc over 10 min; Flow: 20 mL/min) to afford

Example 29

N-{1-[6-(6-Fluoro-1H-indol-3-yl)-hexahydro-pyrrolo[3,2-b]pyrrole-1-carbonyl]-propyl}-2-methylamino-propionamide $^1$H NMR (300 MHz, CDCl$_3$/d$_4$-MeOH), mixture of rotamers: δ10.0 (s, 1H), 8.15 (br s, 1H), 7.91 (dd, J=5.7, 8.7 Hz, 0.8H), 7.53 (dd, J=5.4, 8.7 Hz, 0.2H), 7.39 (s, 0.2H), 7.15 (s, 0.8H), 7.10-7.03 (m, 1H), 6.89-6.83 (m, 1H), 4.80 (app d, J=6.0 Hz, 1H), 4.67 (app t, J=7.2 Hz, 0.8H), 4.45 (app t, J=7.2 Hz, 0.2H), 3.96 (app d, J=5.4 Hz, 1H), 3.73-3.64 (m, 1H), 3.52-3.31 (m, 4H), 2.46 (s, 3H), 2.36-2.29 (m, 1H), 2.16-2.12

(m, 1H), 2.00 (s, 3H), 1.95-1.86 (m, 1H), 1.80-1.71 (m, 1H), 1.37 (d, J=6.9 Hz, 3H), 1.01 (t, J=7.2 Hz, 3H) ppm. $^{13}$C NMR (75 MHz, CDCl$_3$/d$_4$-MeOH), mixture of amide rotamers: δ177.1, 171.8 & 171.0, 161.6 (J$_{CF}$=236.8 Hz), 136.9 & 136.7, 123.0, 121.4 & 121.3, 121.0 (J$_{CF}$=10.0 Hz), 113.2, 107.7 (J$_{CF}$=24.4 Hz), 97.4 (J$_{CF}$=25.9 Hz), 68.6 & 67.9, 60.8, 58.0 & 57.7, 52.8, 50.7, 46.6, 42.1, 32.4 & 32.0, 30.4 & 29.1, 25.1 & 24.6, 22.2, 17.2 & 16.7, 9.9 & 9.7 ppm. Mass spectrum, m/z [416.2] (M+H)+.

Example 30

N-{1-[6-(6-Fluoro-1H-indol-3-yl)-hexahydro-pyrrolo[3,2-b]pyrrole-1-carbonyl]-2-methyl-propyl}-2-methylamino-propionamide $^1$H NMR (300 MHz, CDCl$_3$/d$_4$-MeOH), mixture of amide rotamers: δ9.28 (s, 1H), 7.90 (dd, J=5.1, 8.7 Hz, 0.8H), 7.85 (d, J=8.4 Hz, 1H), 7.32 (s, 0.8H), 7.20 (s, 0.2H), 7.07-7.01 (m, 1H), 6.92-6.85 (m, 1H), 4.73 (d, J=5.7 Hz, 0.8H), 4.66 (dd, J=4.2, 6.6 Hz, 0.2H), 4.49 (d, J=4.5 Hz, 0.2H), 4.35-4.33 (m, 0.2H), 4.19-4.06 (m, 2H), 3.86 (d, J=5.1 Hz, 1H), 3.68-3.59 (m, 1H), 3.40-3.35 (m, 1H), 3.27-3.14 (m, 2H), 2.38 (s, 3H), 2.19-2.04 (m, 2H), 2.02 (s, 3H), 1.32 (d, J=6.6 Hz, 2.4H), 1.27 (d, J=6.9 Hz, 0.6H), 1.02 (d, J=6.6 Hz, 2.4H), 0.97 (d, J=6.3 Hz, 2.4H), 0.72 (d, J=6.6 Hz, 0.6H), 0.47 (d, J=6.6 Hz, 0.6H) ppm. Mass spectrum, m/z [430.3] (M+H)+.

Example 31

N-{1-[6-(6-Fluoro-1H-indol-3-yl)-hexahydro-pyrrolo[3,2-b]pyrrole-1-carbonyl]-2,2-dimethyl-propyl}-2-methylamino-propionamide $^1$H NMR (300 MHz, CDCl$_3$/d$_4$-MeOH), mixture of amide rotamers: δ9.96 (s, 1H), 8.24 (d, J=7.5 Hz, 1H), 8.01 (dd, J=5.7, 9.0 Hz, 0.8H), 7.55 (dd, J=5.7, 9.0 Hz, 0.2H), 7.42 (s, 0.8H), 7.36 (s, 0.2H), 7.12 (dd, J=2.4, 9.9 Hz, 0.2H), 7.05 (dd, J=2.5, 9.9 Hz, 0.8H), 6.91-6.84 (m, 1H), 4.86 (d, J=5.7 Hz, 1H), 4.60 (s, 1H), 4.36 (app t, J=5.1 Hz, 1H), 4.29-4.23 (m, 1H), 4.11 (m, 1H), 3.89-3.82 (m, 1H), 3.55-3.49 (m, 2H), 3.39-3.37 (m, 1H), 2.57 (s, 3H), 2.22-2.17 (m, 1H), 1.49 (d, J=6.9 Hz, 2.4H), 1.40 (d, J=6.9 Hz, 0.6H), 1.10 (s, 8.3H), 0.83 (s, 0.7H) ppm. $^{13}$C NMR (75 MHz, CDCl$_3$/d$_4$-MeOH), mixture of amide rotamers: δ172.2, 170.4, 160.2 (J$_{CF}$=237.1 Hz), 136.8 & 136.8, 123.1, 122.0 & 121.8, 120.3 (J$_{CF}$=9.8 Hz), 112.9, 108.1 (J$_{CF}$=24.8 Hz), 97.6 (J$_{CF}$=25.9 Hz), 68.8, 61.2, 58.5, 58.2, 58.1, 41.9, 35.6, 32.9, 30.0, 26.6, 22.7, 17.7 ppm. Mass spectrum, m/z [444.2] (M+H)+.

Example 32

N-{1-Cyclohexyl-2-[6-(6-fluoro-1H-indol-3-yl)-hexahydro-pyrrolo[3,2-b]pyrrol-1-yl]-2-oxo-ethyl}-2-methylamino-propionamide $^1$H NMR (300 MHz, CDCl$_3$), mixture of amide rotamers: δ8.85 (br s, 1H), 7.88 (app dd, J=9.0, 5.7 Hz, 1H), 7.80 (d, J=9.0 Hz, 1H), 7.08 (s, 1H), 6.99 (dd, J=9.6, 2.1 Hz, 1H), 6.87 (dd, J=9.0, 2.1 Hz, 1H), 4.85 (br s, 4H), 4.67 (d, J=5.4 Hz, 1H), 4.58 (app t, J=8.4 Hz, 1H), 4.14 (app t, J=9.6 Hz, 1H), 4.03 (app t, J=5.1 Hz, 1H), 3.83 (m, 1H), 3.64 (m, 1H), 3.37-3.22 (m, 2H), 3.15 (dd, J=13.8, 7.2 Hz, 1H), 2.35 (s, 3H), 2.01 (br s, 6H, HOAc), 1.75 (m, 6H), 1.31 (d, J=6.6 Hz, 3H), 1.28-1.04 (m, 4H) ppm. $^{13}$C NMR (75 MHz, CDCl$_3$), mixture of amide rotamers: δ174.7, 171.0, 160.3 (d, J$_{CF}$=236.4 Hz), 136.7 (d, J$_{CF}$=12.3 Hz), 123.4, 121.1 (d, J$_{CF}$=3.4 Hz), 120.7 (d, J$_{CF}$=10.0 Hz), 115.6, 108.5 (d, J$_{CF}$=24.3 Hz), 97.6 (d, J$_{CF}$=26.1 Hz), 68.8, 60.8, 59.9, 55.5, 51.9, 47.2, 43.0, 41.0, 34.6, 32.2, 29.9, 28.9, 26.3, 26.1, 19.3 ppm. Mass spectrum, m/z [470.0] (M+H)+.

Example 33

N-{2-[6-(6-Fluoro-1H-indol-3-yl)-hexahydro-pyrrolo[3,2-b]pyrrol-1-yl]-1-hydroxymethyl-2-oxo-ethyl}-2-methylamino-propionamide $^1$H NMR (300 MHz, CDCl$_3$/d$_4$-MeOH), mixture of amide rotamers: δ9.94 (s, 1H), 8.20 (m, 1H), 7.91 (dd, J=5.1, 8.7 Hz, 0.8H), 7.48 (dd, J=5.1, 8.7 Hz, 0.2H), 7.41 (s, 0.2H), 7.37 (s, 0.8H), 7.16-7.03 (m, 1H), 6.89-6.83 (m, 1H), 4.83 (app t, J=5.7 Hz, 0.8H), 4.76 (d, J=5.1 Hz, 0.8H), 4.51 (t, J=6.3 Hz, 0.2H), 4.38 (m, 0.2H), 4.18 (app t, J=5.1 Hz, 0.2H), 3.83 (t, J=5.4 Hz, 0.8H), 3.78-3.69 (m, 2H), 3.59-3.34 (m, 2H), 2.46 (s, 2.4H), 2.36 (s, 0.6H), 2.32-2.03 (m, 1H), 2.01 (s, 3H), 1.36 (d, J=6.9 Hz, 2.4H), 1.26 (d, J=6.6 Hz, 0.6H) ppm. Mass spectrum, m/z [418.1] (M+H)+.

Example 34

N-{2-[6-(6-Fluoro-1H-indol-3-yl)-hexahydro-pyrrolo[3,2-b]pyrrol-1-yl]-1-methoxymethyl-2-oxo-ethyl}-2-methylamino-propionamide $^1$H NMR (300 MHz, CDCl$_3$/d$_4$-MeOH), mixture of amide rotamers: δ9.75 (s, 1H), 8.18 (m, 1H), 7.92 (dd, J=5.4 Hz, 8.7 Hz, 0.8H), 7.46 (dd, J=3.6, 9.0 Hz, 0.2H), 7.33 (s, 0.2H), 7.24 (s, 0.8H), 7.14-7.00 (m, 1H), 6.90-6.81 (m, 1H), 4.93 (t, J=6.3 Hz, 1H), 4.74 (d, J=5.4 Hz, 0.8H), 4.54 (t, J=7.5 Hz, 0.2H), 4.44 (t, J=6.3 Hz, 0.2H), 4.19 (t, J=5.4 Hz, 0.8H), 3.82-3.52 (m, 4H), 3.43 (s, 2.4H), 3.04 (s, 0.6H), 2.43 (s, 3H), 2.40-2.33 (m, 2H), 2.11-2.05 (m, 2H), 2.02 (s, 3H), 1.37 (d, J=6.9 Hz, 2.4H), 1.29 (d, J=6.9 Hz, 0.6H) ppm. $^{13}$C NMR (75 MHz, CDCl$_3$/d$_4$-MeOH), mixture of amide rotamers: δ176.9, 173.0, 169.2, 160.2 (J$_{CF}$=237.4 Hz), 136.7, 136.6, 123.1 & 122.3, 121.4, 120.3 (J$_{CF}$=10.0 Hz), 113.4, 108.2 (J$_{CF}$=24.4 Hz), 97.5 (J$_{CF}$=25.9 Hz), 72.4 & 72.2, 68.9 & 67.8, 63.3, 60.8, 59.3, 58.8 & 58.6, 58.1, 46.9, 44.9 & 44.7, 41.5, 33.2 & 32.7, 30.3 & 29.6, 22.4, 17.9 & 17.4 ppm. Mass spectrum, m/z [432.2] (M+H)+.

Example 35

N-{1-[6-(6-Fluoro-1H-indol-3-yl)-hexahydro-pyrrolo[3,2-b]pyrrole-1-carbonyl]-2-methoxy-propyl}-2-methylamino-propionamide $^1$H NMR (CDCl$_3$, 300 MHz), mixture of amide rotamers: δ8.80 (br s, 1H) 7.95-7.86 (m, 1.6H), 7.79-7.70 (m, 0.4H), 7.55-7.43 (m, 6H), 7.13 (s, 0.6H), 7.01 (s, 0.4H), 6.98-6.80 (m, 3H), 4.89-4.74 (m, 2.6H), 4.52-4.44 (m, 0.4H), 4.10-3.43 (m, 10H), 3.39 (s, 3H), 3.36-3.18 (m, 6H), 3.01 (s, 0.4H), 2.90-2.89 (m, 0.6H), 2.44-2.39 (m, 3H), 2.04 (br s, 8H), 2.3-2.25 (m, 3H), 1.34-1.19 (m, 8H), 0.75-0.73 (m, 0.4H), 0.64-0.62 (m, 0.6H) ppm. $^{13}$C NMR (CDCl$_3$, 75 MHz), mixture of amide rotamers: δ176.4, 174.5, 168.9 & 168.8, 160.4 (J$_{CF}$=237.7 Hz), 136.7, 123.4, 122.3, 121.3, 120.8 (J$_{CF}$=10.1 Hz) 114.9 & 114.6, 108.5 (J$_{CF}$=24.5 Hz), 97.6 (J$_{CF}$=25.9 Hz), 71.5, 68.9 & 68.1, 60.6, 59.7, 54.8 & 57.2, 55.5, 54.8 & 54.5, 51.2, 47.4, 42.5, 34.4, 31.6, 22.1, 19.2 & 19.0, 15.5 ppm. Mass spectrum, m/z [446.3] (M+H)+.

Example 36

4-[2-Cyclohexyl-2-(2-methylamino-propionylamino)-acetyl]-3-(6-fluoro-1H-indol-3-yl)-hexahydro-pyrrolo[3,2-b]pyrrole-1-carboxylic acid methyl ester (53)

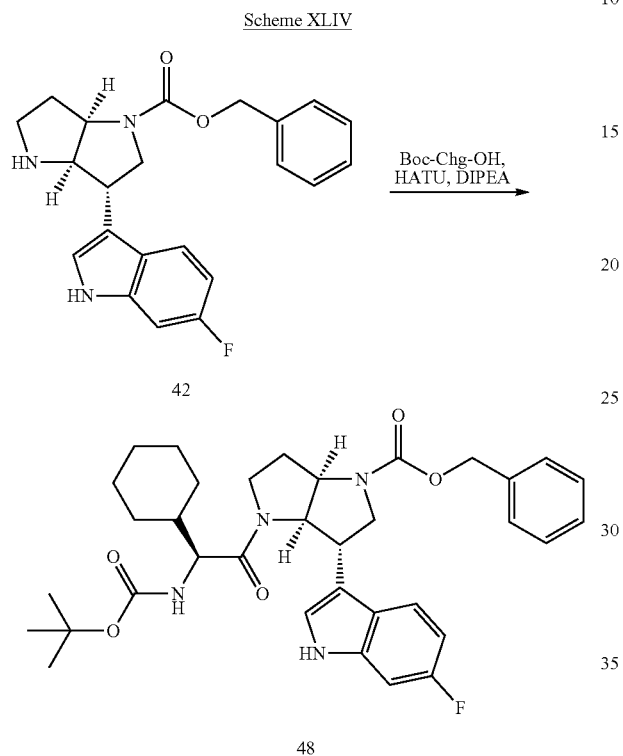

4-(2-tert-Butoxycarbonylamino-2-cyclohexyl-acetyl)-3-(6-fluoro-1H-indol-3-yl)-hexahydro-pyrrolo[3,2-b]pyrrole-1-carboxylic acid benzyl ester (48)

To a solution containing Boc-Chg-OH (600 mg, 2.3 mmol) in anhydrous NMP (6 mL) was cooled to 0° C. HATU (865 mg, 2.3 mmol) and DIPEA (0.67 g, 5.2 mmol) were added followed by the addition of crude 42 (900 mg, 2.4 mmol) in anhydrous NMP (6 mL). The reaction mixture was slowly warmed to ambient temperature. After 16 h, the reaction mixture was diluted with EtOAc and washed successively with 1M HCl, aqueous NaHCO₃, and brine, dried over anhydrous Na₂SO₄, filtered, and concentrated to afford 1.5 g of crude 48 as a light brown-colored foam which was used without further purification. ¹H NMR (300 MHz, CDCl₃), mixture of rotamers: δ8.38 (s, 0.5H), 8.31 (s, 0.5H), 8.19 (dd, J=5.4, 8.7 Hz, 0.5H), 8.12 (dd, J=5.4, 8.7 Hz, 0.5H), 7.44-7.35 (m, 5H), 7.00-6.88 (m, 2H), 6.78 (s, 0.5H), 6.61 (s, 0.5H), 5.38-5.28 (m, 1H), 5.22-5.12 (m, 2H), 4.65 (d, J=4.8 Hz, 0.5H), 4.58 (d, J=5.1 Hz, 0.5H), 4.39-4.31 (m, 2H), 4.23 (d, J=11.7 Hz, 0.5H), 4.16-4.02 (m, 2H), 3.92 (d, J=5.4 Hz, 1H), 3.54-3.43 (m, 2H), 2.47-2.37 (m, 0.5H), 2.29-2.23 (m, 0.5H), 1.93-1.70 (m, 7H), 1.43 (s, 9H), 1.19-1.12 (m, 2H) ppm. Mass spectrum, m/z [619.5] (M+H)+.

{1-Cyclohexyl-2-[6-(6-fluoro-1H-indol-3-yl)-hexahydro-pyrrolo[3,2-b]pyrrol-1-yl]-2-oxo-ethyl}-carbamic acid tert-butyl ester (49)

A 500 mL Parr bottle was charged with crude 48 (1.5 g, 2.4 mmol) and 10% Pd-on-carbon (300 mg) in reagent grade MeOH (20 mL). The mixture was pressurized to 50 PSI H₂ (344.7 KPa) then shaken for 2 h. The catalyst was removed by filtration through diatomaceous earth (Celite®) and the solids were washed with MeOH and EtOAc. The filtrate was concentrated in vacuo to afford 1.1 g of 49 which was used without further purification. ¹H NMR (300 MHz, CDCl₃): δ9.03 (s, 1H), 8.16 (dd, J=5.4 Hz, 8.4 Hz, 1H), 7.57 (s, 1H), 7.00 (d, J=8.7 Hz, 1H), 6.93 (t, J=8.7 Hz, 1H), 5.30 (d, J=8.7 Hz, 1H), 4.76 (m, 1H), 4.30-4.20 (m, 4H), 3.89 (m, 2H), 3.55 (m, 1H), 3.48 (s, 3H), 2.73-2.69 (m, 1H), 2.05-1.99 (m, 1H), 1.74-1.65 (m, 8H), 1.43 (s, 9H), 1.26-1.06 (m, 2H) ppm. Mass spectrum, m/z [485.3] (M+H)+.

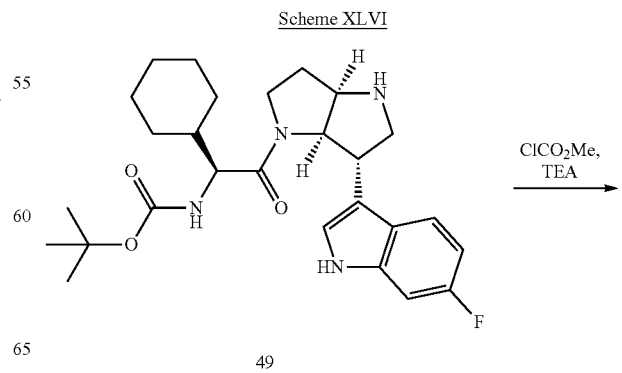

-continued

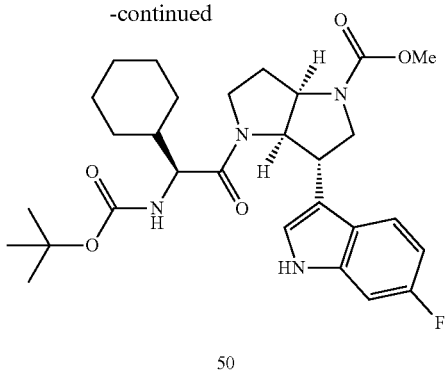

50

4-(2-tert-Butoxycarbonylamino-2-cyclohexyl-acetyl)-3-(6-fluoro-1H-indol-3-yl)-hexahydro-pyrrolo[3,2-b]pyrrole-1-carboxylic acid methyl ester (50)

A solution containing crude 49 (229 mg, 0.47 mmol) in DCM (5 mL) was cooled to 0° C. TEA (73 mg, 0.72 mmol) was added followed by ethyl chloroformate (73 mg, 0.78 mmol). After 30 min, the reaction mixture was diluted with DCM and washed successively with 1M HCl and brine, dried over anhydrous $Na_2SO_4$, filtered, and concentrated. The crude product was purified by flash silica gel chromatography (2:1 hexanes/EtOAc to 1:1 hexanes/EtOAc) to afford 226 mg (88%) of 50 as an off-white-colored foam. $^1$H NMR (300 MHz, $CDCl_3$): δ8.25-8.14 (m, 1H), 8.10 (s, 1H), 7.03-6.97 (m, 1H), 6.95-6.83 (m, 1H), 5.36-5.32 (m, 1H), 4.63 (dd, J=5.4, 19.8 Hz, 1H), 4.39-4.34 (m, 1H), 4.26-4.22 (m, 1H), 4.09-4.04 (m, 2H), 3.95 (app t, J=5.7 Hz, 1H), 3.80 (s, 3H), 3.53-3.48 (m, 2H), 2.49-2.43 (m, 0.5H), 2.31-2.24 (m, 0.5H), 1.94-1.88 (m, 1H), 1.77-1.65 (m, 6H), 1.44 (s, 9H), 1.29-1.10 (m, 5H) ppm. Mass spectrum, m/z [543.4] (M+H)+.

Scheme XLVII

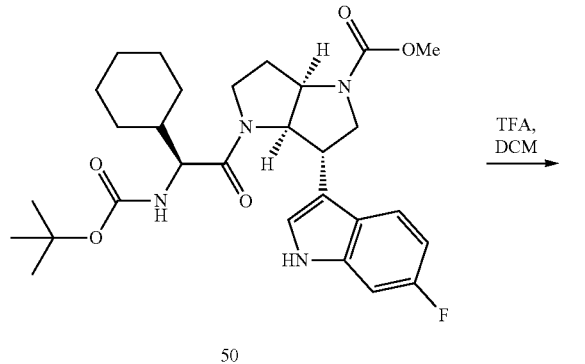

4-(2-Amino-2-cyclohexyl-acetyl)-3-(6-fluoro-1H-indol-3-yl)-hexahydro-pyrrolo[3,2-b]pyrrole-1-carboxylic acid methyl ester (51)

A solution containing 50 (226 mg, 0.42 mmol) in DCM (5 mL) was cooled to 0° C. TFA (2 mL) was added and the reaction mixture was warmed to ambient temperature. After 90 min, the reaction mixture was concentrated in vacuo. The residue was dissolved in EtOAc and the resultant organic solution was washed successively with saturated aqueous $NaHCO_3$ and brine, dried over anhydrous $Na_2SO_4$, filtered, and concentrated to afford 172 mg of 51 as an off-white-colored foam which was used without further purification. Mass spectrum, m/z [443.3] (M+H)+.

Scheme XLVIII

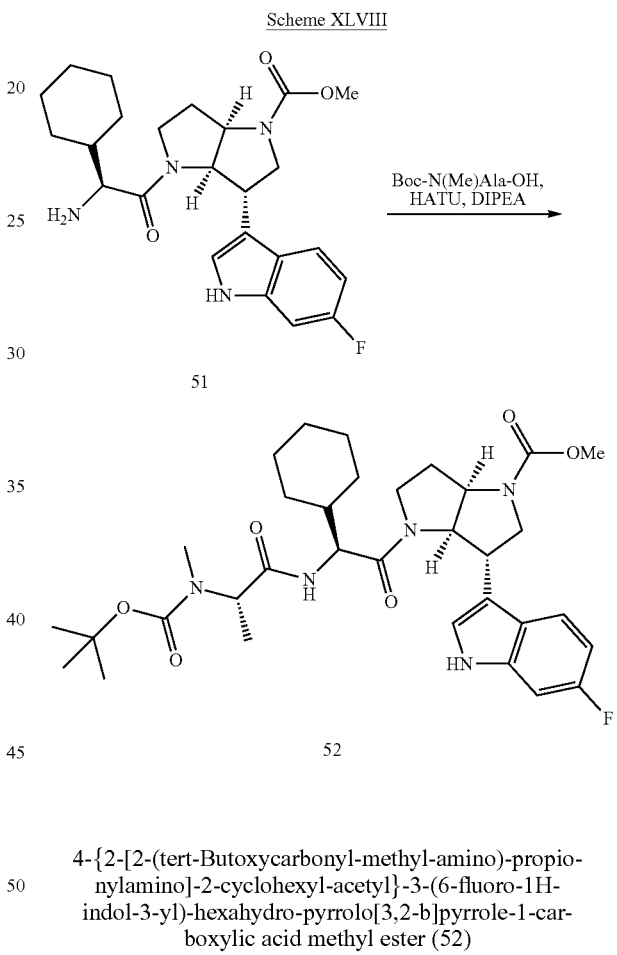

4-{2-[2-(tert-Butoxycarbonyl-methyl-amino)-propionylamino]-2-cyclohexyl-acetyl}-3-(6-fluoro-1H-indol-3-yl)-hexahydro-pyrrolo[3,2-b]pyrrole-1-carboxylic acid methyl ester (52)

To a solution containing Boc-N(Me)Ala-OH (76 mg, 0.37 mmol) in anhydrous NMP (4 mL) was cooled to 0° C. HATU (141 mg, 0.37 mmol) and DIPEA (148 mg, 1.14 mmol) were added followed by the addition of crude 51 (172 mg, 0.39 mmol) in anhydrous NMP (5 mL). The reaction mixture was slowly warmed to ambient temperature. After 16 h, the reaction mixture was diluted with EtOAc and washed successively with 1M HCl, aqueous $NaHCO_3$, and brine, dried over anhydrous $Na_2SO_4$, filtered, and concentrated to afford 255 mg of crude 52 as an off-white-colored foam which was used without further purification. Mass spectrum, m/z [628.5] (M+H)+.

Scheme XLIX

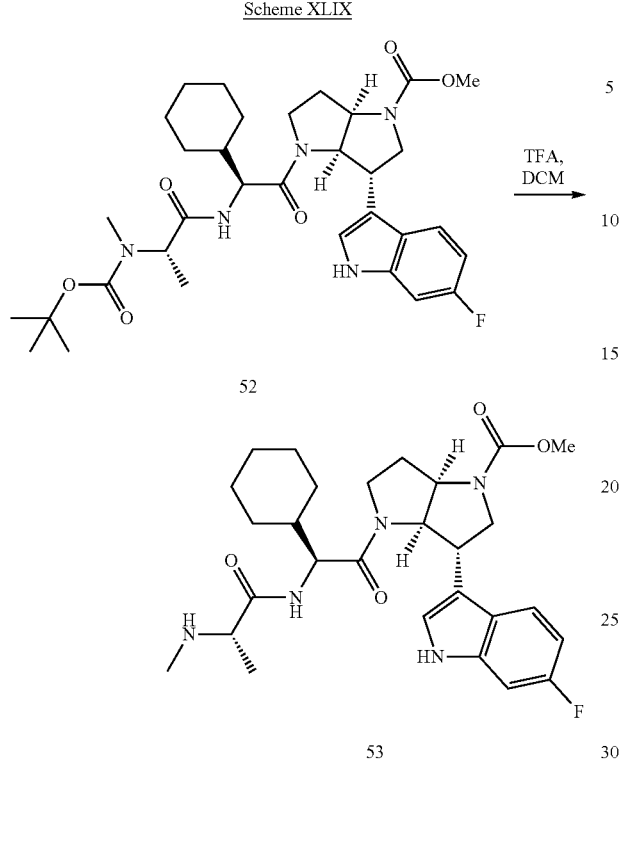

4-[2-Cyclohexyl-2-(2-methylamino-propiony-
lamino)-acetyl]-3-(6-fluoro-1H-indol-3-yl)-hexahy-
dro-pyrrolo[3,2-b]pyrrole-1-carboxylic acid methyl
ester (53)

To a solution containing crude 52 (255 mg) in DCM (6 mL) was added TFA (2 mL) at ambient temperature. After 1 h, the reaction mixture was concentrated in vacuo. The residue was dissolved in EtOAc and the resultant organic solution was washed successively with saturated aqueous NaHCO$_3$ and brine, dried over anhydrous Na$_2$SO$_4$, filtered, and concentrated. The crude product was purified by RP-HPLC (2" C18 Dynamax, 10-70% ACN/water containing 0.1% HOAc over 30 min; Flow: 40 mL/min) to afford 91 mg (41%, 3 steps) of 53.HOAc as a white solid. $^1$H NMR (300 MHz, CDCl$_3$), mixture of amide rotamers: δ8.29 (br s, 1H), 8.19 (dd, J=5.7, 8.1 Hz, 0.5H), 8.10 (dd, J=6.9, 8.2 Hz, 0.5H), 7.75 (app d, J=8.7 Hz, 1H), 7.02-6.95 (m, 1H), 6.92-6.83 (m, 2H), 4.66-4.58 (m, 2H), 4.36 (app t, J=3.9 Hz, 0.5H), 4.27-4.17 (m, 2H), 4.05-3.95 (m, 2H), 3.78 (s, 3H), 3.55-3.49 (m, 2H), 3.15 (app q, J=6.9 Hz, 1H), 2.88 (m, 2H), 2.40 (s, 3H), 2.27 (dd, J=5.7, 13.5 Hz, 0.5H), 1.95-1.67 (m, 6H), 1.32 (d, J=6.9 Hz, 3H), 1.26-1.04 (m, 4H) ppm. $^{13}$C NMR (75 MHz, CDCl$_3$), mixture of amide rotamers: δ175.2, 171.1, 160.5 (J$_{CF}$=237.7 Hz), 155.7 & 155.3, 136.7 & 136.5, 123.6 & 123.6, 121.5 & 121.3, 121.1 & 121.2, 120.2 (J$_{CF}$=6.3 Hz), 116.4 & 116.1, 108.7 (J$_{CF}$=24.2 Hz), 97.4 (J$_{CF}$=25.8 Hz), 68.8 & 67.9, 60.7, 60.2 & 60.1, 55.5, 53.0 & 52.9, 51.2, 47.2, 41.2, 39.4 & 39.2, 35.0, 32.0 & 30.9, 29.9, 28.9, 26.4 & 26.1, 19.5 ppm. Mass spectrum, m/z [528.4] (M+H)+.

Example 37

N-{1-Cyclohexyl-2-[6-(6-fluoro-1H-indol-3-yl)-4-
(2,2,2-trifluoro-acetyl)-hexahydro-pyrrolo[3,2-b]
pyrrol-1-yl]-2-oxo-ethyl}-2-methylamino-propiona-
mide

Scheme L

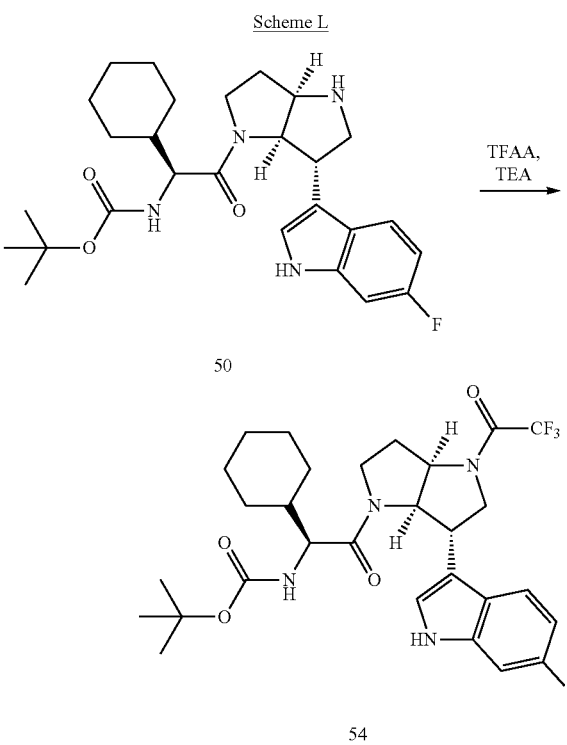

{1-Cyclohexyl-2-[6-(6-fluoro-1H-indol-3-yl)-4-(2,2,
2-trifluoro-acetyl)-hexahydro-pyrrolo[3,2-b]pyrrol-
1-yl]-2-oxo-ethyl}-carbamic acid tert-butyl ester (54)

A solution containing amine 50 (215 mg, 0.44 mmol) in DCM (6 mL) was cooled to 0° C. TEA (145 mg, 1.43 mmol) was added followed by trifluoroacetic anhydride (151 mg, 0.72 mmol) and the reaction mixture was warmed to ambient temperature. After 30 min, the reaction mixture was diluted with DCM and the resulting organic solution was washed successively with 1M HCl and brine, dried over anhydrous Na$_2$SO$_4$, filtered, and concentrated to afford a mixture of 54 together with the trifluoroacetylated indole impurity. The crude residue was dissolved in MeOH (10 mL) and treated with K$_2$CO$_3$ (50 mg) at ambient temperature. After 20 min, the reaction mixture was acidified (pH~2) by the addition of 1M HCl and the aqueous solution was extracted with EtOAc. The organic extract was washed with brine, dried over anhydrous Na$_2$SO$_4$, filtered, and concentrated to afford 245 mg of 54 which was used without further purification. Mass spectrum, m/z [581.4] (M+H)+.

N-{1-Cyclohexyl-2-[6-(6-fluoro-1H-indol-3-yl)-4-
(2,2,2-trifluoro-acetyl)-hexahydro-pyrrolo[3,2-b]
pyrrol-1-yl]-2-oxo-ethyl}-2-methylamino-propiona-
mide—was prepared from 54 in a fashion analogous
to that described in Schemes XLVII through XLIX $^1$H NMR (300 MHz, CDCl$_3$): δ8.21 (dd, J=5.7, 8.7 Hz, 1H), 8.09 (s, 1H), 7.73 (d, J=9.3 Hz, 1H), 7.02 (dd, J=1.8, 9.3 Hz, 1H), 6.83 (s, 1H), 4.69 (d, J=5.1 Hz, 1H), 4.60-4.54 (m, 2H), 4.37-4.25 (m, 2H), 4.11 (d, J=5.7 Hz, 1H), 3.74 (dd, J=6.0, 11.7 Hz, 1H), 3.49-3.39 (m, 1H), 3.10 (app q, J=7.2 Hz, 1H), 2.43 (s, 3H), 1.76 (m, 9H), 1.34 (d, J=6.9 Hz, 3H), 1.23-1.04 (m, 3H) ppm. $^{13}$C NMR (75 MHz, CDCl$_3$), mixture of amide rotamers: δ175.2, 171.2, 160.4 ($J_{CF}$=238.2 Hz), 136.4 & 136.2, 123.1, 121.0 ($J_{CF}$=10.1 Hz), 119.6 & 118.1, 115.0 & 114.3, 108.9 ($J_{CF}$=24.4 Hz), 97.3 ($J_{CF}$=26.1 Hz), 66.4, 62.0, 60.1, 55.3, 51.4, 46.9, 40.8, 39.9, 34.9, 29.8, 29.7, 28.9, 26.1, 25.9, 19.4 ppm. Mass spectrum, m/z [566.4] (M+H)+.

Example 38

N-{2-[4-Benzoyl-6-(6-fluoro-1H-indol-3-yl)-hexahydro-pyrrolo[3,2-b]pyrrol-1-yl]-1-cyclohexyl-2-oxo-ethyl}-2-methylamino-propionamide

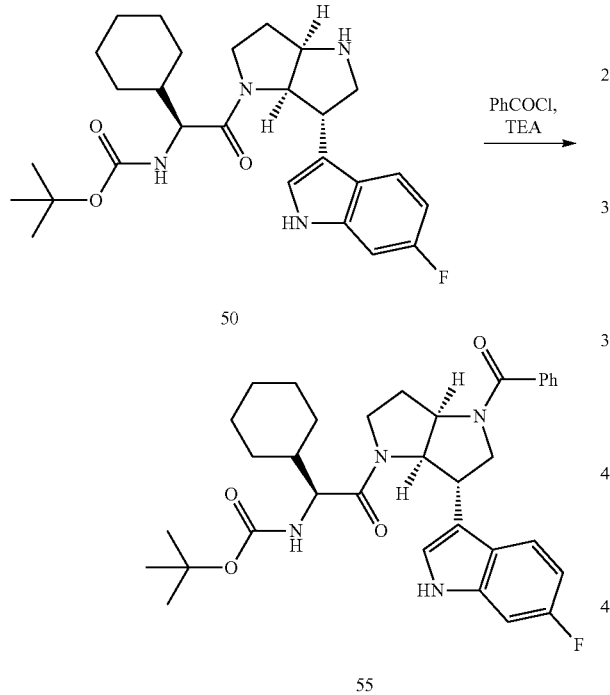

{2-[4-Benzoyl-6-(6-fluoro-1H-indol-3-yl)-hexahydro-pyrrolo[3,2-b]pyrrol-1-yl]-1-cyclohexyl-2-oxo-ethyl}-carbamic acid tert-butyl ester (55)

A solution containing amine 50 (258 mg, 0.5 mmol) in DCM (8 mL) was cooled to 0° C. TEA (73 mg, 0.72 mmol) was added followed by benzoyl chloride (85 mg, 0.61 mmol) and the reaction mixture was warmed to ambient temperature. After 20 min, the reaction mixture was diluted with DCM and the resulting organic solution was washed successively with 1M HCl and brine, dried over anhydrous Na$_2$SO$_4$, filtered, and concentrated. The crude product was purified by flash silica gel chromatography (hexanes/EtOAc, 1:1) to afford 278 mg (94%) of 55 as an off-white-colored foam. Mass spectrum, m/z [589.4] (M+H)+.

N-{2-[4-Benzoyl-6-(6-fluoro-1H-indol-3-yl)-hexahydro-pyrrolo[3,2-b]pyrrol-1-yl]-1-cyclohexyl-2-oxo-ethyl}-2-methylamino-propionamide was prepared from 55 in a fashion analogous to that described in Schemes XLVII through XLIX $^1$H NMR (300 MHz, CDCl$_3$), mixture of amide rotamers: δ8.14 (s, 1H), 8.10 (dd, J=5.4, 8.4 Hz, 1H), 7.73 (d, J=9.3 Hz, 1H), 7.64-7.61 (2H), 7.48-7.42 (m, 4H), 7.09-6.88 (m, 2H), 6.61 (s, 1H), 4.79 (app t, J=7.8 Hz, 1H), 4.72-4.63 (m, 1H), 4.56-4.46 (m, 1H), 4.34 (app t, J=9.6 Hz, 1H), 3.96 (m, 1H), 3.85-3.83 (m, 2H), 3.65-3.55 (m, 1H), 3.13 (app q, J=6.9 Hz, 1H), 2.96 (m, 2H), 2.46 (m, 1H), 2.41 (s, 3H), 1.80 (m, 6H), 1.33 (d, J=6.9 Hz, 3H), 1.25-1.11 (m, 3H) ppm. $^{13}$C NMR (75 MHz, CDCl$_3$), mixture of amide rotamers: δ175.1, 171.2, 170.1, 160.5 ($J_{CF}$=238.3 Hz), 136.5 & 136.4, 136.3, 130.9, 129.1, 128.8, 127.7, 126.7, 123.4, 121.0 ($J_{CF}$=10.1 Hz), 119.9 & 119.8, 115.8, 108.7 ($J_{CF}$=24.4 Hz), 97.5 ($J_{CF}$=26.2 Hz), 67.4, 60.5, 60.3, 55.5, 54.9, 47.8, 41.2, 40.3, 35.1, 31.5, 30.0, 29.0, 26.4, 26.2, 19.6 ppm. Mass spectrum, m/z [574.4] (M+H)+.

Example 39

N-{1-Cyclohexyl-2-[6-(6-fluoro-1H-indol-3-yl)-4-phenylacetyl-hexahydro-pyrrolo[3,2-b]pyrrol-1-yl]-2-oxo-ethyl}-2-methylamino-propionamide

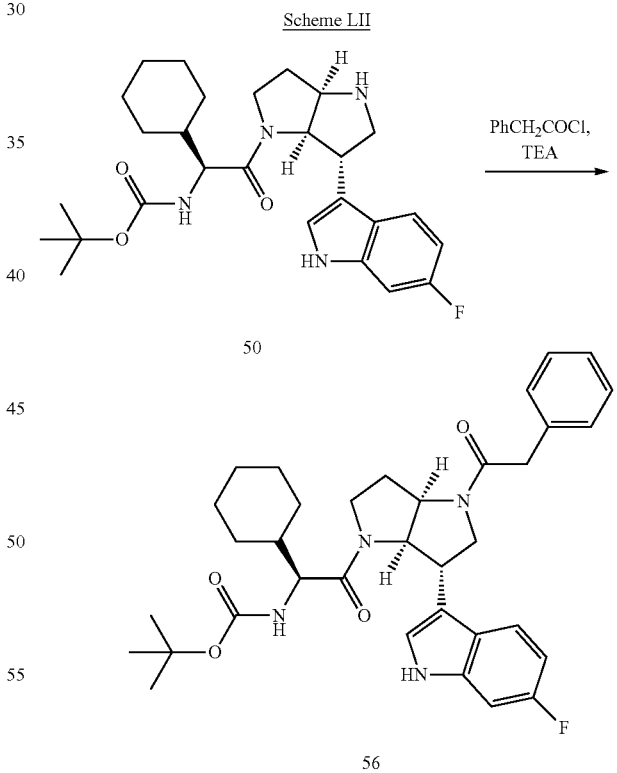

{1-Cyclohexyl-2-[6-(6-fluoro-1H-indol-3-yl)-4-phenylacetyl-hexahydro-pyrrolo[3,2-b]pyrrol-1-yl]-2-oxo-ethyl}-carbamic acid tert-butyl ester (56)

A solution containing amine 50 (296 mg, 0.61 mmol) in DCM (8 mL) was cooled to 0° C. TEA (145 mg, 1.43 mmol) was added followed by phenylacetyl chloride (105 mg, 0.68 mmol) and the reaction mixture was warmed to ambient temperature. After 40 min, the reaction mixture was diluted with DCM and the resulting organic solution was washed successively with 1M HCl and brine, dried over anhydrous Na$_2$SO$_4$, filtered, and concentrated. The crude product was purified by flash silica gel chromatography (1:1 hexanes/ EtOAc to 1:2 hexanes/EtOAc) to afford 244 mg (66%) of 56 as an off-white-colored foam. $^1$H NMR (300 MHz, CDCl$_3$), mixture of amide rotamers: δ8.27 (s, 0.7H), 8.20 (s, 0.3H), 8.02 (dd, J=5.1, 8.4 Hz, 0.7H), 7.35-7.27 (m, 5H), 6.96-6.89 (m, 2H), 6.53 (s, 0.3H), 6.14 (s, 0.7H), 5.34 (d, J=9.3 Hz, 0.7H), 4.77 (d, J=5.1 Hz, 0.3H), 4.51-4.38 (m, 2H), 4.34-4.28 (m, 1H), 4.12 (app q, J=6.9 Hz, 1H), 4.04-3.89 (m, 2H), 3.77 (s, 1H), 3.51-3.42 (m, 0.7H), 3.30-3.20 (m, 0.3H), 2.60-2.53 (m, 1H), 1.76-1.63 (m, 6H), 1.44 (s, 9H), 1.19-1.05 (m, 5H) ppm. Mass spectrum, m/z [603.4] (M+H)+.

N-{1-Cyclohexyl-2-[6-(6-fluoro-1H-indol-3-yl)-4-phenylacetyl-hexahydro-pyrrolo[3,2-b]pyrrol-1-yl]-2-oxo-ethyl}-2-methylamino-propionamide was prepared from 56 in a fashion analogous to that described in Schemes XLVII through XLIX $^1$H NMR (300 MHz, CDCl$_3$), mixture of amide rotamers: δ8.13 (s, 1H), 8.07-7.99 (m, 1H), 7.68 (d, J=9.3 Hz, 1H), 7.32-7.26 (m, 5H), 6.97-6.85 (m, 2H), 6.54 (s, 0.3H), 6.16 (s, 0.7H), 4.59-4.54 (m, 1H), 4.50 (m, 1H), 4.15 (app t, J=9.3 Hz, 1H), 3.95 (m, 2H), 3.77 (m, 1H), 3.53-3.48 (m, 1H), 3.28-3.26 (m, 1H), 3.11-3.05 (m, 1H), 2.56 (dd, J=4.8, 13.2 Hz, 1H), 2.42-2.38 (m, 3H), 2.19 (m, 2H), 2.06 (s, 1H), 1.76-1.71 (m, 6H), 1.32 (d, J=6.3 Hz, 3H), 1.25-1.00 (m, 3H) ppm. $^{13}$C NMR (75 MHz, CDCl$_3$), mixture of amide rotamers: δ175.2 & 175.1, 170.8 & 170.7, 170.2 & 169.8, 160.2 (J$_{CF}$=237.9 Hz), 136.2 & 135.9, 129.1, 128.9, 128.8, 127.7, 127.1, 123.3 & 123.2, 120.6 (J$_{CF}$=10.0 Hz), 119.8, 115.6 & 115.2, 108.5 (J$_{CF}$=24.4 Hz), 97.2 (J$_{CF}$=26.2 Hz), 68.9 & 67.1, 60.5, 60.2 & 59.9, 55.2 & 55.1, 52.0, 47.0, 43.5, 41.1 & 40.9, 39.2 & 38.9, 34.9, 30.1, 29.7, 28.8 & 28.7, 26.1, 25.9 & 25.7, 19.5 & 19.4 ppm. Mass spectrum, m/z [588.4] (M+H)+.

Example 40

N-{1-Cyclohexyl-2-[4-cyclopropanecarbonyl-6-(6-fluoro-1H-indol-3-yl)-hexahydro-pyrrolo[3,2-b]pyrrol-1-yl]-2-oxo-ethyl}-2-methylamino-propionamide Scheme LIII

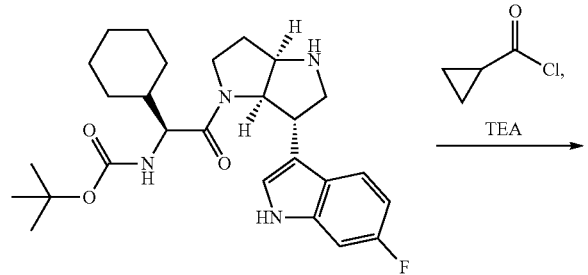

50

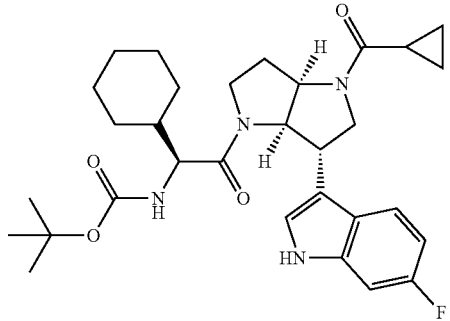

57

{1-Cyclohexyl-2-[4-cyclopropanecarbonyl-6-(6-fluoro-1H-indol-3-yl)-hexahydro-pyrrolo[3,2-b]pyrrol-1-yl]-2-oxo-ethyl}-carbamic acid tert-butyl ester (57)

A solution containing amine 50 (197 mg, 0.41 mmol) in DCM (10 mL) was cooled to 0° C. TEA (73 mg, 0.72 mmol) was added followed by cyclopropanecarbonyl chloride (57 mg, 0.55 mmol) and the reaction mixture was warmed to ambient temperature. After 16 h, the reaction mixture was diluted with DCM and the resulting organic solution was washed successively with 1M HCl and brine, dried over anhydrous Na$_2$SO$_4$, filtered, and concentrated to afford 247 mg of 57 as a yellow-colored oil which was used without further purification. $^1$H NMR (300 MHz, CDCl$_3$), mixture of amide rotamers: δ8.70 (s, 0.5H), 8.60 (s, 0.5H), 8.25 (dd, J=5.4, 8.7 Hz, 0.5H), 8.10 (dd, J=5.1, 8.7 Hz, 0.5H), 7.03-6.99 (m, 1H), 6.97-6.89 (m, 1H), 6.80 (s, 1H), 5.38 (app t, J=9.3 Hz, 1H), 4.81 (d, J=5.1 Hz, 1H), 4.57-4.50 (m, 2H), 4.37 (app t, J=7.8 Hz, 1H), 4.24 (d, J=10.5 Hz, 1H), 4.16-4.04 (m, 2H), 3.93 (d, J=5.4 Hz, 1H), 3.81-3.73 (m, 1H), 3.54-3.40 (m, 2H), 2.41-2.37 (m, 1H), 1.79-1.60 (m, 8H), 1.45 (s, 9H), 1.21-1.09 (m, 6H), 1.04-1.01 (m, 3H), 0.91-0.86 (m, 1H) ppm. Mass spectrum, m/z [553.4] (M+H)+.

{1-Cyclohexyl-2-[4-cyclopropanecarbonyl-6-(6-fluoro-1H-indol-3-yl)-hexahydro-pyrrolo[3,2-b]pyrrol-1-yl]-2-oxo-ethyl}-2-methylamino-propionamide was prepared from 57 in a fashion analogous to that described in Schemes XLVII through XLIX $^1$H NMR (300 MHz, CDCl$_3$), mixture of amide rotamers: δ8.59 (s, 0.5H), 8.49 (s, 0.5H), 8.22 (dd, J=5.4, 8.7 Hz, 0.5H), 8.07 (dd, J=5.1, 8.7 Hz, 0.5H), 7.75 (app t, J=9.9 Hz, 1H), 7.00 (dd, J=2.1, 9.9 Hz, 1H), 6.96-6.89 (m, 1H), 6.81 (s, 1H), 4.81 (d, J=7.8 Hz, 0.5H), 4.65-4.87 (m, 1H), 4.32-4.21 (m, 1H), 4.16-4.08 (m, 1H), 3.98 (dd, J=5.1, 32 Hz, 1H), 3.83-3.78 (m, 0.5H), 3.56-3.43 (m, 2H), 3.11-3.07 (m, 1H), 2.43 (d, J=12.3 Hz, 3H), 1.34-1.08 (m, 9H), 0.88-0.85 (m, 3H) ppm. $^{13}$C NMR (75 MHz, CDCl$_3$), mixture of amide rotamers: δ176.2 & 174.9, 172.7 & 172.2, 170.9 & 170.8, 160.3 (J$_{CF}$=237.7 Hz), 136.5 & 136.4, 136.3 & 136.1, 123.4 & 123.3, 121.2 & 121.1, 120.7 (J$_{CF}$=10.3 Hz), 120.3 & 120.2, 119.9 & 119.8, 116.1 & 115.5, 108.5 (J$_{CF}$=24.5 Hz), 97.3 (J$_{CF}$=26.1 Hz), 68.9 & 67.3, 60.2 & 60.0, 55.3 & 55.2, 51.9 & 50.1, 47.2 & 47.0, 40.9, 39.3 & 38.8, 34.9 & 34.8, 33.1, 30.7, 29.8 & 29.7, 28.8 & 28.7, 26.2 & 26.1, 19.4 & 19.3, 13.2 & 12.5, 8.5 & 8.0, 7.8 & 7.4 ppm. Mass spectrum, m/z [538.3] (M+H)+.

Example 41

[4-[2-Cyclohexyl-2-(2-methylamino-propionylamino)-acetyl]-3-(6-fluoro-1H-indol-3-yl)-hexahydro-pyrrolo[3,2-b]pyrrol-1-yl]-acetic acid ethyl ester

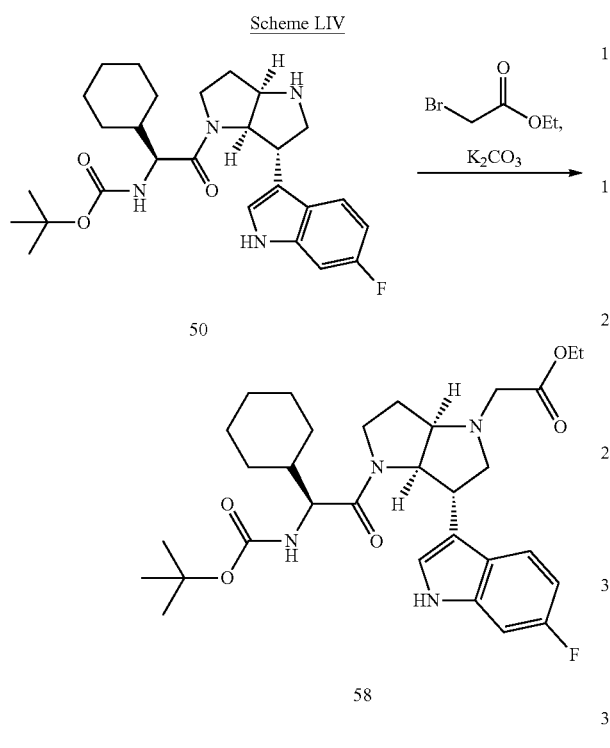

[4-(2-tert-Butoxycarbonylamino-2-cyclohexyl-acetyl)-3-(6-fluoro-1H-indol-3-yl)-hexahydro-pyrrolo[3,2-b]pyrrol-1-yl]-acetic acid ethyl ester (58)

A solution containing amine 50 (200 mg, 0.41 mmol) in ACN (5 mL) was cooled to 0° C. $K_2CO_3$ (63 mg, 0.46 mmol) was added followed by ethyl bromoacetate (75 mg, 0.45 mmol) and the reaction mixture was warmed to ambient temperature. After 16 h, the reaction mixture was diluted with water and extracted with EtOAc. The organic extract was washed with brine, dried over anhydrous $Na_2SO_4$, filtered, and concentrated. The crude product was purified by flash silica gel chromatography (1:1 hexanes/EtOAc) to afford 194 mg (82%) of 58 as an off-white-colored foam. $^1$H NMR (300 MHz, $CDCl_3$), mixture of amide rotamers: δ8.50 (s, 0.8H), 8.29 (s, 0.2H), 7.55 (dd, J=5.4, 8.7 Hz, 1H), 7.11 (s, 1H), 6.99 (d, J=9.0 Hz, 0.2H), 6.82 (d, J=9.6 Hz, 0.8H), 5.30-5.24 (m, 1H), 4.85-4.82 (m, 1H), 4.34 (t, J=6.0 Hz, 1H), 4.23-4.07 (m, 2H), 3.93 (t, J=8.7 Hz, 1H), 3.68-3.64 (m, 2H), 3.59-3.54 (m, 2H), 3.44-3.40 (m, 2H), 2.82 (app t, J=9.0 Hz, 1H), 2.05-2.01 (m, 1H), 1.83-1.65 (m, 6H), 1.38 (s, 9H), 1.28 (t, J=6.9 Hz, 3H), 1.24-1.05 (m, 2H) ppm. Mass spectrum, m/z [571.4] (M+H)+.

[4-[2-Cyclohexyl-2-(2-methylamino-propionylamino)-acetyl]-3-(6-fluoro-1H-indol-3-yl)-hexahydro-pyrrolo[3,2-b]pyrrol-1-yl]-acetic acid ethyl ester was prepared from 58 in a fashion analogous to that described in Schemes XLVII through XLIX $^1$H NMR (300 MHz, $CDCl_3$), mixture of amide rotamers: δ8.77 (s, 0.2H), 8.71 (s, 0.8H), 7.55 (dd, J=6.0, 9.0 1H), 7.09 (s, 1H), 7.00 (d, J=9.9 Hz, 0.2H), 6.84-6.78 (m, 1.8H), 4.85 (t, J=6.0 Hz, 0.8H), 4.76 (t, J=5.4 Hz, 0.2H), 4.63 (t, J=7.8 Hz, 1H), 4.20 (app q, J=7.2 Hz, 2H), 4.06 (t, J=8.7 Hz, 1H), 3.76-3.62 (m, 2H), 3.59-3.54 (m, 2H), 3.48-3.34 (m, 2H), 3.09-2.94 (m, 1H), 2.82 (app t, J=8.7 Hz, 1H), 2.35 (s, 1H), 2.24 (s, 2H), 2.14 (s, 2H), 2.03 (s, 1H), 1.84-1.67 (m, 6H), 1.31-1.22 (m, 7H), 1.17-1.03 (m, 1H) ppm. $^{13}$C NMR (75 MHz, $CDCl_3$), mixture of amide rotamers: δ174.9 & 173.9, 170.7 & 170.5, 169.8, 159.7 ($J_{CF}$=236.5 Hz), 136.6 & 136.5, 123.0, 122.1 & 122.0, 119.6 ($J_{CF}$=10.1 Hz), 116.1, 107.4 ($J_{CF}$=24.4 Hz), 97.4 ($J_{CF}$=25.6 Hz), 67.9, 66.2, 60.8 & 60.7, 60.2, 60.1, 54.7, 53.6, 45.9, 43.6, 41.1, 34.9, 29.9, 28.3, 26.2, 26.0, 25.9, 19.5, 14.3 ppm. Mass spectrum, m/z [556.4] (M+H)+.

Example 42

[4-[2-Cyclohexyl-2-(2-methylamino-propionylamino)-acetyl]-3-(6-fluoro-1H-indol-3-yl)-hexahydro-pyrrolo[3,2-b]pyrrol-1-yl]-acetic acid (60)

[4-[2-Cyclohexyl-2-(2-methylamino-propionylamino)-acetyl]-3-(6-fluoro-1H-indol-3-yl)-hexahydro-pyrrolo[3,2-b]pyrrol-1-yl]-acetic acid (60)

To a solution containing 59 (179 mg, 0.32 mmol) in EtOH (5 mL) was added 1M NaOH (0.5 mL). After 40 min, glacial HOAc (2 mL) was added and the reaction mixture was concentrated in vacuo. The residue was purified by RP-HPLC (Phenomenex Luna C18, 100×21.2 mm, 10-60% ACN/water containing 0.1% HOAc over 30 min; Flow: 20 mL/min) to afford 42 mg (25%) of 60 as a white solid. $^1$H NMR (300 MHz, $d_6$-DMSO), mixture of amide rotamers: δ11.0 (s, 0.2H), 10.9 (s, 0.8H), 7.89 (d, J=9.0 Hz, 1H), 7.61 (dd, J=5.1, 8.4 Hz, 1H), 7.40 (s, 0.2H), 7.29 (s, 0.8H), 7.09 (d, J=10.2 Hz, 1H), 6.83-6.77 (m, 1H), 4.56-4.53 (m, 1H), 4.48-4.45 (m, 1H), 3.94-3.89 (m, 2H), 3.61 (app t, J=5.7 Hz, 1H), 3.53-3.48 (m, 2H), 3.41 (app t, J=8.4 Hz, 1H), 3.31-3.25 (m, 2H), 3.01-2.98 (m, 1H), 2.73 (t, J=8.4 Hz, 1H), 2.51 (s, 3H), 2.15 (s, 3H), 1.66-1.62 (m, 6H), 1.08 (d, J=6.9 Hz, 3H), 1.21-0.90 (m, 2H) ppm. Mass spectrum, m/z [528.3] (M+H)+.

Example 43

N-{1-Cyclohexyl-2-[6-(6-fluoro-1H-indol-3-yl)-4-methanesulfonyl-hexahydro-pyrrolo[3,2-b]pyrrol-1-yl]-2-oxo-ethyl}-2-methylamino-propionamide Scheme LVI

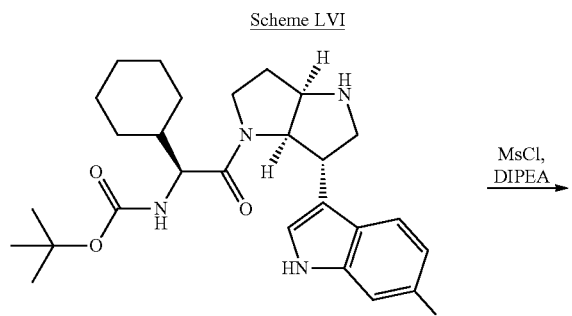

{1-Cyclohexyl-2-[6-(6-fluoro-1H-indol-3-yl)-4-methanesulfonyl-hexahydro-pyrrolo[3,2-b]pyrrol-1-yl]-2-oxo-ethyl}-carbamic acid tert-butyl ester (61)

A solution containing 50 (200 mg, 0.41 mmol) and DIPEA (163 mg, 1.26 mmol) in anhydrous DCM (5 mL) was cooled to 0° C. A solution of MsCl (44 mg, 0.41 mmol) in DCM (0.5 mL) was added followed by the addition of DMAP (5 mg, cat.). After 2 h, the reaction mixture was diluted with DCM and washed successively with 1M HCl and brine, dried over anhydrous Na$_2$SO$_4$, filtered, and concentrated. The crude product was purified by flash silica gel chromatography (1:1 hexanes/EtOAc) to afford 114 mg (49%) of 61 as a white solid. Mass spectrum, m/z [563] (M+H)+.

N-{1-Cyclohexyl-2-[6-(6-fluoro-1H-indol-3-yl)-4-methanesulfonyl-hexahydro-pyrrolo[3,2-b]pyrrol-1-yl]-2-oxo-ethyl}-2-methylamino-propionamide was prepared from 61 in a fashion analogous to that described in Schemes XLVII through XLIX $^1$H NMR (CDCl$_3$, 300 MHz): δ8.47 (br s, 1H), 7.88 (dd, J=5.7, 8.7 Hz, 1H), 7.74 (d, J=9.0 Hz, 1H), 7.18 (s, 1H), 7.00 (dd, 2.4, 9.6 Hz, 1H), 6.89 (ddd, J=2.1 Hz, 2.1 Hz, 9.0 Hz, 1H) 4.77 (app d, J=5.1 Hz, 1H), 4.60 (app t, J=8.4 Hz, 1H), 4.49-4.46 (m, 1H) 4.33-4.27 (m, 1H), 4.00-3.94 (m, 2H), 3.62-3.52 (m, 2H), 3.10 (dd, J=7.2 Hz, 14.1 Hz, 1H), 2.66 (s, 3H), 2.42-2.33 (m, 5H), 2.07-1.99 (m, 2H), 1.86-1.73 (m, 5H), 1.32 (d, J=6.9 Hz, 3H), 1.28-1.04 (m, 4H) ppm. $^{13}$C NMR (CDCl$_3$, 75 MHz) δ175.1, 171.1, 160.2 (J$_{CF}$=238.3 Hz), 136.4, 123.1, 120.9 & 120.4 (J$_{CF}$=10.1 Hz), 114.8, 108.6 (J$_{CF}$=24.4 Hz), 97.4 (J$_{CF}$=25.9 Hz), 68.2, 62.6, 55.3, 53.1, 46.8, 40.8, 39.9, 34.9, 32.6, 29.8, 28.8, 26.1, 25.9, 25.8, 19.4 ppm. Mass spectrum, m/z [548.3] (M)+.

Example 45

N-{1-[6-(6-Fluoro-1H-indol-3-yl)-4-methanesulfonyl-hexahydro-pyrrolo[3,2-b]pyrrole-1-carbonyl]-propyl}-2-methylamino-propionamide (67)

Scheme LVII

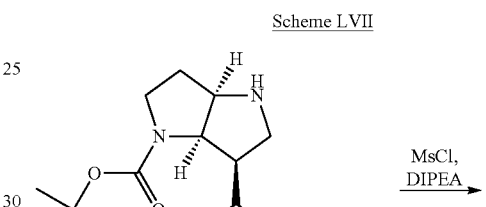

6-(6-Fluoro-1H-indol-3-yl)-4-methanesulfonyl-hexahydro-pyrrolo[3,2-b]pyrrole-1-carboxylic acid tert-butyl ester (62)

A solution containing crude 35 (2.58 g, 7.46 mmol) in DCM (30 mL) was cooled to 0° C. DIPEA (1.45 g, 11.2 mmol) and DMAP (91 mg, 0.74 mmol) were added followed by the addition of MsCl (0.94 g, 8.21 mmol). After 2 h, the reaction mixture was warmed to ambient temperature, diluted with DCM, washed successively with 1M HCl and brine, dried over anhydrous Na$_2$SO$_4$, filtered, and concentrated. The crude product was purified by flash silica gel chromatography (60-80% EtOAc/hexanes) to afford 2.47 g (75%) of 62 as a tan-colored foam. Mass spectrum, m/z [424.1] (M+H)+.

Scheme LVIII

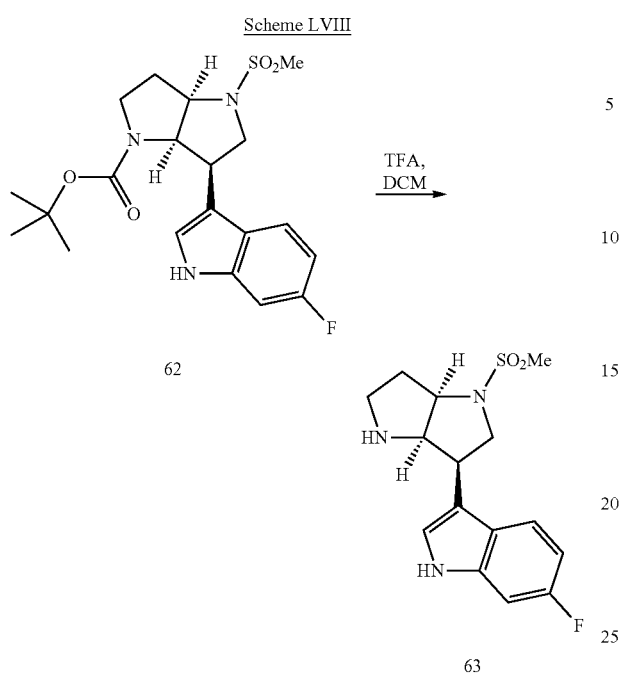

6-Fluoro-3-(1-methanesulfonyl-octahydro-pyrrolo[3,2-b]pyrrol-3-yl)-1H-indole (63)

To a solution containing 62 (2.47 g, 5.83 mmol) in DCM (10 mL) was added TFA (5 mL) at 0° C. After 5 h, the reaction mixture was concentrated in vacuo. The residue was dissolved in EtOAc and the resultant organic solution was washed successively with saturated aqueous NaHCO₃ and brine, dried over anhydrous Na₂SO₄, filtered, and concentrated to afford 1.8 g (95%) of 63 as a white solid which was used without further purification. Mass spectrum, m/z [324.2] (M+H)+.

Scheme LIX

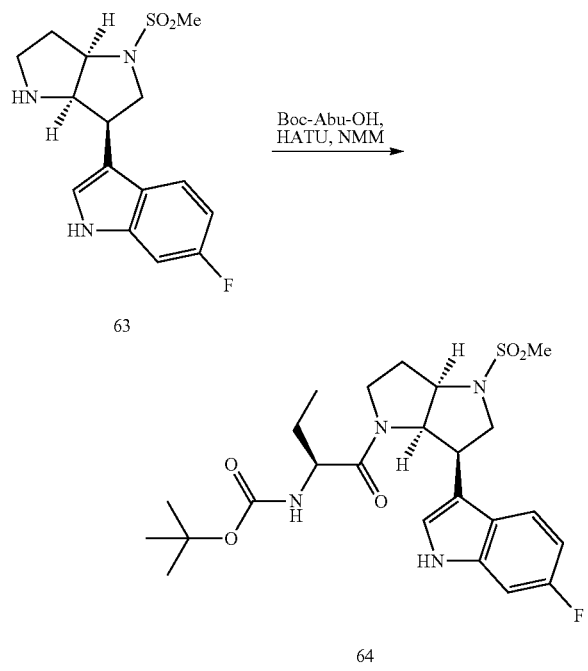

{1-[6-(6-Fluoro-1H-indol-3-yl)-4-methanesulfonyl-hexahydro-pyrrolo[3,2-b]pyrrole-1-carbonyl]-propyl}-carbamic acid tert-butyl ester (64)

To a solution containing Boc-L-Abu-OH (170 mg, 0.83 mmol) in anhydrous NMP (2 mL) was cooled to 0° C. HATU (316 mg, 0.83 mmol) and NMM (115 mg, 1.08 mmol) were added followed by the addition of crude 63 (242 mg, 0.75 mmol) in anhydrous NMP (4 mL). The reaction mixture was slowly warmed to ambient temperature. After 16 h, the reaction mixture was diluted with diethyl ether and EtOAc (10:1) and washed successively with aqueous NaHCO₃ and brine, dried over anhydrous Na₂SO₄, filtered, and concentrated. The crude product was purified by RP-HPLC (2" Dynamax C18, 40-100% ACN/water containing 0.1% HOAc over 30 min; Flow: 40 mL/min) to afford 270 mg (71%) of 64. Mass spectrum, m/z [509.2] (M+H)+.

Scheme LX

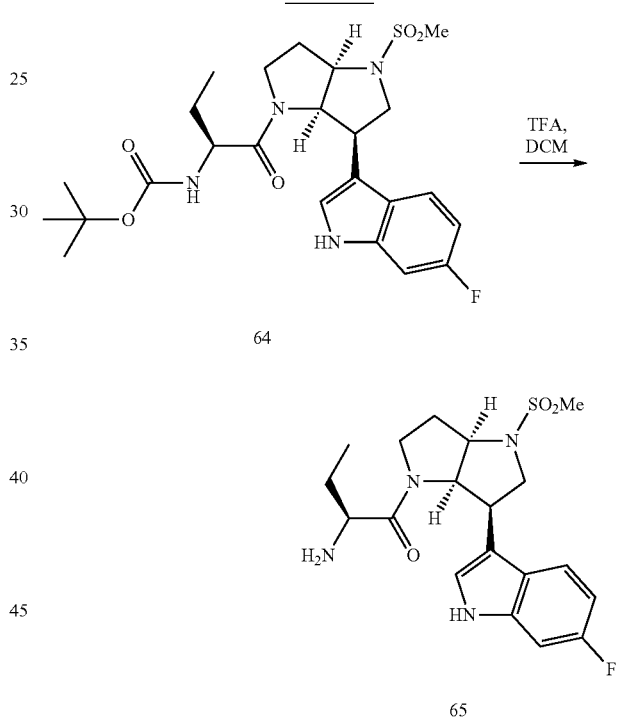

2-Amino-1-[6-(6-fluoro-1H-indol-3-yl)-4-methanesulfonyl-hexahydro-pyrrolo[3,2-b]pyrrol-1-yl]-butan-1-one (65)

To a solution containing 64 (270 mg, 0.53 mmol) in DCM (3 mL) was added TFA (2 mL) at 0° C. After 90 min, the reaction mixture was concentrated in vacuo. The residue was dissolved in EtOAc and the resultant organic solution was washed successively with saturated aqueous NaHCO₃ and brine, dried over anhydrous Na₂SO₄, filtered, and concentrated to afford 150 mg (69%) of 65 which was used without further purification. Mass spectrum, m/z [409.2] (M+H)+.

Scheme LXI

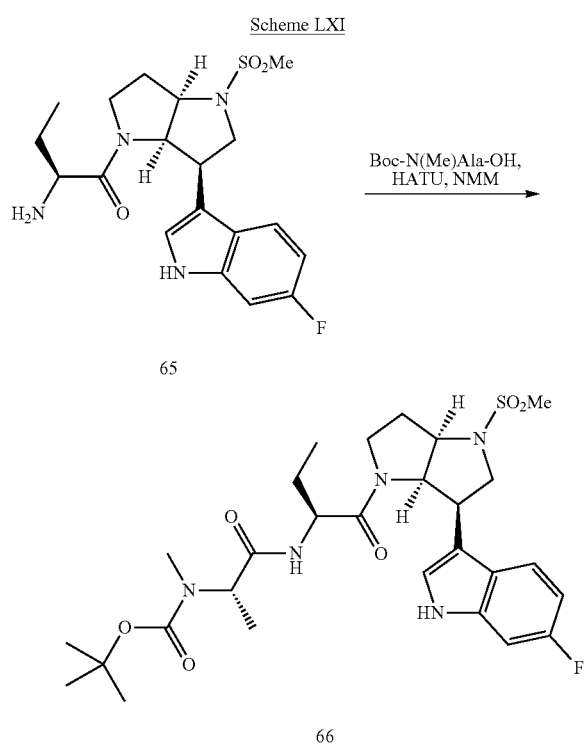

(1-{1-[6-(6-Fluoro-1H-indol-3-yl)-4-methanesulfonyl-hexahydro-pyrrolo[3,2-b]pyrrole-1-carbonyl]-propylcarbamoyl}-ethyl)-methyl-carbamic acid tert-butyl ester (66)

To a solution containing Boc-N(Me)Ala-OH (85 mg, 0.41 mmol) in anhydrous NMP (2 mL) was cooled to 0° C. HATU (156 mg, 0.41 mmol) and NMM (51 mg, 0.5 mmol) were added followed by the addition of crude 65 (150 mg, 0.37 mmol) in anhydrous NMP (4 mL). The reaction mixture was slowly warmed to ambient temperature. After 16 h, the reaction mixture was diluted with diethyl ether and EtOAc (10:1) and washed successively with aqueous NaHCO$_3$ and brine, dried over anhydrous Na$_2$SO$_4$, filtered, and concentrated to afford 160 mg of crude 66 which was used without further purification. Mass spectrum, m/z [594.2] (M+H)+.

Scheme LXII

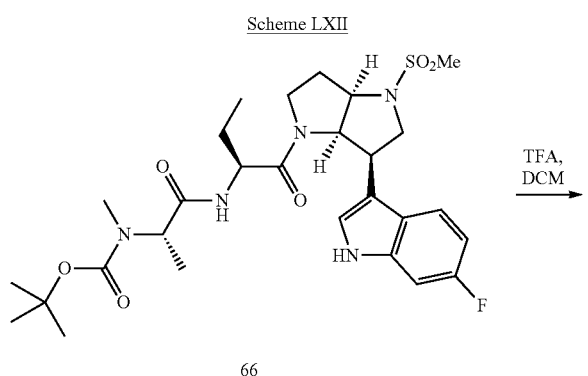

N-{1-[6-(6-Fluoro-1H-indol-3-yl)-4-methanesulfonyl-hexahydro-pyrrolo[3,2-b]pyrrole-1-carbonyl]-propyl}-2-methylamino-propionamide (67)

To a solution containing 66 (160 mg, 0.27 mmol) in DCM (3 mL) was added TFA (3 mL) at 0° C. After 1 h, the reaction mixture was concentrated in vacuo. The residue was dissolved in EtOAc and the resultant organic solution was washed successively with saturated aqueous NaHCO$_3$ and brine, dried over anhydrous Na$_2$SO$_4$, filtered, and concentrated. The crude product was purified by RP-HPLC (2" Dynamax C18, 5-40% ACN/water containing 0.1% HOAc over 30 min; Flow: 40 mL/min) to afford 100 mg (38%, 3 steps) of 67. $^1$H NMR (300 MHz, CDCl$_3$/d$_4$-MeOH), mixture of amide rotamers: δ10.34 (br s, 0.1H), 9.76 (br s, 0.3H), 7.92 (br d, 0.3H), 7.55 (dd, J=8.9, 5.3 Hz, 0.7H), 7.38 (m, 0.3H), 7.35 (s, 0.3H), 7.25 (m, 0.3H), 7.22 (s, 0.7H), 7.02 (m, 1H), 6.82 (dt, J=9.2, 2.0 Hz, 0.7H), 5.11 (t, J=7.8 Hz, 0.7H), 4.79 (m, 0.3H), 4.30 (br s, 2H), 4.24 (m, 1.7H), 4.14 (m, 1.3H), 4.00 (m, 1H), 3.82 (m, 1H), 3.71 (m, 2H), 3.51 (q, J=6.9 Hz, 0.7H), 3.38 (m, 0.3H), 3.29 (m, 0.3H), 3.15 (app q, J=9.0 Hz, 0.7H), 3.01 (s, 0.7H), 2.98 (s, 2.3H), 2.44 (s, 2.3H), 2.34 (s, 0.7H), 2.20 (m, 0.7H), 2.00 (br s, 3.3H), 1.57 (m, 0.3H), 1.35 (d, J=6.9 Hz, 2.3H), 1.17 (d, J=6.9 Hz, 0.7H), 0.71 (m, 1.5H), 0.47 (m, 1.5H) ppm. $^{13}$C NMR (75 MHz, CDCl$_3$/d$_4$-MeOH), mixture of amide rotamers: δ176.6, 171.3, 171.2, 170.7, 170.5, 169.1, 161.6, 158.4, 136.2, 136.0, 135.9, 124.3, 122.9, 122.8, 122.7(2), 120.2, 120.1, 108.3, 108.1, 107.8, 97.6, 97.5, 97.2, 65.0, 64.9, 62.3, 57.9, 57.5, 55.4, 53.4, 52.3, 52.2, 51.7, 47.4, 46.8, 43.1, 38.5, 37.6, 34.4, 33.9, 33.2, 32.2, 32.0, 25.9, 24.2, 22.1, 17.1, 16.8, 10.0, 9.1 ppm. Mass spectrum, m/z [494.2] (M+H)+.

Examples 44, 46-58 were prepared from intermediates 34 and 35 and by using the procedures described in Schemes LVII through LXII by substituting for Boc-Abu-OH with other amino acid reagents including Boc-Val-OH, Boc-Tle-OH, Cbz-Ser(tBu)-OH, Boc-Ser-OH, Boc-Ser(Me)-OH, Cbz-Thr(tBu)-OH, Boc-Thr(tBu)-OH, Boc-Thr-OH, or Boc-Thr(Me)-OH.

Example 46

N-{1-[6-(6-Fluoro-1H-indol-3-yl)-4-methanesulfonyl-hexahydro-pyrrolo[3,2-b]pyrrole-1-carbonyl]-propyl}-2-methylamino-propionamide $^1$H NMR (300 MHz, CDCl$_3$): δ8.22 (s, 1H), 7.92 (dd, J=5.7, 8.7 Hz, 1H), 7.80 (d, J=8.4 Hz, 1H), 7.24 (s, 1H), 7.02 (dd, J=2.1, 9.6 Hz, 1H), 6.96-6.89 (m, 1H), 4.80-4.74 (m, 2H), 4.50 (app t, J=4.8 Hz, 1H), 4.18 (app t, J=9.9 Hz, 1H), 4.02-3.95 (m, 2H), 3.63-3.51 (m, 2H), 3.10 (app q, J=7.2 Hz, 1H), 2.71 (s, 3H), 2.42 (s, 3H), 1.94 (s, 5H), 1.79-1.72 (m, 1H), 1.32 (d, J=6.9 Hz, 3H), 0.99 (t, J=7.5 Hz, 3H) ppm. $^{13}$C NMR (75 MHz, CDCl$_3$): δ174.9, 171.1, 160.2 (J$_{CF}$=238.3 Hz), 136.5 & 136.3, 123.1, 121.0 & 120.9, 120.3 (J$_{CF}$=10.3 Hz), 114.9, 108.6 (J$_{CF}$=24.4 Hz), 97.4 (J$_{CF}$=26.4 Hz), 68.2, 62.5, 60.1, 53.1, 51.8, 46.5, 39.9, 39.3, 34.9, 32.7, 25.8, 19.4, 9.7 ppm. Mass spectrum, m/z [494.3] (M+H)+.

Example 47

N-{1-[6-(6-Fluoro-1H-indol-3-yl)-4-methanesulfonyl-hexahydro-pyrrolo[3,2-b]pyrrole-1-carbonyl]-2-methyl-propyl}-2-methylamino-propionamide $^1$H NMR (300 MHz, CDCl$_3$), mixture of amide rotamers: δ9.61 (br s, 0.2H), 8.55 (br s, 0.8H), 7.60 (app dd, J=8.9, 5.3 Hz, 0.8H), 7.45 (br d, J=9.0 Hz, 0.8H), 7.34 (m, 0.2H), 7.20 (d, J=2.1 Hz, 0.8H), 7.17 (m, 0.2H), 7.12 (s, 0.2H), 6.99 (m, 1H), 6.86 (td, J=9.2, 2.1 Hz, 0.8H), 6.79 (m, 0.2H), 5.16 (app t, J=7.8 Hz, 0.8H), 4.92 (br s, 2H), 4.80 (m, 0.2H), 4.32 (m, 1.7H), 4.17 (m, 0.3H), 4.00 (app q, J=6.3 Hz, 0.8H), 3.79 (m, 3.15H), 3.29 (m, 1H), 3.13 (app q, J=6.9 Hz, 1H), 2.99 (s, 0.5H), 2.95 (s, 2.5H), 2.45 (m, 1H), 2.35 (s, 3H), 2.17 (m, 1H), 2.04 (s, 3H), 1.30 (m, 1H), 1.25 (d, J=6.9 Hz, 2.5H), 1.15 (d, J=6.9 Hz, 0.5H), 0.81 (d, J=6.6 Hz, 0.5H), 0.69 (d, J=6.6 Hz, 0.5H), 0.34 (d, J=6.6 Hz, 2.5H), 0.31 (d, J=6.6 Hz, 2.5H) ppm. $^{13}$C NMR (75 MHz, CDCl$_3$), mixture of amide rotamers: δ174.3, 170.9, 161.9, 158.7, 136.0, 135.8, 124.5, 122.3, 120.6, 120.4, 113.3, 108.9, 108.5, 97.6, 97.3, 65.0, 62.6, 59.9, 55.5, 54.8, 47.9, 46.9, 39.0, 34.9, 34.5, 33.5, 32.2, 30.9, 19.4, 19.3, 16.8 ppm. Mass spectrum, m/z [508.2] (M+H)+.

Example 48

N-{1-[6-(6-Fluoro-1H-indol-3-yl)-4-methanesulfonyl-hexahydro-pyrrolo[3,2-b]pyrrole-1-carbonyl]-2-methyl-propyl}-2-methylamino-propionamide $^1$H NMR (300 MHz, CDCl$_3$): δ8.31 (s, 1H), 7.90 (dd, J=5.1, 8.4 Hz, 1H), 7.76 (d, J=9.3 Hz, 1H), 7.23 (s, 1H), 7.02 (dd, J=1.8, 9.3 Hz, 1H), 6.95-6.88 (m, 1H), 4.78 (d, J=5.1 Hz, 1H), 4.61 (dd, J=7.5, 9.0 Hz, 1H), 4.49 (app t, J=4.5 Hz, 1H), 4.26 (app t, J=9.9 Hz, 1H), 4.01-3.95 (m, 2H), 3.63-3.52 (m, 2H), 3.13 (app q, J=6.6 Hz, 1H), 2.68 (s, 3H), 2.57 (s, 5H), 2.40 (s, 3H), 1.33 (d, J=7.2 Hz, 3H), 1.03 (d, J=6.9 Hz, 3H), 0.99 (d, J=6.6 Hz, 3H) ppm. $^{13}$C NMR (75 MHz, CDCl$_3$): δ175.1, 171.4, 160.4 (J$_{CF}$=238.0 Hz), 136.7 & 136.6, 123.2, 121.3 & 121.2, 120.4 (J$_{CF}$=10.1 Hz), 114.9, 108.7 (J$_{CF}$=26.7 Hz), 97.7 (J$_{CF}$=25.9 Hz), 68.4, 62.8, 60.1, 56.1, 53.4, 46.9, 40.2, 39.3, 34.8, 32.9, 31.6, 19.7, 19.5, 18.2 ppm. Mass spectrum, m/z [508.3] (M+H)+.

Example 49

N-{1-[6-(6-Fluoro-1H-indol-3-yl)-4-methanesulfonyl-hexahydro-pyrrolo[3,2-b]pyrrole-1-carbonyl]-2,2-dimethyl-propyl}-2-methylamino-propionamide $^1$H NMR (300 MHz, CDCl$_3$), mixture of amide rotamers: δ8.51 (br s, 1H), 7.60 (m, 1H), 7.57 (br d, 1H), 7.22 (d, J=2.4 Hz, 1H), 6.97 (dd, J=9.6, 2.1 Hz, 1H), 6.85 (app td, J=9.2, 2.1 Hz, 1H), 5.16 (app t, J=8.0 Hz, 1H), 4.60 (br s, 1H), 4.33 (d, J=9.6 Hz, 1H), 4.23 (dt, J=7.5, 3.6 Hz, 1H), 4.00 (m, 1H), 3.86 (m, 1H), 3.78 (app dd, J=4.7, 10.4 Hz, 1H), 3.69 (app dd, J=7.1, 10.1 Hz, 1H), 3.28 (m, 1H), 3.10 (q, J=6.9 Hz, 1H), 2.93 (s, 3H), 2.44 (m, 1H), 2.33 (s, 3H), 2.16 (m, 1H), 2.02 (br s, 3H), 1.23 (d, J=6.6 Hz, 3H), 0.35 (s, 9H) ppm. $^{13}$C NMR (75 MHz, CDCl$_3$), mixture of amide rotamers: δ174.2, 170.4, 161.9, 158.8, 135.9, 135.8, 124.6, 122.2(2), 120.9, 120.8, 113.9, 108.9, 108.6, 97.5, 97.1, 65.5, 62.7, 59.9, 56.6, 55.9, 48.8, 38.7, 34.9, 34.6, 33.2, 26.9, 25.8, 19.2 ppm. Mass spectrum, m/z [522.2] (M+H)+.

Example 50

N-{1-[6-(6-Fluoro-1H-indol-3-yl)-4-methanesulfonyl-hexahydro-pyrrolo[3,2-b]pyrrole-1-carbonyl]-2,2-dimethyl-propyl}-2-methylamino-propionamide $^1$H NMR (300 MHz, CDCl$_3$): δ8.34 (s, 1H), 7.89-7.85 (m, 2H), 7.21 (s, 1H), 7.01 (dd, J=2.4, 9.9 Hz, 1H), 6.94-6.87 (m, 1H), 4.80 (d, J=5.4 Hz, 1H), 4.67 (d, J=9.3 Hz, 1H), 4.48 (app t, J=4.2 Hz, 1H), 4.28 (app t, J=10.2 Hz, 1H), 3.97 (d, J=10.8 Hz, 1H), 3.91 (d, J=5.4 Hz, 1H), 3.65-3.55 (m, 2H), 3.12 (app q, J=6.9 Hz, 1H), 2.65 (s, 3H), 2.47 (s, 5H), 2.39 (s, 3H), 1.32 (d, J=6.9 Hz, 3H), 1.09 (s, 9H) ppm. $^{13}$C NMR (75 MHz, CDCl$_3$): δ174.9, 170.6, 160.2 (J$_{CF}$=238.0 Hz), 136.5 & 136.3, 123.0, 121.0 & 120.92, 120.3 (J$_{CF}$=10.1 Hz), 114.8, 108.6 (J$_{CF}$=24.4 Hz), 97.4 (J$_{CF}$=25.8 Hz), 68.1, 62.7, 60.1, 57.1, 53.2, 47.5, 40.2, 39.0, 35.5, 34.8, 32.7, 26.7, 19.3 ppm. Mass spectrum, m/z [522.3] (M+H)+.

Example 51

N-{2-[6-(6-Fluoro-1H-indol-3-yl)-4-methanesulfonyl-hexahydro-pyrrolo[3,2-b]pyrrol-1-yl]-1-hydroxymethyl-2-oxo-ethyl}-2-methylamino-propionamide $^1$H NMR (300 MHz, d$_4$-MeOH), mixture of amide rotamers: δ7.55 (app dd, J=8.9, 5.3 Hz, 1H), 7.27 (s, 0.8H), 7.11 (s, 0.2H), 7.03 (app dd, J=9.2, 2.1 Hz, 0.8H), 6.97 (app dd, J=9.8, 2.3 Hz, 0.2H), 6.78 (m, 1H), 5.19 (app t, J=6.3 Hz, 0.2H), 5.09 (t, J=7.8 Hz, 0.8H), 4.76 (app t, J=6.2 Hz, 0.2H), 4.50 (app dd, J=9.3, 3.9 Hz, 0.8H), 4.42 (m, 0.8H), 4.24 (m, 0.2H), 4.10 (m, 0.2H), 3.99 (app q, J=6.6 Hz, 0.8H), 3.86 (m, 1H), 3.76 (m, 2H), 3.60 (m, 0.5H), 3.43 (m, 0.5H), 3.29 (m, 2H), 3.05 (s, 0.6H), 3.03 (s, 2.4H), 2.69 (m, 2H), 2.58 (s, 2.4H), 2.48 (s, 0.6H), 2.39 (m, 0.5H), 2.17 (m, 0.5H), 1.99 (s, 3H), 1.41 (d, J=6.9 Hz, 2.4H), 1.26 (d, J=6.9 Hz, 0.6H) ppm. $^{13}$C NMR (75 MHz, d$_4$-MeOH), mixture of amide rotamers: δ175.3, 169.5, 167.9, 161.5, 136.4, 124.5, 122.9, 120.1, 119.9, 112.3, 107.2, 106.9, 97.1, 96.7, 64.9, 62.6, 60.4, 57.2, 54.9, 54.3, 53.9, 38.7, 33.6, 33.4, 33.2, 30.8, 30.6, 15.2 ppm. Mass spectrum, m/z [496.2] (M+H)+.

Example 52

N-{2-[6-(6-Fluoro-1H-indol-3-yl)-4-methanesulfonyl-hexahydro-pyrrolo[3,2-b]pyrrol-1-yl]-1-hydroxymethyl-2-oxo-ethyl}-2-methylamino-propionamide $^1$H NMR (300 MHz, CDCl$_3$+CD$_3$OD) δ9.70 (s, 1H), 7.81 (dd, J=5.4, 8.7 Hz, 1H), 7.35 (s, 1H), 7.05 (dd, J=2.4, 10.2 Hz, 1H), 6.92-6.85 (m, 1H), 4.86 (app t, J=5.4 Hz, 1H), 4.80 (d, J=5.1 Hz, 1H), 4.53 (app t, J=4.5 Hz, 1H), 4.06 (app t, J=10.2 Hz, 1H), 3.98 (d, J=4.8 Hz, 1H), 3.92 (d, J=11.1 Hz, 1H), 3.83 (d, J=5.7 Hz, 2H), 2.62 (s, 3H), 2.55 (s, 3H), 2.46-2.40 (m, 2H), 1.45 (d, J=6.9 Hz, 3H) ppm. $^{13}$C NMR (75 MHz, CDCl$_3$) δ170.9, 169.1, 160.2 (J$_{CF}$=237.1 Hz), 136.8 & 136.6, 123.1, 121.4 & 121.3, 119.0 (J$_{CF}$=10.0 Hz), 114.4, 108.2 (J$_{CF}$=24.4

Hz), 97.6 (J$_{CF}$=25.9 Hz), 68.45, 62.7, 62.1, 57.8, 53.9, 53.4, 46.7, 39.9, 38.5, 32.8, 32.2, 16.6 ppm. Mass spectrum, m/z [496.2] (M+H)+.

Example 53

N-{2-[6-(6-Fluoro-1H-indol-3-yl)-4-methanesulfonyl-hexahydro-pyrrolo[3,2-b]pyrrol-1-yl]-1-methoxymethyl-2-oxo-ethyl}-2-methylamino-propionamide $^1$H NMR (300 MHz, CDCl$_3$/d$_4$-MeOH), mixture of amide rotamers: δ7.55 (m, 0.8H), 7.39 (m, 0.4H), 7.27 (s, 0.6H), 7.18 (s, 0.2H), 7.11 (m, 0.1H), 7.05 (m, 0.8H), 6.99 (m, 0.3H), 6.84 (m, 0.9H), 5.42 (m, 0.1H), 5.12 (m, 0.9H), 4.75 (m, 0.2H), 4.68 (m, 0.1H), 4.53 (m, 0.5H), 4.42 (m, 0.1H), 4.29 (m, 1H), 4.07 (m, 0.8H), 3.92 (m, 0.2H), 3.84 (m, 0.8H), 3.76 (m, 1.4H), 3.68 (m, 0.6H), 3.38 (m, 1.5H), 3.21 (m, 2.2H), 3.10 (m, 0.3H), 3.01 (s, 3H), 2.99 (s, 3H), 2.50 (m, 1.4H), 2.41 (s, 1.5H), 2.32 (s, 1H), 2.26 (s, 0.5H), 2.19 (m, 1H), 2.01 (s, 6H), 1.33 (d, J=6.9 Hz, 1.7H), 1.26 (d, J=6.6 Hz, 0.7H), 1.13 (d, J=6.9 Hz, 0.6H) ppm. $^{13}$C NMR (75 MHz, CDCl$_3$/d$_4$-MeOH), mixture of amide rotamers: δ176.3, 172.1, 170.6, 170.1, 168.3, 167.8, 161.6, 161.4, 158.4, 158.2, 136.7, 136.0, 135.9, 124.7, 124.2, 123.2, 122.9, 122.8, 120.2, 120.1, 119.8, 119.7, 112.5, 111.4, 109.0, 108.6, 108.3, 108.0, 107.7, 107.5, 98.1, 97.7, 97.6, 97.2, 73.4, 71.9, 70.7, 69.9, 65.5, 65.1, 65.0, 64.7, 62.8, 62.2, 59.2, 58.5, 58.0, 57.7, 57.5, 55.6, 55.1, 53.4, 51.0, 50.3, 50.0, 49.9, 49.6, 49.3, 49.0, 48.7, 48.5, 48.2, 47.5, 47.2, 46.9, 42.8, 39.2, 38.2, 37.4, 37.2, 35.2, 34.1, 33.7, 33.0, 32.5, 32.2, 21.9, 17.6, 17.3, 17.2, 17.0 ppm. Mass spectrum, m/z [510.2] (M+H)+.

Example 55

N-{1-[6-(6-Fluoro-1H-indol-3-yl)-4-methanesulfonyl-hexahydro-pyrrolo[3,2-b]pyrrol-1-carbonyl]-2-hydroxy-propyl}-2-methylamino-propionamide $^1$H NMR (300 MHz, CDCl$_3$/d$_4$-MeOH), mixture of amide rotamers: δ7.37 (app dd, J=8.6, 5.3 Hz, 0.8H), 7.22 (dd, J=7.2, 5.1 Hz, 0.2H), 7.00 (s, 0.8H), 6.83 (s, 0.2H), 6.83 (app dd, J=9.8, 2.0 Hz, 0.8H), 6.77 (dd, J=9.6, 2.1 Hz, 0.2H), 6.62 (m, 1H), 5.10 (app t, J=6.3 Hz, 0.2H), 4.90 (app t, J=7.4 Hz, 0.8H), 4.52 (m, 0.2H), 4.19 (app td, J=7.1, 2.9 Hz, 0.8H), 4.05 (m, 1H), 3.90 (m, 0.2H), 3.80 (app q, J=6.8 Hz, 0.8H), 3.66 (m, 1H), 3.58 (m, 2H), 3.45 (app d, J=11.1 Hz, 0.2H), 3.36 (app q, J=6.9 Hz, 0.8H), 3.23 (app t, J=7.2 Hz, 0.2H), 3.13 (m, 1.4H), 3.01 (m, 0.8H), 2.80 (s, 3H), 2.62 (app d, J=7.5 Hz, 0.5H), 2.25 (s, 2.4H), 2.19 (m, 1H), 2.16 (s, 0.6H), 1.93 (m, 1H), 1.79 (s, 6H), 1.14 (app d, J=6.9 Hz, 2.4H), 0.98 (app d, J=6.9 Hz, 0.6H), 0.76 (app d, J=6.3 Hz, 0.6H), 0.43 (app d, J=6.6 Hz, 2.411) ppm. $^{13}$C NMR (75 MHz, CDCl$_3$/d$_4$-MeOH), mixture of amide rotamers: δ176.5, 171.2, 169.5, 161.4, 158.3, 136.1, 135.9, 124.1, 122.9, 119.7, 119.6, 111.7, 108.8, 107.9, 97.6, 97.3, 68.4, 66.8, 65.0, 64.7, 62.7, 57.5, 57.2, 55.3, 54.8, 53.7, 47.7, 46.8, 42.1, 39.1, 36.7, 34.7, 33.6, 33.3, 31.8, 31.5, 29.5, 21.9, 18.5, 18.3, 16.6, 16.2 ppm. Mass spectrum, m/z [510.2] (M+H)+.

Example 57

N-{1-[6-(6-Fluoro-1H-indol-3-yl)-4-methanesulfonyl-hexahydro-pyrrolo[3,2-b]pyrrol-1-carbonyl]-2-methoxy-propyl}-2-methylamino-propionamide $^1$H NMR (300 MHz, d$_6$-DMSO), mixture of amide rotamers: δ11.0 (br s, 0.2H), 10.90 (br s, 0.8H), 7.74 (d, J=8.4 Hz, 0.8H), 7.57 (app dd, J=8.9, 5.6 Hz, 0.8H), 7.50 (app dd, J=8.7, 5.4 Hz, 0.2H), 7.36 (br d, J=7.5 Hz, 0.2H), 7.16 (br d, 0.8H), 7.14 (br d, 0.2H), 7.02 (app dd, J=10.1, 2.3 Hz, 0.8H), 6.95 (app dd, J=10.1, 2.3 Hz, 0.2H), 6.80 (m, 0.8H), 6.71 (m, 0.2H), 5.16 (app t, J=6.8 Hz, 0.2H), 4.98 (t, J=6.6 Hz, 0.8H), 4.60 (t, J=6.3 Hz, 0.2H), 4.48 (app t, J=5.5 Hz, 0.8H), 4.42 (app dd, J=8.6, 5.2 Hz, 0.8H), 4.20 (app dd, J=7.7, 3.2 Hz, 0.2H), 3.90 (m, 1H), 3.81 (m, 1H), 3.75 (m, 1H), 3.53 (m, 1H), 3.36 (m, 1H), 3.20 (m, 1H), 3.04 (s, 3H), 3.03 (s, 3H), 2.92 (app q, J=6.9 Hz, 0.8H), 2.69 (m, 0.2H), 2.10 (s, 2.4H), 2.02 (s, 0.6H), 1.88 (s, 3H), 1.02 (d, J=6.6 Hz, 2.4H), 0.97 (d, J=6.9 Hz, 0.6H), 0.81 (d, J=6.0 Hz, 0.6H), 0.48 (d, J=6.3 Hz, 2.4H) ppm. $^{13}$C NMR (75 MHz, d$_6$-DMSO), mixture of amide rotamers: δ174.5, 172.9, 172.7, 168.9, 168.3, 161.0, 157.9, 136.6, 136.5, 136.3, 136.1, 125.4, 124.2, 120.6, 120.5, 111.4, 110.4, 107.3, 106.9, 97.7, 97.3, 77.8, 76.5, 64.7, 64.6, 64.3, 63.6, 59.6, 59.4, 57.2, 56.4, 54.3, 54.2, 52.9, 47.9, 46.6, 35.8(2), 34.8, 34.7, 33.7, 21.9, 19.4, 19.2, 15.5, 15.4 ppm. Mass spectrum, m/z [524.2] (M+H)+.

Example 58

N-{1-[6-(6-Fluoro-1H-indol-3-yl)-4-methanesulfonyl-hexahydro-pyrrolo[3,2-b]pyrrole-1-carbonyl]-2-methoxy-propyl}-2-methylamino-propionamide $^1$H NMR (300 MHz, CDCl$_3$): δ8.48 (s, 1H), 7.92 (d, J=7.8 Hz, 1H), 7.83 (dd, J=5.4, 8.7 Hz, 1H), 7.19 (s, 1H), 7.02 (dd, J=2.1, 9.6 Hz, 1H), 6.92-6.86 (m, 1H), 4.90 (dd, J=4.2, 7.8 Hz, 1H), 4.81 (d, J=5.4 Hz, 1H), 4.47 (app t, J=4.5 Hz, 1H), 4.07 (app t, J=10.2 Hz, 1H), 3.98-3.91 (m, 2H), 3.74 (app t, J=6.0 Hz, 1H), 3.69-3.60 (m, 2H), 3.42 (s, 3H), 3.15 (app q, J=6.9 Hz, 1H), 2.64 (s, 3H), 2.42 (s, 3H), 2.38-2.36 (m, 1H), 2.02 (m, 5H), 1.34 (d, J=7.8 Hz, 3H), 1.21 (d, J=6.3 Hz, 3H) ppm. $^{13}$C NMR (75 MHz, CDCl$_3$): δ1757, 169.2, 160.4 (J$_{CF}$=238.0 Hz), 136.7 & 136.5, 123.3, 121.2 & 121.1, 120.5 (J$_{CF}$=10.0 Hz), 115.1, 108.8 (J$_{CF}$=24.5 Hz), 97.6 (J$_{CF}$=25.9 Hz), 68.5, 62.6, 60.3, 57.2, 54.7, 53.2, 47.3, 40.2, 39.5, 35.2, 32.9, 19.6, 15.5 ppm. Mass spectrum, m/z [524.3] (M+H)+.

Example 59

N-{2-[4-Acetyl-6-(6-fluoro-1H-indol-3-yl)-hexahydro-pyrrolo[3,2-b]pyrrol-1-yl]-1-cyclohexyl-2-oxo-ethyl}-2-methylamino-propionamide Scheme LXIII

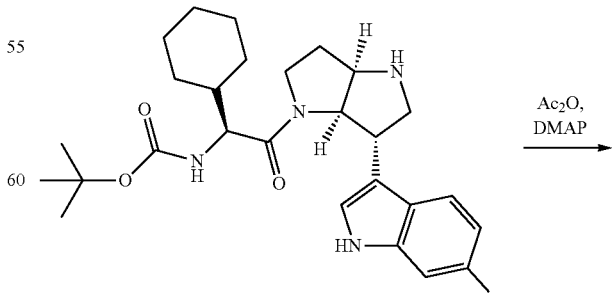

49

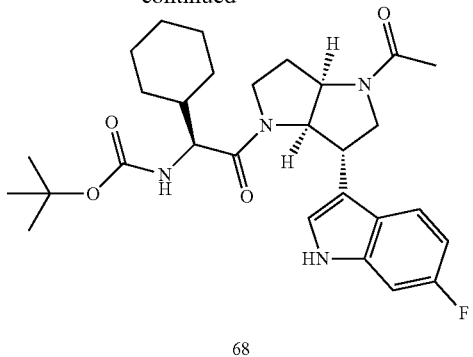

{2-[4-Acetyl-6-(6-fluoro-1H-indol-3-yl)-hexahydro-pyrrolo[3,2-b]pyrrol-1-yl]-1-cyclohexyl-2-oxo-ethyl}-carbamic acid tert-butyl ester (68)

To a solution containing 49 (200 mg, 0.41 mmol) in DCM (5 mL) was added Ac$_2$O (65 mg, 0.63 mmol) and DMAP (5 mg, cat.) at ambient temperature. After 16 h, the reaction mixture was diluted with DCM, washed successively with 1M HCl and brine, dried over anhydrous Na$_2$SO$_4$, filtered, and concentrated to afford 170 mg (78%) of crude 68 which was used without further purification. Mass spectrum, m/z [527] (M+H)+.

N-{2-[4-Acetyl-6-(6-fluoro-1H-indol-3-yl)-hexahydro-pyrrolo[3,2-b]pyrrol-1-yl]-1-cyclohexyl-2-oxo-ethyl}-2-methylamino-propionamide was prepared from 68 in a fashion analogous to that described in Schemes XLVII through XLIX $^1$H NMR (CDCl$_3$, 300 MHz), mixture of amide rotamers: δ8.42 (br s, 0.6H), 8.31 (br s, 0.4H), 8.27-8.23 (m, 0.4H), 8.06-8.01 (m, 0.4H), 7.74 (app t, J=10.2 Hz, 1H), 7.04-6.99 (m, 1H), 6.96-6.89 (m, 1H), 6.81 (dd, J=2.1, 10.5 Hz, 1H), 4.81 (d, J=5.4 Hz, 0.4H), 4.64-4.52 (m, 2.6H), 4.34-4.19 (m, 1.4H), 4.01 (d, J=5.7 Hz, 0.6H), 3.95-3.87 (m, 1H), 3.73-3.66 (m, 0.6H), 3.57-3.38 (m, 1.4H), 3.14-3.06 (m, 1H), 2.52-2.39 (m, 3H), 2.19-2.08 (m, 3H), 2.01 (br s, 3H), 1.87-1.78 (m, 5H), 1.36-1.31 (m, 3H), 1.26-1.00 (m, 4H) ppm. $^{13}$C NMR (CDCl$_3$, 75 MHz), mixture of amide rotamers: δ175.5 & 175.3, 171.1, 169.9 & 169.4, 160.5 ($J_{CF}$=238.3 Hz), 136.8 & 136.6, 136.5 & 136.3, 123.6 & 123.4, 121.5 ($J_{CF}$=10.0 Hz) & 120.9 ($J_{CF}$=10.0 Hz), 120.3 & 119.9, 116.3 & 115.6, 108.9 ($J_{CF}$=24.5 Hz), 97.5 ($J_{CF}$=25.9 Hz), 69.0, 67.6, 60.7 & 60.4, 55.5 & 55.4, 53.2, 49.8, 47.3 & 47.2, 41.2, 39.6 & 39.3, 35.2, 33.1, 30.8, 30.0 & 29.9, 29.1 & 29.0, 26.4 & 26.1, 23.6, 22.1, 19.7 & 19.6 ppm. Mass spectrum, m/z [512.3] (M+H)+.

Examples 60-66 and 94-96 were prepared using the procedures described in Schemes XLIV, XLV, XLVII through XLIX and LXIII by substituting for Boc-Chg-OH with other amino acid reagents including Boc-Abu-OH, Boc-Val-OH, Boc-Tle-OH, Boc-Ser-OH, Cbz-Ser(tBu)-OH, Boc-Ser(Me)-OH, Cbz-Thr(tBu)-OH, Boc-Thr(tBu)-OH, Boc-Thr-OH, or Boc-Thr(Me)-OH and Boc-Ala-OH or Cbz-Ala-OH for Boc-N(Me)Ala-OH or Cbz-N(Me)Ala-OH.

Example 60

N-{1-[4-Acetyl-6-(6-fluoro-1H-indol-3-yl)-hexahydro-pyrrolo[3,2-b]pyrrole-1-carbonyl]-propyl}-2-methylamino-propionamide $^1$H NMR (CDCl$_3$, 300 MHz), mixture of amide rotamers: δ8.54 (br s, 0.6H), 8.42 (br s, 0.4H), 8.21 (dd, J=5.4, 8.7 Hz, 0.4H), 7.98 (dd, J=5.1, 8.7 Hz, 0.6H), 7.83-7.81 (m, 1H), 7.08-6.99 (m, 1H), 6.96-6.89 (m, 1H), 6.84-6.79 (m, 1H), 4.84-4.75 (m, 1.4H), 4.60-4.54 (m, 1.6H), 4.37-3.98 (m, 2H), 3.90-3.86 (m, 1H), 3.74-3.68 (m, 0.6H), 3.52-3.36 (m, 1.4H), 3.19-3.12 (m, 1H), 2.96 (br s, 3.6H), 2.81 (s, 0.4H), 2.55-2.38 (m, 3H), 2.17-1.90 (m, 6H), 1.82-1.70 (m, 1H), 1.35-1.32 (m, 3H), 0.99 (t, J=7.5 Hz, 3H) ppm. $^{13}$C NMR (CDCl$_3$, 75 MHz), mixture of amide rotamers: δ174.8 & 174.6, 170.8, 169.8 & 169.4, 160.3 ($J_{CF}$=237.9 Hz), 136.5 & 136.2, 123.3 & 123.2, 121.1 ($J_{CF}$=10.3 Hz) & 120.5 ($J_{CF}$=10.1 Hz), 120.1 & 119.8, 115.9 & 115.2, 108.6 ($J_{CF}$=24.4 Hz), 97.3 ($J_{CF}$=26.1 Hz), 68.8, 67.4, 60.3 & 60.0, 53.9 & 52.9, 51.8, 49.6, 46.8 & 45.6, 39.4 & 39.1, 34.7 & 33.0, 30.6, 25.8, 23.3, 21.8, 19.2, 9.6 ppm. Mass spectrum, m/z [458.2] (M+H)+.

Example 61

N-{1-[4-Acetyl-6-(6-fluoro-1H-indol-3-yl)-hexahydro-pyrrolo[3,2-b]pyrrole-1-carbonyl]-2-methyl-propyl}-2-methylamino-propionamide $^1$H NMR (300 MHz, CDCl$_3$), mixture of amide rotamers: δ8.62 (s, 0.6H), 8.49 (s, 0.4H), 8.22 (dd, J=5.1, 8.7 Hz, 0.4H), 7.99 (dd, J=5.4, 8.7 Hz, 0.6H), 7.79 (app t, J=8.7 Hz, 1H), 7.04-7.00 (m, 1H), 6.96-6.88 (m, 1H), 6.82 (s, 0.4H), 6.79 (s, 0.6H), 4.82 (d, J=5.4 Hz, 0.4H), 4.6-4.54 (m, 2.6H), 4.30-4.15 (m, 1H), 4.01-3.99 (m, 2H), 3.93-3.86 (m, 2H), 3.74-3.69 (m, 1H), 3.53-3.38 (m, 2H), 3.19-3.12 (m, 1H), 2.54-2.46 (m, 0.6H), 2.43 (s, 1H), 2.39 (s, 2H), 2.17 (s, 2H), 2.12 (s, 1H), 1.36-1.32 (m, 3H), 1.05-0.99 (m, 6H) ppm. $^{13}$C NMR (75 MHz, CDCl$_3$), mixture of amide rotamers: δ175.2 & 175.1, 170.9 & 170.8, 169.7 & 169.2, 160.3 ($J_{CF}$=237.9 Hz), 136.6 & 136.4, 136.3 & 136.1, 123.4 & 123.2, 121.3 & 121.1, 120.6 ($J_{CF}$=10.1 Hz), 120.1 & 120.0, 119.8 & 119.7, 116.0 & 115.3, 108.5 ($J_{CF}$=24.4 Hz), 97.3 ($J_{CF}$=25.9 Hz), 68.8 & 67.3, 60.4 & 60.2, 60.1 & 60.0, 55.9 & 55.7, 52.9, 49.6, 47.0 & 46.9, 39.4 & 39.1, 34.9 & 34.8, 32.9, 31.5 & 30.6, 23.4 & 21.8, 19.5 & 19.4, 19.4, 18.2 & 18.0 ppm. Mass spectrum, m/z [472.3] (M+H)+.

Example 62

N-{1-[4-Acetyl-6-(6-fluoro-1H-indol-3-yl)-hexahydro-pyrrolo[3,2-b]pyrrole-1-carbonyl]-2,2-dimethyl-propyl}-2-methylamino-propionamide $^1$H NMR (CDCl$_3$, 300 MHz), mixture of amide rotamers: δ8.50 (br s, 0.6H), 8.37 (br s, 0.4H), 8.25 (dd, J=5.7, 8.7 Hz, 0.4H), 7.99 (dd, J=5.1, 8.7 Hz, 0.6H), 7.92-7.85 (m, 1H), 7.04-6.99 (m, 1H), 6.97-6.89 (m, 1H), 6.83-6.79 (m, 1H), 4.83 (d, J=5.1 Hz, 0.4H), 4.70-4.52 (m, 2.6H), 4.28-4.17 (m, 1.4H), 3.98-3.85 (m, 1.6H), 3.75-3.69 (m, 0.6H), 3.52-3.39 (m, 1.4H), 3.13-3.07 (m, 1H), 2.42 (s, 1H), 2.38 (s, 2H), 2.16 (s, 2H), 2.11-1.98 (m, 6H), 1.37-1.31 (m, 3H), 1.09 (s, 9H) ppm. $^{13}$C NMR (CDCl$_3$, 75 MHz), mixture of amide rotamers: δ175.1 & 174.9, 170.3, 169.8 & 169.3, 160.3 ($J_{CF}$=237.7 Hz), 136.5 & 136.2, 123.3 & 123.2, 121.2 ($J_{CF}$=9.8 Hz) & 120.5 ($J_{CF}$=10.3 Hz), 120.1 & 119.8, 115.9 & 115.3, 108.6 ($J_{CF}$=24.4 Hz), 97.3 ($J_{CF}$=25.9 Hz) & 97.1 ($J_{CF}$=26.2 Hz), 68.7, 67.3, 60.5 & 60.1, 57.0 & 56.8, 53.0, 49.7, 47.7 & 47.6, 39.7 & 39.3, 35.7, 34.9, 32.9 & 30.6, 26.6, 23.3, 21.8, 19.4 ppm. Mass spectrum, m/z [486.2] (M+H)+.

Example 63

N-{2-[4-Acetyl-6-(6-fluoro-1H-indol-3-yl)-hexahydro-pyrrolo[3,2-b]pyrrol-1-yl]-1-hydroxymethyl-2-oxo-ethyl}-2-methylamino-propionamide $^1$H NMR (CDCl$_3$/d$_4$-MeOH, 300 MHz), mixture of amide rotamers: δ9.47 (br s, 1H), 8.17 (dd, J=5.4, 8.7 Hz, 0.4H), 7.95 (dd, J=5.7, 8.7 Hz, 0.6H), 7.57-7.52 (m, 0.2H), 7.35-7.28 (m, 0.8H), 7.09-7.01 (m, 1H), 6.94-6.87 (m, 1H), 6.81-6.79 (m, 1H), 4.86-4.82 (m, 1H), 4.62-4.47 (m, 1.6H), 4.35-4.32 (m, 0.4H), 4.06-3.94 (m, 1.6H), 3.84-3.76 (m, 3H), 3.60-3.38 (m, 1.4H), 3.24 (br s, MeOH/AcOH/water), 2.44-2.35 (m, 3H), 2.19-2.12 (m, 3H), 2.05-2.00 (m, 2H), 1.38-1.27 (m, 3H) ppm. $^{13}$C NMR (CDCl$_3$, 75 MHz), mixture of amide rotamers: δ174.7, 170.5 & 170.1, 169.4 & 169.3, 160.3 (J$_{CF}$=237.4 Hz), 136.4 & 136.2, 123.4 & 123.2, 120.7 (J$_{CF}$=10.6 Hz) & 120.2 (J$_{CF}$=10.7 Hz), 115.4 & 114.7, 108.2 (J$_{CF}$=24.5 Hz), 97.4 (J$_{CF}$=25.9 Hz) & 97.2, 69.0, 67.7, 62.9 & 62.8, 60.6 & 60.1, 59.2, 53.2 & 53.0, 46.9, 39.2 & 39.1, 33.9 & 32.9, 30.6, 23.1, 21.7, 18.3 ppm. Mass spectrum, m/z [460.2] (M+H)+.

Example 64

N-{2-[4-Acetyl-6-(6-fluoro-1H-indol-3-yl)-hexahydro-pyrrolo[3,2-b]pyrrol-1-yl]-1-methoxymethyl-2-oxo-ethyl}-2-methylamino-propionamide $^1$H NMR (CDCl$_3$, 300 MHz), mixture of amide rotamers: δ8.44 (br s, 0.6H), 8.34 (br s, 0.4H), 8.23 (dd, J=5.1, 8.7 Hz, 0.4H), 8.06-7.99 (m, 0.6H), 7.90-7.78 (m, 1H), 7.06-7.01 (m, 1H), 6.97-6.89 (m, 1H), 6.83-6.79 (m, 1H), 5.06-4.95 (m, 1H), 4.82 (d, J=5.4 Hz, 0.4H), 4.58-4.54 (m, 1.6H), 4.31 (t, J=4.5 Hz, 0.4H), 4.12-3.91 (m, 1.6H), 3.88-3.43 (m, 4H), 3.40-3.36 (m, 3H), 3.20-3.11 (m, 1H), 2.43-2.40 (m, 8H), 2.18-2.08 (m, 5H), 1.35-1.32 (m, 3H) ppm. $^{13}$C NMR (CDCl$_3$, 75 MHz), mixture of amide rotamers: δ175.0 & 174.8, 169.7 & 169.2, 160.3 (J$_{CF}$=239.7 Hz), 136.6 & 136.1, 123.4 & 123.2, 121.2 (J$_{CF}$=9.6 Hz) & 120.6 (J$_{CF}$=10.0 Hz), 119.8 & 119.7, 116.3 & 116.1, 115.5 & 115.4, 108.6 (J$_{CF}$=24.4 Hz), 97.3 (J$_{CF}$=26.1 Hz) & 97.2 (J$_{CF}$=25.9 Hz), 72.9, 72.6 & 72.4, 68.8, 67.5, 60.4 & 60.3, 59.9, 59.3 & 59.2, 52.7, 50.6 & 50.2, 49.4, 47.0 & 46.4, 39.3 & 39.0, 34.9 & 34.8, 33.1 & 32.9, 30.5, 23.4, 21.8, 19.4 & 19.2 ppm. Mass spectrum, m/z [474.1] (M+H)+.

Example 65

N-{1-[4-Acetyl-6-(6-fluoro-1H-indol-3-yl)-hexahydro-pyrrolo[3,2-b]pyrrole-1-carbonyl]-2-hydroxy-propyl}-2-methylamino-propionamide $^1$H NMR (CDCl$_3$/d$_4$-MeOH, 300 MHz), mixture of amide rotamers: δ9.33 (br s, 1H), 8.16 (dd, J=5.7, 8.7 Hz, 0.6H), 8.08 (br, 0.4H), 7.95 (dd, J=5.1, 8.4 Hz, 0.6H), 7.59 (dd, J=6.0, 9.0 Hz, 0.4H), 7.08-7.00 (m, 1H), 6.94-6.85 (m, 1H), 6.82-6.78 (m, 1H), 4.82 (d, J=5.4 Hz, 0.4H), 4.69-4.49 (m, 2.6H), 4.34-4.23 (m, 0.6H), 4.16-4.10 (m, 1.4H), 4.01-3.98 (m, 0.4H), 3.91-3.72 (m, 1.6H), 3.61-3.39 (m, 1.4H), 3.25-3.19 (m, 0.6H), 2.97 (br s, MeOH/AcOH/water), 2.51-2.37 (m, 3H), 2.19-1.98 (m, 5H), 1.39-1.21 (m, 6H) ppm. $^{13}$C NMR (CDCl$_3$, 75 MHz), mixture of amide rotamers: δ175.2, 170.1 & 169.8, 160.3 (J$_{CF}$=237.7 Hz), 136.3, 123.3 & 123.2, 120.9 & 120.2 (J$_{CF}$=9.8 Hz), 115.5 & 114.8, 108.3 (J$_{CF}$=25.2 Hz), 97.4 (J$_{CF}$=26.2 Hz) & 97.3, 68.8, 67.9 & 67.7, 67.5, 60.5 & 60.1, 59.6, 55.4, 53.0, 47.1, 39.4 & 39.2, 34.3 & 33.0, 30.6, 23.2 & 21.7, 19.1 & 18.7 ppm. Mass spectrum, m/z [474.2] (M+H)+.

Example 66

N-{1-[4-Acetyl-6-(6-fluoro-1H-indol-3-yl)-hexahydro-pyrrolo[3,2-b]pyrrole-1-carbonyl]-2-methoxy-propyl}-2-methylamino-propionamide $^1$H NMR (CDCl$_3$, 300 MHz), mixture of amide rotamers: δ8.41 (br s, 0.6H), 8.30 (br s, 0.4H), 8.24 (dd, J=5.1, 8.7 Hz, 0.4H), 8.00 (dd, J=5.4, 8.4 Hz, 0.6H), 7.91-7.87 (m, 1H), 7.05-7.00 (m, 1H), 6.97-6.89 (m, 1H), 6.84-6.80 (m, 1H), 4.94-4.84 (m, 1.5H), 4.62-4.55 (m, 1.5H), 4.30 (t, J=5.1 Hz, 0.5H), 4.11-3.99 (m, 1.5H), 3.91-3.86 (m, 1H), 3.76-3.71 (m, 1.5H), 3.61-3.49 (m, 0.5H), 3.44-3.39 (m, 3H), 3.20-3.12 (m, 1H), 2.66 (br s, 5H), 2.53-2.43 (m, 3H), 2.17-2.07 (m, 6H), 1.36-1.32 (m, 3H), 1.23-1.20 (m, 3H) ppm. $^{13}$C NMR (CDCl$_3$, 75 MHz), mixture of amide rotamers: δ175.0 & 174.8, 169.7 & 169.3, 168.7, 160.3 (J$_{CF}$=237.9 Hz), 136.5 & 136.1, 123.3 & 123.2, 121.2 (J$_{CF}$=10.0 Hz) & 120.6 (J$_{CF}$=9.8 Hz), 119.8 & 119.7, 116.0 & 115.3, 108.6 (J$_{CF}$=24.5 Hz), 97.4 (J$_{CF}$=26.2 Hz) & 97.2 (J$_{CF}$=26.2 Hz), 68.9 & 67.5, 60.3 & 59.9, 57.1 & 56.9, 54.6 & 54.2, 52.8, 49.5, 47.3, 39.4 & 39.1, 34.7, 33.0 & 30.6, 23.4 & 21.8, 19.2, 15.3 & 15.2 ppm. Mass spectrum, m/z [488.2] (M+H)+.

Examples 67-74 were prepared using the procedures described in Schemes XXV through XXXI, XLIV, XLV, XLVII through XLIX, and LXIII and by substituting 6-F indole with 5-F indole and Boc-Chg-OH with other amino acid reagents including Boc-Abu-OH, Boc-Val-OH, Boc-Tle-OH, Boc-Ser-OH, Cbz-Ser(tBu)-OH, Boc-Ser(Me)-OH, Cbz-Thr(tBu)-OH, Boc-Thr(tBu)-OH, Boc-Thr-OH, or Boc-Thr(Me)-OH.

Example 67

N-{1-[4-Acetyl-6-(5-fluoro-1H-indol-3-yl)-hexahydro-pyrrolo[3,2-b]pyrrole-1-carbonyl]-propyl}-2-methylamino-propionamide $^1$H NMR (CDCl$_3$, 300 MHz), mixture of amide rotamers: δ8.46 (br s, 0.6H), 8.34 (br s, 0.4H), 8.01 (dd, J=2.4, 9.9 Hz, 0.4H), 7.86 (t, J=6.0 Hz, 1H), 7.74 (dd, J=2.7, 9.6 Hz, 0.6H), 7.32-7.23 (m, 1H), 6.99-6.87 (m, 2H), 4.83-4.73 (m, 1H), 4.61-4.55 (m, 1.6H), 4.30 (t, J=4.8 Hz, 0.4H), 4.19-4.04 (m, 1H), 3.96-3.86 (m, 1.4H), 3.73-3.68 (m, 0.6H), 3.53-3.36 (m, 1H), 3.22-3.13 (m, 1H), 3.05 (br s, 4H), 2.55-2.48 (m, 1H), 2.46 (s, 1H), 2.42 (s, 2H), 2.17-2.13 (m, 3H), 2.09-1.89 (m, 3H), 1.82-1.70 (m, 1H), 1.38-1.32 (m, 3H), 1.02-0.97 (m, 2.6H), 0.87-0.81 (m, 0.4H) ppm. $^{13}$C NMR (CDCl$_3$, 75 MHz), mixture of amide rotamers: δ174.8 & 174.6, 170.8, 169.8 & 169.3, 157.9 (J$_{CF}$=235.1 Hz), 133.1 & 132.7, 127.1, 121.4 (J$_{CF}$=21.9 Hz) 115.9 & 115.3, 111.7 & 111.6, 111.1 (J$_{CF}$=26.8 Hz) & 110.9 (J$_{CF}$=26.5 Hz), 105.3 (J$_{CF}$=24.1 Hz) & 104.6 (J$_{CF}$=23.9 Hz), 68.7, 67.4 & 67.2, 60.3 & 69.9, 52.9, 51.7, 49.5, 46.7, 39.4 & 39.2, 34.7, 33.0, 30.7, 25.7, 23.3, 21.9 & 21.2, 19.2, 9.6 ppm. Mass spectrum, m/z [458.2] (M+H)+.

Example 68

N-{1-[4-Acetyl-6-(5-fluoro-1H-indol-3-yl)-hexahydro-pyrrolo[3,2-b]pyrrole-1-carbonyl]-2-methyl-propyl}-2-methylamino-propionamide $^1$H NMR (CDCl$_3$, 300 MHz), mixture of amide rotamers: δ8.36 (br s, 0.6H), 8.24 (br s, 0.4H), 8.03 (dd, J=2.4, 9.6 Hz, 0.4H), 7.82-7.74 (m, 1.6H), 7.28-7.23 (m, 0.4H), 6.99-6.86 (m, 1.6H), 4.81 (d, J=5.4 Hz, 0.4H), 4.65-4.54 (m, 2.6H), 4.31-4.13 (m, 1.4H), 3.97-3.85 (m, 1.6H), 3.74-3.68 (m, 0.6H), 3.55-3.38 (m, 1.4H), 3.17-3.08 (m, 1H), 2.53-2.47 (m, 1H), 2.45 (s, 1H), 2.41 (s, 2H), 2.21-1.94 (m, 10H), 1.38-1.32 (m, 3H), 1.05-0.98 (m, 6H) ppm. $^{13}$C NMR (CDCl$_3$, 75 MHz), mixture of amide rotamers: δ175.4 & 175.2, 170.8, 169.7 & 169.2, 157.9 (J$_{CF}$=235.1 Hz), 133.1 & 132.7, 127.1, 121.5 (J$_{CF}$=21.9 Hz), 116.1 & 115.5, 111.7 & 111.5, 111.1 (J$_{CF}$=26.2 Hz) & 110.9 (J$_{CF}$=26.8 Hz), 105.4 (J$_{CF}$=23.9 Hz) & 104.7 (J$_{CF}$=23.9 Hz), 68.6, 67.2, 60.4 & 60.1, 55.8 & 55.6, 52.9, 49.5, 46.9, 39.4 & 39.1, 34.9, 33.0, 31.4 & 30.6, 23.3, 21.9, 19.5, 18.1 & 17.9 ppm. Mass spectrum, m/z [472.2] (M+H)+.

Example 69

N-{1-[4-Acetyl-6-(5-fluoro-1H-indol-3-yl)-hexahydro-pyrrolo[3,2-b]pyrrole-1-carbonyl]-2,2-dimethyl-propyl}-2-methylamino-propionamide $^1$H NMR (CDCl$_3$, 300 MHz), mixture of amide rotamers: δ8.54 (br s, 0.6H), 8.38 (br s, 0.4H), 8.04 (dd, J=2.7, 9.9 Hz, 0.4H), 7.93-7.86 (m, 1H), 7.72 (dd, J=2.4, 9.6 Hz, 0.6H), 7.27-7.22 (m, 0.4H), 6.98-6.85 (m, 1.6H), 4.81 (d, J=5.4 Hz, 0.4H), 4.69-4.52 (m, 2.6H), 4.29-4.16 (m, 1.4H), 3.92-3.83 (m, 1.6H), 3.74-3.69 (m, 0.6H), 3.55-3.39 (m, 1.4H), 3.17-3.08 (m, 1H), 2.53-2.46 (m, 1H), 2.44 (s, 1H), 2.39 (s, 2H), 2.28 (br s, 3H), 2.15-2.06 (m, 5H), 1.36-1.31 (m, 3H), 1.09 (s, 9H) ppm. $^{13}$C NMR (CDCl$_3$, 75 MHz), mixture of amide rotamers: δ175.1 & 175.0, 170.2 & 170.1, 169.7 & 169.3, 157.9 (J$_{CF}$=234.5 Hz), 133.1 & 132.7, 127.1, 121.4 (J$_{CF}$=18.7 Hz) 116.1 & 115.5, 111.8 & 111.5, 111.1 (J$_{CF}$=26.4 Hz) & 110.9 (J$_{CF}$=26.8 Hz), 105.4 (J$_{CF}$=24.4 Hz) & 104.7 (J$_{CF}$=23.9 Hz), 68.6, 67.1, 60.4 & 60.1, 57.0 & 56.8, 53.0, 49.6, 47.6, 39.7 & 39.3, 35.7, 34.9, 32.9, 30.7, 26.7, 23.3, 21.9, 19.4 ppm. Mass spectrum, m/z [486.3] (M+H)+.

Example 70

N-{2-[4-Acetyl-6-(5-fluoro-1H-indol-3-yl)-hexahydro-pyrrolo[3,2-b]pyrrol-1-yl]-1-cyclohexyl-2-oxo-ethyl}-2-methylamino-propionamide $^1$H NMR (CDCl$_3$, 300 MHz), mixture of amide rotamers: δ8.59 (br s, 0.6H), 8.45 (br s, 0.4H), 8.02 (dd, J=2.1, 9.6 Hz, 0.4H), 7.81-7.74 (m, 1.6H), 7.27-7.22 (m, 0.4H), 6.98-6.85 (m, 1.6H), 4.80 (d, J=5.4 Hz, 0.4H), 4.65-4.52 (m, 2.6H), 4.30-4.17 (m, 1.4H), 3.98-3.86 (m, 1.4H), 3.72-3.66 (m, 0.6H), 3.53-3.38 (m, 1.6H), 3.18-3.09 (m, 1H), 2.62-2.47 (br m, 4H), 2.44 (s, 1H), 2.39 (s, 2H), 2.18-1.97 (m, 5H), 1.87-1.68 (m, 5H), 1.36-1.31 (m, 3H), 1.27-1.05 (m, 4H) ppm. $^{13}$C NMR (CDCl$_3$, 75 MHz), mixture of amide rotamers: δ175.2 & 175.0, 170.8, 169.8 & 169.3, 157.8 (J$_{CF}$=234.8 Hz), 133.1 & 132.8, 127.1, 121.4 (J$_{CF}$=20.7 Hz), 115.9 & 115.3, 111.8 & 111.6, 111.3 (J$_{CF}$=26.5 Hz) & 110.9 (J$_{CF}$=26.5 Hz), 105.3 (J$_{CF}$=23.9 Hz) & 104.7 (J$_{CF}$=23.9 Hz), 68.7, 67.2, 60.5 & 60.1, 55.3 & 55.2, 52.9, 49.6, 47.0, 40.9, 39.4 & 39.0, 34.8, 32.9, 30.6, 29.8, 28.8, 26.1 & 25.9, 23.3, 21.8, 19.4 ppm. Mass spectrum, m/z [512.3] (M+H)+.

Example 71

N-{1-[4-Acetyl-6-(5-fluoro-1H-indol-3-yl)-hexahydro-pyrrolo[3,2-b]pyrrole-1-carbonyl]-2-methoxy-propyl}-2-methylamino-propionamide $^1$H NMR (CDCl$_3$, 300 MHz), mixture of amide rotamers: δ8.38 (br s, 0.6H), 8.26 (br s, 0.4H), 8.04 (dd, J=2.4, 9.9 Hz, 0.4H), 7.93 (app t, J=7.5 Hz, 1H), 7.76 (dd, J=2.4, 9.6 Hz, 0.6H), 7.30-7.24 (m, 0.4H), 7.29-7.23 (m, 1H), 6.99-6.87 (m, 2H), 4.93-4.83 (m, 1.4H), 4.63-4.55 (m, 1.6H), 4.29 (t, J=4.8 Hz, 0.4H), 4.09-3.95 (m, 1.6H), 3.88-3.84 (m, 1H), 3.76-3.70 (m, 1.6H), 3.61-3.49 (m, 1H), 3.44 (s, 2H), 3.40 (s, 1H), 3.22-3.09 (m, 1.4H), 2.48-2.43 (m, 3H), 2.17-2.00 (m, 7H), 1.35-1.31 (m, 3H), 1.23-1.19 (m, 3H) ppm. $^{13}$C NMR (CDCl$_3$, 75 MHz), mixture of amide rotamers: δ175.4 & 175.2, 169.9 & 169.4, 168.8, 158.1 (J$_{CF}$=235.1 Hz), 133.3 & 132.7, 127.3, 121.6 (J$_{CF}$=21.3 Hz), 116.2 & 115.6, 112.0 & 111.8, 111.3 (J$_{CF}$=26.8 Hz) & 111.1 (J$_{CF}$=26.5 Hz), 105.6 (J$_{CF}$=23.8 Hz) & 104.8 (J$_{CF}$=23.9 Hz), 69.0 & 67.6, 60.5 & 60.3, 57.2, 54.7 & 54.3, 53.0, 49.6 & 47.5, 39.7 & 39.4, 35.1, 33.2, 30.9, 23.6, 22.1, 19.5, 15.6 & 15.4 ppm. Mass spectrum, m/z [488.2] (M+H)+.

Example 72

N-{2-[4-Acetyl-6-(5-fluoro-1H-indol-3-yl)-hexahydro-pyrrolo[3,2-b]pyrrol-1-yl]-1-methoxymethyl-2-oxo-ethyl}-2-methylamino-propionamide $^1$H NMR (CDCl$_3$, 300 MHz), mixture of amide rotamers: δ8.35 (br s, 0.6H), 8.25 (br s, 0.4H), 8.05 (dd, J=2.4, 9.6 Hz, 0.4H), 7.94-7.89 (m, 0.6H), 7.79 (dd, J=2.1, 9.6 Hz, 1H), 7.30-7.24 (m, 0.4H), 7.00-6.87 (m, 1.6H), 5.05-496 (m, 1H), 4.81 (d, J=5.4 Hz, 0.4H), 4.60-4.56 (m, 1.4H), 4.33-4.29 (m, 0.4H), 4.11-3.93 (m, 1.6H), 3.88-3.84 (m, 0.6H), 3.80-3.46 (m, 3.6H), 3.41-3.36 (m, 3H), 3.18-3.09 (m, 1H), 2.52-2.42 (m, 3.4H), 2.18-2.07 (m, 3.6H), 1.35-1.30 (m, 3H) ppm. $^{13}$C NMR (CDCl$_3$, 75 MHz), mixture of amide rotamers: δ175.2 & 175.0, 169.6 & 169.1, 157.9 (J$_{CF}$=234.8 Hz), 133.1 & 132.7, 127.2, 121.4 (J$_{CF}$=23.6 Hz), 116.2, 111.8 & 111.6, 111.3 (J$_{CF}$=26.5 Hz), 105.2 & 104.8 (J$_{CF}$=23.6 Hz), 73.1 & 72.5, 68.8, 67.4, 60.3 & 60.0, 59.3, 52.6, 50.5 & 49.2, 46.9 & 46.4, 39.1 & 38.8, 35.0, 32.9, 30.6, 23.4, 21.9, 19.3 ppm. Mass spectrum, m/z [474.2] (M+H)+.

Example 73

N-{2-[4-Acetyl-6-(5-fluoro-1H-indol-3-yl)-hexahydro-pyrrolo[3,2-b]pyrrol-1-yl]-1-hydroxymethyl-2-oxo-ethyl}-2-methylamino-propionamide $^1$H NMR (CDCl$_3$/d$_4$-MeOH, 300 MHz), mixture of amide rotamers: δ7.95 (d, J=9.9 Hz, 0.4H), 7.73 (d, J=9.6 Hz, 0.6H), 7.31-7.26 (m, 1H), 6.97-6.87 (m, 2H), 4.88-4.82 (m, 1H), 4.62-4.48 (m, 1.6H), 4.38-4.36 (m, 0.4H), 4.17-4.11 (m, 0.4H), 4.07-4.01 (m, 1H), 3.94-3.79 (m, 1.6H), 3.71 (br s, MeOH/AcOH/water), 3.39-3.37 (m, 1H), 3.25-3.12 (m, 1H), 2.44-2.39 (m, 3H), 2.18-2.14 (m, 3H), 2.06-1.99 (m, 2H), 1.36-1.26 (m, 3H) ppm. Mass spectrum, m/z [460.2] (M+H)+.

Example 74

N-{1-[4-Acetyl-6-(5-fluoro-1H-indol-3-yl)-hexahydro-pyrrolo[3,2-b]pyrrole-1-carbonyl]-2-hydroxypropyl}-2-methylamino-propionamide $^1$H NMR (CDCl$_3$/d$_4$-MeOH, 300 MHz), mixture of amide rotamers: δ9.38 (br s, 1H), 7.95 (dd, J=2.4, 9.9 Hz, 0.4H), 7.72 (dd, J=2.4, 10.2 Hz, 0.6H), 7.30-7.42 (m, 1H), 6.98-6.89 (m, 1H), 6.87 (s, 1H), 4.81 (d, J=5.4 Hz, 0.4H), 4.69-4.49 (m, 2.4H), 4.33-4.23 (m, 0.6H), 4.19-4.09 (m, 1.4H), 3.97-3.95 (m, 0.6H), 3.89-3.86 (m, 1H), 3.79-3.73 (m, 0.6H), 3.57-3.38 (m, 1.4H), 3.26-3.20 (m, 1H), 3.11 (br s, MeOH/AcOH/water), 2.50-2.46 (m, 0.6H), 2.44-2.41 (m, 3H), 2.17-1.95 (m, 5H), 1.37-1.33 (m, 3H), 1.24 (d, J=6.0 Hz, 3H) ppm. $^{13}$C NMR (CDCl$_3$, 75 MHz), mixture of amide rotamers: δ175.5 & 175.3, 170.5 & 170.1, 157.9 (J$_{CF}$=234.3 Hz), 133.4& 133.1, 127.1, 121.8 & 121.6 (J$_{CF}$=12.4 Hz), 115.4& 114.8, 112.0, 110.8 (J$_{CF}$=26.5 Hz) & 110.7 (J$_{CF}$=26.5 Hz), 105.0 (J$_{CF}$=24.4 Hz) & 104.5 (J$_{CF}$=23.9 Hz), 68.9, 67.9, 67.6, 60.7 & 60.2, 59.7, 55.9 & 55.8, 53.1, 47.2, 39.5 & 39.3, 34.3 & 33.1, 30.7, 23.3 & 21.8, 19.4 & 19.2, 18.9 & 18.8 ppm. Mass spectrum, m/z [474.1] (M+H)+.

Example 75

N-{1-Cyclohexyl-2-[6-(6-fluoro-1H-indol-3-yl)-4-pyrimidin-2-yl-hexahydro-pyrrolo[3,2-b]pyrrol-1-yl]-2-oxo-ethyl}-2-methylamino-propionamide Scheme LXIV

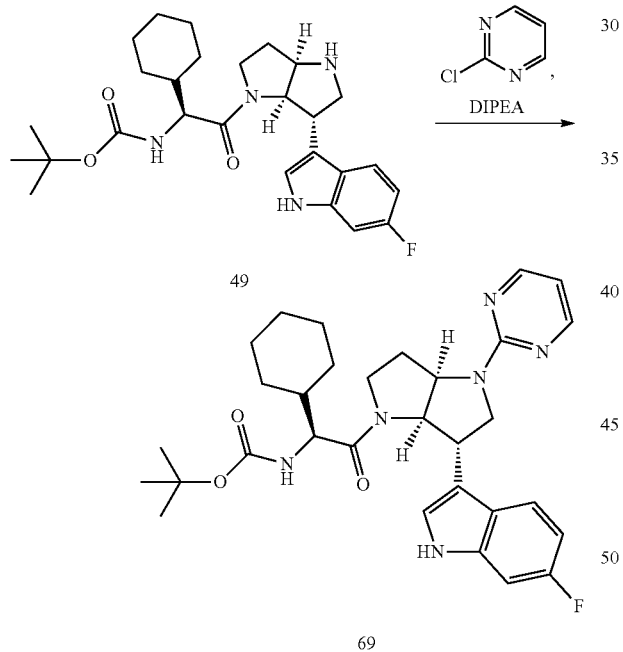

{1-Cyclohexyl-2-[4-(6-fluoro-1H-indol-3-yl)-4-pyrimidin-2-yl-hexahydro-pyrrolo[3,2-b]pyrrol-1-yl]-2-oxo-ethyl}-carbamic acid tert-butyl ester (69)

To a solution containing 49 (375 mg, 0.77 mmol) in anhydrous DMF (5 mL) was added DIPEA (118 mg, 0.92 mmol) and 2-chloropyrimidine (97 mg, 0.85 mmol) at ambient temperature. The reaction mixture was warmed to 70° C. After 16 h, the reaction mixture was cooled to ambient temperature and diluted with water and subsequently extracted with diethyl ether. The organic extract was washed successively with water and brine, dried over anhydrous Na$_2$SO$_4$, filtered, and concentrated. The crude product was purified by flash silica gel chromatography (1:1 hexanes/EtOAc) to afford 260 mg (60%) of 69 as a white solid. Mass spectrum, m/z [563] (M+H)+.

N-{1-Cyclohexyl-2-[6-(6-fluoro-1H-indol-3-yl)-4-pyrimidin-2-yl-hexahydro-pyrrolo[3,2-b]pyrrol-1-yl]-2-oxo-ethyl}-2-methylamino-propionamide was prepared from 69 in a fashion analogous to that described in Schemes 47 through 49: $^1$H NMR (CDCl$_3$, 300 MHz): δ8.38 (d, J=4.8 Hz, 2H), 8.19 (dd, J=5.4, 8.5 Hz, 1H), 8.09 (br s, 1H), 7.74 (d, J=9.0 Hz, 1H), 6.99-6.89 (m, 2H), 6.68 (s, 1H), 6.59 (t, J=4.8 Hz, 1H), 4.72 (d, J=5.4 Hz, 1H), 4.67-4.57 (m, 2H), 4.49 (d, J=11.7 Hz, 1H), 4.18 (t, J=9.6 Hz, 1H), 4.07 (d, J=5.4 Hz, 1H), 3.71 (dd, J=6.0, 11.7 Hz, 1H), 3.52-3.43 (m, 1H), 3.11 (dd, J=7.2, 14.1 Hz, 1H), 2.52-2.46 (m, 1H), 2.42 (s, 3H), 2.09-1.97 (m, 5H), 1.87-1.67 (m, 6H), 1.32 (d, J=6.9 Hz, 3H), 1.26-1.04 (m, 5H) ppm. $^{13}$C NMR (CDCl$_3$, 75 MHz) δ175.1, 170.8, 160.3 (J$_{CF}$=237.0 Hz), 159.8, 157.9, 136.3, 123.5, 121.1 (J$_{CF}$=10.0 Hz), 120.0, 116.7, 110.0, 108.5 (J$_{CF}$=24.2 Hz), 97.1 (J$_{CF}$=26.2 Hz), 68.2, 60.3, 60.2, 55.2, 51.2, 47.2, 41.1, 38.9, 34.9, 30.7, 29.8, 28.8, 26.2, 25.9, 19.5 ppm. Mass spectrum, m/z [546.6] (M)+.

Example 76

N-{2-[4-(4-Chloro-pyrimidin-2-yl)-6-(6-fluoro-1H-indol-3-yl)-hexahydro-pyrrolo[3,2-b]pyrrol-1-yl]-1-cyclohexyl-2-oxo-ethyl}-2-methylamino-propionamide was prepared using the procedures described in Scheme LXIV and Schemes XLVII-XLIX by substituting 2-chloropyrimidine with 2,4-dichloropyrimidine: $^1$H NMR (CDCl$_3$, 300 MHz): δ8.24-8.12 (m, 3H), 7.77 (d, J=9.0 Hz, 1H), 7.03-6.91 (m, 2H), 6.66 (s, 1H), 6.38-6.28 (m, 1H), 4.84-4.57 (m, 3H), 4.34-4.08 (m, 3H), 3.69-3.66 (m, 1H), 3.46 (br s, 1H), 3.12 (dd, J=6.9, 13.8 Hz, 1H), 2.43 (s, 3H), 2.08-1.69 (m, 10H), 1.32 (d, J=7.2 Hz, 3H), 1.28-1.05 (m, 5H) ppm. $^{13}$C NMR (CDCl$_3$, 75 MHz) δ175.2, 171.0, 160.7, 160.4 (J$_{CF}$=238.3 Hz), 156.9, 136.3, 123.2, 120.7 (J$_{CF}$=10.0 Hz), 119.8, 115.7, 108.8 (J$_{CF}$=24.4 Hz), 102.0, 97.3 (J$_{CF}$=25.6 Hz), 68.5, 60.9, 60.2, 55.3, 51.0, 47.0, 40.9, 39.0, 35.0, 29.8, 28.9, 26.2, 25.9, 19.4 ppm. Mass spectrum, m/z [582.2] (M)+.

Example 77

N-{1-[6-(6-Fluoro-1H-indol-3-yl)-4-pyrimidin-2-yl-hexahydro-pyrrolo[3,2-b]pyrrole-1-carbonyl]-2-methyl-propyl}-2-methylamino-propionamide (75)

Scheme LXV

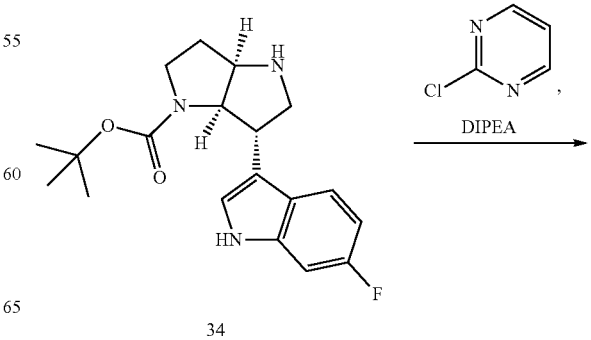

-continued

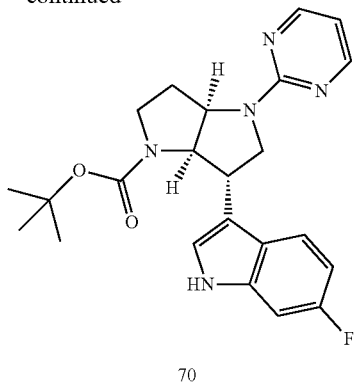

70

6-(6-Fluoro-1H-indol-3-yl)-4-pyrimidin-2-yl-hexahydro-pyrrolo[3,2-b]pyrrole-1-carboxylic acid tert-butyl ester (70)

A solution containing 34 (370 mg, 1.07 mmol), DIPEA (163 mg, 1.26 mmol), and 2-chloropyrimidine (135 mg, 1.17 mmol) in anhydrous DMF (6 mL) was warmed to 70° C. After 16 h, the reaction mixture was cooled to ambient temperature and diluted with water and subsequently extracted with diethyl ether. The organic extract was washed successively with water and brine, dried over anhydrous $Na_2SO_4$, filtered, and concentrated. The crude product was purified by flash silica gel chromatography (1:1 hexanes/EtOAc) to afford 210 mg (46%) of 70 as a white solid. Mass spectrum, m/z [424] (M+H)+.

Scheme LXVI

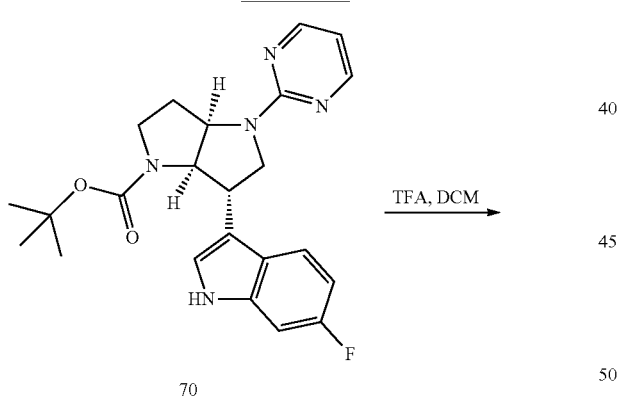

6-Fluoro-3-(1-pyrimidin-2-yl-octahydro-pyrrolo[3,2-b]pyrrol-3-yl)-1H-indole (71)

To a solution containing 70 (210 mg, 0.49 mmol) in DCM (10 mL) was added TFA (4 mL) at 0° C. After 2.5 h, the reaction mixture was concentrated in vacuo. The residue was dissolved in EtOAc and the resultant organic solution was washed successively with saturated aqueous $NaHCO_3$ and brine, dried over anhydrous $Na_2SO_4$, filtered, and concentrated to afford 150 mg (93%) of 71 which was used without further purification. Mass spectrum, m/z [324] (M+H)+.

Scheme LXVII

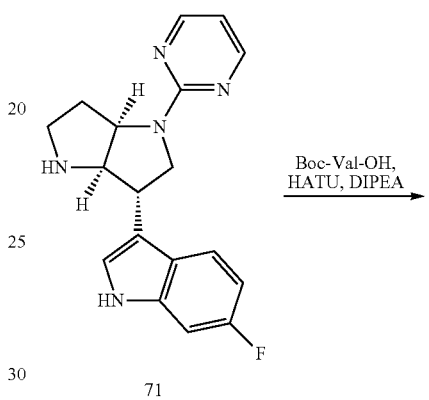

71

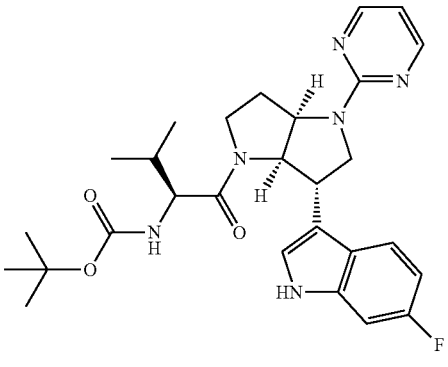

72

{1-[6-(6-Fluoro-1H-indol-3-yl)-4-pyrimidin-2-yl-hexahydro-pyrrolo[3,2-b]pyrrole-1-carbonyl]-2-methyl-propyl}-carbamic acid tert-butyl ester (72)

To a solution containing Boc-Val-OH (106 mg, 0.48 mmol) in anhydrous NMP (3 mL) was cooled to 0° C. HATU (185 mg, 0.48 mmol) and DIPEA (67 mg, 0.52 mmol) were added followed by the addition of crude 71 (150 mg, 0.46 mmol) in anhydrous NMP (3 mL). After 2.5 h, the reaction mixture was diluted with diethyl ether and washed successively with water, aqueous $NaHCO_3$, water, and brine, dried over anhydrous $Na_2SO_4$, filtered, and concentrated. The crude product was purified by flash silica gel chromatography (1:1 hexanes/EtOAc) to afford 210 mg (86%) of 72 as a white-colored foam. Mass spectrum, m/z [523] (M+H)+.

Scheme LXVIII

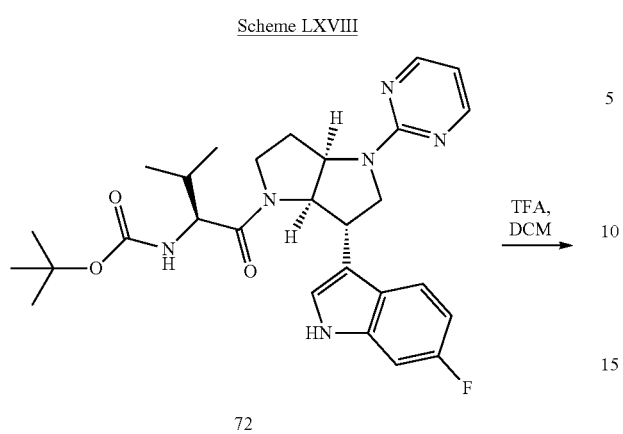

72

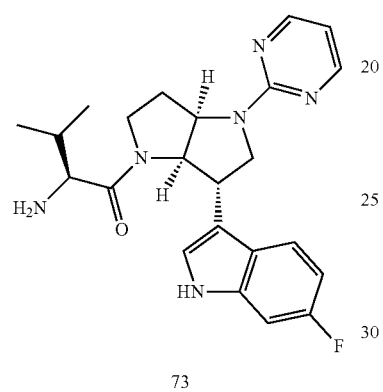

73

2-Amino-1-[6-(6-fluoro-1H-indol-3-yl)-4-pyrimidin-2-yl-hexahydro-pyrrolo[3,2-b]pyrrol-1-yl]-3-methyl-butan-1-one (73)

To a solution containing 72 (210 mg, 0.40 mmol) in DCM (10 mL) was added TFA (4 mL) at 0° C. After 90 min, the reaction mixture was concentrated in vacuo. The residue was dissolved in EtOAc and the resultant organic solution was washed successively with saturated aqueous NaHCO$_3$ and brine, dried over anhydrous Na$_2$SO$_4$, filtered, and concentrated to afford 148 mg (87%) of 73 which was used without further purification. Mass spectrum, m/z [423] (M+H)+.

Scheme LXIX

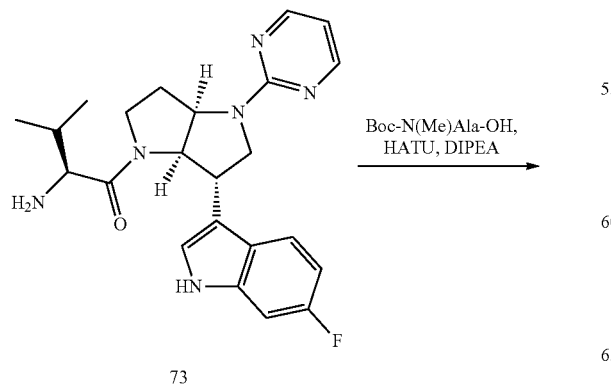

73

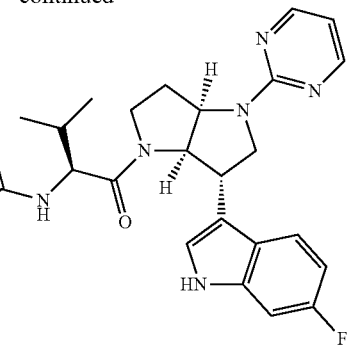

74

(1-{1-[6-(6-Fluoro-1H-indol-3-yl)-4-pyrimidin-2-yl-hexahydro-pyrrolo[3,2-b]pyrrole-1-carbonyl]-2-methyl-propylcarbamoyl}-ethyl)-methyl-carbamic acid tert-butyl ester (74)

To a solution containing Boc-N(Me)Ala-OH (75 mg, 0.37 mmol) in anhydrous NMP (3 mL) was cooled to 0° C. HATU (140 mg, 0.37 mmol) and DIPEA (52 mg, 0.42 mmol) were added followed by the addition of 73 (148 mg, 0.35 mmol) in anhydrous NMP (3 mL). The reaction mixture was slowly warmed to ambient temperature. After 4 h, the reaction mixture was diluted with diethyl ether and washed successively with water, aqueous NaHCO$_3$, water and brine, dried over anhydrous Na$_2$SO$_4$, filtered, and concentrated to afford 202 mg of crude 74 which was used without further purification. Mass spectrum, m/z [608] (M+H)+.

Scheme LXX

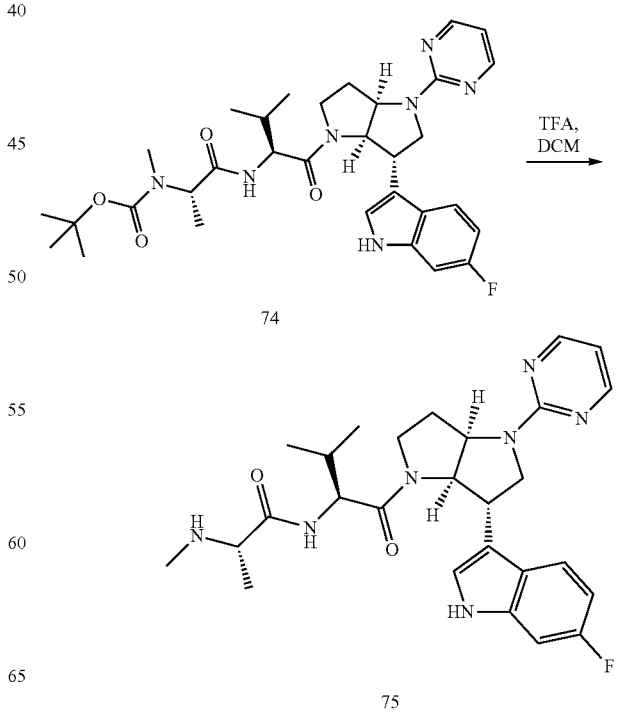

N-{1-[6-(6-Fluoro-1H-indol-3-yl)-4-pyrimidin-2-yl-hexahydro-pyrrolo[3,2-b]pyrrole-1-carbonyl]-2-methyl-propyl}-2-methylamino-propionamide (75)

To a solution containing 74 (202 mg, 0.33 mmol) in DCM (10 mL) was added TFA (4 mL) at 0° C. After 2 h, the reaction mixture was concentrated in vacuo. The residue was dissolved in EtOAc and the resultant organic solution was washed successively with saturated aqueous NaHCO$_3$ and brine, dried over anhydrous Na$_2$SO$_4$, filtered, and concentrated. The crude product was purified by RP-HPLC (2" Dynamax C18, 10-70% ACN/water containing 0.1% HOAc over 30 min; Flow: 40 mL/min) to afford 125 mg (61%, 3 steps) of 75. $^1$H NMR (CDCl$_3$, 300 MHz): δ8.37 (dd, J=6.0, 10.5 Hz, 2H), 8.19 (s, 1H), 8.11 (dd, J=5.4, 8.7 Hz, 1H), 7.82 (d, J=8.7 Hz, 1H), 6.99-6.88 (m, 2H), 6.74-6.68 (m 1H), 6.62-6.58 (m, 1H), 4.74-4.60 (m, 1H), 4.48-4.44 (m, 1H) 4.16-4.04 (m, 2H), 3.69 (dd, J=6.0, 11.4 Hz, 1H), 3.51-3.42 (m, 1H), 3.26 (dd, J=6.6, 13.5 Hz, 1H), 2.76 (br s, 4H), 2.53-2.47 (m, 1H), 2.44-2.39 (m, 3H), 2.21-2.01 (m, 3H), 1.39-1.32 (m, 3H), 1.06-0.96 (m, 6H) ppm. $^{13}$C NMR (CDCl$_3$, 75 MHz) δ173.9, 170.8, 160.2 (J$_{CF}$=237.4 Hz), 159.8, 136.2, 123.4, 120.9 (J$_{CF}$=10.1 Hz), 116.6, 110.1, 108.5 (J$_{CF}$=24.5 Hz), 97.2 (J$_{CF}$=26.2 Hz), 68.2, 60.3, 59.7, 55.9, 51.4, 47.2, 38.9, 34.2, 31.5, 30.7, 19.4, 18.8, 18.0 ppm. Mass spectrum, m/z [508.3] (M)+.

Examples 78-83 were prepared from intermediates 34 and 35 using the procedures described in Schemes XLVII through XLIX and Schemes LXVII through LXX by substituting Boc-Val-OH with other mino acid reagents including Boc-Abu-OH, Boc-Tle-OH, Boc-Ser-OH, Cbz-Ser(tBu)-OH, Boc-Ser(Me)-OH, Cbz-Thr(tBu)-OH, Boc-Thr(tBu)-OH, Boc-Thr-OH, or Boc-Thr(Me)-OH.

Example 78

N-{1-[6-(6-Fluoro-1H-indol-3-yl)-4-pyrimidin-2-yl-hexahydro-pyrrolo[3,2-b]pyrrole-1-carbonyl]-propyl}-2-methylamino-propionamide $^1$H NMR (300 MHz, CDCl$_3$), mixture of amide rotamers: δ8.37 (d, J=4.5 Hz, 2H), 8.28 (br s, 1H), 8.11 (app dd, J=8.7, 5.4 Hz, 1H), 7.88 (d, J=8.4 Hz, 1H), 6.97 (app dd, J=9.6, 2.1 Hz, 1H), 6.91 (m, 1H), 6.70 (d, J=0.9 Hz, 1H), 6.58 (app t, J=4.8 Hz, 1H), 4.79 (app q, J=7.2 Hz, 1H), 4.73 (d, J=5.1 Hz, 1H), 4.60 (t, J=4.8 Hz, 1H), 4.46 (d, J=12.0 Hz, 1H), 4.07 (br s, 2H), 4.02 (app d, J=6.3 Hz, 1H), 3.67 (dd, J=11.7, 5.7 Hz, 1H), 3.43 (m, 1H), 3.23 (app q, J=6.9 Hz, 1H), 2.50 (dd, J=13.2, 5.4 Hz, 1H), 2.42 (s, 3H), 2.05 (s, 1.5H), 2.01 (m, 1H), 1.91 (m, 1H), 1.75 (m, 1H), 1.35 (d, J=6.6 Hz, 3H), 0.98 (t, J=7.5 Hz, 3H) ppm. $^{13}$C NMR (75 MHz, CDCl$_3$), mixture of amide rotamers: δ175.4, 174.0, 170.9, 161.9, 159.9, 158.8, 158.1, 136.5, 136.3, 123.5, 121.1, 121.0, 120.3, 116.6, 110.2, 108.8, 108.4, 97.5, 97.1, 68.4, 60.3, 59.7, 52.0, 51.4, 47.0, 39.1, 34.4, 30.9, 25.9, 21.6, 19.0, 9.7 ppm. Mass spectrum, m/z [494.2] (M+H)+.

Example 79

N-{1-[6-(6-Fluoro-1H-indol-3-yl)-4-pyrimidin-2-yl-hexahydro-pyrrolo[3,2-b]pyrrole-1-carbonyl]-2,2-dimethyl-propyl}-2-methylamino-propionamide $^1$H NMR (300 MHz, CDCl$_3$), mixture of amide rotamers: δ8.36 (app d, J=4.8 Hz, 2H), 8.30 (br s, 1H), 8.15 (app dd, J=8.7, 5.4 Hz, 1H), 7.87 (d, J=9.3 Hz, 1H), 6.92 (m, 2H), 6.67 (d, J=1.8 Hz, 1H), 6.57 (app t, J=4.8 Hz, 1H), 4.72 (m, 2H), 4.57 (t, J=4.8 Hz, 1H), 4.46 (br d, J=11.7 Hz, 1H), 4.15 (app t, J=9.5 Hz, 1H), 4.01 (d, J=5.7 Hz, 1H), 3.70 (app dd, J=11.7, 6.0 Hz, 1H), 3.46 (m, 1H), 3.34 (br s, 2H), 3.15 (app q, J=6.6 Hz, 1H), 2.46 (app dd, J=13.2, 5.4 Hz, 1H), 2.39 (s, 3H), 2.05 (s, 1.3H), 1.99 (m, 1H), 1.32 (d, J=6.6 Hz, 3H), 1.08 (s, 9H) ppm. $^{13}$C NMR (75 MHz, CDCl$_3$), mixture of amide rotamers: δ174.8, 170.4, 161.9, 159.9, 158.7, 158.1, 136.5, 136.3, 123.6, 121.2, 121.1, 120.3, 120.2, 116.7, 110.1, 108.7, 108.4, 97.4, 97.1, 68.3, 60.4, 60.1, 57.1, 51.5, 48.1, 39.4, 35.9, 34.8, 30.8, 26.8, 19.3 ppm. Mass spectrum, m/z [522.2] (M+H)+.

Example 80

N-{2-[6-(6-Fluoro-1H-indol-3-yl)-4-pyrimidin-2-yl-hexahydro-pyrrolo[3,2-b]pyrrol-1-yl]-1-hydroxymethyl-2-oxo-ethyl}-2-methylamino-propionamide $^1$H NMR (300 MHz, CDCl$_3$), mixture of amide rotamers: δ8.26 (d, J=4.8 Hz, 2H), 7.96 (app dd, J=8.7, 5.4 Hz, 1H), 6.90 (app dd, J=9.8, 2.3 Hz, 1H), 6.77 (app td, J=9.2, 6.8 Hz, 1H), 6.60 (s, 1H), 6.52 (app t, J=4.8 Hz, 1H), 4.78 (app t, J=5.4 Hz, 1H), 4.64 (app d, J=5.4 Hz, 1H), 4.53 (app t, J=4.8 Hz, 1H), 4.29 (d, J=11.7 Hz, 1H), 3.91 (m, 2H), 3.75 (app d, J=5.7 Hz, 1H), 3.63 (dd, J=11.4, 5.7 Hz, 1H), 3.43 (m, 1H), 3.34 (app q, J=6.8 Hz, 1H), 2.40 (m, 1H), 2.38 (s, 3H), 1.95 (m, 1H), 1.90 (s, 3H), 1.30 (d, J=6.9 Hz, 3H) ppm. $^{13}$C NMR (75 MHz, CDCl$_3$), mixture of amide rotamers: δ176.5, 173.0, 169.0, 161.6, 159.4, 158.4, 158.0, 136.5, 136.3, 123.3, 120.4, 120.3, 115.8, 110.0, 107.9, 107.6, 97.3, 97.0, 68.4, 62.3, 60.2, 58.4, 53.6, 51.3, 47.0, 38.9, 32.8, 30.7, 22.0, 17.3 ppm. Mass spectrum, m/z [496.2] (M+H)+.

Example 81

N-{2-[6-(6-Fluoro-1H-indol-3-yl)-4-pyrimidin-2-yl-hexahydro-pyrrolo[3,2-b]pyrrol-1-yl]-1-methoxymethyl-2-oxo-ethyl}-2-methylamino-propionamide $^1$H NMR (300 MHz, CDCl$_3$), mixture of amide rotamers: δ8.37 (m, 2H), 8.19 (br s, 1H), 8.15 (m, 1H), 7.89 (br d, J=8.1 Hz, 1H), 6.97 (m, 1H), 6.92 (m, 1H), 6.67 (d, J=1.8 Hz, 1H), 6.57 (m, 1H), 5.02 (m, 1H), 4.72 (d, J=5.4 Hz, 1H), 4.59 (t, J=4.7 Hz, 1H), 4.47 (d, J=11.7 Hz, 1H), 4.07 (m, 1H), 3.97 (m, 1H), 3.68 (m, 3H), 3.54 (m, 3H), 3.36 (s, 3H), 3.15 (m, 1H), 2.48 (dd, J=13.2, 5.7 Hz, 1H), 2.42 (s, 3H), 2.05 (s, 1.5H), 1.99 (m, 1H), 1.32 (d, J=6.6 Hz, 3H) ppm. $^{13}$C NMR (75 MHz, CDCl$_3$), mixture of amide rotamers: δ174.8, 169.2, 161.9, 159.8, 158.8, 158.1, 136.5, 136.3, 123.6, 121.2, 121.1, 120.2, 120.2, 116.8, 110.1, 108.7, 108.4, 97.4, 97.1, 73.0, 72.7, 68.5, 60.3, 60.0, 59.9, 59.5, 59.3, 51.1, 50.8, 50.4, 47.3, 39.2, 38.9, 34.9, 34.8, 30.9, 19.4, 19.2 ppm. Mass spectrum, m/z [510.2] (M+H)+.

Example 82

N-{1-[6-(6-Fluoro-1H-indol-3-yl)-4-pyrimidin-2-yl-hexahydro-pyrrolo[3,2-b]pyrrole-1-carbonyl]-2-hydroxy-propyl}-2-methylamino-propionamide $^1$H NMR (300 MHz, CDCl$_3$), mixture of amide rotamers: δ8.26 (d, J=5.1 Hz, 2H), 7.95 (app dd, J=8.6, 5.6 Hz, 1H), 6.90 (dd, J=9.6, 2.4 Hz, 1H), 6.76 (m, 1H), 6.60 (s, 1H), 6.52 (t, J=4.8 Hz, 1H), 4.63 (app d, J=5.4 Hz, 1H), 4.57 (app d, J=5.1 Hz, 1H), 4.52 (app t, J=4.8 Hz, 1H), 4.31 (d, J=11.4 Hz, 1H), 3.99 (m, 2H), 3.62 (app dd, J=11.9, 5.9 Hz, 1H), 3.41 (m, 2H), 2.39 (s, 3H), 2.37 (m, 1H), 1.95 (m, 1H), 1.90 (s, 3H), 1.31 (d, J=6.9 Hz, 3H), 1.17 (d, J=6.6 Hz, 3H) ppm. $^{13}$C NMR (75 MHz, CDCl$_3$), mixture of amide rotamers: δ172.6, 169.6, 159.4, 158.4, 158.0, 136.5, 136.3, 123.2, 120.4, 120.3, 115.6, 110.0, 107.9, 107.6, 97.3, 97.0, 86.7, 68.3, 67.5, 60.2, 58.2, 56.8, 51.4, 47.2, 38.8, 32.5, 30.6, 21.9, 19.3, 17.1 ppm. Mass spectrum, m/z [510.2] (M+H)+.

Example 83

N-{1-[6-(6-Fluoro-1H-indol-3-yl)-4-pyrimidin-2-yl-hexahydro-pyrrolo[3,2-b]pyrrole-1-carbonyl]-2-methoxy-propyl}-2-methylamino-propionamide $^1$H NMR (300 MHz, CDCl$_3$), mixture of amide rotamers: δ8.38 (d, J=4.5 Hz, 2H), 8.21 (br s, 1H), 8.16 (app dd, J=8.7, 5.4 Hz, 1H), 7.88 (d, J=7.8 Hz, 1H), 6.98 (app dd, J=9.8, 2.3 Hz, 1H), 6.93 (m, 1H), 6.69 (d, J=2.1 Hz, 1H), 6.59 (app t, J=4.8 Hz, 1H), 4.90 (dd, J=8.1, 4.5 Hz, 1H), 4.76 (d, J=5.4 Hz, 1H), 4.59 (t, J=4.8 Hz, 1H), 4.49 (d, J=11.7 Hz, 1H), 4.02 (m, 2H), 3.74 (m, 2H), 3.53 (m, 1H), 3.39 (s, 3H), 3.34 (br s, 2H), 3.20 (app q, J=6.9 Hz, 1H), 2.49 (dd, J=13.2, 5.7 Hz, 1H), 2.44 (s, 3H), 2.06 (s, 1.5H), 2.01 (m, 1H), 1.34 (d, J=6.9 Hz, 3H), 1.22 (d, J=6.0 Hz, 3H) ppm. $^{13}$C NMR (75 MHz, CDCl$_3$), mixture of amide rotamers: δ174.9, 168.9, 161.9, 159.9, 158.8, 158.1, 136.5, 136.3, 123.6, 121.3, 121.1, 120.2, 120.2, 116.7, 110.1, 108.8, 108.4, 97.4, 97.1, 68.5, 60.2, 59.9, 57.1, 54.8, 51.3, 47.6, 39.2, 34.7, 30.9, 19.3, 15.5 ppm. Mass spectrum, m/z [524.2] (M+H)+.

Example 84

4-[2-Cyclohexyl-2-(2-methylamino-propionylamino)-acetyl]-3S-(6-fluoro-1H-indol-3-yl)-6-hydroxy-hexahydro-pyrrolo[3,2-b]pyrrole-1-carboxylic acid benzyl ester (94)

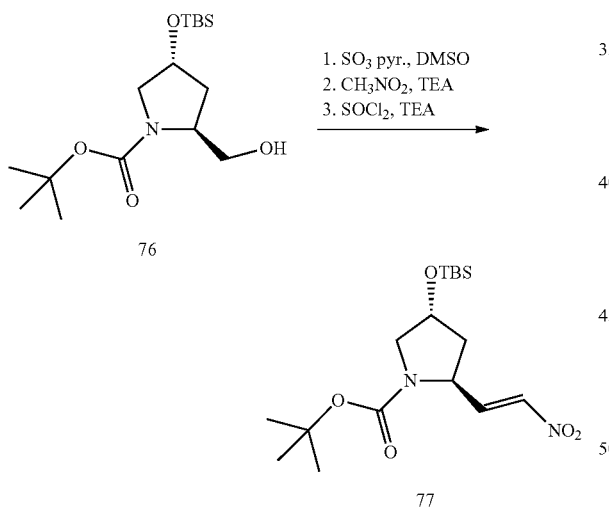

Scheme LXXI 4-(tert-Butyl-dimethyl-silanyloxy)-2-(2-nitro-vinyl)-pyrrolidine-1-carboxylic acid tert-butyl ester (77)

To a solution of 76 (25.8 g, 77.8 mmol) in DMSO (60 mL) and CH$_2$Cl$_2$ (300 mL) at 0° C. were added Et$_3$N (54 mL, 389.1 mmol) and SO$_3$.pyridine complex (49.5 g, 311.2 mmol). The reaction mixture was then allowed to stir for 2 h at 0° C. Upon complete consumption of 76 by TLC analysis, the reaction mixture was diluted with EtOAc and washed successively with dilute aqueous HCl and brine and concentrated. The resultant residue was dissolved in 1:1 Et$_2$O/hexanes, washed with 1M HCl and brine to remove residual DMSO. The organic extracts were dried over anhydrous Na$_2$SO$_4$, filtered, and concentrated to afford the desired prolinal (25.4 g, 99%) as a pale yellow oil which was used without further purification.

To a solution of prolinal (25.4 g, 77.1 mmol) in CH$_3$NO$_2$ (128 mL) at 0° C. was added Et$_3$N (10 mL). The reaction mixture was then stirred for an additional 17 h warming gradually to ambient temperature. The reaction mixture was concentrated and the residue was concentrated twice from toluene to remove any residual water. The crude alcohols (29.8 g, 99%) were used without further purification.

To a solution of alcohols (29.8 g, 76.4 mmol) and Et$_3$N (42.6 mL, 305.9 mmol) in CH$_2$Cl$_2$ (400 mL) at −78° C. was added dropwise a solution of SOCl$_2$ (7.2 mL, 99.4 mmol) in CH$_2$Cl$_2$ over a period of 1 h during which time the reaction mixture became brown-colored and heterogeneous. The reaction mixture was then stirred for an additional 15 min, after which time it was concentrated to form a brown-colored residue. The residue was slurried in 10% EtOAc/hexanes and purified by flash silica gel chromatography (10-15% EtOAc/hexanes) to afford 77 (15.1 g, 53%) as an orange solid. $^1$H NMR (300 MHz, CDCl$_3$): δ7.08 (dd, J=6.9, 13.5 Hz, 1H), 6.96 (d, J=13.5 Hz, 1H), 4.51 (dd, J=6.3, 35.8 Hz, 1H), 4.29 (s, 1H), 3.51-3.36 (m, 2H), 2.08 (ddd, J=3.3, 7.5, 11.4 Hz, 1H), 1.79 (s, 1H), 1.38 (s, 9H), 0.79 (s, 9H), 0.05 (s, 6H) ppm.

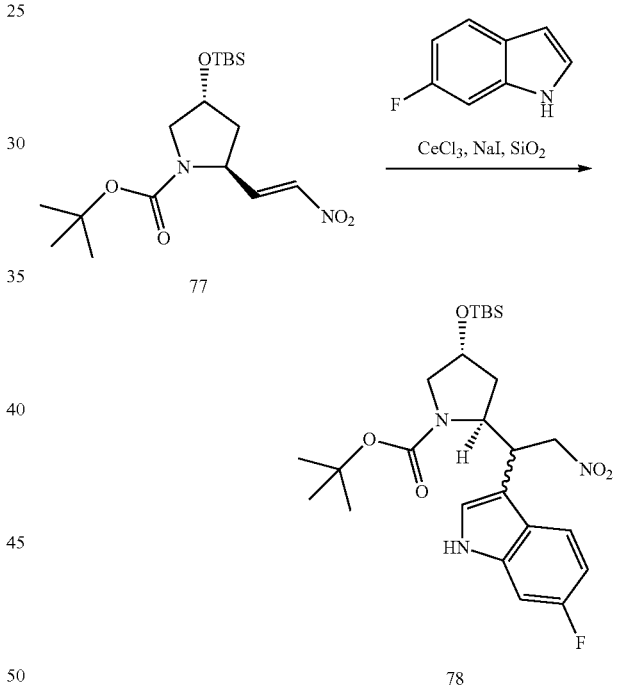

Scheme LXXII 4-(tert-Butyl-dimethyl-silanyloxy)-2-[1-(6-fluoro-1H-indol-3-yl)-2-nitro-ethyl]-pyrrolidine-1-carboxylic acid tert-butyl ester (78)

To a solution of CeCl$_3$.7H$_2$O (6.06 g, 40.6 mmol) and NaI (2.44 g, 16.2 mmol) in MeOH (200 mL) was added SiO$_2$ (30 g). The resulting pale yellow solution was evaporated to dryness to afford a fine yellow powder. To this solid was added 6-fluoroindole (6.59 g, 48.7 mmol) and a solution of 77 (15.1 g, 40.6 mmol) in anhydrous CH$_3$CN (150 mL). The heterogeneous reaction mixture was evaporated to dryness and allowed to stand 72 h at ambient temperature. The reaction mixture was diluted with CH$_2$Cl$_2$ and additional silica gel (150 mL) was added. The mixture was concentrated to dryness and the product was eluted by flash silica gel chromatography (15-25% EtOAc/hexanes) to afford 78 (15.3 g, 75%) as an inseparable mixture of diastereomers. Mass spectrum, m/z [508.2] (M+H)+.

Scheme LXXIII

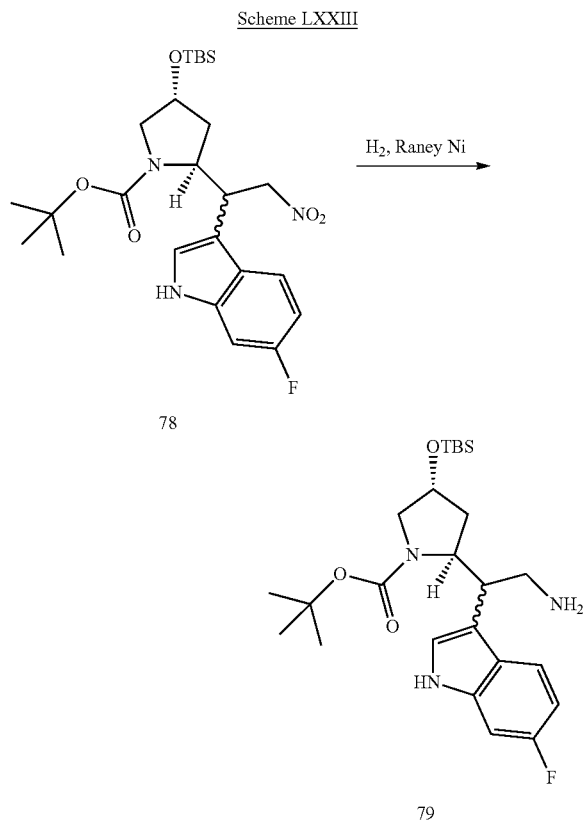

2-[2-Amino-1-(6-fluoro-1H-indol-3-yl)-ethyl]-4-(tert-butyl-dimethyl-silanyloxy)-pyrrolidine-1-carboxylic acid tert-butyl ester (79)

To a solution of 78 (10.1 g, 20.0 mmol) in EtOH (150 mL) in a Parr bottle was added an aqueous suspension of Raney Ni (6 pipettes). The bottle was evacuated and flushed with $H_2$ five times, charged to 50 PSI $H_2$ (344.7 KPa) and shaken for 2.5 h. The reaction mixture was filtered through diatomaceous earth (Celite®) and concentrated to afford 79 (9.3 g, 97%) as an off-white powder which was used without further purification. Mass spectrum, m/z [478.2] (M+H)+.

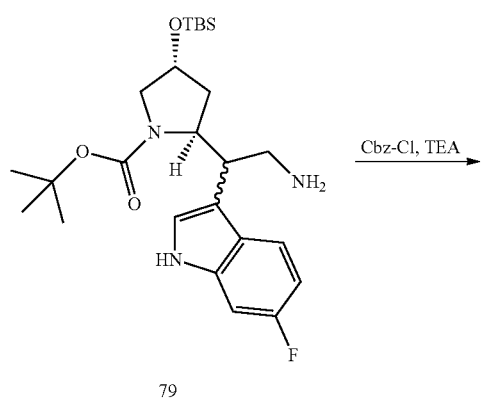

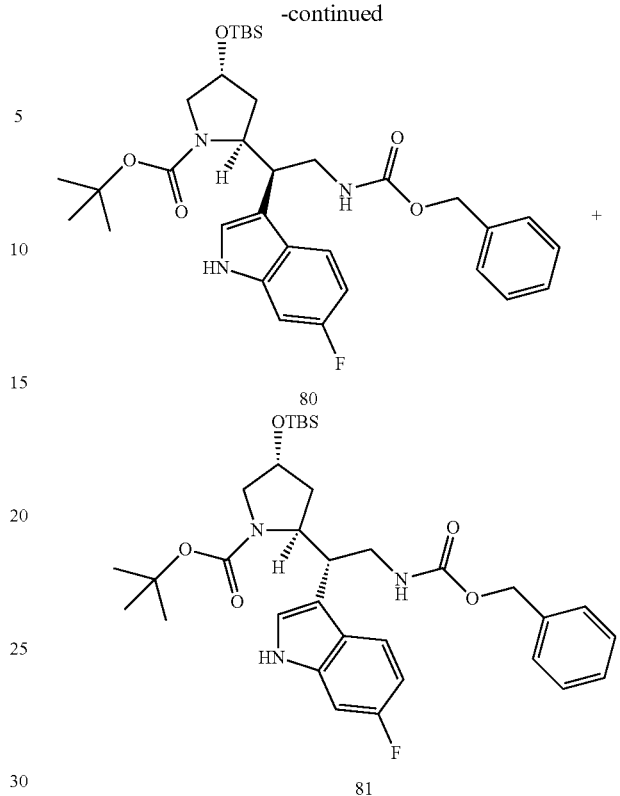

2R-[2-Benzyloxycarbonylamino-1R-(6-fluoro-1H-indol-3-yl)-ethyl]-4R-(tert-butyl-dimethyl-silanyloxy)-pyrrolidine-1-carboxylic acid tert-butyl ester (80) and 2R-[2-Benzyloxycarbonylamino-1S-(6-fluoro-1H-indol-3-yl)-ethyl]-4R-(tert-butyl-dimethyl-silanyloxy)-pyrrolidine-1-carboxylic acid tert-butyl ester (81)

To a solution of 79 (9.3 g, 19.4 mmol) in $CH_2Cl_2$ (100 mL) at 0° C. were added TEA (7.1 mL, 50.6 mmol) and Cbz-Cl (3.56 mL, 25.3 mmol). The reaction mixture was allowed to stir for an additional 17 h warming gradually to ambient temperature. Upon completion, the reaction mixture was diluted with $CH_2Cl_2$ and washed sequentially with 1M HCl, $NaHCO_3$ (sat.) and brine. The organic extracts were dried over anhydrous $Na_2SO_4$, filtered and concentrated and the residue was purified via flash silica gel chromatography (5:1→2:1 hexanes/EtOAc) to afford 9.53 g (80%) of the indole addition products as an ~1:1 mixture of two diastereomers [TLC: 2:1 hexanes/EtOAc, $R_f$(80)=0.43, $R_f$(81)=0.45]. The diastereomers were separated by reverse-phase HPLC (2" Dynamax C18, 60-100% ACN/$H_2O$ containing 0.1% HOAc; Flow: 40 mL/min). The product-containing fractions were combined and concentrated to remove ACN and the resulting aqueous solutions were dissolved in EtOAc and washed successively with $NaHCO_3$ (sat.) and brine, dried over anhydrous $Na_2SO_4$, filtered and concentrated to afford 80 (4.74 g, 37%) and 81 (3.46 g, 27%) as off-white-colored foams.

80: $^1$H NMR (300 MHz, CDCl$_3$): δ8.42 (m, 1H), 7.62 (m, 1H), 7.44 (m, 4H), 7.18-6.94 (m, 3H), 5.48 (m, 1H), 5.16 (m, 2H), 4.61 (m, 1H), 4.0-3.80 (m, 2H), 3.68-3.54 (m, 2H), 3.35 (dd, J=3.9, 11.1 Hz, 1H), 3.01 (dd, J=4.9, 11.1 Hz, 1H), 1.92 (m, 2H), 1.67 (s, 9H), 0.94 (s, 9H), 0.01 (m, 6H) ppm. Mass spectrum, m/z [612.3] (M+H)+.

81: $^1$H NMR (300 MHz, CDCl$_3$): δ8.68 (s, 1H), 7.26 (dd, J=5.1, 8.7 Hz, 1H), 7.60 (m, 5H), 7.25 (d, J=9.3 Hz, 1H), 7.14-7.06 (m, 2H), 6.71 (s, 1H), 5.37 (d, J=22.8 Hz, 2H), 4.77 (s, 1H), 3.81 (m, 1H), 3.66 (m, 1H), 3.56 (dd, J=4.2, 13.2 Hz,

2H), 3.48-3.38 (m, 2H), 3.12 (dd, J=5.7, 11.1 Hz, 1H), 2.05 (m, 2H), 1.75 (s, 9H), 0.96 (s, 9H), 0.01 (d, J=8.7 Hz, 6H) ppm. Mass spectrum, m/z [612.3] (M+H)+.

Scheme LXXV

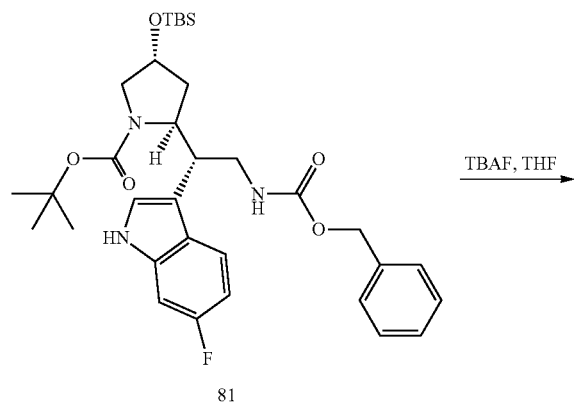

2-[2-Benzyloxycarbonylamino-1S-(6-fluoro-1H-indol-3-yl)-ethyl]-4-hydroxy-pyrrolidine-1-carboxylic acid tert-butyl ester (82)

To a solution of 81 (3.74 g, 6.11 mmol) in THF (30 mL) at ambient temperature was added TBAF (1M/THF, 9.17 mL) and the reaction mixture was stirred for an additional 4.5 h. Upon completion, the reaction mixture was concentrated and the residue dissolved in EtOAc and washed successively with 1M HCl, NaHCO₃ (sat.), and brine. The organic extracts were dried over anhydrous Na₂SO₄, filtered and concentrated to afford 82 (3.47 g, quant.) as an off-white-colored foamy solid that was used without further purification. Mass spectrum, m/z [498.2] (M+H)+.

Scheme LXXVI

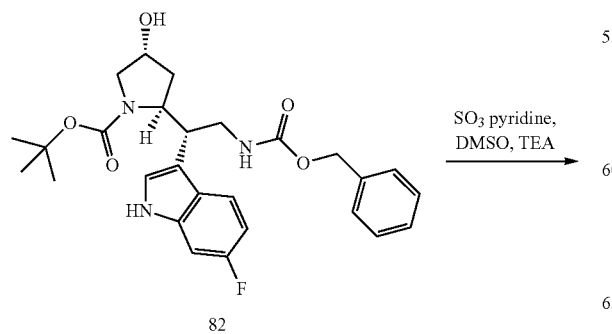

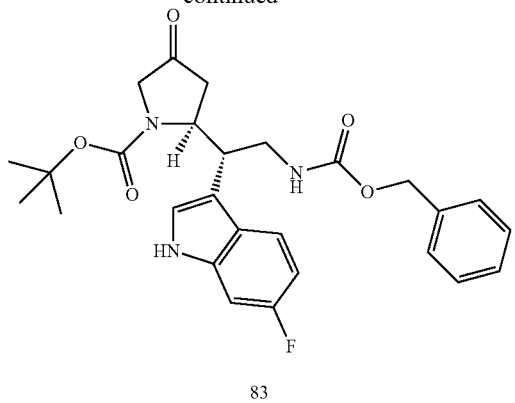

2-[2-Benzyloxycarbonylamino-1S-(6-fluoro-1H-indol-3-yl)-ethyl]-4-oxo-pyrrolidine-1-carboxylic acid tert-butyl ester (83)

To a solution of 82 (3.04 g, 6.11 mmol) in DMSO (15 mL) and CH₂Cl₂ (45 mL) at 0° C. were added TEA (5.1 mL, 36.7 mmol) and SO₃.pyridine complex (3.89 g, 24.4 mmol). The resultant yellow reaction mixture was stirred for an additional 30 min at 0° C. then warmed to ambient temperature. After 4 h, the reaction mixture was diluted with CH₂Cl₂ and washed successively with 1M HCl, NaHCO₃ (sat.), and brine. The organic phase was dried over anhydrous Na₂SO₄, filtered, and concentrated to afford a white solid. The crude product was adsorbed onto silica gel and purified via flash chromatography (1:1 hexanes/EtOAc) to afford 83 (2.73 g, 90%) as a foamy white solid. $^1$H NMR (300 MHz, CDCl₃): δ8.43 (br s, 1H), 7.39 (m, 6H), 6.98 (d, J=7.8 Hz, 1H), 6.83 (m, 2H), 6.34 (br s, 1H), 5.12 (dd, J=12.3, 30.1 Hz, 2H), 4.91 (d, J=8.4 Hz, 1H), 3.72-3.53 (m, 3H), 3.22 (m, 1H), 2.87 (d, J=19.2 Hz, 1H), 2.71 (dd, J=9.6, 18 Hz, 1H), 2.32 (d, J=18.3 Hz, 1H), 1.52 (s, 9H) ppm. Mass spectrum, m/z [498.2] (M+H)+.

Scheme LXXVII

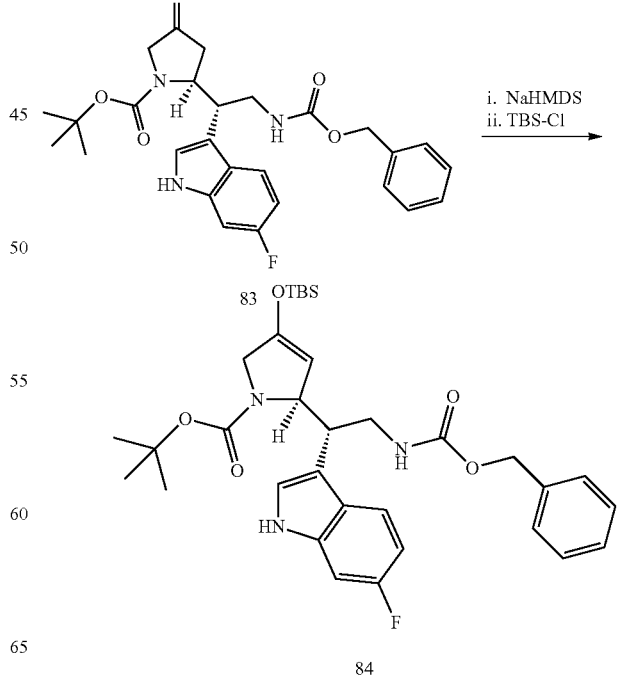

2-[2-Benzyloxycarbonylamino-1S-(6-fluoro-1H-indol-3-yl)-ethyl]-4-(tert-butyl-dimethyl-silanyloxy)-2,5-dihydro-pyrrole-1-carboxylic acid tert-butyl ester (84)

To a solution of 83 (2.73 g, 5.51 mmol) in THF (25 mL) at −78° C. was added dropwise a solution of NaHMDS (1M/THF, 17.1 mL) over 15 min. The resultant yellow reaction mixture was stirred an additional 45 min at −78° C. To the reaction mixture was then added a solution of TBSCl (2.57 g, 17.1 mmol) in THF (10 mL) dropwise over 10 min. The reaction mixture was then stirred an additional 5 h at −78° C. The reaction mixture was warmed to 0° C. and quenched with NH$_4$Cl (sat.), extracted three times with EtOAc, and the combined organic extracts were washed with brine and concentrated. The residue was adsorbed onto silica gel and purified by flash chromatography (4:1 hexanes/EtOAc) to afford 84 (3.56 g, 89%) as a foamy white solid. $^1$H NMR (300 MHz, CDCl$_3$): δ7.67 (dd, J=6.0, 8.7 Hz, 1H), 7.31 (m, 5H), 7.12 (dd, J=2.1, 10.8 Hz, 1H), 6.88 (m, 2H), 5.28-4.66 (m, 4H), 4.34 (m, 1H), 3.93 (m, 1H), 3.79-3.42 (m, 4H), 1.62 (s, 3H), 1.52 (s, 6H), 0.88 (m, 18H), 0.57 (m, 3H), 0.07 (m, 9H) ppm. Mass spectrum, m/z [724.4] (M)+.

tion mixture was slowly warmed to ambient temperature. After 21 h, the reaction mixture was cooled to 0° C. and quenched with aqueous Na$_2$S$_2$O$_3$. After the xotherm had subsided, the reaction mixture was extracted three times with EtOAc. The combined organic extracts were washed with brine and dried over anhydrous Na$_2$SO$_4$, filtered, and concentrated. The crude residue was purified by flash silica gel chromatography (3:1-1:1 hexanes/EtOAc) to afford 85 (1.87 g, 61%) as a white solid. $^1$H NMR (300 MHz, CDCl$_3$): δ8.38 (br s, 1H), 7.59 (s, 1H), 7.30 (m, 5H), 7.07 (d, J=1.8 Hz, 1H), 7.01 (d, J=9.6 Hz, 1H), 6.86 (d, J=8.1 Hz, 1H), 5.42 (br s, 1H), 5.05 (dd, J=12.3, 24.9 Hz, 2H), 4.03 (m, 3H), 3.83-3.68 (m, 3H), 3.52 (m, 1H), 2.87 (m, 1H), 1.37 (s, 9H), 0.86 (s, 9H), 0.59 (s, 6H) ppm. Mass spectrum, m/z [724.4] (M+Na)+.

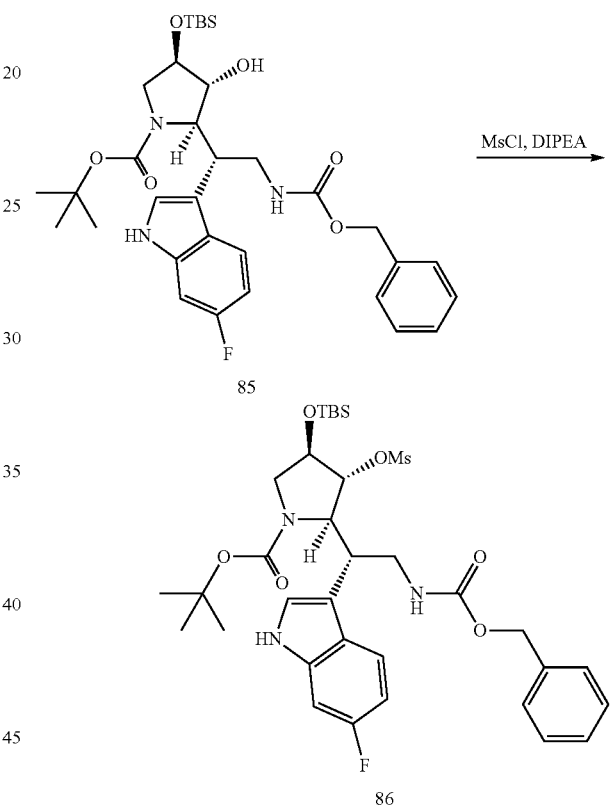

Scheme LXXIX

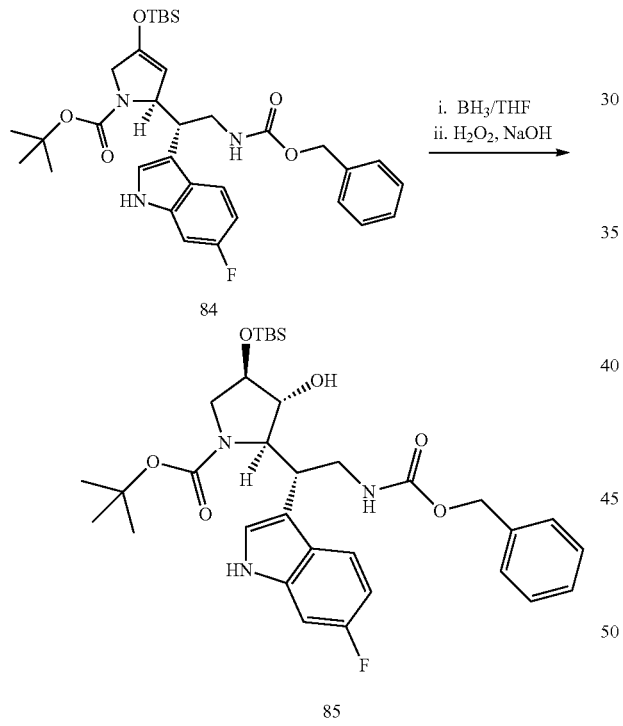

Scheme LXXVIII

2-[2-Benzyloxycarbonylamino-1S-(6-fluoro-1H-indol-3-yl)-ethyl]-4-(tert-butyl-dimethyl-silanyloxy)-3-hydroxy-pyrrolidine-1-carboxylic acid tert-butyl ester (85)

To a solution of 84 (3.56 g, 4.92 mmol) in THF (100 mL) at −30° C. was added BH$_3$.THF (1M/THF, 24.6 mL) in one portion The reaction mixture was stirred for 30 min at −30° C. then warmed to ambient temperature and stirred for an additional 1.5 h. The reaction mixture was then cooled to 0° C. and 1M NaOH (26 mL) and 30% H$_2$O$_2$ (13 mL) were slowly added during which time bubbling was observed. The reac-

2-[2-Benzyloxycarbonylamino-1S-(6-fluoro-1H-indol-3-yl)-ethyl]-4-(tert-butyl-dimethyl-silanyloxy)-3-methanesulfonyloxy-pyrrolidine-1-carboxylic acid tert-butyl ester (86)

To a solution of 85 (1.87 g, 2.98 mmol) in CH$_2$Cl$_2$ (30 mL) at 0° C. were added DIPEA (1.06 mL, 5.96 mmol), DMAP (50 mg.), and MsCl (237 µL). The reaction mixture was stirred at 0° C. for 2 h during which time the reaction mixture became heterogeneous. The reaction mixture was diluted with CH$_2$Cl$_2$ and washed successively with 1M HCl, NaHCO$_3$ (sat.), and brine. The organic phase was dried over anhydrous Na$_2$SO$_4$, filtered, and concentrated. The crude residue was purified by flash silica gel chromatography (2:1 hexanes/EtOAc) to afford 86 (2.44 g, quant.) as a foamy white solid. $^1$H NMR (300 MHz, CDCl$_3$): δ8.40 (br s, 1H), 7.63 (s, 1H), 7.31 (m, 5H), 7.11 (s, 1H), 7.02 (d, J=8.1 Hz, 1H), 6.88 (dd, J=1.8, 9.3 Hz, 1H), 5.45 (br s, 1H), 5.07 (m, 2H), 4.82 (s, 1H), 4.38 (s, 1H), 4.28 (s, 1H), 3.73-3.61 (m, 3H), 2.91 (s, 1H), 2.46 (s, 3H), 1.44 (s, 9H), 0.86 (s, 9H), 0.09 (d, J=13.2 Hz, 6H) ppm. Mass spectrum, m/z [728.3] (M+Na)+.

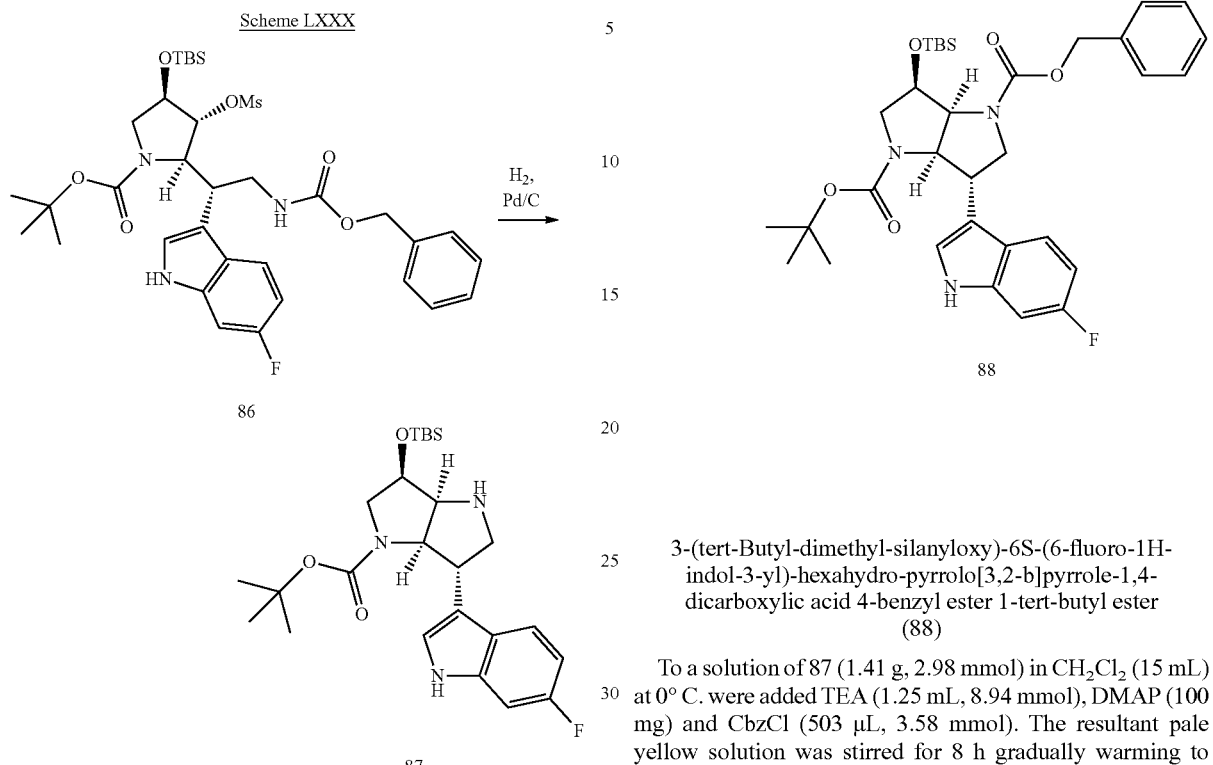

3-(tert-Butyl-dimethyl-silanyloxy)-6S-(6-fluoro-1H-indol-3-O-hexahydro-pyrrolo[3,2-b]pyrrole-1-carboxylic acid tert-butyl ester (87)

To a solution of 86 (2.10 g, 2.97 mmol) in THF (5 mL) and MeOH (20 mL) in a Parr bottle was added 10% Pd/C (150 mg). The flask was evacuated and flushed with $H_2$ five times, then charged to 50 PSI $H_2$ (344.7 KPa) and shaken for 4.5 h. The reaction mixture was filtered and concentrated. The residue was dissolved in EtOAc and washed successively with aqueous $NaHCO_3$ (sat.) and brine. The organic phase was dried over anhydrous $Na_2SO_4$, filtered, and concentrated to afford 87 (1.69 g, quant.) as a white solid which was used without further purification. Mass spectrum, m/z [476.2] (M+H)+.

3-(tert-Butyl-dimethyl-silanyloxy)-6S-(6-fluoro-1H-indol-3-yl)-hexahydro-pyrrolo[3,2-b]pyrrole-1,4-dicarboxylic acid 4-benzyl ester 1-tert-butyl ester (88)

To a solution of 87 (1.41 g, 2.98 mmol) in $CH_2Cl_2$ (15 mL) at 0° C. were added TEA (1.25 mL, 8.94 mmol), DMAP (100 mg) and CbzCl (503 μL, 3.58 mmol). The resultant pale yellow solution was stirred for 8 h gradually warming to ambient temperature. The reaction mixture was diluted with $CH_2Cl_2$ and washed successively with 1M HCl, $NaHCO_3$ (sat.), and brine. The organic phase was dried over anhydrous $Na_2SO_4$, filtered, and concentrated. The crude residue was purified by flash silica gel chromatography (4:1-2:1 hexanes/EtOAc) to afford 88 (1.70 g, 93%) as a foamy white solid. $^1$H NMR (300 MHz, $CDCl_3$): δ8.08 (m, 1H), 7.50 (ddd, J=5.4, 8.4, 10.8 Hz, 1H), 7.32 (m, 5H), 7.02 (d, J=9.3 Hz, 1H), 6.92 (s, 1H), 6.86 (dd, J=3.0, 9.6 Hz, 1H), 5.38-4.96 (m, 3H), 4.50 (m, 3H), 3.89 (m, 3H), 3.68 (m, 1H), 3.51 (d, J=12.3 Hz, 1H), 1.44 (m, 3H), 0.89 (m, 15H), 0.06 (dd, J=13.2, 24.0 Hz, 6H) ppm. Mass spectrum, m/z [610.2] (M+H)+.

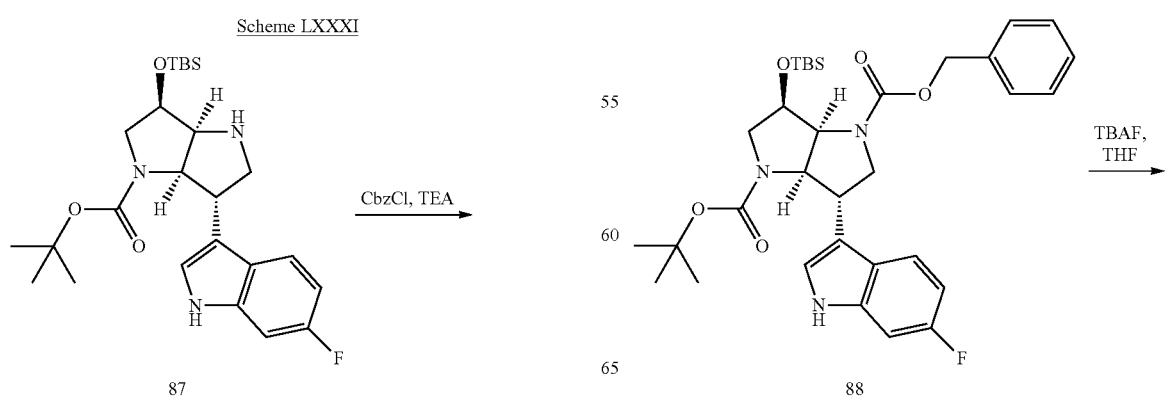

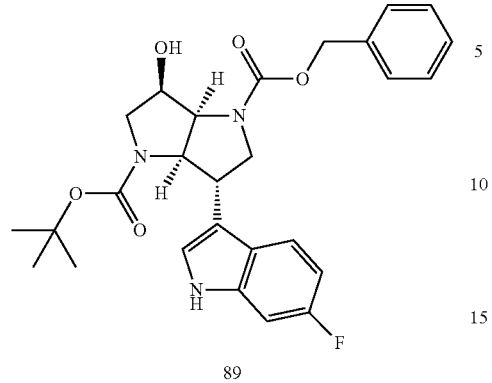

89

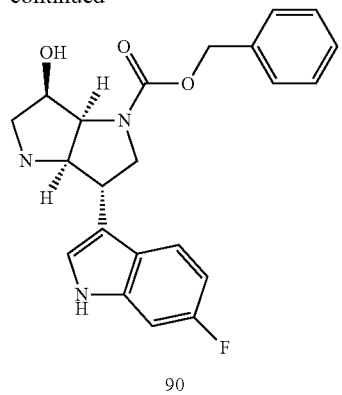

90

3-(6-Fluoro-1H-indol-3-yl)-6S-hydroxy-hexahydro-pyrrolo[3,2-b]pyrrole-1,4-dicarboxylic acid 1-benzyl ester 4-tert-butyl ester (89)

To a solution of 88 (1.70 g, 2.79 mmol) in THF (15 mL) at ambient temperature was added 1M TBAF/THF (4.19 mL). The reaction mixture was then stirred for an additional 2 h. The reaction mixture was concentrated and the residue was dissolved in EtOAc, washed successively with 1M HCl, NaHCO$_3$ (sat.), and brine, dried over anhydrous Na$_2$SO$_4$, filtered, and concentrated. The residue was purified by normal phase HPLC (Dynamax 2" SiO$_2$, 20-100% EtOAc/hexanes over 30 min; Flow: 40 mL/min) to afford 89 (570 mg, 41%) as a foamy off-white solid. $^1$H NMR (300 MHz, CDCl$_3$), mixture of carbamate rotamers: δ 8.06-7.95 (m, 2H), 7.38 (m, 4H), 7.00 (d, J=13.5 Hz, 1H), 6.91 (d, J=7.5 Hz, 1H), 6.70 (s, 0.3H), 6.58 (s, 0.7H), 5.34-5.15 (m, 2H), 4.58-4.33 (m, 3H), 4.20 (d, J=11.4 Hz, 2H), 4.03 (m, 1H), 3.94 (m, 1H), 3.75 (m, 1H), 3.22 (d, J=9.9 Hz, 0.3H), 3.12 (d, J=9.9 Hz, 0.7 Hz), 1.52 (s, 6H), 1.39 (s, 3H) ppm. Mass spectrum, m/z [496.1] (M+H)+.

3-(6-Fluoro-1H-indol-3-yl)-6S-hydroxy-hexahydro-pyrrolo[3,2-b]pyrrole-1-carboxylic acid benzyl ester (90)

To a solution of 89 (570 mg, 1.15 mmol) in CH$_2$Cl$_2$ (6 mL) at 0° C. was added TFA (2 mL). The reaction mixture was stirred at 0° C. for 2.5 h during which time the solution became pink-colored. The reaction mixture was concentrated and the residue was dissolved in EtOAc and washed successively with aqueous NaHCO$_3$ (sat.), and brine. The organic phase was dried over anhydrous Na$_2$SO$_4$, filtered, and concentrated to afford 90 (430 mg, 95%) as an off-white solid which was used without further purification. Mass spectrum, m/z [438.2] (M+H)+.

Scheme LXXXIV

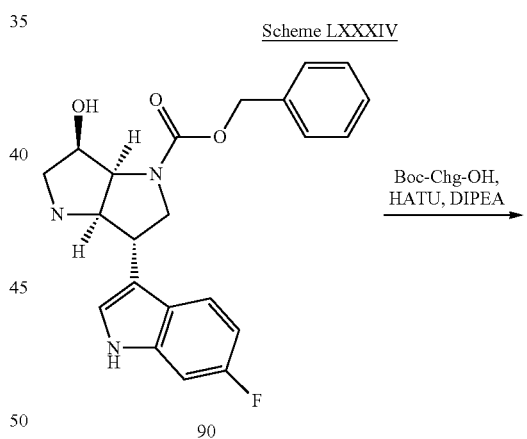

Boc-Chg-OH, HATU, DIPEA

90

Scheme LXXXIII

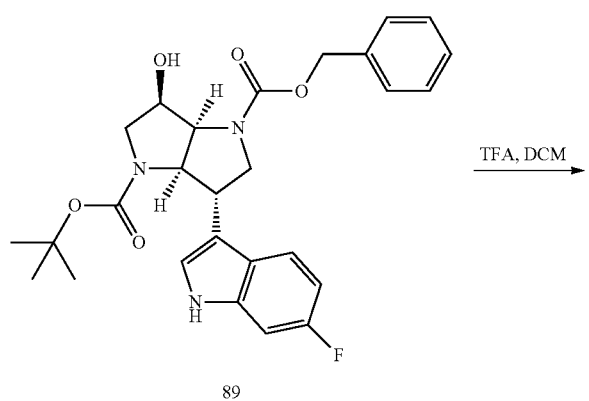

89

TFA, DCM

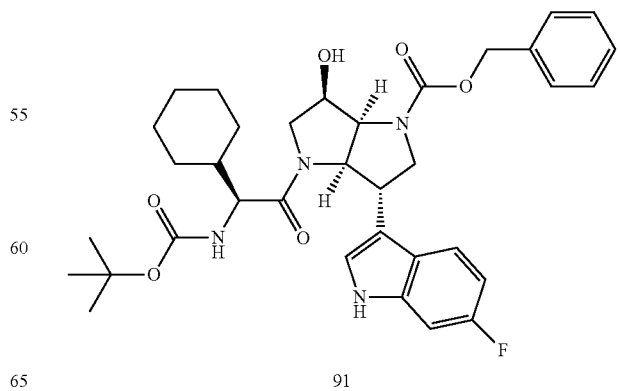

91

4-(2-tert-Butoxycarbonylamino-2-cyclohexyl-acetyl)-3S-(6-fluoro-1H-indol-3-yl)-6-hydroxy-hexahydro-pyrrolo[3,2-b]pyrrole-1-carboxylic acid benzyl ester (91)

To a solution of Boc-Chg-OH (309 mg, 1.20 mmol) and HATU (455 mg, 1.20 mmol) in NMP (1.5 mL) at 0° C. was added DIPEA (418 μL, 2.40 mmol) and the resultant pale yellow solution stirred for 30 min at 0° C. To the reaction mixture was added a solution of 90 (430 mg, 1.09 mmol) in NMP (3 mL) and the reaction mixture was stirred for an additional 3 h warming gradually to ambient temperature. The reaction mixture was diluted with EtOAc and washed successively with 1M HCl, NaHCO$_3$ (sat.), and brine. The organic phase was dried over anhydrous Na$_2$SO$_4$, filtered, and concentrated. The residue was purified by flash silica gel chromatography (2:1-1:1 hexanes/EtOAc) to afford 91 (680 mg, 98%) as an off-white foam. $^1$H NMR (300 MHz, CDCl$_3$): δ8.12 (dd, J=5.4, 8.4 Hz, 1H), 7.99 (s, 1H), 7.41 (s, 4H), 6.98 (dd, J=2.1, 9.6 Hz, 1H), 6.93 (dt, J=1.8, 9.6 Hz, 1H), 6.56 (s, 1H), 5.33-5.16 (m, 2H), 4.70 (d, J=4.8 Hz, 1H), 4.53 (s, 1H), 4.42 (t, J=4.8, 4.8 Hz, 1H), 4.36-4.19 (m, 3H), 3.91 (d, J=4.8 Hz, 1H), 3.58 (dd, J=5.7, 11.7 Hz, 1H), 3.33 (t, J=9.6 Hz, 1H), 1.72 (m, 4H), 1.44 (s, 9H), 1.17 (m, 4H) ppm. Mass spectrum, m/z [677.3] (M+H)+.

Scheme LXXXV

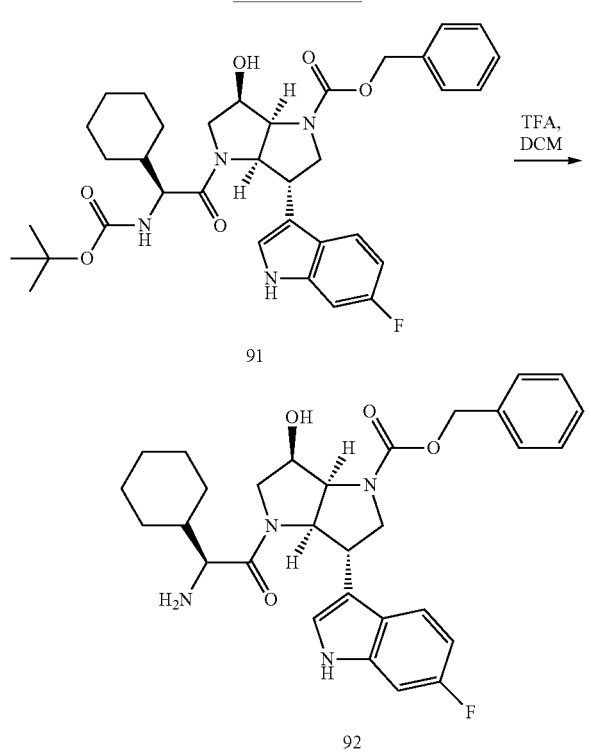

4-(2-Amino-2-cyclohexyl-acetyl)-3S-(6-fluoro-1H-indol-3-yl)-6-hydroxy-hexahydro-pyrrolo[3,2-b]pyrrole-1-carboxylic acid benzyl ester (92)

To a solution of 91 (680 mg, 1.07 mmol) in CH$_2$Cl$_2$ (4 mL) at 0° C. was added TFA (2 mL). After 3 h, the reaction mixture was concentrated and the residue dissolved in EtOAc and washed successively with NaHCO$_3$ (sat.), and brine. The organic phase was dried over anhydrous Na$_2$SO$_4$, filtered, and concentrated to afford 92 (610 mg, quant.) as a brown solid which was used without further purification. Mass spectrum, m/z [577.3] (M+H)+.

Scheme LXXXVI

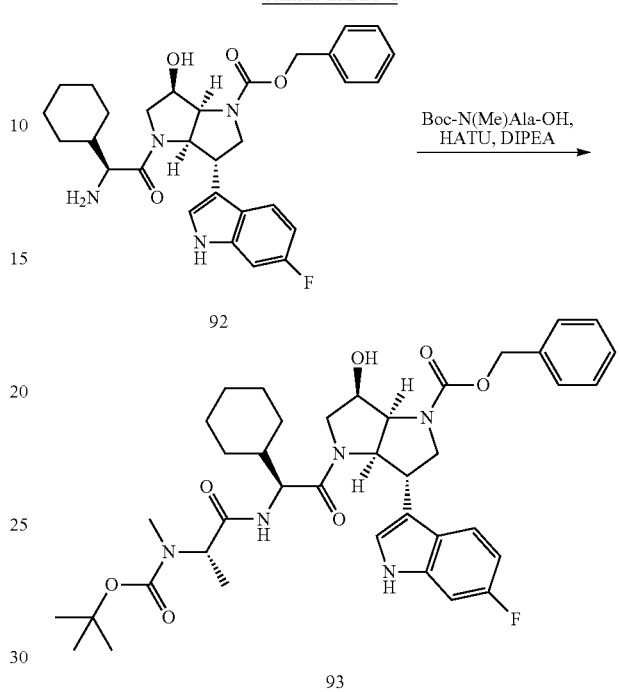

4-{2-[2-(tert-Butoxycarbonyl-methyl-amino)-propionylamino]-2-cyclohexyl-acetyl}-3S-(6-fluoro-1H-indol-3-yl)-6-hydroxy-hexahydro-pyrrolo[3,2-b]pyrrole-1-carboxylic acid benzyl ester (93)

To a solution of Boc-N(Me)Ala-OH (240 mg, 1.18 mmol) and HATU (449 mg, 1.18 mmol) in NMP (1.5 mL) at 0° C. was added DIPEA (411 μL, 2.36 mmol) and the resultant pale yellow solution was maintained at 0° C. After 30 min, a solution of 92 (572 mg, 1.07 mmol) in NMP (3 mL) was added and the reaction mixture was allowed to slowly warm to ambient temperature. After 2 h, the reaction mixture was diluted with EtOAc and washed successively with 1M HCl, NaHCO$_3$ (sat.), and brine. The organic phase was dried over anhydrous Na$_2$SO$_4$, filtered, and concentrated to afford 93 (790 mg) as an off-white solid which was used without further purification. Mass spectrum, m/z [720.4] (M+H)+.

Scheme LXXXVII

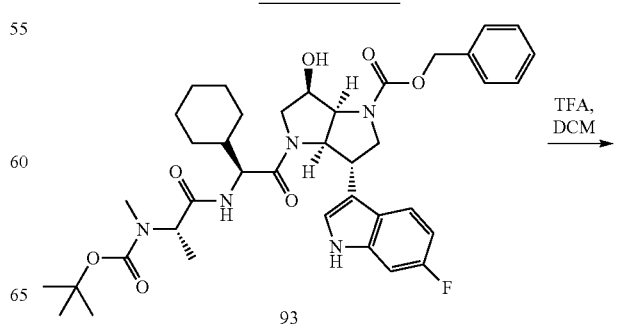

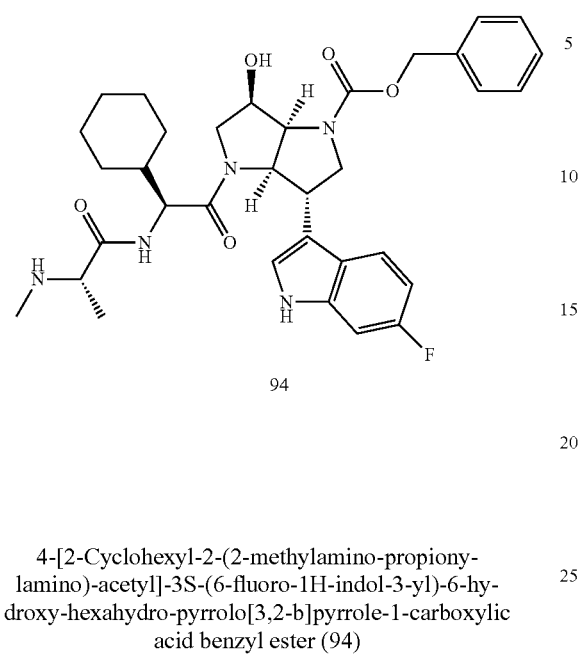

4-[2-Cyclohexyl-2-(2-methylamino-propionylamino)-acetyl]-3S-(6-fluoro-1H-indol-3-yl)-6-hydroxy-hexahydro-pyrrolo[3,2-b]pyrrole-1-carboxylic acid benzyl ester (94)

To a solution of 93 (770 mg, 1.07 mmol) in CH$_2$Cl$_2$ (5 mL) at 0° C. was added TFA (2 mL). After 2.5 h, the reaction mixture was concentrated and the residue was dissolved in EtOAc and washed successively with NaHCO$_3$ (sat.), and brine. The organic phase was dried over anhydrous Na$_2$SO$_4$, filtered, and concentrated to afford 94 (700 mg, quant.) as an off-white solid. A portion of crude residue (340 mg) was dissolved in H$_2$O and purified by reverse-phase HPLC (2" Dynamax C18, 10-60% ACN/H$_2$O containing 0.1% HOAc over 30 min; Flow: 40 mL/min). The product-containing fractions were combined and lyophilized to afford 94 (241 mg) as a white solid. $^1$H NMR (DMSO, 300 MHz): δ10.93 (d, J=12.6 Hz, 1H), 8.10 (m, 1.5H), 7.98 (dd, J=5.4, 8.7 Hz, 0.5H), 7.30 (m, 4H), 7.25 (m, 1H), 7.15 (t, J=3.0 Hz, 0.5H), 7.11 (t, J=2.4 Hz, 0.5H), 6.88 (m, 2H), 5.20 (d, J=12.9 Hz, 1H), 5.03 (dd, J=8.4, 12.9 Hz, 1H), 4.68 (app. t, J=6.3 Hz, 1H), 4.42 (m, 2H), 4.24 (m, 2H), 4.16-4.06 (m, 2H), 3.58 (d, J=5.7 Hz, 2H), 3.52-3.36 (m, 4H), 3.25 (dt, J=3.6, 9.6 Hz, 1H), 3.10 (dd, J=6.3, 13.5 Hz, 1H), 2.51 (app. t, J=1.8 Hz, 1H), 2.21 (s, 2H), 1.82-1.58 (m, 4H), 1.24-0.85 (m, 6H) ppm. $^{13}$C NMR (DMSO, 75 MHz), mixture of amide rotamers: δ174.6, 170.8 & 170.7, 159.8 (J$_{CF}$=246.6 Hz), 156.0 & 155.9, 138.0 & 137.6, 137.0 & 136.9, 129.1, 128.9, 128.5 & 128.1, 128.0, 127.6, 124.0 (J$_{CF}$=6.9 Hz), 121.9, 120.9, 115.1 & 115.0, 107.6 (J$_{CF}$=24.6 Hz), 98.0 (J$_{CF}$=25.4 Hz), 71.1 & 70.8, 67.1 & 66.7, 66.6 & 66.1, 62.2 & 61.6, 59.3, 55.2, 52.6, 41.3, 34.5, 29.8, 28.8, 26.5, 26.2 & 26.1, 19.3 ppm. Mass spectrum, m/z [620.3] (M+H)+.

Example 85 was prepared from 94 via hydrogenation as described in Scheme XLIII.

Example 86

N-{1-Cyclohexyl-2-[6R-(6-fluoro-1H-indol-3-yl)-3-hydroxy-hexahydro-pyrrolo[3,2-b]pyrrol-1-yl]-2-oxo-ethyl}-2-methylamino-propionamide (109)

Scheme LXXXVIII

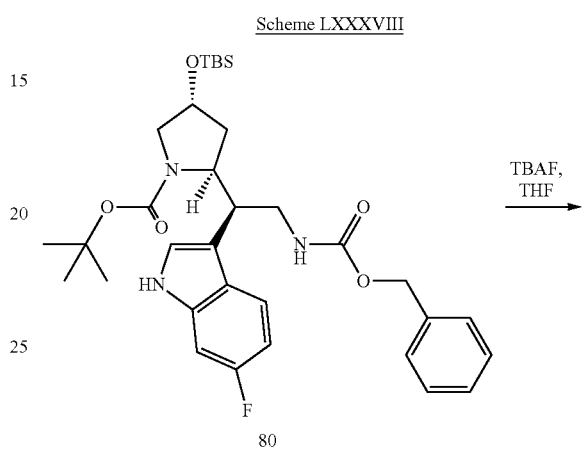

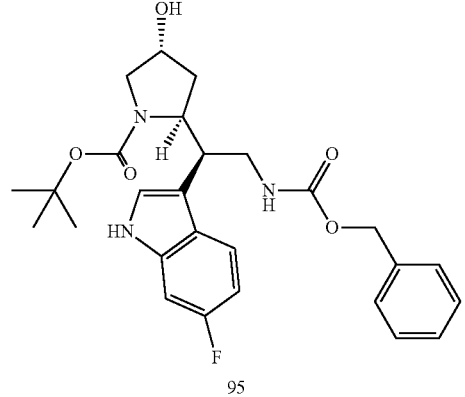

2-[2-Benzyloxycarbonylamino-1R-(6-fluoro-1H-indol-3-yl)-ethyl]-4-hydroxy-pyrrolidine-1-carboxylic acid tert-butyl ester (95)

To a solution of 80 (5.15 g, 8.42 mmol) in THF (42 mL) at ambient temperature was added 1M TBAF/THF (12.63 mL). After 5 h, the reaction mixture was concentrated and the residue dissolved in EtOAc and washed successively with 1M HCl, NaHCO$_3$ (sat.), and brine. The organic phase was dried over anhydrous Na$_2$SO$_4$, filtered, and concentrated to afford 95 (4.97 g, quant.) as an off-white foamy solid that was taken forward without further purification. Mass spectrum, m/z [498.2] (M+H)+.

Scheme LXXXIX

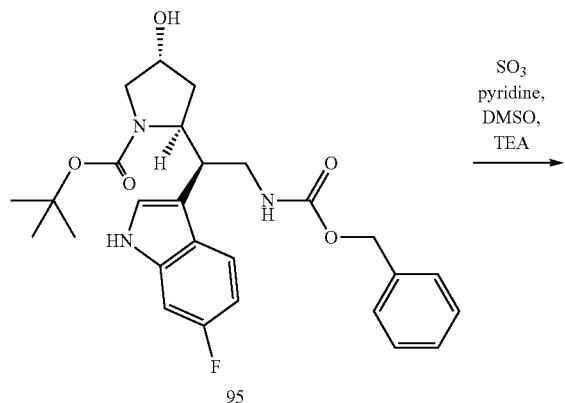

Scheme XC

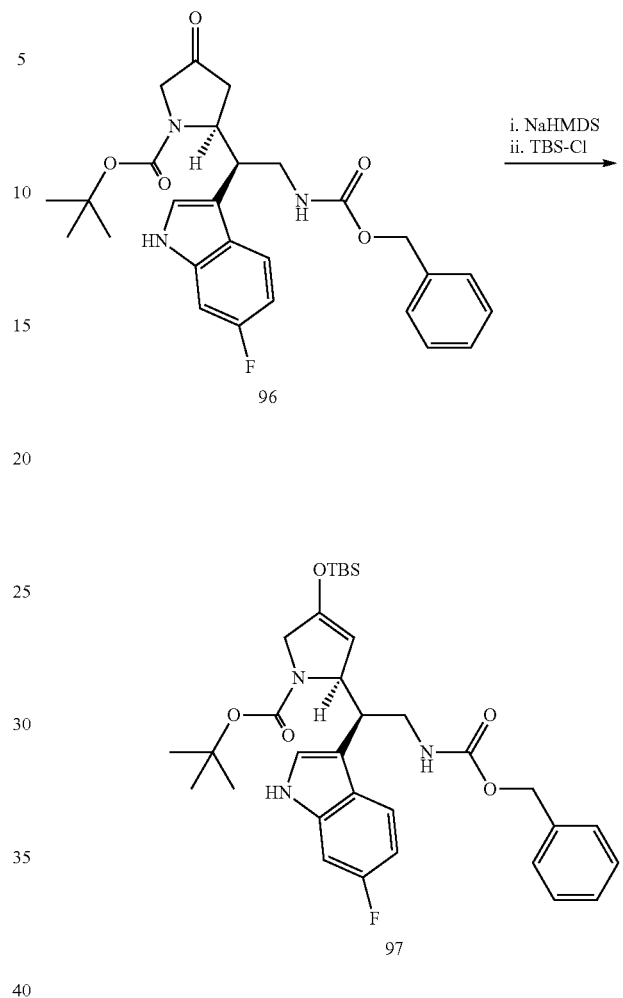

2-[2-Benzyloxycarbonylamino-1R-(6-fluoro-1H-indol-3-yl)-ethyl]-4-oxo-pyrrolidine-1-carboxylic acid tert-butyl ester (96)

To a solution of 95 (4.19 g, 8.42 mmol) in DMSO (15 mL) and CH$_2$Cl$_2$ (45 mL) at 0° C. were added TEA (7.03 mL, 50.5 mmol) and SO$_3$.pyridine complex (5.36 g, 33.6 mmol). The resultant yellow reaction mixture was stirred for an additional 30 min at 0° C. then warmed to ambient temperature. After 2.5 h, the reaction mixture was diluted with CH$_2$Cl$_2$ and washed with 30% citric acid, NaHCO$_3$ (sat.), and brine. The organic phase was dried over anhydrous Na$_2$SO$_4$, filtered, and concentrated. The crude product was purified by flash silica gel chromatography (2:1-1:1 hexanes/EtOAc) to afford 96 (3.97 g, 95%) as a foamy white solid. $^1$H NMR (300 MHz, CDCl$_3$): δ8.44 (m, 1H), 7.42 (dd, J=5.7, 8.7 Hz, 1H), 7.33 (m, 4H), 6.99 (dd, J=2.1, 9.3 Hz, 2H), 6.93-6.81 (m, 2H), 5.18 (m, 1H), 5.03 (m, 2H), 4.77 (m, 1H), 3.70 (m, 2H), 3.53 (d, J=19.5 Hz, 1H), 3.40 (m, 2H), 2.63-2.50 (m, 3H), 1.52 (m, 9H) ppm. Mass spectrum, m/z [498.2] (M+H)+.

2-[2-Benzyloxycarbonylamino-1R-(6-fluoro-1H-indol-3-yl)-ethyl]-4-(tert-butyl-dimethyl-silanyloxy)-2,5-dihydro-pyrrole-1-carboxylic acid tert-butyl ester (97)

To a solution of 96 (2.37 g, 4.78 mmol) in THF (20 mL) at −78° C. was added NaHMDS (1M/THF, 14.8 mL) over 20 min. The resultant yellow reaction mixture was stirred an additional 40 min at −78° C. To the reaction mixture was added a solution of TBSCl (2.23 g, 14.8 mmol) in THF (10 mL) dropwise over 10 min. After 4 h at −78° C., the reaction mixture was warmed to 0° C. and quenched with NH$_4$Cl (sat.). The mixture was extracted with EtOAc, and the combined organic extracts were washed with brine and concentrated. The residue was purified by flash silica gel chromatography (4:1 hexanes/EtOAc) to afford 97 (2.73 g, 79%) as a foamy white solid. $^1$H NMR (300 MHz, CDCl$_3$): δ7.48 (m, 1H), 7.30 (m, 5H), 7.10 (dd, J=1.9, 10.8 Hz, 1H), 6.80 (ddd, J=1.8, 1.8, 9.0 Hz, 1H), 5.04 (m, 2H), 4.88-4.79 (m, 1H), 4.62 (s, 1H), 3.85-3.65 (m, 3H), 3.42 (m, 1H), 3.12 (dd, J=3.3, 13.5 Hz, 1H), 1.61-1.42 (m, 9H), 0.98-0.86 (m, 18H), 0.56 (m, 5H), 0.08 (m, 7H) ppm. Mass spectrum, m/z [724.4] (M)+.

Scheme XCI

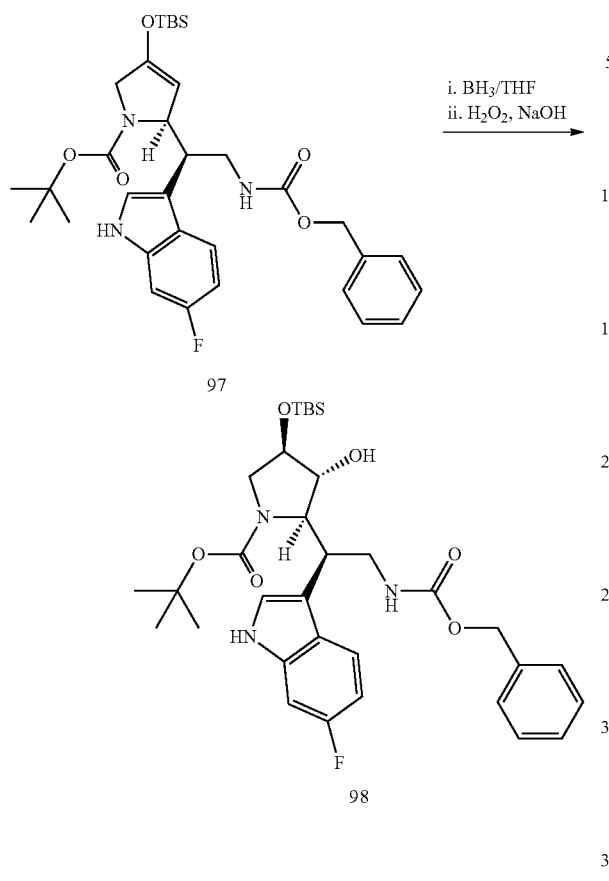

Scheme XCII

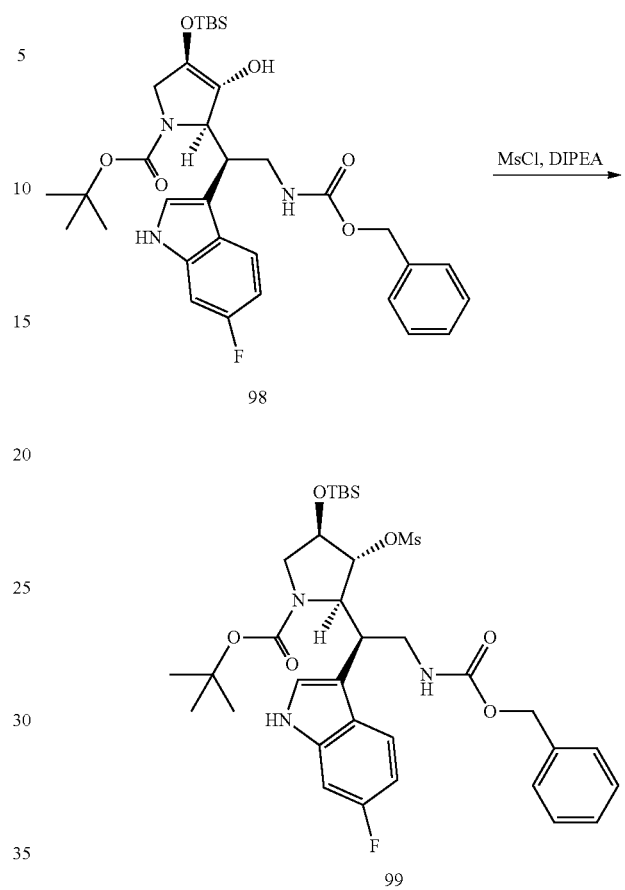

2-[2-Benzyloxycarbonylamino-1R-(6-fluoro-1H-indol-3-yl)-ethyl]-4-(tert-butyl-dimethyl-silanyloxy)-3-hydroxy-pyrrolidine-1-carboxylic acid tert-butyl ester (98)

To a solution of 97 (2.73 g, 3.78 mmol) in THF (75 mL) at −30° C. was added $BH_3$.THF (1M/THF, 18.8 mL) in one portion The reaction mixture was stirred for 15 min at −30° C. then warmed to ambient temperature and stirred for an additional 3 h. The reaction mixture was then cooled to 0° C. and 1M NaOH (20 mL) and 30% $H_2O_2$ (10 mL) were slowly added. When the bubling had subsided, the reaction mixture was allowed to slowly warm to ambient temperature. After 4 h, the reaction mixture was recooled to 0° C. and quenched with aqueous $Na_2S_2O_3$. The mixture was extracted three times with EtOAc and the combined organic extracts were washed with brine and dried over anhydrous $Na_2SO_4$, filtered, and concentrated. The crude residue was purified by flash silica gel column (3:1-1:1 hexanes/EtOAc) to afford 98 (1.75 g, 60%) as a white solid. $^1$H NMR (300 MHz, $CDCl_3$): δ8.57 (s, 0.6H), 8.45 (s, 0.4H), 7.53 (dd, J=5.7, 9.0 Hz, 1H), 7.32-7.14 (m, 4H), 6.97 (m, 1H), 6.23 (s, 0.3H), 5.77 (s, 0.7H), 4.21-4.06 (m, 2H), 3.89-3.90 (m, 2H), 3.64 (m, 1H), 3.27 (m, 1H), 2.91 (m, 1H), 2.52 (m, 1H), 1.50 (m, 9H), 0.85 (s, 9H), 0.03 (m, 6H) ppm. Mass spectrum, m/z [650.3] (M+Na)+.

2-[2-Benzyloxycarbonylamino-1R-(6-fluoro-1H-indol-3-yl)-ethyl]-4-(tert-butyl-dimethyl-silanyloxy)-3-methanesulfonyloxy-pyrrolidine-1-carboxylic acid tert-butyl ester (99)

To a solution of 98 (1.75 g, 2.79 mmol) in $CH_2Cl_2$ (30 mL) at 0° C. were added DIPEA (993 μL, 5.58 mmol), DMAP (50 mg.), and MsCl (220 μL, 2.84 mmol)). The reaction mixture was stirred at 0° C. during which time the reaction mixture became heterogeneous. After 2 h, the reaction mixture was diluted with $CH_2Cl_2$ and washes successively with 1M HCl, $NaHCO_3$ (sat.), and brine. The organic phase was dried over anhydrous $Na_2SO_4$, filtered, and concentrated. The crude residue was purified by flash silica gel chromatography (2:1 hexanes/EtOAc) to afford 99 (2.44 g, quant.) as a foamy white solid. $^1$H NMR (300 MHz, $CDCl_3$): δ8.22 (m, 1H), 7.68-7.55 (m, 1H), 7.27 (m, 4H), 7.05 (m, 1H), 6.96 (m, 1H), 6.83 (dd, J=9.3, 16.5 Hz, 1H), 5.86 (d, J=5.7 Hz, 1H), 4.91 (m, 2H), 4.61-4.48 (m, 2H), 4.40 (d, J=4.8 Hz, 1H), 3.82 (ddd, J=4.2, 4.2, 13.8 Hz, 1H), 3.54 (m, 1H), 3.36 (m, 2H), 2.47-2.28 (m, 3H), 1.60-1.53 (m, 9H), 0.92 (m, 9H), 0.06 (m, 6H) ppm. Mass spectrum, m/z [728.3] (M+Na)+.

Scheme XCIII

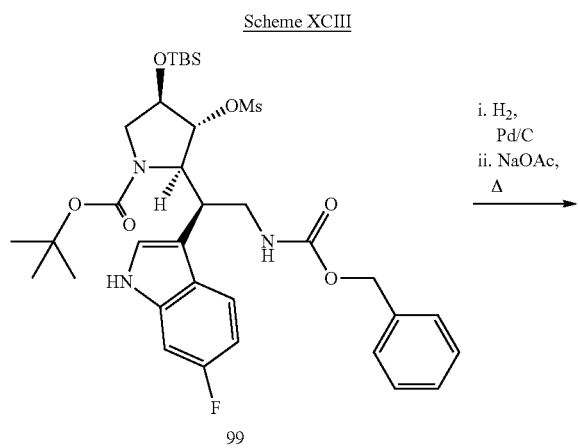

Scheme XCIV

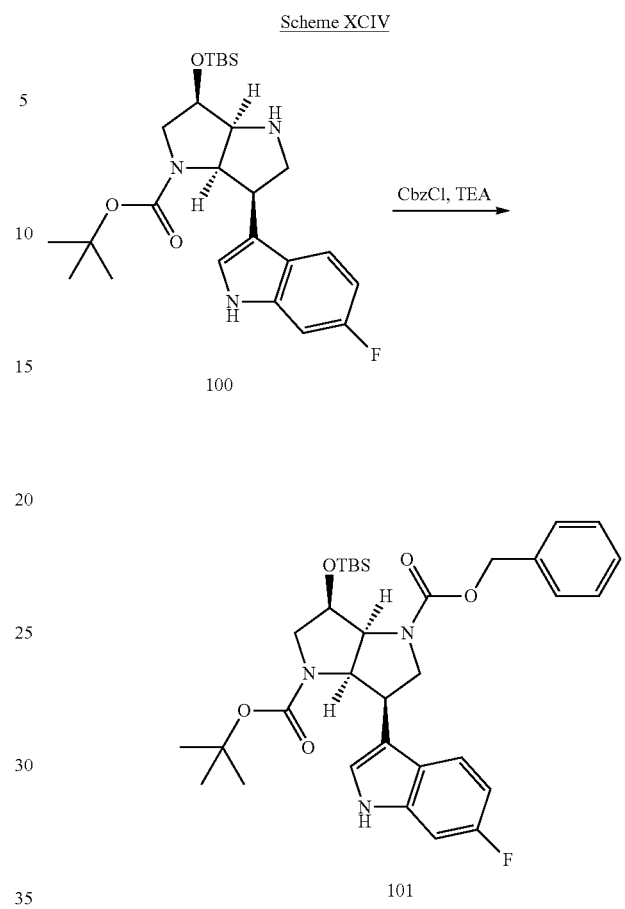

3-(tert-Butyl-dimethyl-silanyloxy)-6R-(6-fluoro-1H-indol-3-yl)-hexahydro-pyrrolo[3,2-b]pyrrole-1-carboxylic acid tert-butyl ester (100)

To a solution of 99 (1.83 g, 2.59 mmol) in MeOH (50 mL) in a Parr bottle was added 10% Pd/C (100 mg). The flask was evacuated and flushed with H$_2$ five times, then charged to 50 PSI H$_2$ (344.7 KPa) and shaken. After 2.5 h, the mixture was filtered through a Millipore filter and concentrated to afford a mixture of anticipated acyclic amine and 100 (1.47 g) as a white solid. Mass spectrum, m/z [572.3] (M+H)+.

To this mixture of cyclic and acyclic amines (1.47 g) in EtOH (30 mL) at ambient temperature was added NaOAc (253 mg, 3.09 mmol) and the mixture was warmed in a preheated oil bath (80° C.). After 15 min, the reaction mixture was concentrated and the residue dissolved in EtOAc, washed with water and brine. The organic phase was dried over anhydrous Na$_2$SO$_4$, filtered, and concentrated to afford 100 (1.28 g, quant.) as a foamy off-white solid. $^1$H NMR (300 MHz, CDCl$_3$): δ9.0 (br s, 1H), 7.48 (dd, J=1.2, 11.1 Hz, 1H), 6.89 (m, 2H), 4.62 (t, J=6.0 Hz, 1H), 4.44 (dd, J=7.8, 15.6 Hz, 1H), 4.33 (t, J=6.6 Hz, 1H), 4.20 (m, 1H), 4.00 (m, 1H), 3.57 (dd, J=7.2, 10.2 Hz, 1H), 3.16 (t, J=12.3 Hz, 1H), 2.96 (t, J=9.9 Hz, 1H), 0.97 (m, 9H), 0.73 (m, 9H), 0.18 (m, 6H) ppm. Mass spectrum, m/z [476.2] (M+H)+.

3-(tert-Butyl-dimethyl-silanyloxy)-6R-(6-fluoro-1H-indol-3-yl)-hexahydro-pyrrolo[3,2-b]pyrrole-1,4-dicarboxylic acid 4-benzyl ester 1-tert-butyl ester (101)

To a solution of 100 (1.22 g, 2.57 mmol) in CH$_2$Cl$_2$ (13 mL) at 0° C. were added TEA (716 µL, 5.14 mmol), DMAP (50 mg), and CbzCl (434 µL, 3.08 mmol). The resultant pale yellow solution was warmed gradually to ambient temperature. After 14 h, the reaction mixture was diluted with CH$_2$Cl$_2$ and washed successively with 1M HCl, NaHCO$_3$ (sat.), and brine. The organic phase was dried over anhydrous Na$_2$SO$_4$, filtered, and concentrated. The crude residue was purified by flash silica gel chromatography (3:1 hexanes/EtOAc) to afford 101 (1.02 g, 65%) as a foamy white solid. $^1$H NMR (300 MHz, CDCl$_3$), mixture of carbamate rotamers: δ8.52 (m, 1H), 7.48 (dd, J=5.7, 8.1 Hz, 1H), 7.34 (m, 5H), 7.04 (d, J=9.3 Hz, 1H), 6.97 (s, 1H), 6.89 (t, J=9.9 Hz, 1H), 5.42 (d, J=12.3 Hz, 0.5H), 5.12 (dd, J=12.6, 32.4 Hz, 1H), 4.85 (m, 1H), 4.70 (d, J=6.8 Hz, 0.5H), 4.59 (m, 1H), 4.37-4.23 (m, 1H), 4.16 (dd, J=2.8, 8.4 Hz, 0.5H), 4.06 (dd, J=6.9, 10.8 Hz, 0.5H), 3.71 (m, 1H), 3.32 (t, J=12.3 Hz, 1H), 3.03 (m, 1H), 0.91 (m, 9H), 0.68 (m, 9H), 0.14 (m, 6H) ppm. Mass spectrum, m/z [610.2] (M+H)+.

Scheme XCV

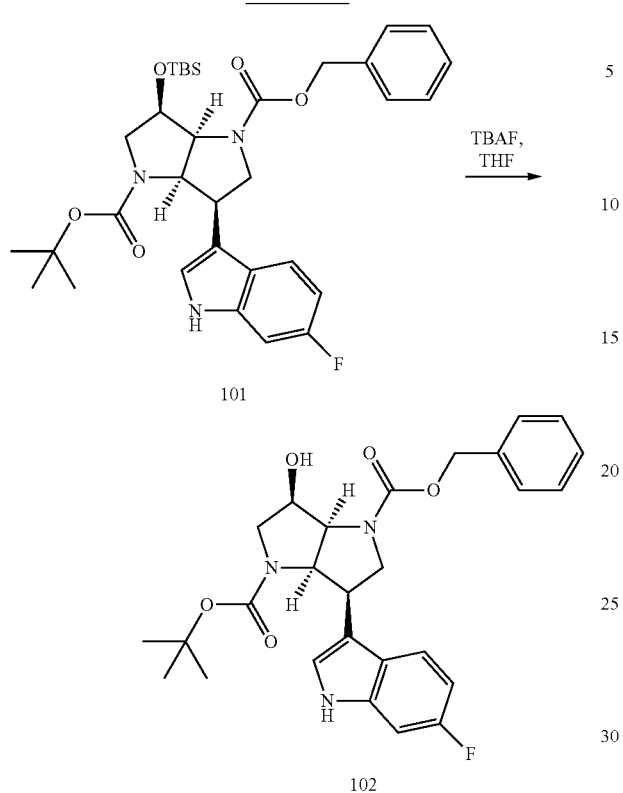

3-(6-Fluoro-1H-indol-3-yl)-6R-hydroxy-hexahydro-pyrrolo[3,2-b]pyrrole-1,4-dicarboxylic acid 1-benzyl ester 4-tert-butyl ester (102)

To a solution of 101 (1.0 g, 1.64 mmol) in THF (10 mL) at ambient temperature was added 1M TBAF/THF (2.46 mL). After 2 h, the reaction mixture was concentrated and the residue was dissolved in EtOAc, washed successively with 1M HCl, NaHCO$_3$ (sat.), and brine, dried over anhydrous Na$_2$SO$_4$, filtered, and concentrated to afford 102 (870 mg, quant.) as a foamy off-white solid which was used without further purification. Mass spectrum, m/z [496.1] (M+H)+.

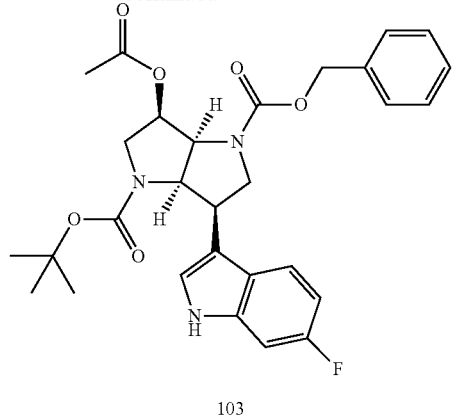

3-Acetoxy-6R-(6-fluoro-1H-indol-3-yl)-hexahydro-pyrrolo[3,2-b]pyrrole-1,4-dicarboxylic acid 4-benzyl ester 1-tert-butyl ester (103)

To a solution of 102 (813 mg, 1.64 mmol) in CH$_2$Cl$_2$ (10 mL) at 0° C. were added TEA (447 µL, 3.28 mmol), DMAP (50 mg), and Ac$_2$O (186 µL, 1.97 mmol). The resultant yellow solution was slowly warmed to ambient temperature. After 2.5 h, the reaction mixture was diluted with CH$_2$Cl$_2$ and washed successively with 1M HCl, NaHCO$_3$ (sat.), and brine. The organic phase was dried over anhydrous Na$_2$SO$_4$, filtered, and concentrated. The crude residue was purified by flash silica gel chromatography (1:1 hexanes/EtOAc) to afford 103 (730 mg, 83%) as a foamy white solid. $^1$H NMR (300 MHz, CDCl$_3$): δ8.37 (br s, 1H), 7.49 (m, 1H), 7.37 (m, 5H), 7.06 (d, J=8.4 Hz, 1H) 6.99 (s, 1H), 6.90 (t, J=9.3 Hz, 1H), 5.31-5.08 (m, 3H), 4.95 (m, 1H), 4.65 (m, 1H), 4.21 (m, 2H), 3.70 (dd, J=7.2, 12.6 Hz, 1H), 3.42 (t, J=6.0 Hz, 1H), 3.18 (t, J=11.1 Hz, 1H), 1.96-1.81 (m, 3H), 0.77 (m, 9H) ppm. Mass spectrum, m/z [538.2] (M+H)+.

Scheme XCVI

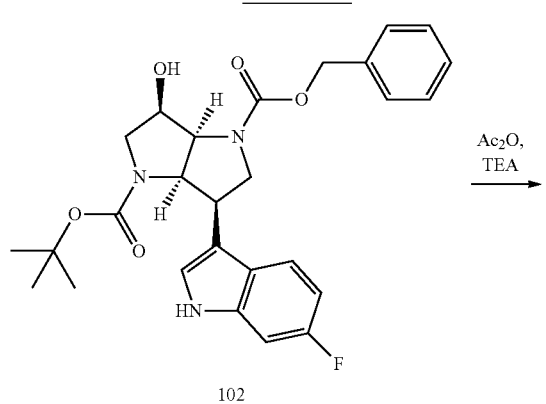

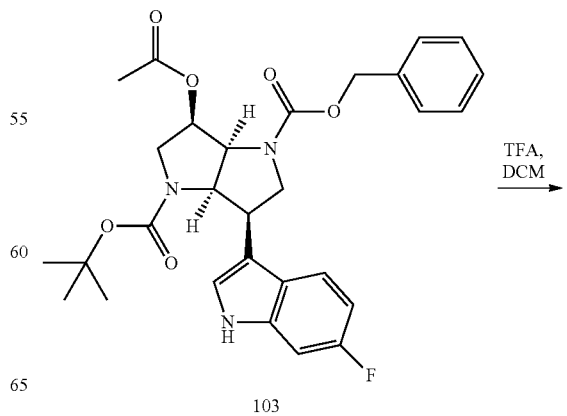

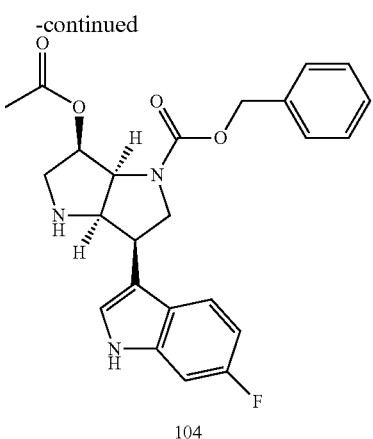

6-Acetoxy-3R-(6-fluoro-1H-indol-3-yl)-hexahydro-pyrrolo[3,2-b]pyrrole-1-carboxylic acid benzyl ester (104)

To a solution of 103 (730 mg, 1.36 mmol) in CH₂Cl₂ (6 mL) at 0° C. was added TFA (3 mL). After 2 h, the magenta-colored reaction mixture was concentrated. The residue was dissolved in EtOAc and washed successively with NaHCO₃ (sat.), and brine. The organic phase was dried over anhydrous Na₂SO₄, filtered, and concentrated to afford 104 (540 mg, 91%) as an off-white solid which was used without further purification. Mass spectrum, m/z [438.2] (M+H)+.

6-Acetoxy-4-(2-tert-butoxycarbonylamino-2-cyclo-hexyl-acetyl)-3R-(6-fluoro-1H-indol-3-yl)-hexahy-dro-pyrrolo[3,2-b]pyrrole-1-carboxylic acid benzyl ester (105)

To a solution of Boc-Chg-OH (349 mg, 1.36 mmol) and HATU (517 mg, 1.36 mmol) in NMP (2 mL) at 0° C. was added DIPEA (428 µL, 2.46 mmol) and the resultant pale yellow solution was stirred for 30 min at 0° C. To the reaction mixture was added a solution of 104 (540 mg, 1.23 mmol) in NMP (6 mL) and the reaction mixture was allowed to warm to ambient temperature. After 16 h, the reaction mixture was diluted with EtOAc and washed successively with 1M HCl, NaHCO₃ (sat.), and brine. The organic phase was dried over anhydrous Na₂SO₄, filtered, and concentrated. The residue was purified by flash silica gel chromatography (2:1-1:1 hexanes/EtOAc) to afford 105 (750 mg, 90%) as an off-white foam. ¹H NMR (300 MHz, CDCl₃): δ8.24 (d, J=13.5 Hz, 1H), 7.61 (dd, J=5.1, 8.4 Hz, 1H), 7.39 (m, 5H), 6.93 (m, 3H), 5.39 (m, 1H), 5.22 (d, J=12.3 Hz, 2H), 5.13 (m, 1H), 4.99 (d, J=9.0 Hz, 1H), 4.86 (d, J=29.1 Hz, 2H), 4.25 (m, 1H), 4.13 (m, 1H), 4.05 (m, 1H), 3.87 (dt, J=7.5, 11.4 Hz, 1H), 3.57 (t, J=11.1 Hz, 1H), 3.17 (m, 1H), 1.91-1.81 (m, 3H), 1.53 (m, 2H), 1.35 (m, 9H), 1.27 (m, 2H), 0.97 (m, 4H), 0.55 (m, 2H) ppm. Mass spectrum, m/z [677.3] (M+H)+.

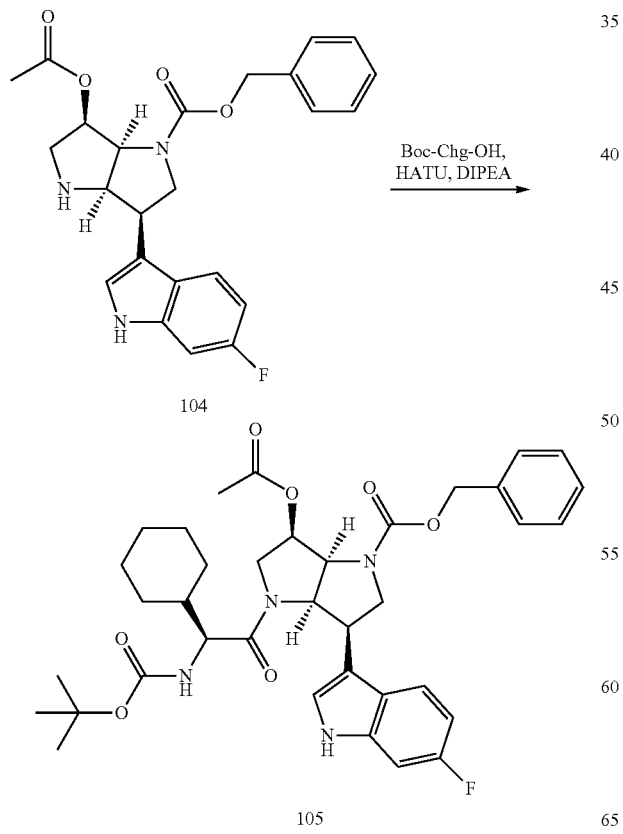

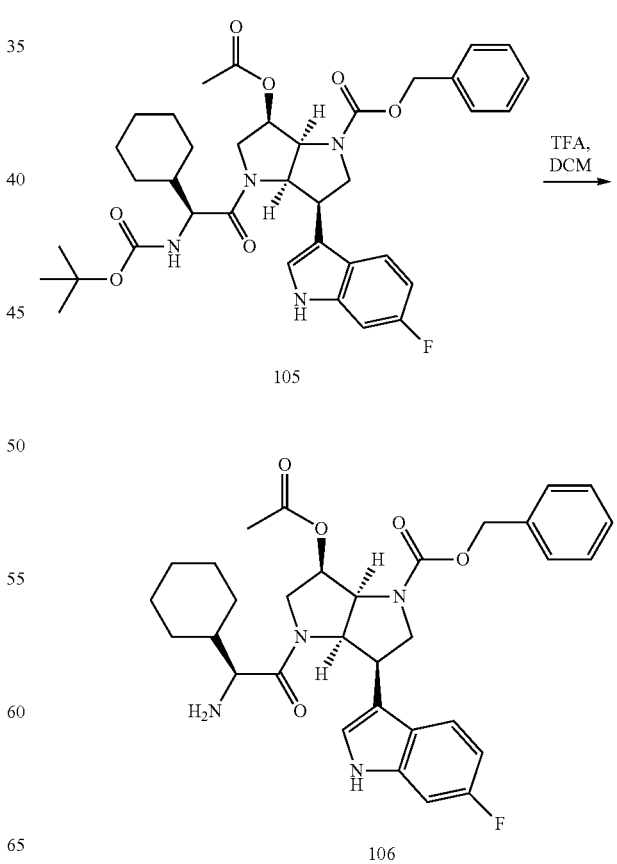

6-Acetoxy-4-(2-amino-2-cyclohexyl-acetyl)-3R-(6-fluoro-1H-indol-3-yl)-hexahydro-pyrrolo[3,2-b]pyrrole-1-carboxylic acid benzyl ester (106)

To a solution of 105 (188 mg, 0.27 mmol) in CH$_2$Cl$_2$ (5 mL) at 0° C. was added TFA (3 mL). After 2.5 h, the pink-colored reaction mixture was concentrated and the residue was dissolved in EtOAc and washed successively with NaHCO$_3$ (sat.), and brine. The organic phase was dried over anhydrous Na$_2$SO$_4$, filtered, and concentrated to afford 106 (160 mg, quant.) as a brown solid which was used without further purification. Mass spectrum, m/z [577.3] (M+H)+.

Scheme C

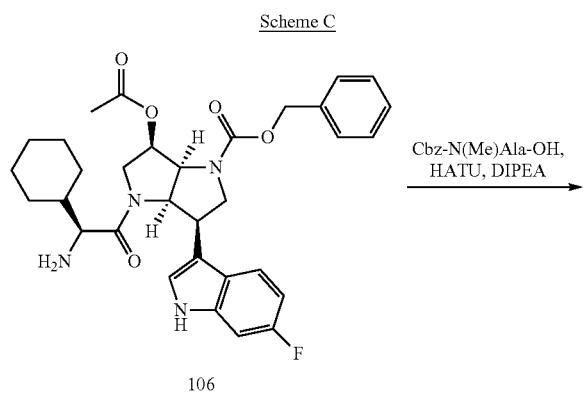

106

Cbz-N(Me)Ala-OH,
HATU, DIPEA
→

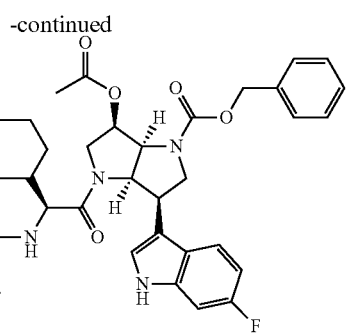

107

6-Acetoxy-4-{2-[2-(benzyloxycarbonyl-methyl-amino)-propionylamino]-2-cyclohexyl-acetyl}-3R-(6-fluoro-1H-indol-3-yl)-hexahydro-pyrrolo[3,2-b]pyrrole-1-carboxylic acid benzyl ester (107)

To a solution of Cbz-N(Me)Ala-OH (73 mg, 0.30 mmol) and HATU (116 mg, 0.30 mmol) in NMP (1 mL) at 0° C. was added DIPEA (97 μL, 0.55 mmol) and the resultant pale yellow solution was maintained at 0° C. After 30 min, a solution of 106 (160 mg, 0.27 mmol) in NMP (2 mL) was added and the reaction mixture was allowed to slowly warm to ambient temperature. After 16 h, the reaction mixture was diluted with EtOAc and washed successively with 1M HCl, NaHCO$_3$ (sat.), and brine. The organic phase was dried over anhydrous Na$_2$SO$_4$, filtered, and concentrated to afford 107 (230 mg, quant.) as a brown solid which was used without further purification. Mass spectrum, m/z [796.4] (M+H)+.

Scheme CI

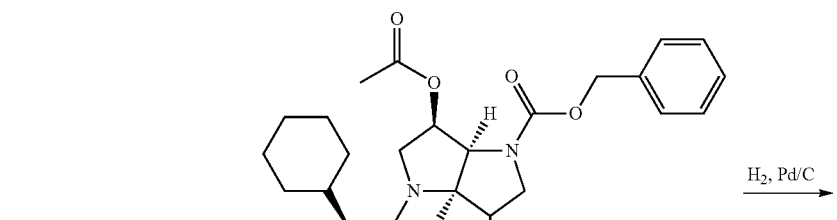

107

H$_2$, Pd/C
→

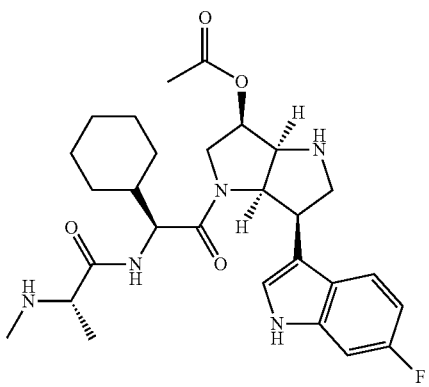

108

Acetic acid 1-[2-cyclohexyl-2-(2-methylamino-propionylamino)-acetyl]-6R-(6-fluoro-1H-indol-3-yl)-octahydro-pyrrolo[3,2-b]pyrrol-3-yl ester (108)

To a solution of 107 (221 mg, 0.27 mmol) in MeOH (15 mL) in a Parr bottle was added 10% Pd/C (50 mg). The flask was evacuated and flushed with $H_2$ five times, then charged to 50 PSI $H_2$ (344.7 KPa) and shaken. After 2 h, the reaction mixture was filtered through a Millipore filter and concentrated to afford 108 (130 mg, 88%) as a white solid that was used without further purification. Mass spectrum, m/z [528.3] (M+H)+.

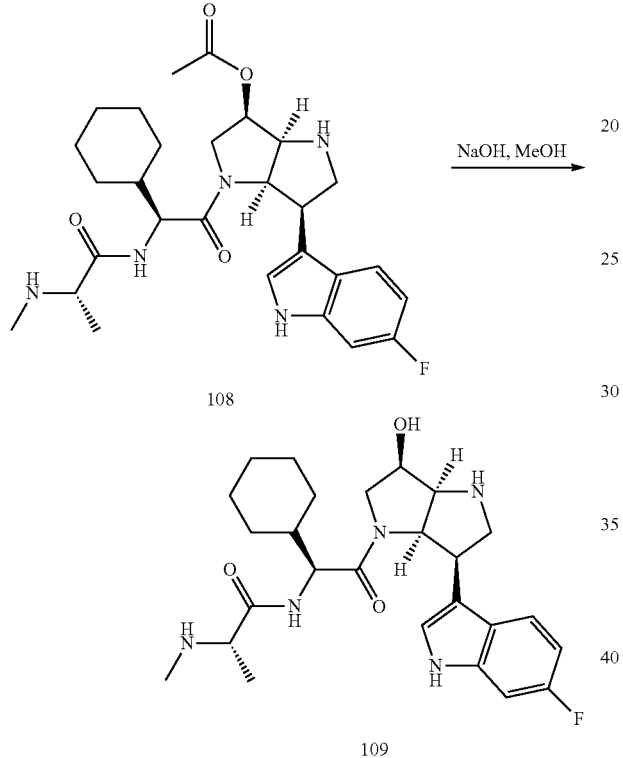

N-{1-Cyclohexyl-2-[6R-(6-fluoro-1H-indol-3-yl)-3-hydroxy-hexahydro-pyrrolo[3,2-b]pyrrol-1-yl]-2-oxo-ethyl}-2-methylamino-propionamide (109)

To a solution of 108 (130 mg, 0.24 mmol) in MeOH (5 mL) at ambient temperature was added 1M NaOH (2 mL). After 3 h, solid NaOH (3 pellets) was added. After 72 h, the reaction mixture was neutralized with HOAc and concentrated. The residue was dissolved in $H_2O$ and purified by reverse-phase HPLC (2" Dynamax C18, 10-60% ACN/$H_2O$ containing 0.1% HOAc over 30 min; Flow: 40 mL/min). The product-containing fractions were combined and lyophilized to afford 109 (84 mg, 70%) as a white solid. $^1$H NMR (300 MHz, $d_6$-DMSO): δ10.42 (s, 1H), 7.25-7.18 (m, 2H), 6.78 (d, J=1.5 Hz, 1H), 6.61 (dd, J=2.4, 10.2 Hz, 1H), 6.41 (dt, J=2.4, 10.5 Hz, 1H), 4.66 (t, J=7.2 Hz, 1H), 3.83 (dd, J=6.3, 9.0 Hz, 2H), 3.62-3.45 (m, 3H), 3.23 (dt, J=7.2, 10.8 Hz, 1H), 2.79 (dd, J=7.5, 10.8 Hz, 1H), 2.52 (m, 2H), 2.14 (s, 1H), 1.72 (s, 2H), 1.52 (s, 3H), 1.08 (m, 2H), 0.65 (d, J=6.6 Hz, 2H), 0.52 (m, 2H), 0.34 (m, 2H), 0.05 (m, 2H) ppm. $^{13}$C NMR (75 MHz, $d_6$-DMSO): δ174.5, 173.0, 169.2, 160.9, 157.8, 136.4, 136.2, 125.4, 123.7, 120.8, 120.7, 111.7, 107.0, 106.8, 97.4, 97.1, 69.4, 62.9, 62.15, 59.7, 54.1, 53.9, 52.7, 43.5, 34.7, 29.6, 27.2, 26.4, 26.2, 26.1, 22.1, 19.7 ppm. Mass spectrum, m/z [486.3] (M+H)+.

Example 108

4-[2-Cyclohexyl-2-(2-methylamino-propionylamino)-acetyl]hexahydro-pyrrolo[3,2-b]pyrrole-1-carboxylic acid benzyl ester (117)

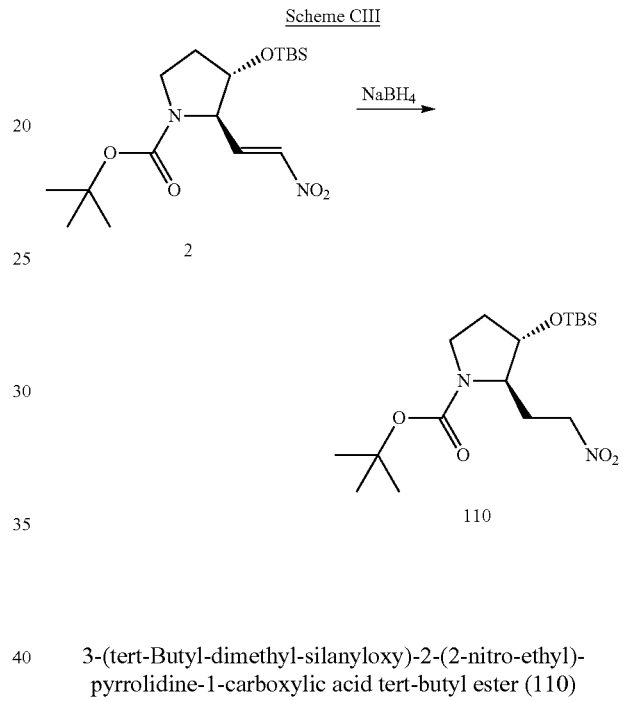

3-(tert-Butyl-dimethyl-silanyloxy)-2-(2-nitro-ethyl)-pyrrolidine-1-carboxylic acid tert-butyl ester (110)

At ambient temperature, NaBH$_4$ (0.24 g, 6.36 mmol) was added portionwise to a solution containing 2 (2.37 g, 6.36 mmol) in THF (100 mL) and water (20 mL). After 2 h, the reaction mixture was poured onto a mixture of dilute aqueous HCl, EtOAc, and ice. The organic layer was separated and washed successively with 1M HCl, brine, dried over anhydrous Na$_2$SO$_4$, filtered, and concentrated to afford 2.5 g (quant.) of 110 which was used without further purification. $^1$H NMR (300 MHz, CDCl$_3$): δ4.46 (m, 2H), 4.04 (br s, 1H), 3.74-3.40 (m, 3H), 3.29 (app t, J=8.4 Hz, 1H), 2.15-1.85 (m, 3H), 1.45 (s, 9H), 0.86 (s, 9H), 0.07 (s, 6H) ppm.

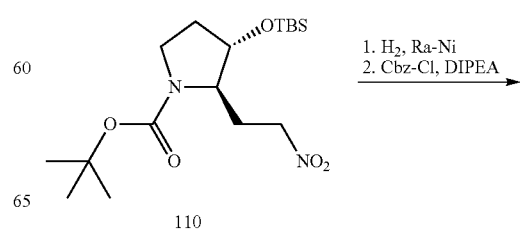

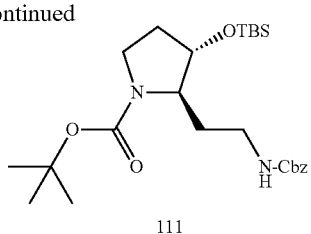

111

2-(2-Benzyloxycarbonylamino-ethyl)-3-hydroxy-pyrrolidine-1-carboxylic acid tert-butyl ester (111)

A 500 mL Parr bottle was charged with crude 110 (2.5 g) and Raney-Ni (~2 mL, 2400, slurry in water) in abs. EtOH (30 mL). The bottle was pressurized to 55 PSI $H_2$ (379.2 KPa) and shaken for 2 h. The catalyst was removed by filtration through diatomaceous earth (Celite®) and washed with EtOH and water. The filtrate was concentrated in vacuo and the residue was dissolved in EtOAc, washed with aqueous $NaHCO_3$, brine, dried over anhydrous $Na_2SO_4$, filtered, and concentrated to afford 2.3 g of crude amine which was used without further purification.

A solution containing the crude amine (2.3 g) in DCM (20 mL) was cooled to 0° C. DIPEA (1.03 g, 8.01 mmol) was added followed by the addition of Cbz-Cl (1.13 g, 6.67 mmol). The reaction mixture was allowed to slowly warm to ambient temperature. After 16 h, the reaction mixture was diluted with DCM and washed successively with 1M HCl, brine, dried over anhydrous $Na_2SO_4$, filtered, and concentrated. The crude product was purified by flash silica gel chromatography (9:1 to 4:1 hexanes/EtOAc) to afford 2.37 g (78% from 2) of 111. $^1$H NMR (300 MHz, $CDCl_3$): δ 7.30 (m, 5H), 6.12 (m, 1H), 5.06 (m, 4H), 3.94 (m, 1H), 3.70 (m, 1H), 3.47-3.41 (m, 2H), 3.26 (app t, J=9.0 Hz, 1H), 2.95 (m, 1H), 1.91-1.56 (m, 2H), 1.40 (s, 9H), 0.81 (s, 9H), 0.00 (s, 6H) ppm. Mass spectrum, m/z [479.2] (M+H)+.

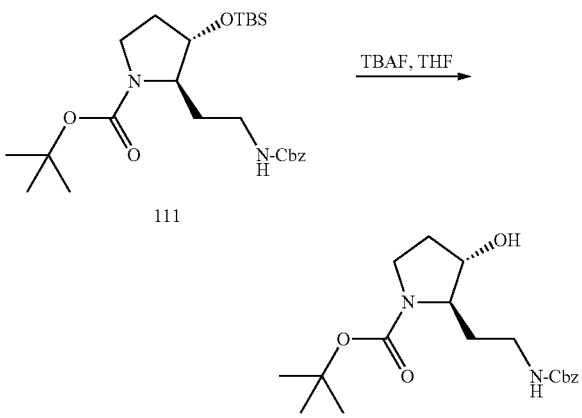

2-(2-Benzyloxycarbonylamino-ethyl)-3-hydroxy-pyrrolidine-1-carboxylic acid tert-butyl ester (112)

A solution containing 111 (2.37 g, 4.95 mmol) in THF (25 mL) was cooled to 0° C. TBAF (1M in THF, 5.5 mL) was added and the reaction mixture was slowly warmed to ambient temperature. After 16 h, the reaction mixture was diluted with EtOAc and washed successively with 1M HCl, brine, dried over anhydrous $Na_2SO_4$, filtered, and concentrated. The crude product was purified by flash silica gel chromatography (1:1 to 1:3 hexanes/EtOAc) to afford 1.68 g (93%) of 112 as a white-colored foam. Mass spectrum, m/z [365.1] (M+H)+.

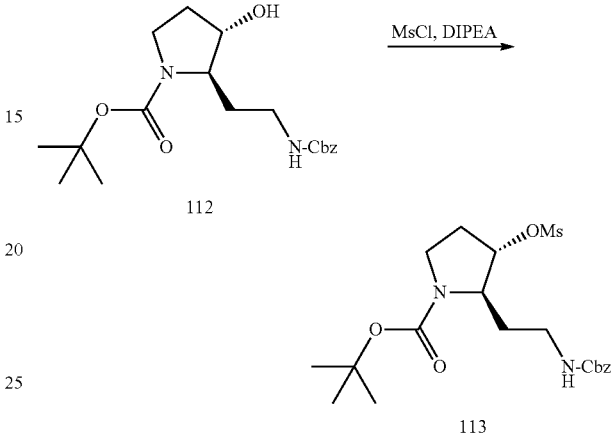

2-(2-Benzyloxycarbonylamino-ethyl)-3-methane-sulfonyloxy-pyrrolidine-1-carboxylic acid tert-butyl ester (113)

A solution containing 112 (1.68 g, 4.60 mmol) and DIPEA (0.71 g, 5.53 mmol) in DCM (20 mL) was cooled to 0° C. MsCl (0.52 g, 4.60 mmol) was added. After 1 h, the reaction mixture was diluted with EtOAc and washed successively with dilute aqueous HCl, brine, dried over anhydrous $Na_2SO_4$, filtered, and concentrated. The crude product was purified by flash silica gel chromatography (1:1 to 1:3 hexanes/EtOAc) to afford 2.6 g (quant.) of 113.

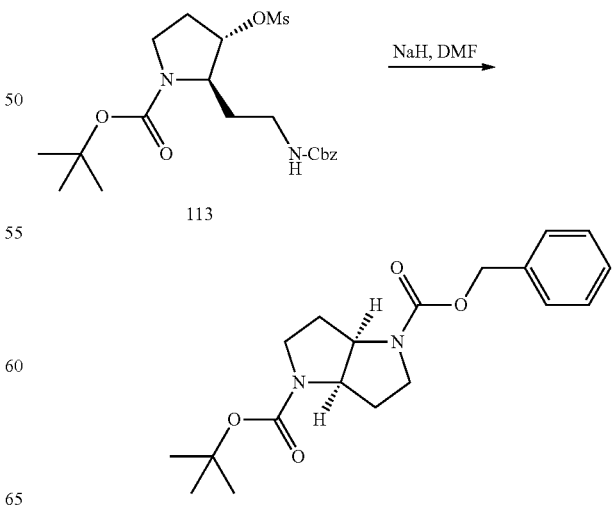

Hexahydro-pyrrolo[3,2-b]pyrrole-1,4-dicarboxylic acid 1-benzyl ester 4-tert-butyl ester (114)

A solution containing 113 (2.6 g) in DMF (20 mL) was cooled to 0° C. NaH (60%, 0.28 g, 6.91 mmol) was added in one portion. After 10 min, the reaction mixture was carefully quenched by the addition of saturated aqueous NH$_4$Cl. The mixture was diluted with diethyl ether and water and the layers were separated. The ether layer was washed five times with water to remove DMF then once with brine. The combined aqueous washes were back-extracted with diethyl ether. The combined ether extracts were dried over anhydrous Na$_2$SO$_4$, filtered, and concentrated to afford 1.59 g of crude 114 which was used without further purification. $^1$H NMR (300 MHz, CDCl$_3$): δ7.36 (m, 5H), 5.15 (m, 2H), 4.35 (m, 2H), 3.77-3.66 (m, 2H), 3.26-3.14 (m, 2H), 2.26 (m, 1H), 2.23 (m, 1H), 1.94 (m, 2H), 1.46 (s, 9H) ppm.

Scheme CVIII

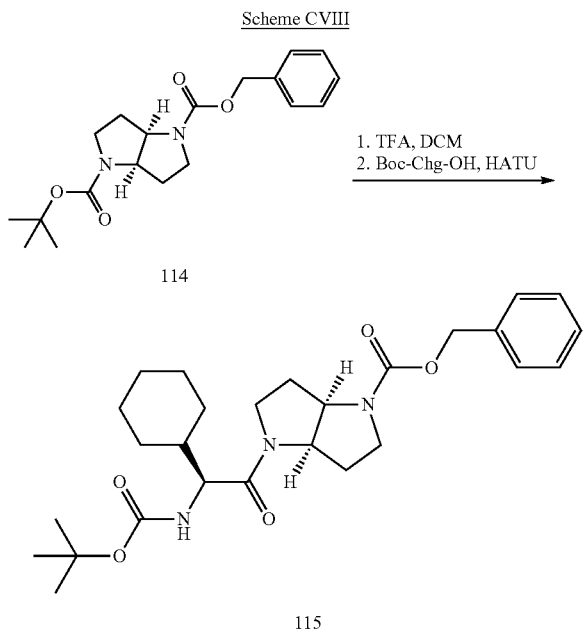

4-(2-tert-Butoxycarbonylamino-2-cyclohexyl-acetyl)-hexahydro-pyrrolo[3,2-b]pyrrole-1-carboxylic acid benzyl ester (115)

TFA (5 mL) was added to a solution containing crude 114 (1.5 g) in DCM (20 mL) at 0° C. After 90 min, an additional portion of TFA (2 mL) was added. After 1 h, the reaction mixture was carefully quenched by the addition of saturated aqueous NaHCO$_3$. The mixture was then diluted with EtOAc and water and the layers were separated. The organic phase was washed three times with aqueous NaHCO$_3$ then once with brine. The combined aqueous washes were back-extracted with EtOAc and the combined organic extracts were dried over anhydrous Na$_2$SO$_4$, filtered, and concentrated to afford crude amine (1 g) which was used without further purification. $^1$H NMR (300 MHz, CDCl$_3$): δ7.36 (m, 5H), 5.15 (m, 2H), 4.32 (m, 1H), 3.91 (m, 1H), 3.66 (app quint., J=8.7 Hz, 1H), 3.39 (m, 1H), 2.95 (m, 2H), 2.75 (m, 2H), 2.07-1.91 (m, 2H) ppm. Mass spectrum, m/z [247.2] (M+H)+.

A solution containing crude amine (1 g), Boc-Chg-OH (1.15 g, 4.46 mmol), and HATU (1.85 g, 4.87 mmol) in NMP (25 mL) was cooled to 0° C. DIPEA (0.68 g, 5.27 mmol) was added and the reaction mixture was slowly warmed to ambient temperature. After 16 h, the reaction mixture was diluted with diethyl ether and washed successively with 1M HCl, water, aqueous NaHCO$_3$, filtered, and concentrated. The crude product was purified by flash silica gel chromatography (2:1 to 1:3 hexanes/EtOAc) to afford 1.39 g (62% from 112) of 115. $^1$H NMR (300 MHz, CDCl$_3$): δ7.36 (m, 5H), 5.24-5.07 (m, 3H), 4.57 (app t, J=5.2 Hz, 1H), 4.36 (m, 1H), 4.26 (m, 1H), 3.98-3.94 (m, 1H), 3.81-3.71 (m, 1H), 3.33 (m, 1H), 3.13 (m, 1H), 2.22 (m, 2H), 2.00 (m, 2H), 1.80-1.50 (m, 5H), 1.42 (s, 9H), 1.32-0.95 (m, 5H) ppm.

Scheme CIX

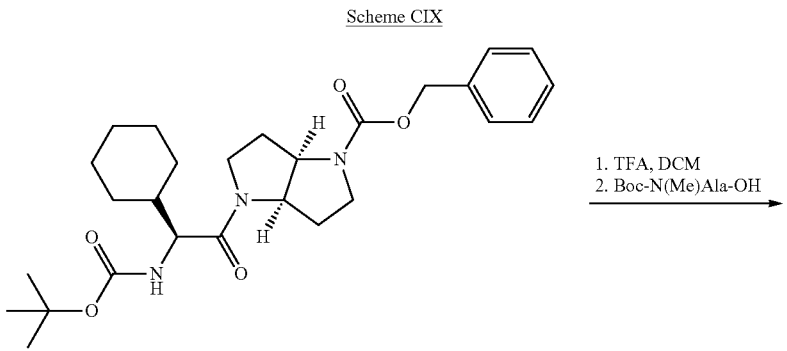

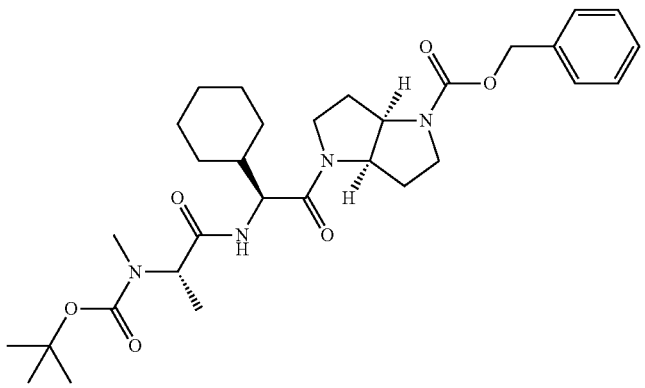

116

4-{2-[2-(tert-Butoxycarbonyl-methyl-amino)-propionylamino]-2-cyclohexyl-acetyl}-hexahydro-pyrrolo[3,2-b]pyrrole-1-carboxylic acid benzyl ester (116)

TFA (6 mL) was added to a solution containing crude 115 (0.8 g, 1.64 mmol) in DCM (20 mL) at 0° C. After 75 min, the reaction mixture was carefully quenched by the addition of saturated aqueous $NaHCO_3$. The mixture was then diluted with EtOAc and water and the layers were separated. The organic phase was washed three times with aqueous $NaHCO_3$ then once with brine. The combined aqueous washes were back-extracted with EtOAc and the combined organic extracts were dried over anhydrous $Na_2SO_4$, filtered, and concentrated to afford crude amine (0.65 g) which was used without further purification. $^1$H NMR (300 MHz, $CDCl_3$): δ7.36 (m, 5H), 5.16 (m, 3H), 4.59 (m, 1H), 4.38 (m, 1H), 3.74 (m, 2H), 3.31 (m, 1H), 3.14 (m, 1H), 2.23 (m, 1H), 1.75-1.50 (m, 5H), 1.28-0.93 (m, 5H) ppm.

A solution containing crude amine (0.65 g), Boc-N(Me)Ala-OH (368 mg, 1.81 mmol), and HATU (751 mg, 1.97 mmol) in NMP (20 mL) was cooled to 0° C. DIPEA (276 mg, 2.14 mmol) was added and the reaction mixture was slowly warmed to ambient temperature. After 16 h, the reaction mixture was diluted with diethyl ether and washed successively with 1M HCl, water, aqueous $NaHCO_3$, filtered, and concentrated to afford 0.9 g of crude 116 which was used without further purification. $^1$H NMR (300 MHz, $CDCl_3$): δ7.36 (m, 5H), 5.16 (m, 3H), 4.64 (m, 1H), 4.54 (m, 2H), 4.37 (m, 1H), 3.99 (m, 1H), 3.78 (m, 1H), 3.36 (m, 1H), 3.13 (m, 1H), 2.79 (s, 3H), 2.23 (m, 1H), 1.99 (m, 1H), 2.79-2.55 (m, 5H), 1.48 (s, 9H), 1.32 (d, J=7.0 Hz, 3H), 1.28-0.92 (m, 5H) ppm.

Scheme CX

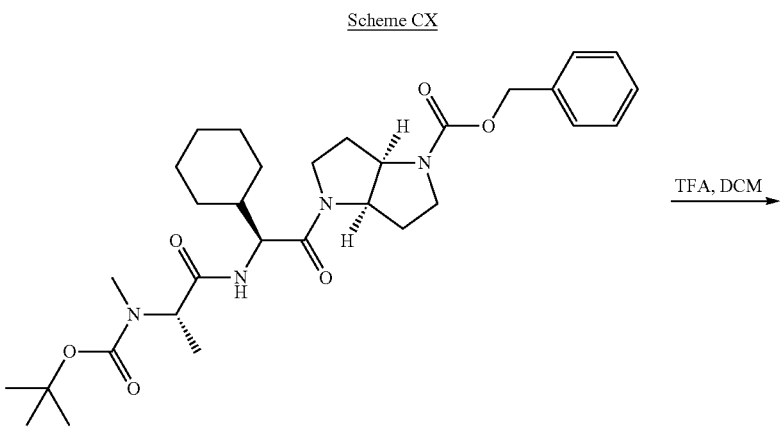

116

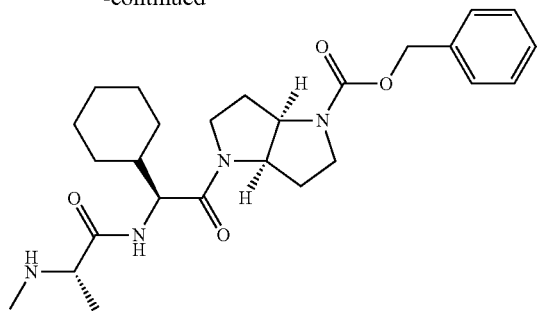

117

4-[2-Cyclohexyl-2-(2-methylamino-propionylamino)-acetyl]-hexahydro-pyrrolo[3,2-b]pyrrole-1-carboxylic acid benzyl ester (117)

TFA (5 mL) was added to a solution containing crude 116 (0.9 g) in DCM (20 mL) at 0° C. After 90 min, another portion of TFA (2 mL) was added. After 75 min, the reaction mixture was carefully quenched by the addition of saturated aqueous NaHCO$_3$. The mixture was then diluted with EtOAc and water and the layers were separated. The organic phase was washed three times with aqueous NaHCO$_3$ then once with brine. The combined aqueous washes were back-extracted with EtOAc and the combined organic extracts were dried over anhydrous Na$_2$SO$_4$, filtered, and concentrated. The crude product was purified by reverse-phase HPLC [2" Dynamax C18; Method: 10-55% ACN/water containing 0.1% HOAc over 30 min; Flow: 40 mL/min]. The product-containing fractions were pooled, frozen, and lyophilized to afford 410 mg (53% from 115) of 117 as a white-colored solid. $^1$H NMR (300 MHz, d$_6$-DMSO), mixture of carbamate rotomers: δ7.67 (d, J=8.7 Hz, 1H), 7.34-7.28 (m, 5H), 5.17-5.05 (m, 2H), 4.52 (m, 2H), 4.34 (m, 1H), 4.00 (m, 1H), 3.75 (m, 1H), 3.33 (m, 1H), 3.14-3.01 (m, 2H), 2.35 (br s, 3H), 2.30 (m, 1H), 1.90 (m, 1H), 1.69-1.60 (m, 5H), 1.27 (d, J=6.9 Hz, 3H), 1.18-0.94 (m, 5H) ppm. $^{13}$C NMR (75 MHz, d$_6$-DMSO), mixture of carbamate rotomers: δ174.7, 174.4 172.9, 170.1, 170.0, 154.1, 154.0, 137.5, 129.1, 128.5, 128.2, 128.1, 66.7, 66.6, 63.0, 61.9, 61.6, 60.9, 59.5, 55.2, 54.7, 46.7, 46.1, 45.6, 41.5, 34.5, 32.3, 31.2, 30.7, 30.1, 29.6, 29.5, 28.9, 28.7, 26.4, 26.2, 26.1, 26.0, 22.0, 19.5, 19.4 ppm. Mass spectrum, m/z [471.0] (M+H)+.

Example 109

N-[1-Cyclohexyl-2-(hexahydro-pyrrolo[3,2-b]pyrrol-1-yl)-2-oxo-ethyl]-2-methylamino-propionamide (118)

Scheme CXI

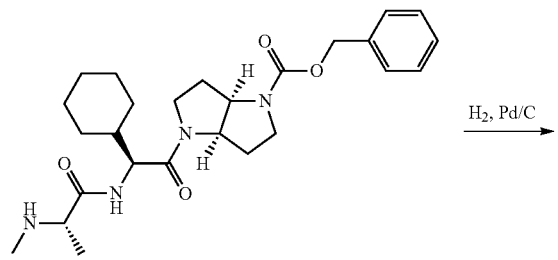

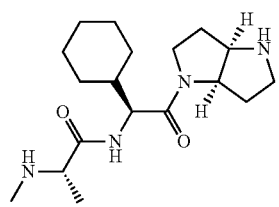

118

N-[1-Cyclohexyl-2-(hexahydro-pyrrolo[3,2-b]pyrrol-1-yl)-2-oxo-ethyl]-2-methylamino-propionamide (118)

A 500 mL Parr bottle was charged with 117 (190 mg, 0.40 mmol) and 10% Pd-on-carbon (~0.5 g) in MeOH (20 mL). The bottle was pressurized to 55 PSI H$_2$ (379.2 KPa) and shaken for 3 h. The catalyst was removed by filtration through diatomaceous earth (Celite®) and washed with EtOAc and MeOH. The filtrate was concentrated in vacuo and the residue was purified by reverse-phase HPLC [Phenomenex Luna C18, 100×21.2 mm, 5-50% ACN/water containing 0.1% HOAc over 30 min; Flow: 20 mL/min]. The product-containing fraction was diluted with water, frozen, and lyophilized to afford 70 mg (52%) of 118.HOAc as a white-colored solid. $^1$H NMR (300 MHz, d$_6$-DMSO), mixture of amide rotomers: δ9.72 (br s, 1H), 8.80 (d, J=8.1 Hz, 1H), 4.50 (m, 1H), 4.35 (m, 1H), 4.18 (app t, J=6.6 Hz, 1H), 3.99 (app t, J=9.3 Hz, 1H), 3.85 (app q, J=6.6 Hz, 1H), 3.75 (m, 1H), 3.36 (br s, 3H), 3.21 (m, 1H), 2.98 (m, 1H), 2.44 (s, 3H), 2.36 (m, 1H), 2.14 (m, 2H), 1.99 (m, 1H), 1.71-1.51 (m, 5H), 1.34 (d, J=6.9 Hz, 3H), 1.14-0.98 (m, 5H) ppm. $^{13}$C NMR (75 MHz, d$_6$-DMSO), mixture of amide rotomers: δ169.5, 169.3, 61.9, 61.3, 56.4, 56.3, 46.9, 45.3, 31.6, 31.3, 29.4, 28.8, 26.3, 26.2, 26.0, 16.4 ppm. Mass spectrum, m/z [337.2] (M+H)+.

Example 110

N-(1-Cyclohexyl-2-{4-[2-cyclohexyl-2-(2-methylamino-propionylamino)-acetyl]-hexahydro-pyrrolo[3,2-b]pyrrol-1-yl}-2-oxo-ethyl)-2-methylamino-propionamide (120)

{2-[4-(2-tert-Butoxycarbonylamino-2-cyclohexyl-acetyl)-hexahydro-pyrrolo[3,2-b]pyrrol-1-yl]-1-cyclohexyl-2-oxo-ethyl}-carbamic acid tert-butyl ester (119)

A 500 mL Parr bottle was charged with 115 (670 mg, 1.37 mmol) and 10% Pd-on-carbon (~0.5 g) in MeOH (25 mL). The bottle was pressurized to 55 PSI $H_2$ (379.2 KPa) and shaken for 3 h. The catalyst was removed by filtration through diatomaceous earth (Celite®) and washed with EtOAc and MeOH. The filtrate was concentrated in vacuo to afford the crude amine (0.49 g, quant.) which was used without further purification.

A solution containing crude amine (0.49 g), Boc-Chg-OH (390 mg, 1.51 mmol), and HATU (630 mg, 1.65 mmol) in NMP (20 mL) was cooled to 0° C. DIPEA (231 mg, 1.79 mmol) was added and the reaction mixture was slowly warmed to ambient temperature. After 16 h, the reaction mixture was diluted with diethyl ether and washed successively with 1M HCl, water, aqueous $NaHCO_3$, filtered, and concentrated. The crude product was purified by flash silica gel chromatography (1:1 to 1:3 hexanes/EtOAc) to afford 0.77 g (94%) of 119. $^1$H NMR (300 MHz, $CDCl_3$), mixture of carbamate rotomers: δ5.19 (d, J=9.0 Hz, 2H), 4.72 (m, 1H), 4.56 (m, 2H), 4.48 (m, 1H), 4.27 (m, 2H), 3.98 (m, 2H), 3.43-3.09 (m, 2H), 2.42-2.21 (m, 2H), 1.80-1.55 (m, 10H), 1.42 (s, 18H), 1.30-0.98 (m, 10H) ppm. Mass spectrum, m/z [591.2] (M+H)+.

Scheme CXII

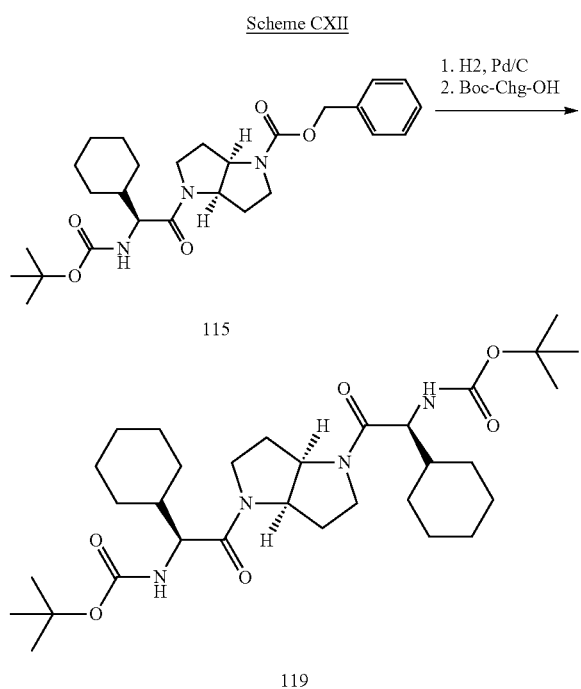

Scheme CXIII

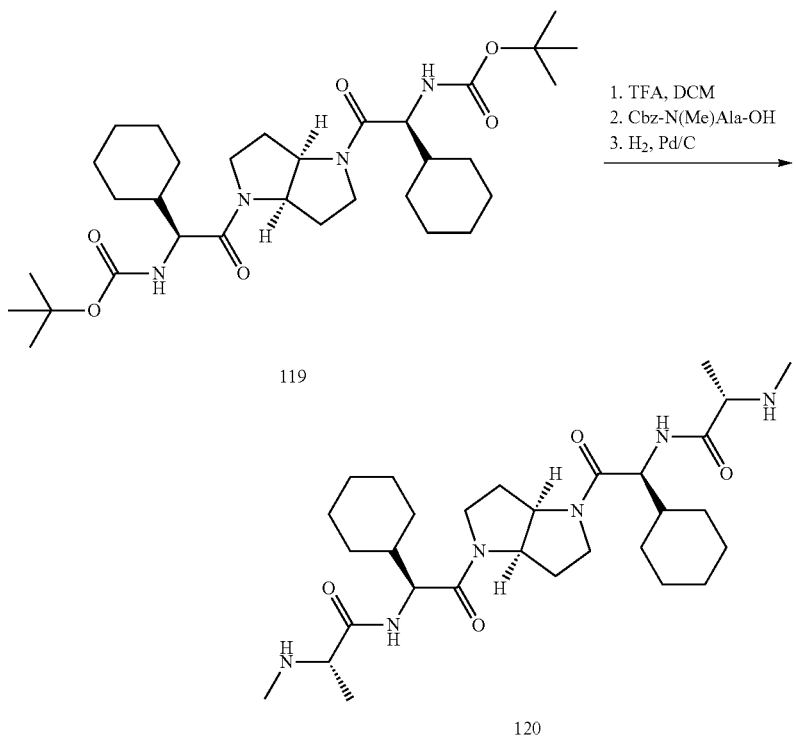

N-(1-Cyclohexyl-2-{4-[2-cyclohexyl-2-(2-methylamino-propionylamino)-acetyl]-hexahydro-pyrrolo[3,2-b]pyrrol-1-yl}-2-oxo-ethyl)-2-methylamino-propionamide (120)

TFA (6 mL) was added to a solution containing 119 (770 mg, 1.30 mmol) in DCM (20 mL) at 0° C. then slowly warmed to ambient temperature After 2 h, the reaction mixture was concentrated in vacuo. The resultant bis-acetate salt was dissolved in water (2 mL) and passed through an anion exchange column (BIORAD AG 1-X8, 200-400 mesh, acetate form) that had been previously equilibrated with 1M HCl and then washed with water. The amine-containing fractions were lyophilized to dryness [TLC: 40:10:2 DCM/MeOH/NH$_4$OH, R$_f$(amine.2HCl)=0.5; ninhydrin-positive].

A solution containing crude amine.2HCl (0.52 g), Cbz-N(Me)Ala-OH (560 mg, 2.35 mmol), and HATU (940 mg, 2.46 mmol) in NMP (20 mL) was cooled to 0° C. DIPEA (660 mg, 5.00 mmol) was added and the reaction mixture was slowly warmed to ambient temperature. After 16 h, the reaction mixture was diluted with diethyl ether and washed successively with 1M HCl, water, aqueous NaHCO$_3$, filtered, and concentrated. The crude product was purified by reverse-phase HPLC [2″ Dynamax C18; Method: 10-55% ACN/water containing 0.1% HOAc over 30 min; Flow: 40 mL/min]. The product-containing fractions were combined, diluted with aqueous NaHCO$_3$, and extracted with EtOAc. The organic extracts were washed with brine, dried over anhydrous Na$_2$SO$_4$, filtered, and concentrated to afford 0.9 g of crude bis-Cbz-120. Mass spectrum, m/z [829.3] (M)+.

A solution containing bis-Cbz-120 (0.9 g) and 10% Pd-on-carbon (200 mg) in MeOH (20 mL) was placed in a Parr bottle and pressurized to 55 PSI H$_2$ (379.2 KPa). After shaking for 2 h, the catalyst was removed by filtration through diatomaceous earth (Celite®). The solids were washed with MeOH and EtOAc and the filtrate was concentrated in vacuo. The crude product was purified by reverse-phase HPLC [2″ Dynamax C18; Method: 10-55% ACN/water containing 0.1% HOAc over 30 min; Flow: 40 mL/min] and the product-containing fractions were diluted with water, frozen, and lyophilized to dryness to afford 496 mg (68% from 119) of 120 as a white-colored solid. $^1$H NMR (300 MHz, d$_6$-DMSO), mixture of amide rotomers: δ8.73 (d, J=7.9 Hz, 2H), 4.60-4.33 (m, 4H), 3.99 (app t, J=9.3 Hz, 2H), 3.93-2.96 (m, 8H), 2.41 (s, 6H), 2.12 (m, 2H), 1.91 (m, 2H), 1.80-1.60 (m, 10H), 1.32 (d, J=6.7 Hz, 6H), 1.15-0.99 (m, 10H) ppm. $^{13}$C NMR (75 MHz, d$_6$-DMSO), mixture of amide rotomers: d169.9, 169.7, 63.0, 61.4, 56.8, 56.3, 55.7, 47.0, 45.9, 31.7, 30.9, 30.1, 29.3, 29.0, 26.3, 26.2, 26.1, 16.8 ppm. Mass spectrum, m/z [561.3] (M)+.

Example 111
N-{1-Cyclohexyl-2-[4-[2-cyclohexyl-2-(2-methylamino-propionylamino)-acetyl]-6-(6-fluoro-1H-indol-3-yl)-hexahydro-pyrrolo[3,2-b]pyrrol-1-yl]-2-oxo-ethyl}-2-methylamino-propionamide (124)

Scheme CXIV

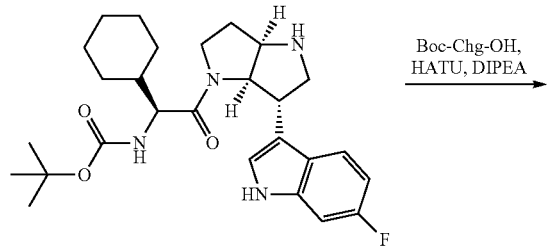

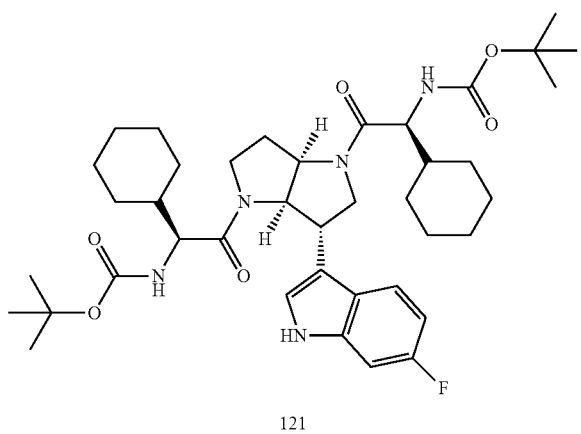

121

{2-[4-(2-tert-Butoxycarbonylamino-2-cyclohexylacetyl)-6-(6-fluoro-1H-indol-3-yl)-hexahydro-pyrrolo[3,2-b]pyrrol-1-yl]-1-cyclohexyl-2-oxo-ethyl}-carbamic acid tert-butyl ester (121)

To a solution containing Boc-Chg-OH (167 mg, 0.64 mmol) in anhydrous NMP (6 mL) was cooled to 0° C. HATU (247 mg, 0.64 mmol) and DIPEA (94 mg, 0.73 mmol) were added followed by the addition of crude 49 (300 mg, 0.62 mmol). The reaction mixture was slowly warmed to ambient temperature. After 16 h, the reaction mixture was diluted with diethyl ether and washed successively with water, 1M HCl, water, aqueous NaHCO$_3$, and brine, dried over anhydrous Na$_2$SO$_4$, filtered, and concentrated. The crude product was purified by flash silica gel chromatography (2:1-1:1 hexanes/EtOAc) to afford 370 mg (82%) of 121 as a white solid. $^1$H NMR (300 MHz, CDCl$_3$), mixture of rotomers: δ8.32 (dd, J=5.4, 8.7 Hz, 0.4H, minor rotomer), 8.21 (dd, J=5.7, 9.0 Hz, 1.6H, major rotomer), 8.12 (br s, 0.4H), 8.06 (br s, 1.6H), 7.06 (m, 2H), 7.01 (m, 2H), 6.98 (m, 2H), 6.94 (m, 2H), 5.31 (app d, J=9.3 Hz, 2H), 5.22 (app d, J=9.6 Hz, 2H), 4.60 (d, J=5.1 Hz, 2H), 4.46-4.32 (m, 10H), 4.04 (d, J=5.7 Hz, 2H), 3.64 (dd, J=6.0, 10.8 Hz, 2H), 3.33 (m, 2H), 2.43 (dd, J=5.4, 13.4 Hz, 2H), 1.89-1.55 (m, 10H), 1.47 (s, 3.6H, minor rotomer), 1.44 (s, 14.4H, major rotomer), 1.28-1.02 (m, 10H) ppm. Mass spectrum, m/z [724.5] (M+H)+.

Scheme CXV

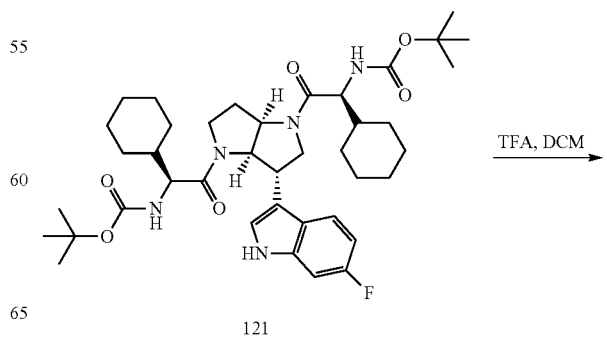

121

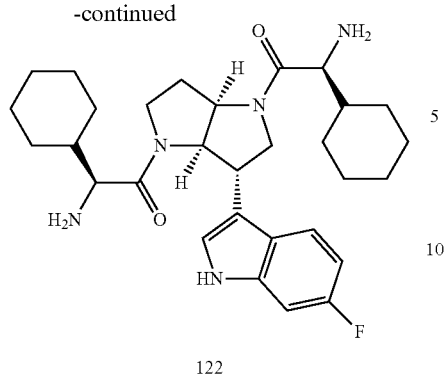

122

2-Amino-1-[4-(2-amino-2-cyclohexyl-acetyl)-6-(6-fluoro-1H-indol-3-yl)-hexahydro-pyrrolo[3,2-b]pyrrol-1-yl]-2-cyclohexyl-ethanone (122)

To a solution containing 121 (370 mg, 0.51 mmol) in DCM (10 mL) at 0° C. was added TFA (4 mL). After 2 h, the reaction mixture was concentrated in vacuo. The residue was dissolved in DCM and the organic solution was washed successively with saturated aqueous NaHCO$_3$ and brine, dried over anhydrous Na$_2$SO$_4$, filtered, and concentrated to afford 210 mg of 122 which was used without further purification. Mass spectrum, m/z [523.3] (M)+.

Scheme CXVI

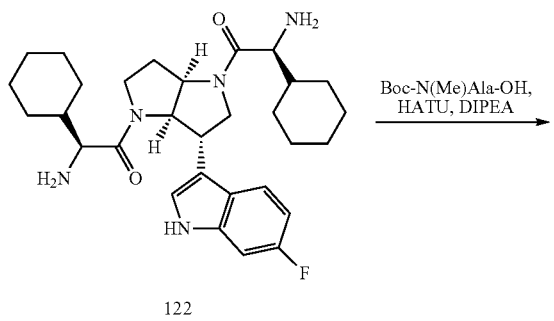

122

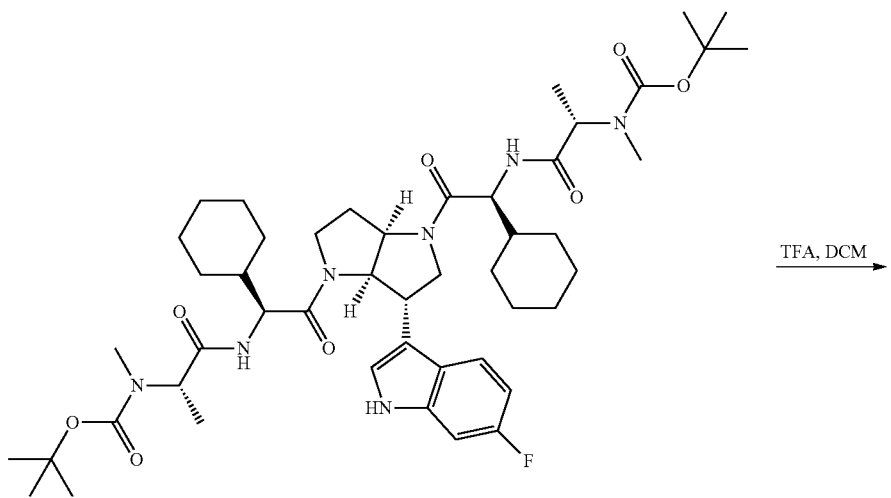

123

(1-{2-[4-{2-[2-(tert-Butoxycarbonyl-methyl-amino)-propionylamino]-2-cyclohexyl-acetyl}-6-(6-fluoro-1H-indol-3-yl)-hexahydro-pyrrolo[3,2-b]pyrrol-1-yl]-1-cyclohexyl-2-oxo-ethylcarbamoyl}-ethyl)-methyl-carbamic acid tert-butyl ester (123)

To a solution containing Boc-N(Me)Ala-OH (167 mg, 0.82 mmol) in anhydrous NMP (3 mL) was cooled to 0° C. HATU (312 mg, 0.82 mmol) and DIPEA (126 mg, 0.97 mmol) were added followed by the addition of crude 122 (205 mg, 0.39 mmol) in anhydrous NMP (3 mL). The reaction mixture was slowly warmed to ambient temperature. After 16 h, the reaction mixture was diluted with diethyl ether and washed successively with water, 1M HCl, water, aqueous NaHCO$_3$, and brine, dried over anhydrous Na$_2$SO$_4$, filtered, and concentrated to afford 346 mg of crude 123 as a white solid which was used without further purification. Mass spectrum, m/z [894.8] (M)+.

Scheme CXVII

123

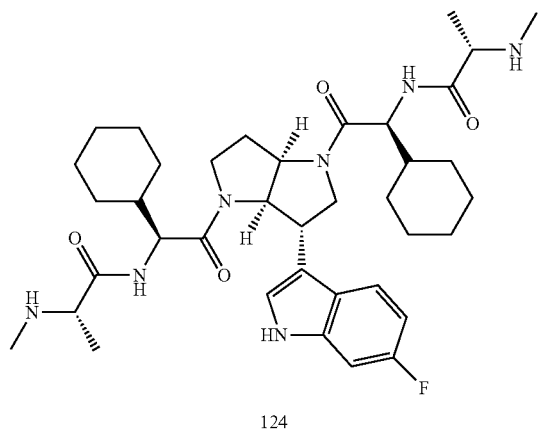

124

N-{1-Cyclohexyl-2-[4-[2-cyclohexyl-2-(2-methylamino-propionylamino)-acetyl]-6-(6-fluoro-1H-indol-3-yl)-hexahydro-pyrrolo[3,2-b]pyrrol-1-yl]-2-oxo-ethyl}-2-methylamino-propionamide (124)

To a solution containing crude 123 (340 mg, 0.38 mmol) in DCM (10 mL) was added TFA (4 mL) at 0° C. After 3 h, the pink-colored reaction mixture was concentrated in vacuo. The residue was dissolved in DCM and the resultant organic solution was washed successively with saturated aqueous NaHCO$_3$ and brine, dried over anhydrous Na$_2$SO$_4$, filtered, and concentrated. The crude product was purified by RP-HPLC (Phenomenex Luna C18, 100×21.2 mm, 10-50% ACN/water containing 0.1% HOAc over 20 min; Flow: 20 mL/min) to afford 133 mg (37%, 3 steps) of 124 following lyophilization. $^1$H NMR (300 MHz, CDCl$_3$), mixture of amide rotamers: δ8.46 (br s, 1H), 8.30 (dd, J=5.1, 8.4 Hz, 0.4H, minor rotamer), 8.22 (dd, J=5.7, 9.0 Hz, 1.6H, major rotamer), 7.72 (m, 4H), 7.18 (m, 2H), 7.03-6.80 (m, 6H), 4.67-4.57 (m, 2H), 4.74-4.38 (m, 2H), 4.23 (app t, J=9.6 Hz, 1H), 4.03 (d, J=5.7 Hz, 1H), 3.65 (dd, J=6.0, 10.8 Hz, 1H), 3.48 (m, 0.4H, minor rotamer), 3.36 (m, 1.6H, major rotamer), 3.08 (m, 2H), 2.43 (s, 4.8H, major rotamer), 2.40 (s, 1.2H, mino rotamer), 1.95-1.62 (m, 10H), 1.34 (d, J=6.9 Hz, 3H), 1.32 (d, J=6.9 Hz, 3H), 1.28-1.08 (m, 10H) ppm. $^{13}$C NMR (75 MHz, CDCl$_3$), mixture of amide rotamers: δ175.5, 175.1, 170.9, 170.8, 160.1 (d, J$_{CF}$=235.8 Hz), 136.3 (d, J$_{CF}$=12.6 Hz), 123.4, 121.1, 115.0, 108.3 (d, J$_{CF}$=24.3 Hz), 97.1 (d, J$_{CF}$=25.8 Hz), 67.1, 60.5, 60.4, 60.2, 55.2, 55.1, 51.6, 47.2, 40.9, 40.7, 39.5, 35.1, 33.2, 30.0, 29.7, 29.6, 29.0, 28.7, 26.2, 26.1, 26.0, 25.9, 19.7, 19.5 ppm. Mass spectrum, m/z [694.3] (M+H)+.

Using the procedures outlined in the schemes presented above and where necessary the appropriate amino acid reagents, one can prepare the compounds presented in TABLES 1, 2, and 3. The results of testing compounds for their binding affinities (K$_D$) to XIAP BIR-3 and cIAP-1 BIR-3 and for their ability to inhibit the growth (CC$_{50}$) of an ovarian cancer cell line, SK-OV-3, are reported as ranges in TABLES 1, 2, and 3.

TABLE 1

| Example | Structure | K$_D$ (XIAP BIR3) μM | K$_D$ (c-IAP-1 BIR3) μM | CC$_{50}$ (SK-OV-3) μM |
|---|---|---|---|---|
| 1 | 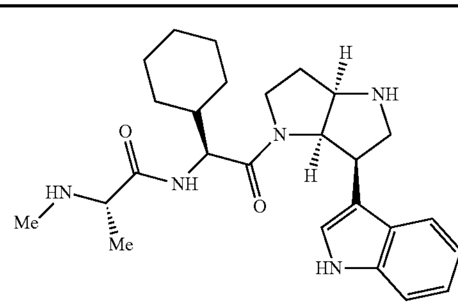 | D | D | C |

TABLE 1-continued
| Example | Structure | $K_D$ (XIAP BIR3) μM | $K_D$ (c-IAP-1 BIR3) μM | $CC_{50}$ (SK-OV-3) μM |
|---|---|---|---|---|
| 2 | 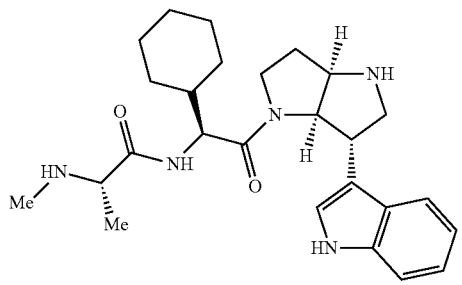 [SMILES: CN[C@@H](C)C(=O)N[C@H](C(=O)N1CC[C@H]2NC[C@H](c3c[nH]c4ccccc34)[C@H]21)C1CCCCC1] | A | A | B |
| 3 | 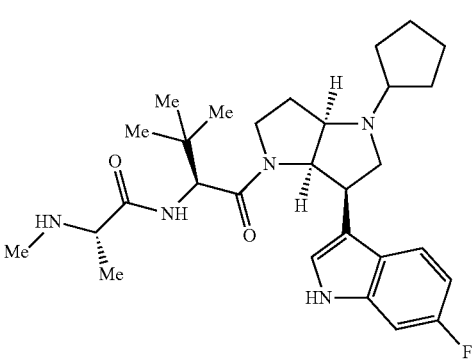 [SMILES: CN[C@@H](C)C(=O)N[C@H](C(=O)N1CC[C@@H]2[C@H]1[C@H](c1c[nH]c3cc(F)ccc13)CN2C1CCCC1)C(C)(C)C] | C | C | C |
| 4 | 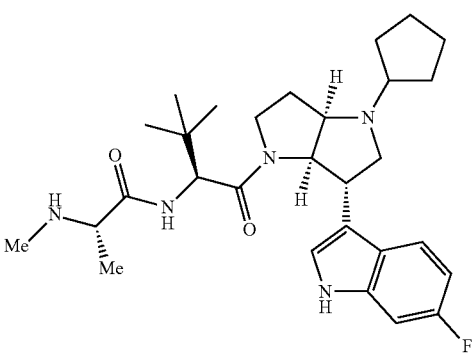 [SMILES: CN[C@@H](C)C(=O)N[C@H](C(=O)N1CC[C@@H]2[C@H]1[C@@H](c1c[nH]c3cc(F)ccc13)CN2C1CCCC1)C(C)(C)C] | A | A | A |
| 5 | 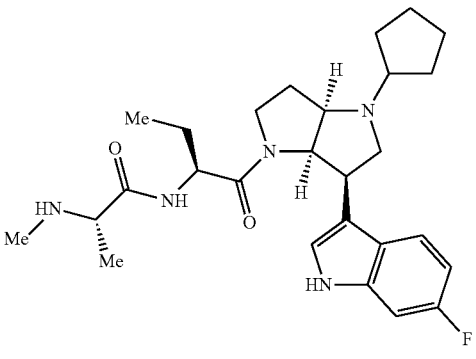 [SMILES: CC[C@H](NC(=O)[C@H](C)NC)C(=O)N1CC[C@@H]2[C@H]1[C@H](c1c[nH]c3cc(F)ccc13)CN2C1CCCC1] | D | B | C |

TABLE 1-continued

| Example | Structure | $K_D$ (XIAP BIR3) μM | $K_D$ (c-IAP-1 BIR3) μM | $CC_{50}$ (SK-OV-3) μM |
|---|---|---|---|---|
| 6 | 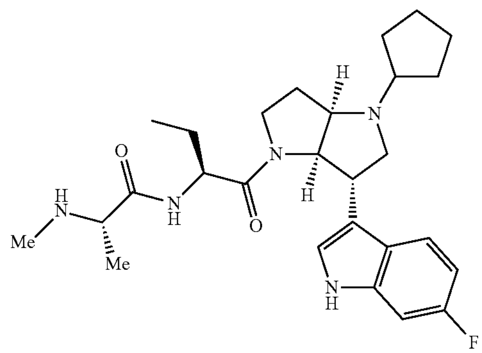 [SMILES: CC[C@H](NC(=O)[C@H](C)NC)C(=O)N1CC[C@@H]2[C@H]1[C@@H](c1c[nH]c3cc(F)ccc13)CN2C1CCCC1] | B | B | B |
| 7 | 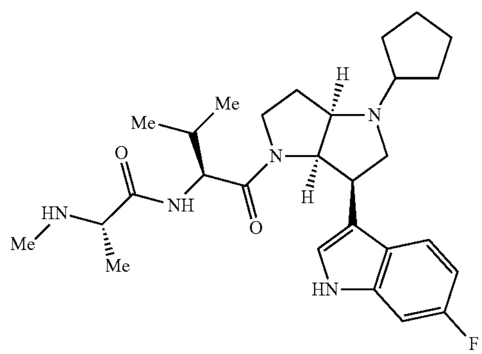 [SMILES: CN[C@@H](C)C(=O)N[C@H](C(=O)N1CC[C@@H]2[C@H]1[C@H](c1c[nH]c3cc(F)ccc13)CN2C1CCCC1)C(C)C] | C | B | C |
| 8 | 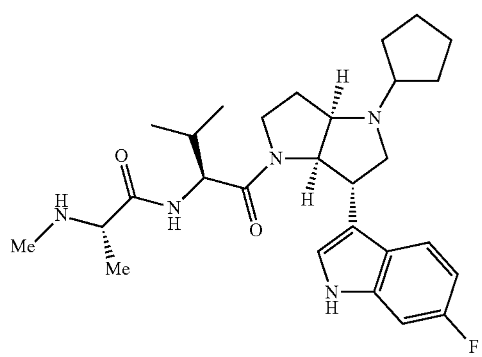 [SMILES: CN[C@@H](C)C(=O)N[C@H](C(=O)N1CC[C@@H]2[C@H]1[C@@H](c1c[nH]c3cc(F)ccc13)CN2C1CCCC1)C(C)C] | B | A | B |
| 9 | 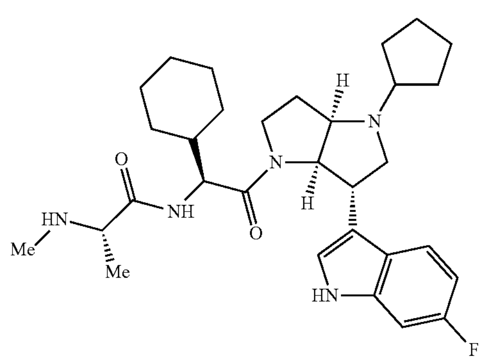 [SMILES: CN[C@@H](C)C(=O)N[C@H](C(=O)N1CC[C@@H]2[C@H]1[C@@H](c1c[nH]c3cc(F)ccc13)CN2C1CCCC1)C1CCCCC1] | B | A | A |

TABLE 1-continued

| Example | Structure | $K_D$ (XIAP BIR3) μM | $K_D$ (c-IAP-1 BIR3) μM | $CC_{50}$ (SK-OV-3) μM |
|---|---|---|---|---|
| 10 | 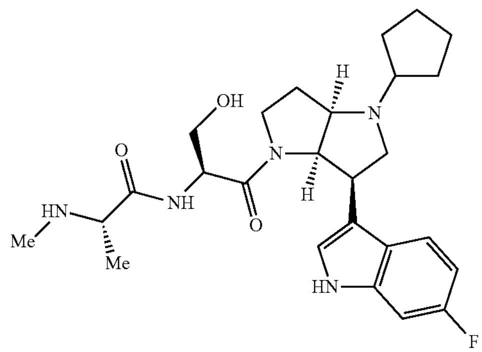 [SMILES: CN[C@@H](C)C(=O)N[C@@H](CO)C(=O)N1CC[C@@H]2[C@H]1[C@H](c1c[nH]c3cc(F)ccc13)CN2C1CCCC1] | D | B | C |
| 11 | 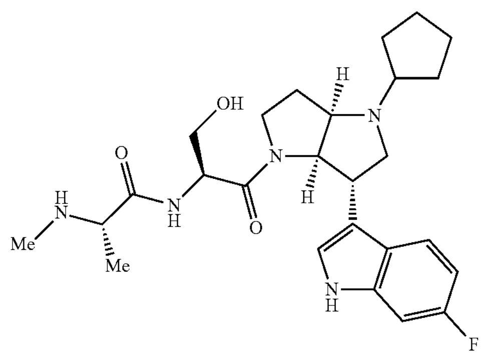 [SMILES: CN[C@@H](C)C(=O)N[C@@H](CO)C(=O)N1CC[C@@H]2[C@H]1[C@@H](c1c[nH]c3cc(F)ccc13)CN2C1CCCC1] | B | A | D |
| 12 | 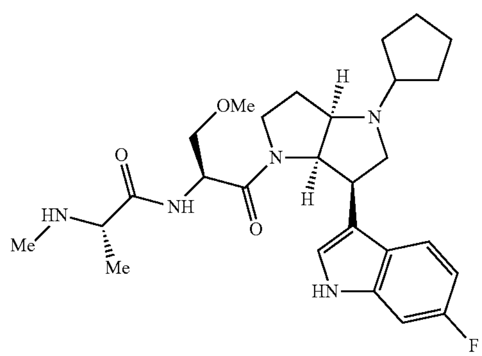 [SMILES: CN[C@@H](C)C(=O)N[C@@H](COC)C(=O)N1CC[C@@H]2[C@H]1[C@H](c1c[nH]c3cc(F)ccc13)CN2C1CCCC1] | C | A | D |
| 13 | 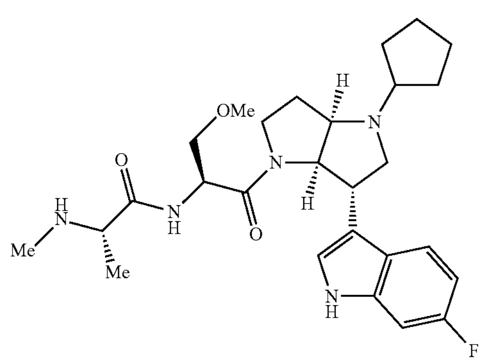 [SMILES: CN[C@@H](C)C(=O)N[C@@H](COC)C(=O)N1CC[C@@H]2[C@H]1[C@@H](c1c[nH]c3cc(F)ccc13)CN2C1CCCC1] | C | B | C |

TABLE 1-continued

| Example | Structure | K_D (XIAP BIR3) μM | K_D (c-IAP-1 BIR3) μM | CC_{50} (SK-OV-3) μM |
|---------|-----------|---------------------|------------------------|----------------------|
| 14 | 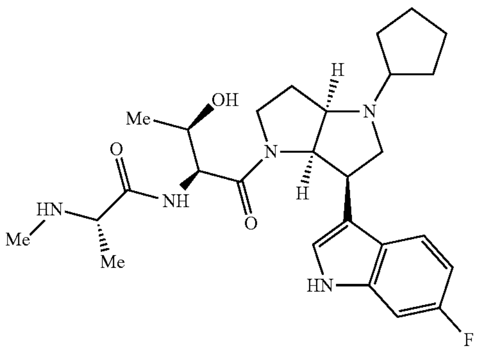 [SMILES: CN[C@@H](C)C(=O)N[C@H](C(=O)N1CC[C@@H]2[C@H]1[C@H](c1c[nH]c3cc(F)ccc13)CN2C1CCCC1)[C@@H](C)O] | D | B | D |
| 15 | 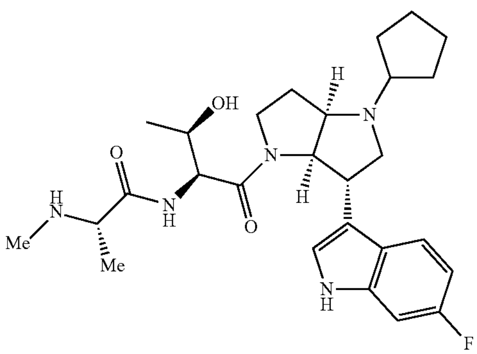 [SMILES: CN[C@@H](C)C(=O)N[C@H](C(=O)N1CC[C@@H]2[C@H]1[C@@H](c1c[nH]c3cc(F)ccc13)CN2C1CCCC1)[C@@H](C)O] | B | B | B |
| 16 | 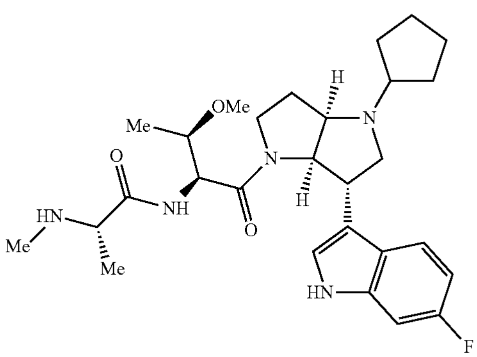 [SMILES: CN[C@@H](C)C(=O)N[C@H](C(=O)N1CC[C@@H]2[C@H]1[C@@H](c1c[nH]c3cc(F)ccc13)CN2C1CCCC1)[C@@H](C)OC] | B | A | B |
| 17 | 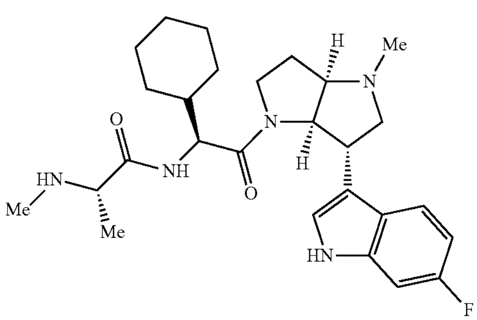 [SMILES: CN[C@@H](C)C(=O)N[C@H](C(=O)N1CC[C@@H]2[C@H]1[C@@H](c1c[nH]c3cc(F)ccc13)CN2C)C1CCCCC1] | B | A | B |

TABLE 1-continued

| Example | Structure | $K_D$ (XIAP BIR3) μM | $K_D$ (c-IAP-1 BIR3) μM | $CC_{50}$ (SK-OV-3) μM |
|---|---|---|---|---|
| 18 | 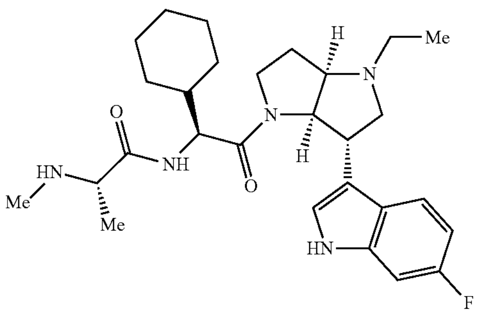 [SMILES: CCN1C[C@H](c2c[nH]c3cc(F)ccc23)[C@@H]2[C@H]1CCN2C(=O)[C@@H](NC(=O)[C@H](C)NC)C1CCCCC1] | B | A | B |
| 19 | 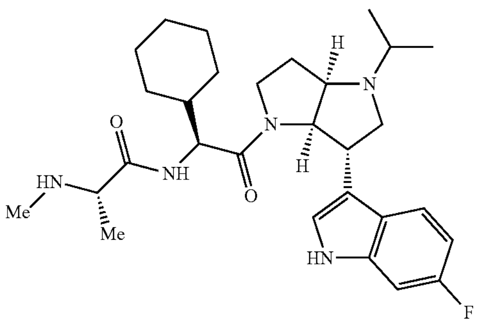 [SMILES: CN[C@@H](C)C(=O)N[C@H](C(=O)N1CC[C@@H]2[C@H]1[C@@H](c1c[nH]c3cc(F)ccc13)CN2C(C)C)C1CCCCC1] | C | A | B |
| 20 | 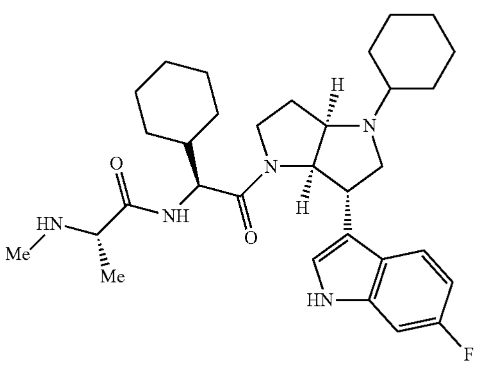 [SMILES: CN[C@@H](C)C(=O)N[C@H](C(=O)N1CC[C@@H]2[C@H]1[C@@H](c1c[nH]c3cc(F)ccc13)CN2C1CCCCC1)C1CCCCC1] | A | A | B |
| 21 | 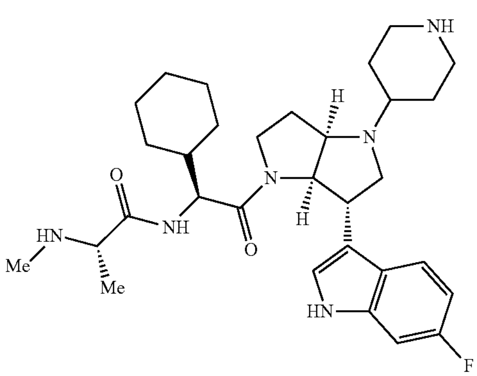 [SMILES: CN[C@@H](C)C(=O)N[C@H](C(=O)N1CC[C@@H]2[C@H]1[C@@H](c1c[nH]c3cc(F)ccc13)CN2C1CCNCC1)C1CCCCC1] | B | A | D |

TABLE 1-continued

| Example | Structure | $K_D$ (XIAP BIR3) μM | $K_D$ (c-IAP-1 BIR3) μM | $CC_{50}$ (SK-OV-3) μM |
|---------|-----------|---------------------|------------------------|------------------------|
| 22 | 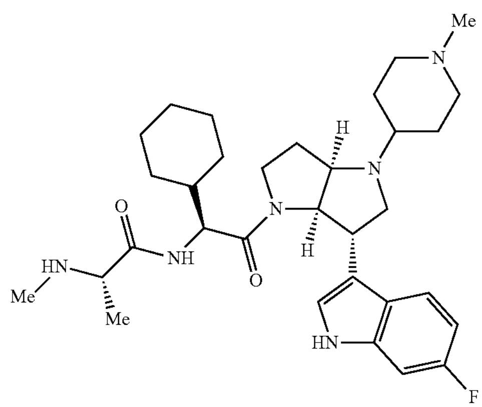 [SMILES: CN[C@@H](C)C(=O)N[C@H](C(=O)N1CC[C@@H]2[C@H]1[C@@H](c1c[nH]c3cc(F)ccc13)CN2C1CCN(C)CC1)C1CCCCC1] | B | A | B |
| 23 | 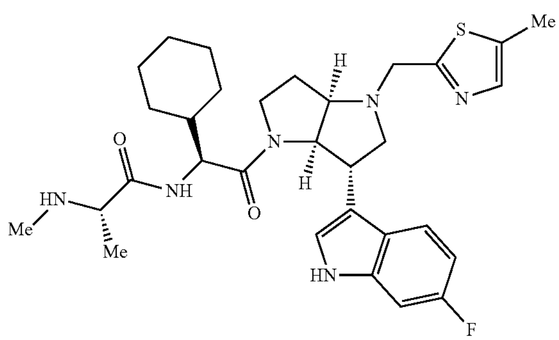 [SMILES: CN[C@@H](C)C(=O)N[C@H](C(=O)N1CC[C@@H]2[C@H]1[C@@H](c1c[nH]c3cc(F)ccc13)CN2Cc1ncc(C)s1)C1CCCCC1] | A | A | A |
| 24 | 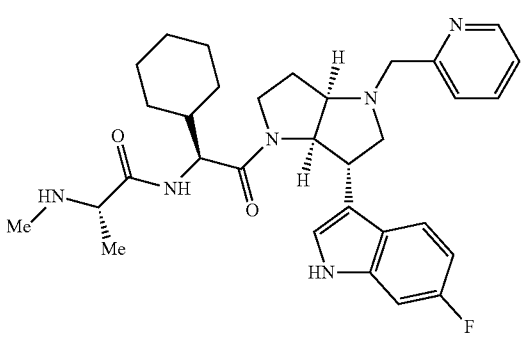 [SMILES: CN[C@@H](C)C(=O)N[C@H](C(=O)N1CC[C@@H]2[C@H]1[C@@H](c1c[nH]c3cc(F)ccc13)CN2Cc1ccccn1)C1CCCCC1] | A | A | A |
| 25 | 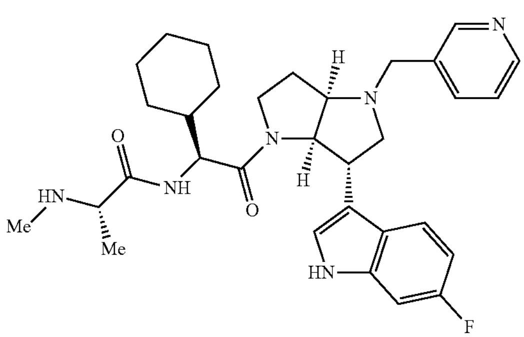 [SMILES: CN[C@@H](C)C(=O)N[C@H](C(=O)N1CC[C@@H]2[C@H]1[C@@H](c1c[nH]c3cc(F)ccc13)CN2Cc1cccnc1)C1CCCCC1] | A | A | B |

TABLE 1-continued
| Example | Structure | $K_D$ (XIAP BIR3) μM | $K_D$ (c-IAP-1 BIR3) μM | $CC_{50}$ (SK-OV-3) μM |
|---|---|---|---|---|
| 26 | 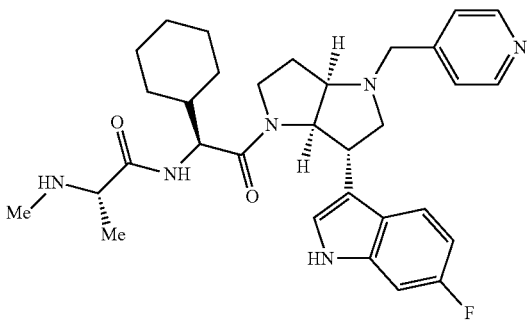 [SMILES: CN[C@@H](C)C(=O)N[C@H](C(=O)N1CC[C@@H]2[C@H]1[C@@H](c1c[nH]c3cc(F)ccc13)CN2Cc1ccncc1)C1CCCCC1] | A | A | A |
| 27 | 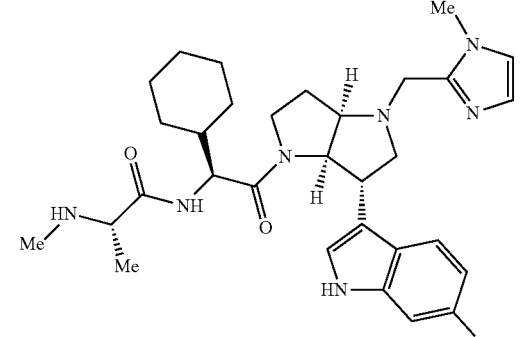 | A | A | C |
| 28 | 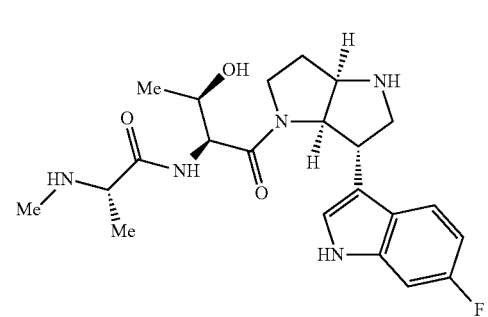 [SMILES: CN[C@@H](C)C(=O)N[C@H](C(=O)N1CC[C@H]2NC[C@H](c3c[nH]c4cc(F)ccc34)[C@H]21)[C@@H](C)O] | B | A | C |
| 29 | 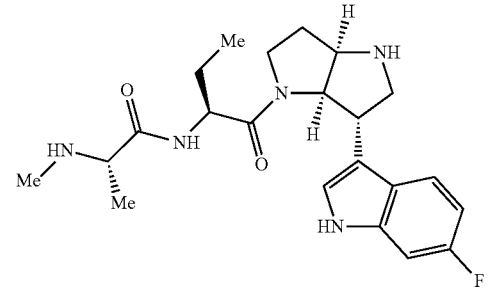 [SMILES: CC[C@H](NC(=O)[C@H](C)NC)C(=O)N1CC[C@H]2NC[C@H](c3c[nH]c4cc(F)ccc34)[C@H]21] | A | A | B |

TABLE 1-continued
| Example | Structure | $K_D$ (XIAP BIR3) μM | $K_D$ (c-IAP-1 BIR3) μM | $CC_{50}$ (SK-OV-3) μM |
|---|---|---|---|---|
| 30 | 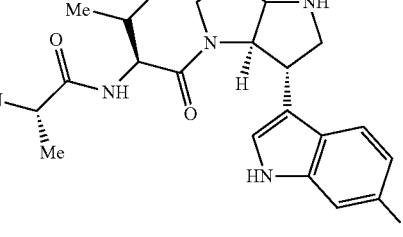 | A | A | A |
| 31 | 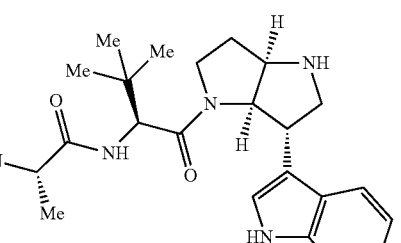 | B | A | A |
| 32 | 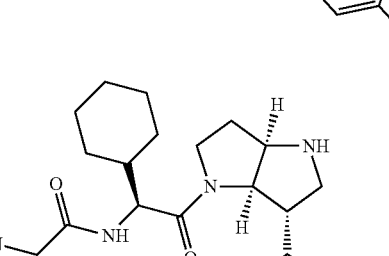 | A | A | A |
| 33 | 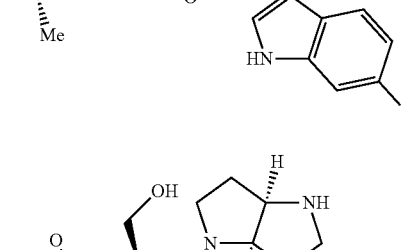 | A | A | C |
| 34 | 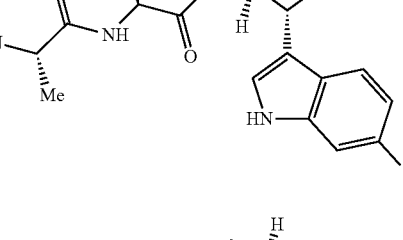 | A | A | C |

TABLE 1-continued

| Example | Structure | $K_D$ (XIAP BIR3) µM | $K_D$ (c-IAP-1 BIR3) µM | $CC_{50}$ (SK-OV-3) µM |
|---|---|---|---|---|
| 35 | 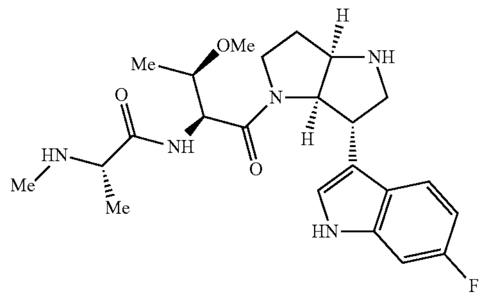 [SMILES: CN[C@@H](C)C(=O)N[C@H](C(=O)N1CC[C@H]2NC[C@H](c3c[nH]c4cc(F)ccc34)[C@H]21)[C@@H](C)OC] | A | A | A |
| 36 | 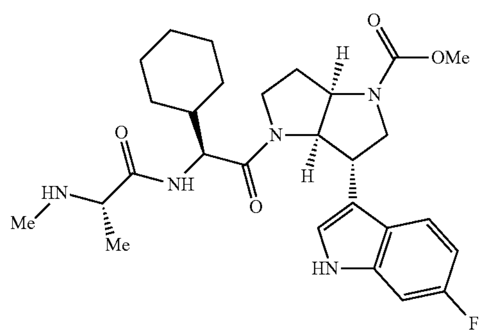 | A | A | A |
| 37 | 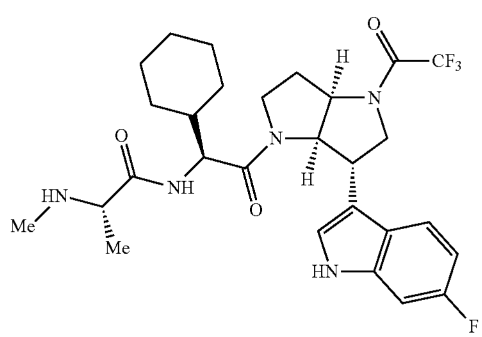 [SMILES: CN[C@@H](C)C(=O)N[C@H](C(=O)N1CC[C@@H]2[C@H]1[C@@H](c1c[nH]c3cc(F)ccc13)CN2C(=O)C(F)(F)F)C1CCCCC1] | A | A | A |
| 38 | 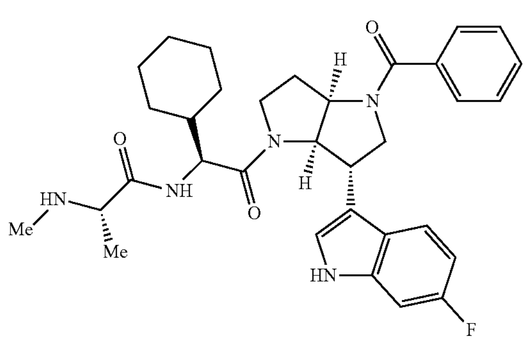 [SMILES: CN[C@@H](C)C(=O)N[C@H](C(=O)N1CC[C@@H]2[C@H]1[C@@H](c1c[nH]c3cc(F)ccc13)CN2C(=O)c1ccccc1)C1CCCCC1] | A | A | A |

TABLE 1-continued
| Example | Structure | $K_D$ (XIAP BIR3) μM | $K_D$ (c-IAP-1 BIR3) μM | $CC_{50}$ (SK-OV-3) μM |
|---|---|---|---|---|
| 39 | 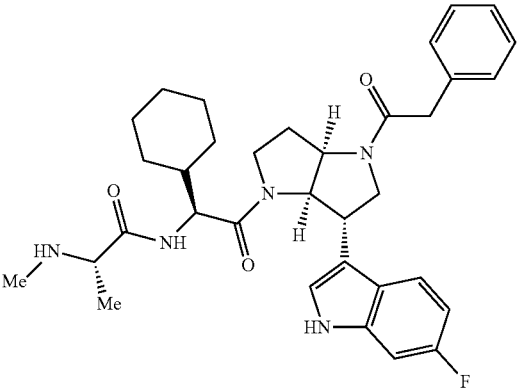 [SMILES: CN[C@@H](C)C(=O)N[C@H](C(=O)N1CC[C@@H]2[C@H]1[C@@H](c1c[nH]c3cc(F)ccc13)CN2C(=O)Cc1ccccc1)C1CCCCC1] | A | A | A |
| 40 | 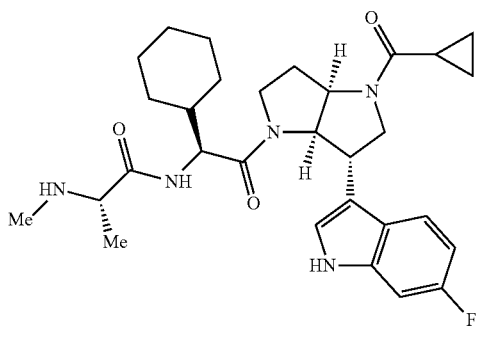 [SMILES: CN[C@@H](C)C(=O)N[C@H](C(=O)N1CC[C@@H]2[C@H]1[C@@H](c1c[nH]c3cc(F)ccc13)CN2C(=O)C1CC1)C1CCCCC1] | A | A | A |
| 41 | 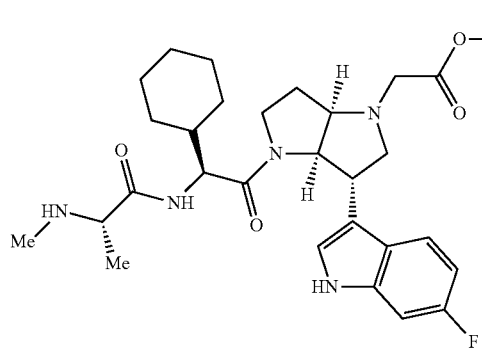 | A | A | B |
| 42 | 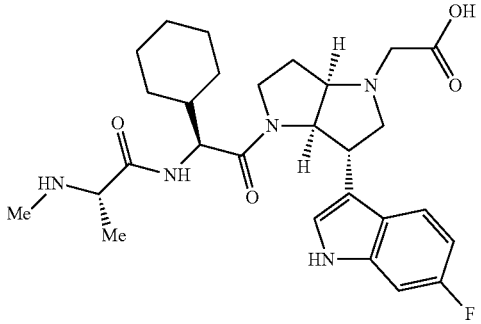 [SMILES: CN[C@@H](C)C(=O)N[C@H](C(=O)N1CC[C@@H]2[C@H]1[C@@H](c1c[nH]c3cc(F)ccc13)CN2CC(=O)O)C1CCCCC1] | B | A | C |

TABLE 1-continued
| Example | Structure | $K_D$ (XIAP BIR3) μM | $K_D$ (c-IAP-1 BIR3) μM | $CC_{50}$ (SK-OV-3) μM |
|---|---|---|---|---|
| 43 | 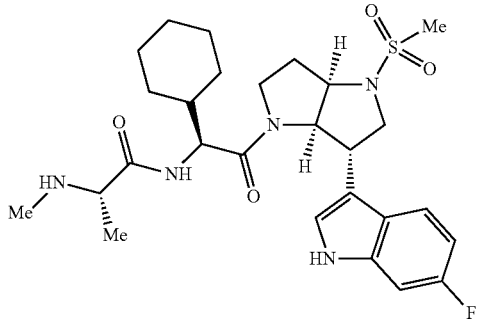 [SMILES: CN[C@@H](C)C(=O)N[C@H](C(=O)N1CC[C@@H]2[C@H]1[C@@H](c1c[nH]c3cc(F)ccc13)CN2S(C)(=O)=O)C1CCCCC1] | A | A | A |
| 44 | 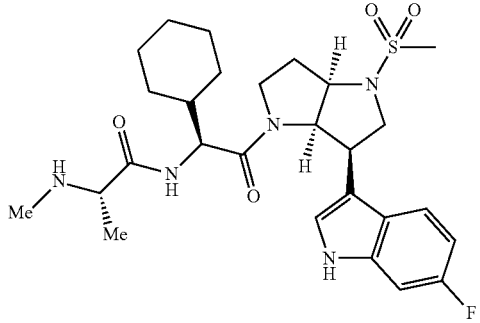 [SMILES: CN[C@@H](C)C(=O)N[C@H](C(=O)N1CC[C@@H]2[C@H]1[C@H](c1c[nH]c3cc(F)ccc13)CN2S(C)(=O)=O)C1CCCCC1] | C | B | C |
| 45 | 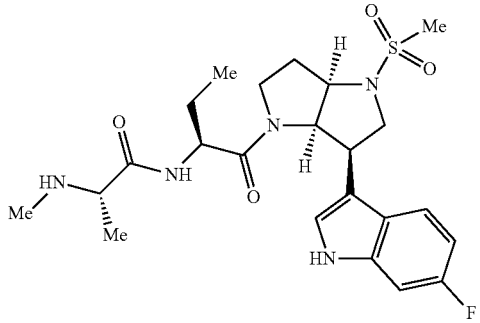 [SMILES: CC[C@H](NC(=O)[C@H](C)NC)C(=O)N1CC[C@@H]2[C@H]1[C@H](c1c[nH]c3cc(F)ccc13)CN2S(C)(=O)=O] | D | C | D |
| 46 | 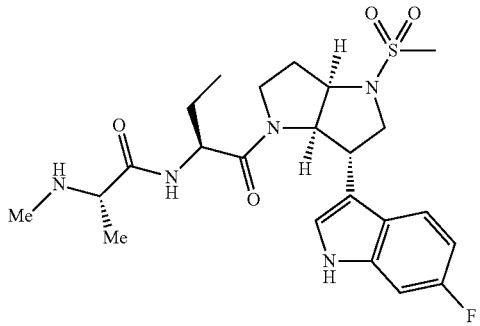 [SMILES: CC[C@H](NC(=O)[C@H](C)NC)C(=O)N1CC[C@@H]2[C@H]1[C@@H](c1c[nH]c3cc(F)ccc13)CN2S(C)(=O)=O] | A | A | A |

TABLE 1-continued
| Example | Structure | $K_D$ (XIAP BIR3) μM | $K_D$ (c-IAP-1 BIR3) μM | $CC_{50}$ (SK-OV-3) μM |
|---|---|---|---|---|
| 47 | 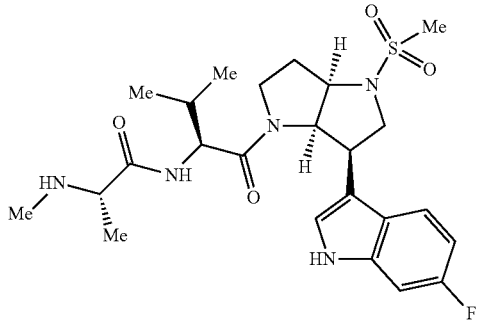 [SMILES: CN[C@@H](C)C(=O)N[C@H](C(=O)N1CC[C@@H]2[C@H]1[C@H](c1c[nH]c3cc(F)ccc13)CN2S(C)(=O)=O)C(C)C] | B | B | D |
| 48 | 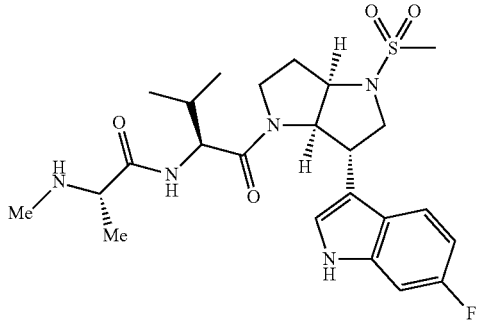 [SMILES: CN[C@@H](C)C(=O)N[C@H](C(=O)N1CC[C@@H]2[C@H]1[C@@H](c1c[nH]c3cc(F)ccc13)CN2S(C)(=O)=O)C(C)C] | A | A | A |
| 49 | 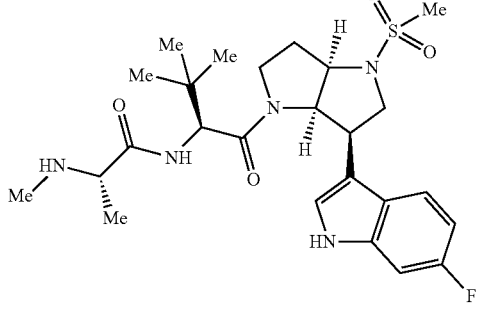 | C | B | D |
| 50 | 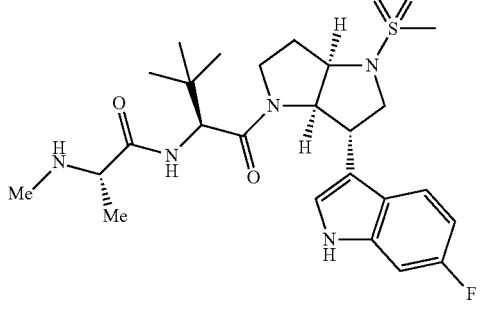 | A | A | A |

TABLE 1-continued

| Example | Structure | $K_D$ (XIAP BIR3) μM | $K_D$ (c-IAP-1 BIR3) μM | $CC_{50}$ (SK-OV-3) μM |
|---|---|---|---|---|
| 51 | 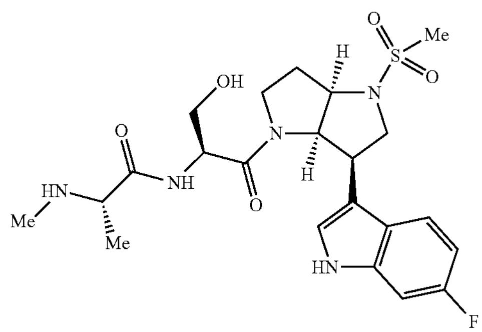 [SMILES: CN[C@@H](C)C(=O)N[C@@H](CO)C(=O)N1CC[C@@H]2[C@H]1[C@H](c1c[nH]c3cc(F)ccc13)CN2S(C)(=O)=O] | D | C | D |
| 52 | 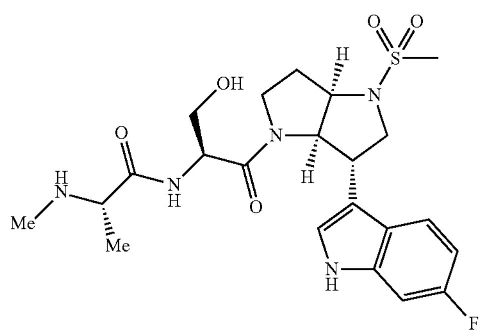 [SMILES: CN[C@@H](C)C(=O)N[C@@H](CO)C(=O)N1CC[C@@H]2[C@H]1[C@@H](c1c[nH]c3cc(F)ccc13)CN2S(C)(=O)=O] | A | A | C |
| 53 | 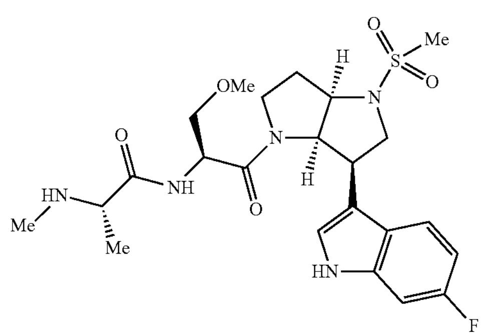 [SMILES: CN[C@@H](C)C(=O)N[C@@H](COC)C(=O)N1CC[C@@H]2[C@H]1[C@H](c1c[nH]c3cc(F)ccc13)CN2S(C)(=O)=O] | D | C | D |
| 54 | 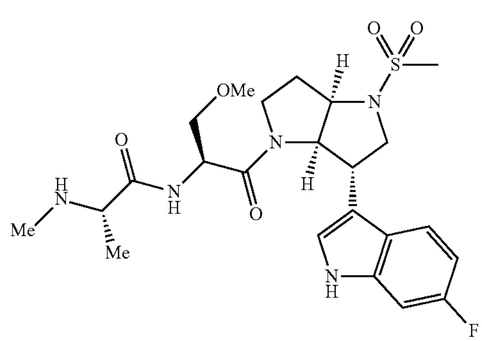 [SMILES: CN[C@@H](C)C(=O)N[C@@H](COC)C(=O)N1CC[C@@H]2[C@H]1[C@@H](c1c[nH]c3cc(F)ccc13)CN2S(C)(=O)=O] | A | A | B |

TABLE 1-continued
| Example | Structure | $K_D$ (XIAP BIR3) μM | $K_D$ (c-IAP-1 BIR3) μM | $CC_{50}$ (SK-OV-3) μM |
|---|---|---|---|---|
| 55 | 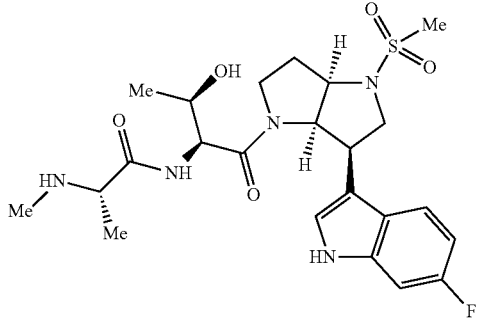 [SMILES: CN[C@@H](C)C(=O)N[C@H](C(=O)N1CC[C@@H]2[C@H]1[C@H](c1c[nH]c3cc(F)ccc13)CN2S(C)(=O)=O)[C@@H](C)O] | D | C | D |
| 56 | 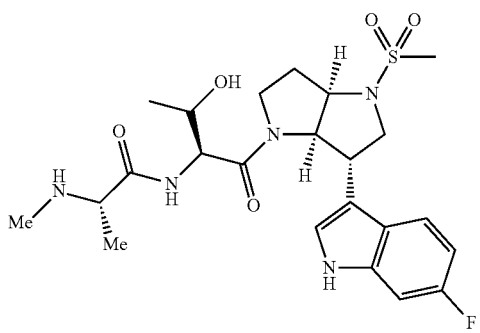 [SMILES: CN[C@@H](C)C(=O)N[C@H](C(=O)N1CC[C@@H]2[C@H]1[C@@H](c1c[nH]c3cc(F)ccc13)CN2S(C)(=O)=O)C(C)O] | A | A | A |
| 57 | 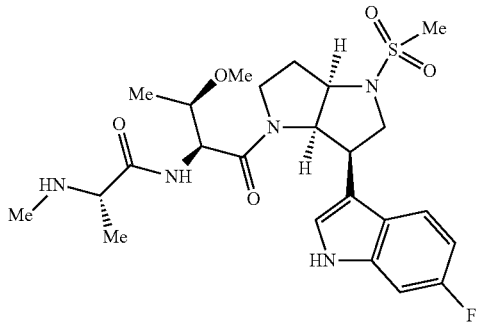 [SMILES: CN[C@@H](C)C(=O)N[C@H](C(=O)N1CC[C@@H]2[C@H]1[C@H](c1c[nH]c3cc(F)ccc13)CN2S(C)(=O)=O)[C@@H](C)OC] | D | B | D |
| 58 | 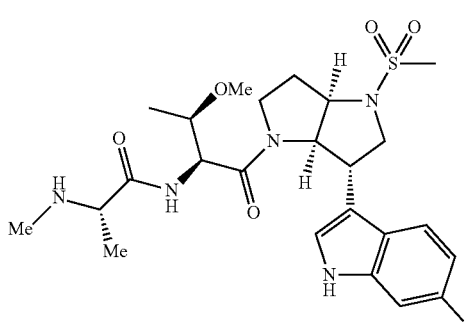 | A | A | A |

TABLE 1-continued

| Example | Structure | $K_D$ (XIAP BIR3) μM | $K_D$ (c-IAP-1 BIR3) μM | $CC_{50}$ (SK-OV-3) μM |
|---|---|---|---|---|
| 59 | 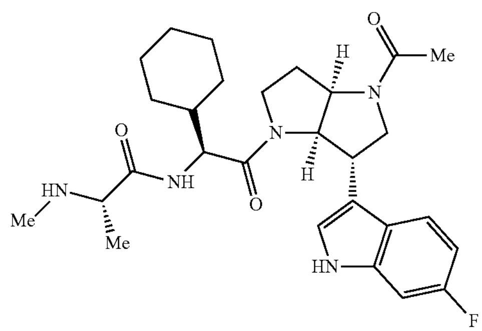 [SMILES: CN[C@@H](C)C(=O)N[C@H](C(=O)N1CC[C@@H]2[C@H]1[C@@H](c1c[nH]c3cc(F)ccc13)CN2C(C)=O)C1CCCCC1] | A | A | A |
| 60 | 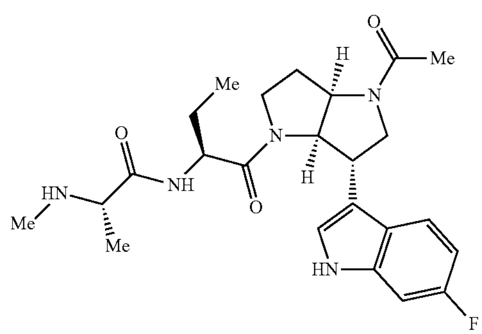 [SMILES: CC[C@H](NC(=O)[C@H](C)NC)C(=O)N1CC[C@@H]2[C@H]1[C@@H](c1c[nH]c3cc(F)ccc13)CN2C(C)=O] | A | A | A |
| 61 | 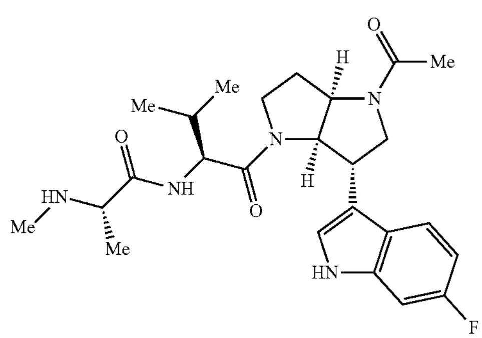 [SMILES: CN[C@@H](C)C(=O)N[C@H](C(=O)N1CC[C@@H]2[C@H]1[C@@H](c1c[nH]c3cc(F)ccc13)CN2C(C)=O)C(C)C] | A | A | A |
| 62 | 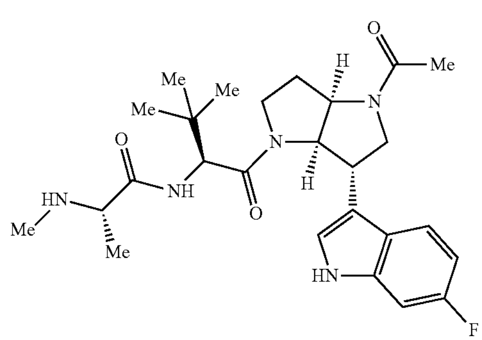 [SMILES: CN[C@@H](C)C(=O)N[C@H](C(=O)N1CC[C@@H]2[C@H]1[C@@H](c1c[nH]c3cc(F)ccc13)CN2C(C)=O)C(C)(C)C] | A | A | A |

TABLE 1-continued
| Example | Structure | $K_D$ (XIAP BIR3) μM | $K_D$ (c-IAP-1 BIR3) μM | $CC_{50}$ (SK-OV-3) μM |
|---|---|---|---|---|
| 63 | 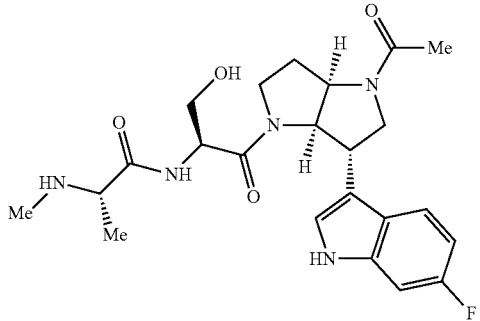 | A | A | C |
| 64 | 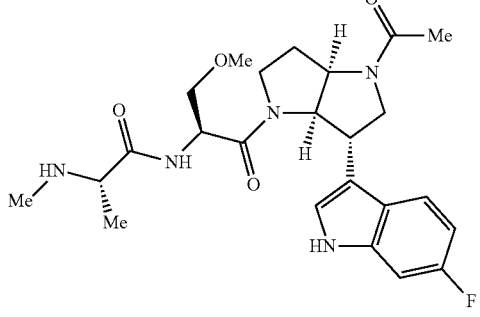 | B | A | B |
| 65 | 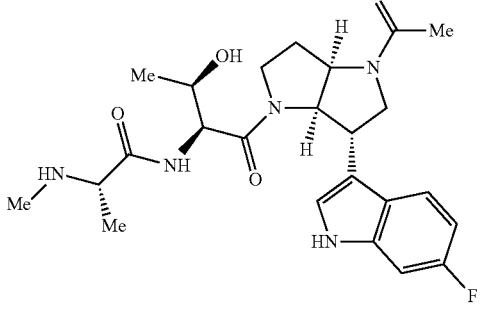 | A | A | B |
| 66 | 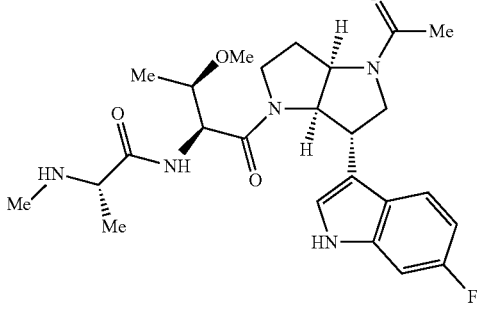 | A | A | A |

TABLE 1-continued
| Example | Structure | $K_D$ (XIAP BIR3) μM | $K_D$ (c-IAP-1 BIR3) μM | $CC_{50}$ (SK-OV-3) μM |
|---|---|---|---|---|
| 67 | 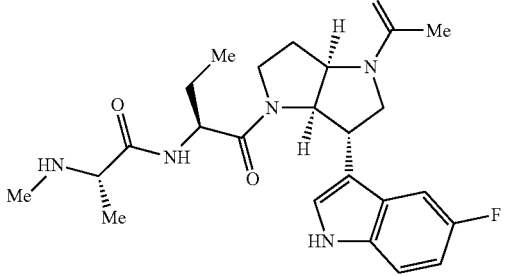 | A | A | B |
| 68 | 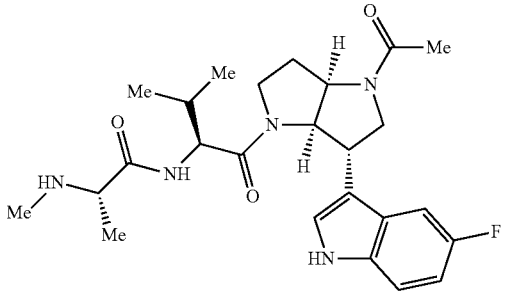 [SMILES: CN[C@@H](C)C(=O)N[C@H](C(=O)N1CC[C@@H]2[C@H]1[C@@H](c1c[nH]c3ccc(F)cc13)CN2C(C)=O)C(C)C] | A | A | A |
| 69 | 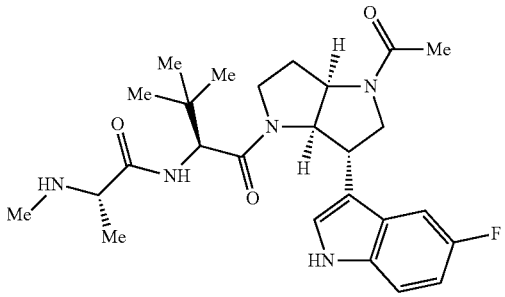 [SMILES: CN[C@@H](C)C(=O)N[C@H](C(=O)N1CC[C@@H]2[C@H]1[C@@H](c1c[nH]c3ccc(F)cc13)CN2C(C)=O)C(C)(C)C] | A | A | A |
| 70 | 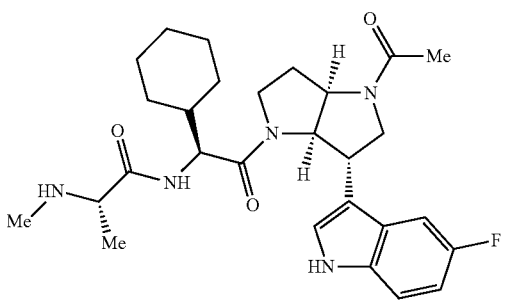 [SMILES: CN[C@@H](C)C(=O)N[C@H](C(=O)N1CC[C@@H]2[C@H]1[C@@H](c1c[nH]c3ccc(F)cc13)CN2C(C)=O)C1CCCCC1] | A | A | A |
| 71 | 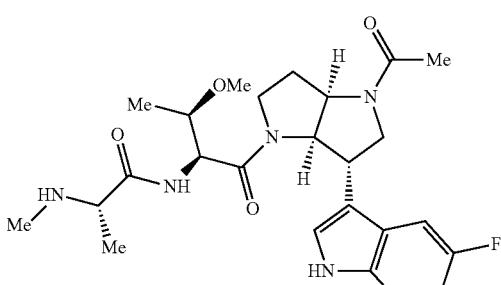 | A | A | A |

TABLE 1-continued
| Example | Structure | $K_D$ (XIAP BIR3) μM | $K_D$ (c-IAP-1 BIR3) μM | $CC_{50}$ (SK-OV-3) μM |
|---|---|---|---|---|
| 72 | 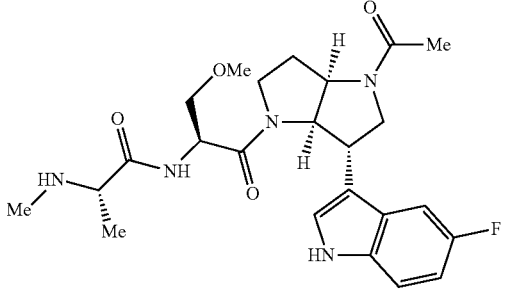 [SMILES: CN[C@@H](C)C(=O)N[C@@H](COC)C(=O)N1CC[C@@H]2[C@H]1[C@@H](c1c[nH]c3ccc(F)cc13)CN2C(C)=O] | A | A | C |
| 73 | 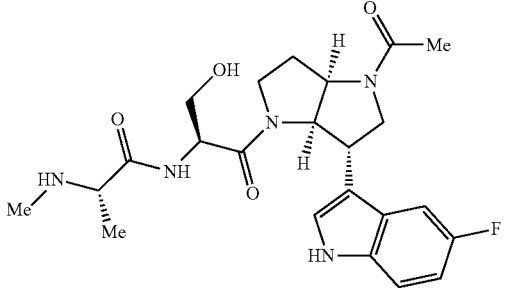 [SMILES: CN[C@@H](C)C(=O)N[C@@H](CO)C(=O)N1CC[C@@H]2[C@H]1[C@@H](c1c[nH]c3ccc(F)cc13)CN2C(C)=O] | A | A | C |
| 74 | 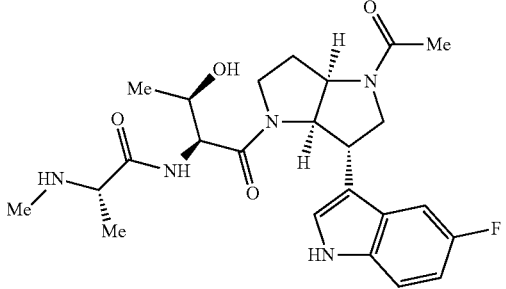 [SMILES: CN[C@@H](C)C(=O)N[C@H](C(=O)N1CC[C@@H]2[C@H]1[C@@H](c1c[nH]c3ccc(F)cc13)CN2C(C)=O)[C@@H](C)O] | A | A | B |
| 75 | 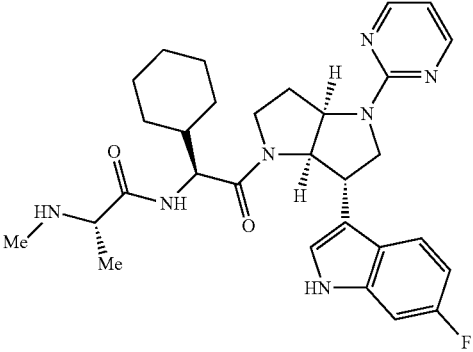 [SMILES: CN[C@@H](C)C(=O)N[C@H](C(=O)N1CC[C@@H]2[C@H]1[C@@H](c1c[nH]c3cc(F)ccc13)CN2c1ncccn1)C1CCCCC1] | A | A | A |

TABLE 1-continued

| Example | Structure | $K_D$ (XIAP BIR3) μM | $K_D$ (c-IAP-1 BIR3) μM | $CC_{50}$ (SK-OV-3) μM |
|---------|-----------|---------------------|-------------------------|------------------------|
| 76 | 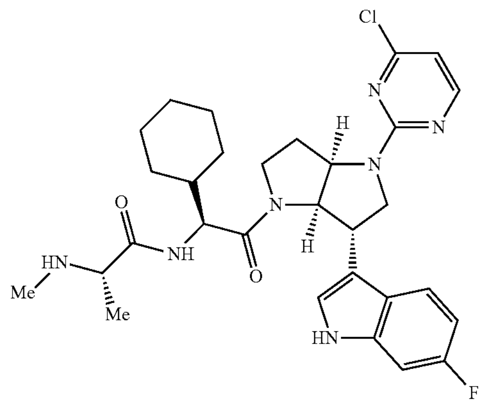 [SMILES: CN[C@@H](C)C(=O)N[C@H](C(=O)N1CC[C@@H]2[C@H]1[C@@H](c1c[nH]c3cc(F)ccc13)CN2c1nccc(Cl)n1)C1CCCCC1] | A | A | A |
| 77 | 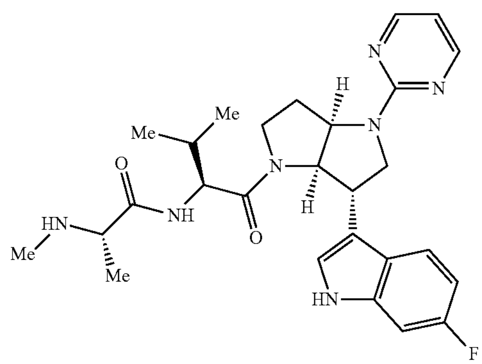 [SMILES: CN[C@@H](C)C(=O)N[C@H](C(=O)N1CC[C@@H]2[C@H]1[C@@H](c1c[nH]c3cc(F)ccc13)CN2c1ncccn1)C(C)C] | A | A | A |
| 78 | 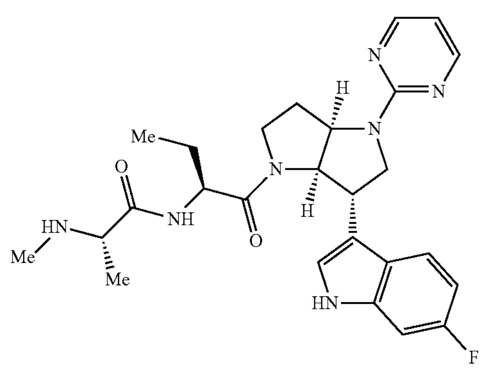 [SMILES: CC[C@H](NC(=O)[C@H](C)NC)C(=O)N1CC[C@@H]2[C@H]1[C@@H](c1c[nH]c3cc(F)ccc13)CN2c1ncccn1] | B | A | A |
| 79 | 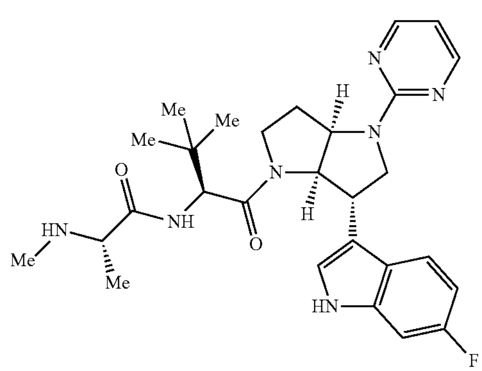 [SMILES: CN[C@@H](C)C(=O)N[C@H](C(=O)N1CC[C@@H]2[C@H]1[C@@H](c1c[nH]c3cc(F)ccc13)CN2c1ncccn1)C(C)(C)C] | A | A | A |

TABLE 1-continued

| Example | Structure | $K_D$ (XIAP BIR3) μM | $K_D$ (c-IAP-1 BIR3) μM | $CC_{50}$ (SK-OV-3) μM |
|---|---|---|---|---|
| 80 | 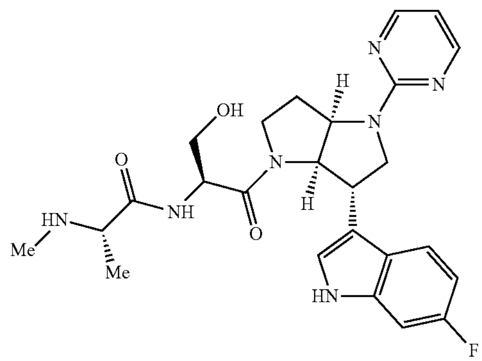 [SMILES: CN[C@@H](C)C(=O)N[C@@H](CO)C(=O)N1CC[C@@H]2[C@H]1[C@@H](c1c[nH]c3cc(F)ccc13)CN2c1ncccn1] | A | A | A |
| 81 | 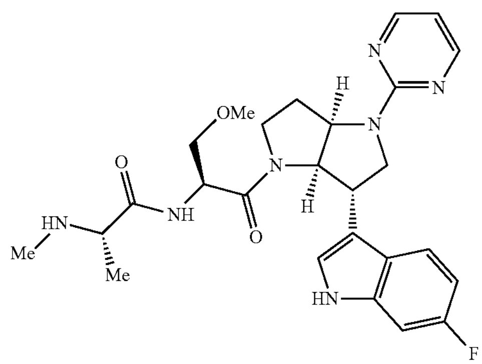 [SMILES: CN[C@@H](C)C(=O)N[C@@H](COC)C(=O)N1CC[C@@H]2[C@H]1[C@@H](c1c[nH]c3cc(F)ccc13)CN2c1ncccn1] | A | A | A |
| 82 | 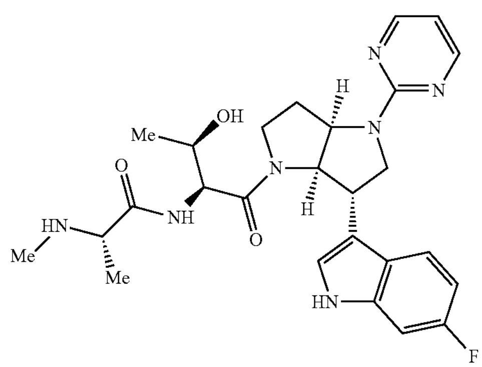 [SMILES: CN[C@@H](C)C(=O)N[C@H](C(=O)N1CC[C@@H]2[C@H]1[C@@H](c1c[nH]c3cc(F)ccc13)CN2c1ncccn1)[C@@H](C)O] | A | A | A |
| 83 | 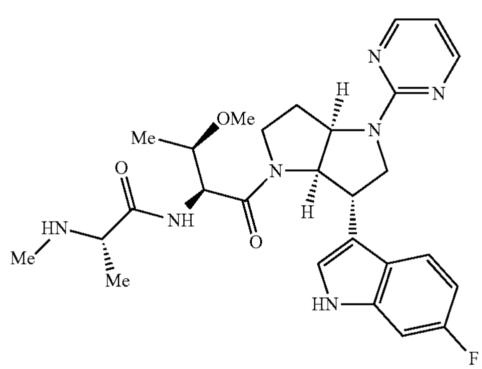 [SMILES: CN[C@@H](C)C(=O)N[C@H](C(=O)N1CC[C@@H]2[C@H]1[C@@H](c1c[nH]c3cc(F)ccc13)CN2c1ncccn1)[C@@H](C)OC] | A | A | A |

TABLE 1-continued
| Example | Structure | $K_D$ (XIAP BIR3) μM | $K_D$ (c-IAP-1 BIR3) μM | $CC_{50}$ (SK-OV-3) μM |
|---|---|---|---|---|
| 84 | 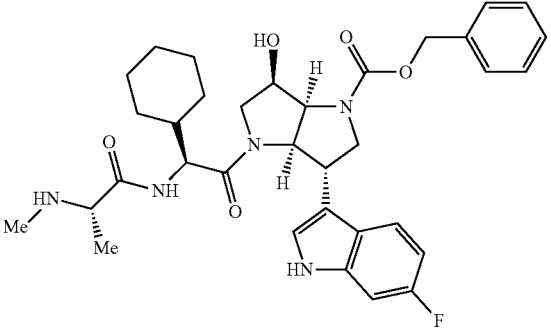 [SMILES: CN[C@@H](C)C(=O)N[C@H](C(=O)N1C[C@@H](O)[C@@H]2[C@H]1[C@@H](c1c[nH]c3cc(F)ccc13)CN2C(=O)OCc1ccccc1)C1CCCCC1] | A | A | A |
| 85 | 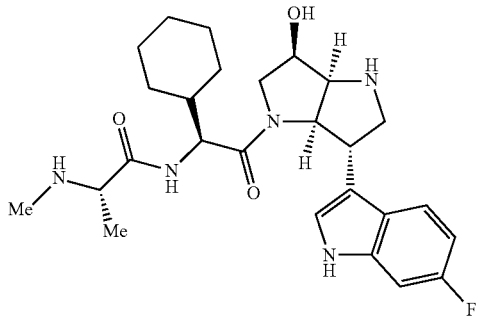 [SMILES: CN[C@@H](C)C(=O)N[C@H](C(=O)N1C[C@@H](O)[C@H]2NC[C@H](c3c[nH]c4cc(F)ccc34)[C@H]21)C1CCCCC1] | B | A | B |
| 86 | 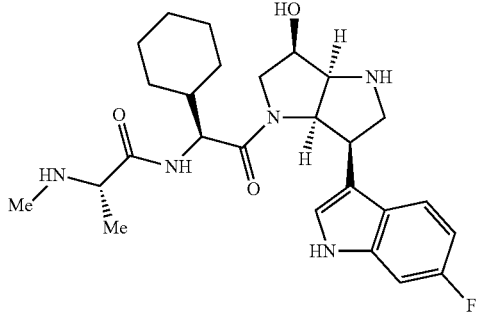 [SMILES: CN[C@@H](C)C(=O)N[C@H](C(=O)N1C[C@@H](O)[C@H]2NC[C@@H](c3c[nH]c4cc(F)ccc34)[C@H]21)C1CCCCC1] | D | B | D |
| 87 | 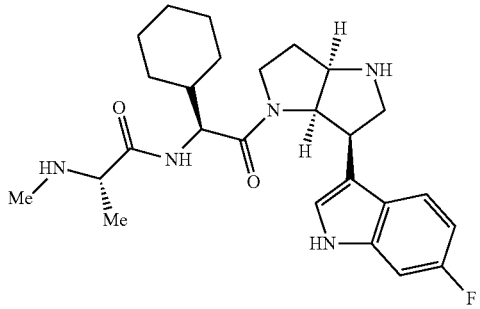 [SMILES: CN[C@@H](C)C(=O)N[C@H](C(=O)N1CC[C@H]2NC[C@@H](c3c[nH]c4cc(F)ccc34)[C@H]21)C1CCCCC1] | D | C | D |

TABLE 1-continued
| Example | Structure | $K_D$ (XIAP BIR3) µM | $K_D$ (c-IAP-1 BIR3) µM | $CC_{50}$ (SK-OV-3) µM |
|---|---|---|---|---|
| 88 | 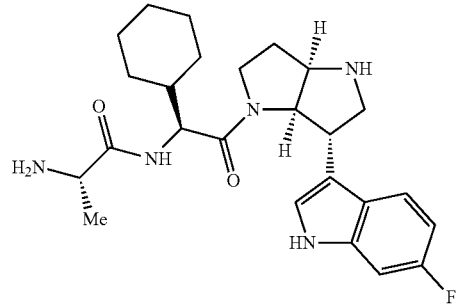 [SMILES: C[C@H](N)C(=O)N[C@H](C(=O)N1CC[C@H]2NC[C@H](c3c[nH]c4cc(F)ccc34)[C@H]21)C1CCCCC1] | A | A | D |
| 89 | 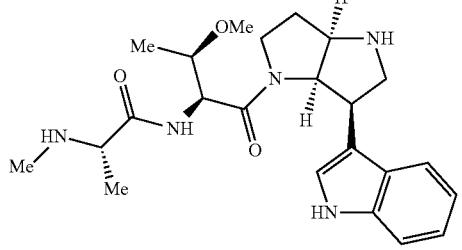 | D | B | D |
| 90 | 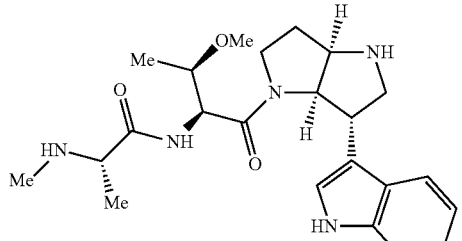 | A | A | C |
| 91 | 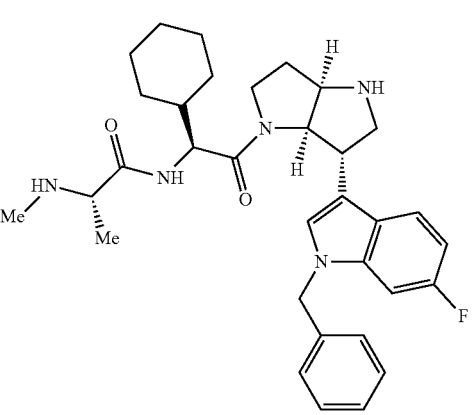 [SMILES: CN[C@@H](C)C(=O)N[C@H](C(=O)N1CC[C@H]2NC[C@H](c3cn(Cc4ccccc4)c4cc(F)ccc34)[C@H]21)C1CCCCC1] | A | A | B |

TABLE 1-continued

| Example | Structure | $K_D$ (XIAP BIR3) μM | $K_D$ (c-IAP-1 BIR3) μM | $CC_{50}$ (SK-OV-3) μM |
|---|---|---|---|---|
| 92 | 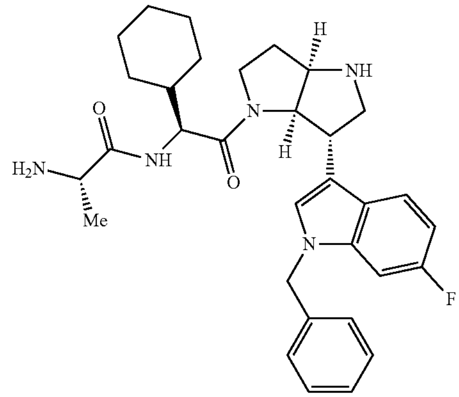 [SMILES: C[C@H](N)C(=O)N[C@H](C(=O)N1CC[C@H]2NC[C@H](c3cn(Cc4ccccc4)c4cc(F)ccc34)[C@H]21)C1CCCCC1] | A | A | C |
| 93 | 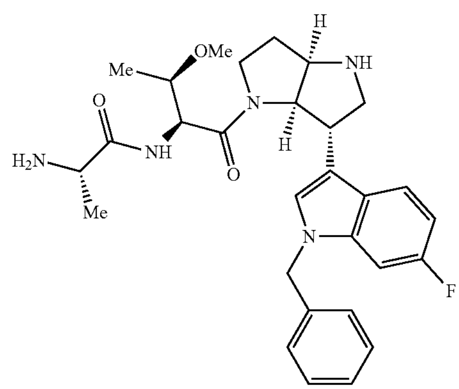 [SMILES: CO[C@H](C)[C@H](NC(=O)[C@H](C)N)C(=O)N1CC[C@H]2NC[C@H](c3cn(Cc4ccccc4)c4cc(F)ccc34)[C@H]21] | A | A | C |
| 94 | 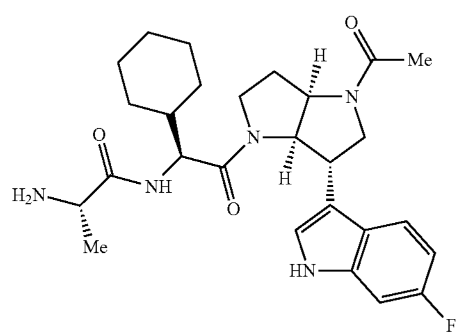 [SMILES: CC(=O)N1C[C@H](c2c[nH]c3cc(F)ccc23)[C@@H]2[C@H]1CCN2C(=O)[C@@H](NC(=O)[C@H](C)N)C1CCCCC1] | A | A | C |
| 95 | 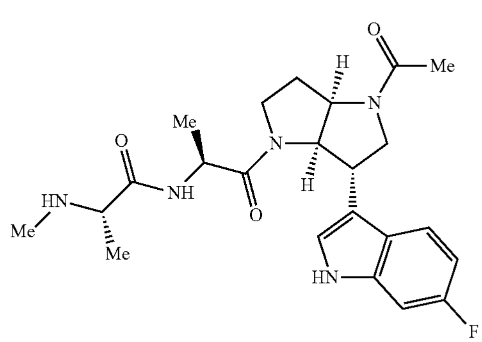 | A | A | B |

TABLE 1-continued

| Example | Structure | $K_D$ (XIAP BIR3) μM | $K_D$ (c-IAP-1 BIR3) μM | $CC_{50}$ (SK-OV-3) μM |
|---|---|---|---|---|
| 96 | 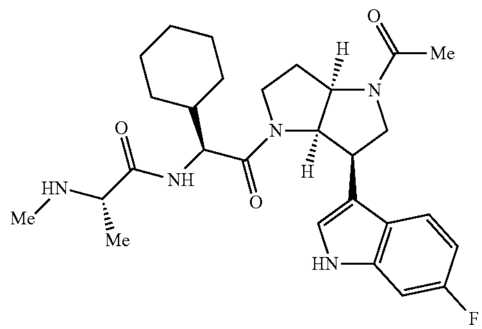 [SMILES: CN[C@@H](C)C(=O)N[C@H](C(=O)N1CC[C@@H]2[C@H]1[C@H](c1c[nH]c3cc(F)ccc13)CN2C(C)=O)C1CCCCC1] | C | B | C |
| 97 | 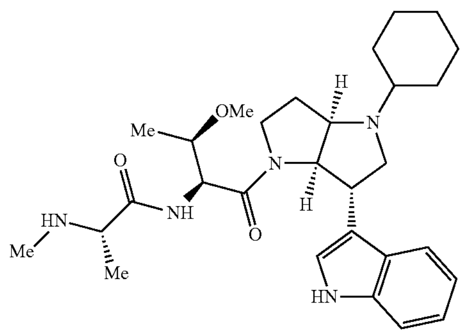 [SMILES: CN[C@@H](C)C(=O)N[C@H](C(=O)N1CC[C@@H]2[C@H]1[C@@H](c1c[nH]c3ccccc13)CN2C1CCCCC1)[C@@H](C)OC] | C | B | B |
| 98 | 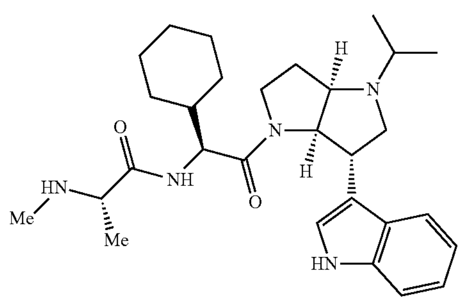 [SMILES: CN[C@@H](C)C(=O)N[C@H](C(=O)N1CC[C@@H]2[C@H]1[C@@H](c1c[nH]c3ccccc13)CN2C(C)C)C1CCCCC1] | C | B | B |
| 99 | 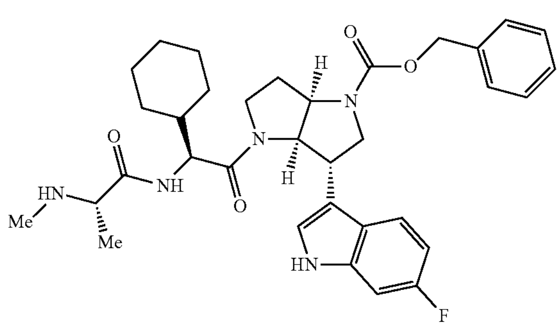 [SMILES: CN[C@@H](C)C(=O)N[C@H](C(=O)N1CC[C@@H]2[C@H]1[C@@H](c1c[nH]c3cc(F)ccc13)CN2C(=O)OCc1ccccc1)C1CCCCC1] | A | A | A |

TABLE 1-continued

| Example | Structure | $K_D$ (XIAP BIR3) μM | $K_D$ (c-IAP-1 BIR3) μM | $CC_{50}$ (SK-OV-3) μM |
|---|---|---|---|---|
| 100 | 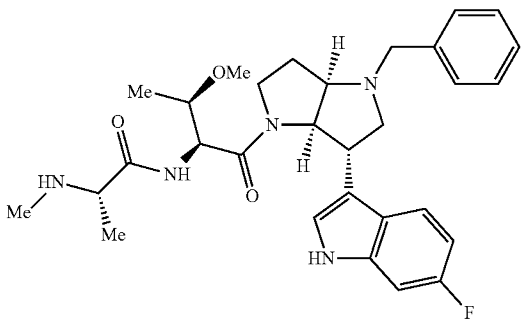 [SMILES: CN[C@@H](C)C(=O)N[C@H](C(=O)N1CC[C@@H]2[C@H]1[C@@H](c1c[nH]c3cc(F)ccc13)CN2Cc1ccccc1)[C@@H](C)OC] | A | A | A |
| 101 | 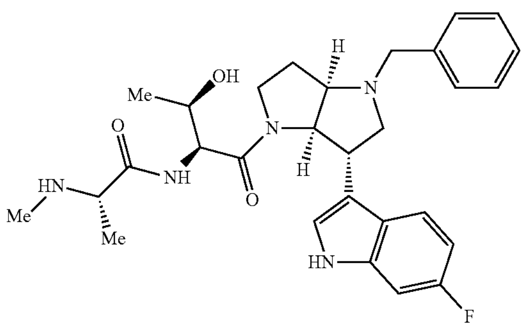 [SMILES: CN[C@@H](C)C(=O)N[C@H](C(=O)N1CC[C@@H]2[C@H]1[C@@H](c1c[nH]c3cc(F)ccc13)CN2Cc1ccccc1)[C@@H](C)O] | B | A | B |
| 102 | 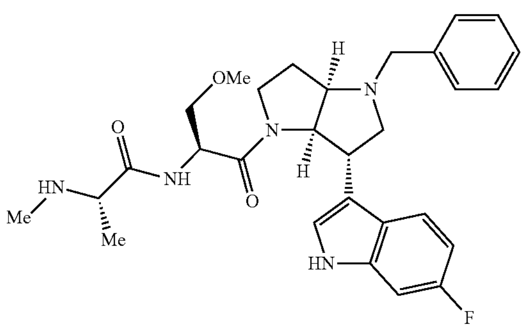 [SMILES: CN[C@@H](C)C(=O)N[C@@H](COC)C(=O)N1CC[C@@H]2[C@H]1[C@@H](c1c[nH]c3cc(F)ccc13)CN2Cc1ccccc1] | C | B | C |
| 103 | 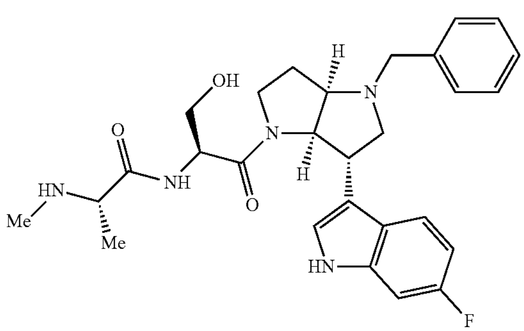 [SMILES: CN[C@@H](C)C(=O)N[C@@H](CO)C(=O)N1CC[C@@H]2[C@H]1[C@@H](c1c[nH]c3cc(F)ccc13)CN2Cc1ccccc1] | C | B | C |

TABLE 1-continued

| Example | Structure | K_D (XIAP BIR3) μM | K_D (c-IAP-1 BIR3) μM | CC_50 (SK-OV-3) μM |
|---|---|---|---|---|
| 104 | 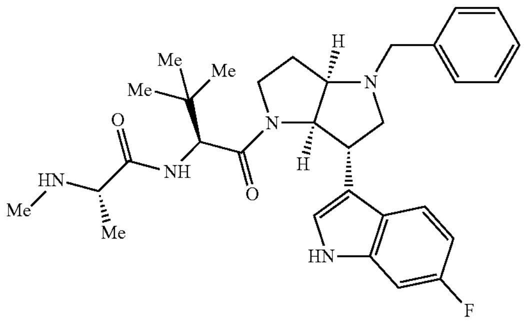 [SMILES: CN[C@@H](C)C(=O)N[C@H](C(=O)N1CC[C@@H]2[C@H]1[C@@H](c1c[nH]c3cc(F)ccc13)CN2Cc1ccccc1)C(C)(C)C] | A | A | A |
| 105 | 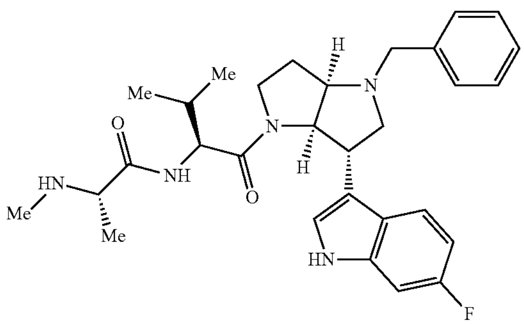 [SMILES: CN[C@@H](C)C(=O)N[C@H](C(=O)N1CC[C@@H]2[C@H]1[C@@H](c1c[nH]c3cc(F)ccc13)CN2Cc1ccccc1)C(C)C] | B | A | A |
| 106 | 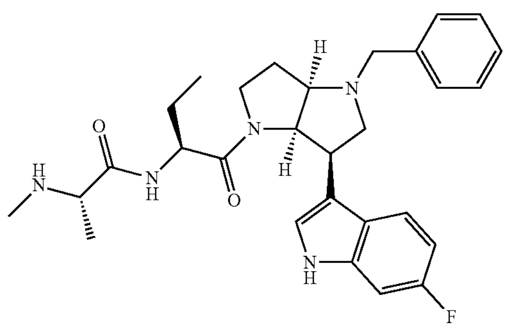 [SMILES: CC[C@H](NC(=O)[C@H](C)NC)C(=O)N1CC[C@@H]2[C@H]1[C@H](c1c[nH]c3cc(F)ccc13)CN2Cc1ccccc1] | D | B | C |
| 107 | 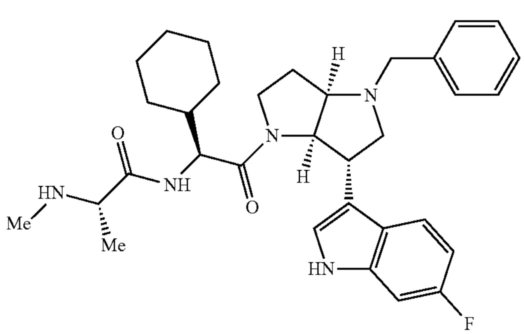 [SMILES: CN[C@@H](C)C(=O)N[C@H](C(=O)N1CC[C@@H]2[C@H]1[C@@H](c1c[nH]c3cc(F)ccc13)CN2Cc1ccccc1)C1CCCCC1] | A | A | B |

TABLE 2

| Example | Structure | $K_D$ (XIAP BIR3) μM | $K_D$ (c-IAP-1 BIR3) μM | $CC_{50}$ (SK-OV-3) μM |
|---|---|---|---|---|
| 108 | 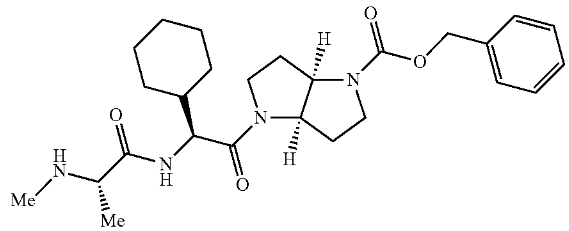 [SMILES: CN[C@@H](C)C(=O)N[C@H](C(=O)N1CC[C@@H]2[C@H]1CCN2C(=O)OCc1ccccc1)C1CCCCC1] | C | A | B |
| 109 | 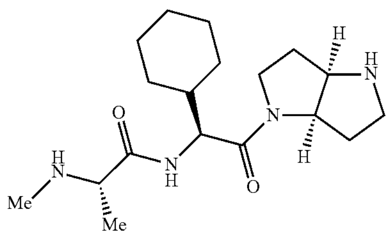 [SMILES: CN[C@@H](C)C(=O)N[C@H](C(=O)N1CC[C@H]2NCC[C@H]21)C1CCCCC1] | C | B | D |

TABLE 3

| Entry | Structure | $K_D$ (XIAP BIR3) μM | $K_D$ (c-IAP-1 BIR3) μM | $CC_{50}$ (SK-OV-3) μM |
|---|---|---|---|---|
| 110 | 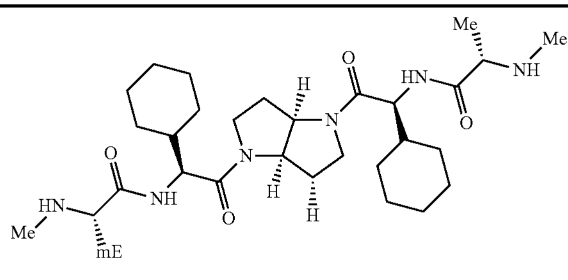 | C | A | C |
| 111 | 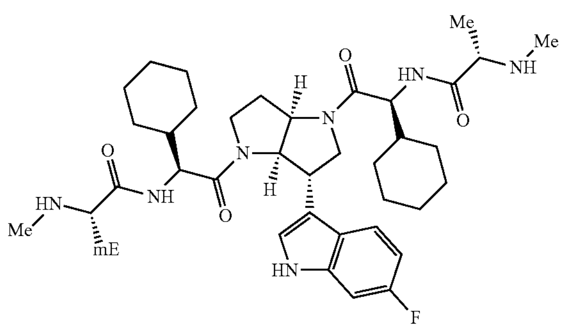 | A | A | A |

It is intended that the present invention encompass compounds that are synthesized in vitro using laboratory techniques, such as those well known to synthetic chemists; or synthesized using in vivo techniques, such as through metabolism, fermentation, digestion, and the like. It is also contemplated that the compounds of the present invention may be synthesized using a combination of in vitro and in vivo techniques.

The present invention also includes isotopically-labelled compounds, which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine and chlorine, such as $^2H$, $^3H$, $^{13}C$, $^{14}C$, $^{15}N$, $^{16}O$, $^{17}O$, $^{31}P$, $^{32}P$, $^{35}S$, $^{18}F$, and $^{36}Cl$.

Compounds of the present invention that contain the aforementioned isotopes and/or other isotopes of other atoms are within the scope of this invention. Certain isotopically-labelled compounds of the present invention, for example those into which radioactive isotopes such as $^3H$ and $^{14}C$ are incorporated, are useful in drug and/or substrate tissue distribution assays. Tritiated, i.e., $^3$H, and carbon-14, i.e., $^{14}$C, isotopes are particularly preferred for their ease of preparation and detection. Further, substitution with heavier isotopes such as deuterium, i.e., $^2$H, can afford certain therapeutic advantages resulting from greater metabolic stability, for example increased in vivo half-life or reduced dosage requirements and, hence, may be preferred in some circumstances. Isotopically labelled compounds of this invention can generally be prepared by substituting a readily available isotopically labelled reagent for a non-isotopically labelled reagent.

The compounds of the present invention may exist in unsolvated forms as well as solvated forms, including hydrated forms. The compounds of the present invention (e.g., compounds of Formula I, IS, IR, II, IIS, IIR, III, IIIS and IIIR) also are capable of forming both pharmaceutically acceptable salts, including but not limited to acid addition and/or base addition salts. Furthermore, compounds of the present invention may exist in various solid states including an amorphous form (noncrystalline form), and in the form of clathrates, prodrugs, polymorphs, bio-hydrolyzable esters, racemic mixtures, non-racemic mixtures, or as purified stereoisomers including, but not limited to, optically pure enantiomers and diastereomers. In general, all of these forms can be used as an alternative form to the free base or free acid forms of the compounds, as described above and are intended to be encompassed within the scope of the present invention.

A "polymorph" refers to solid crystalline forms of a compound. Different polymorphs of the same compound can exhibit different physical, chemical and/or spectroscopic properties. Different physical properties include, but are not limited to stability (e.g., to heat or light), compressibility and density (important in formulation and product manufacturing), and dissolution rates (which can affect bioavailability). Different physical properties of polymorphs can affect their processing.

A "clathrate" means a compound or a salt thereof in the form of a crystal lattice that contains spaces (e.g., channels) that have a guest molecule (e.g., a solvent or water) trapped within.

As noted above, the compounds of the present invention can be administered, inter alia, as pharmaceutically acceptable salts, esters, amides or prodrugs. The term "salts" refers to inorganic and organic salts of compounds of the present invention. The salts can be prepared in situ during the final isolation and purification of a compound, or by separately reacting a purified compound in its free base or acid form with a suitable organic or inorganic base or acid and isolating the salt thus formed. Representative salts include the hydrobromide, hydrochloride, sulfate, bisulfate, nitrate, acetate, oxalate, palmitiate, stearate, laurate, borate, benzoate, lactate, phosphate, tosylate, citrate, maleate, fumarate, succinate, tartrate, naphthylate, mesylate, glucoheptonate, lactobionate, and laurylsulphonate salts, and the like. The salts may include cations based on the alkali and alkaline earth metals, such as sodium, lithium, potassium, calcium, magnesium, and the like, as well as non-toxic ammonium, quaternary ammonium, and amine cations including, but not limited to, ammonium, tetramethylammonium, tetraethylammonium, methylamine, dimethylamine, trimethylamine, triethylamine, ethylamine, and the like. See, for example, S. M. Berge, et al., "Pharmaceutical Salts," J Pharm Sci, 66: 1-19 (1977).

Examples of pharmaceutically acceptable esters of the compounds of the present invention include $C_1$-$C_8$ alkyl esters. Acceptable esters also include $C_5$-$C_7$ cycloalkyl esters, as well as arylalkyl esters such as benzyl. $C_1$-$C_4$ alkyl esters are commonly used. Esters of compounds of the present invention may be prepared according to methods that are well known in the art.

Examples of pharmaceutically acceptable amides of the compounds of the present invention include amides derived from ammonia, primary $C_1$-$C_8$ alkyl amines, and secondary $C_1$-$C_8$ dialkyl amines. In the case of secondary amines, the amine may also be in the form of a 5 or 6 membered heterocycloalkyl group containing at least one nitrogen atom. Amides derived from ammonia, $C_1$-$C_3$ primary alkyl amines and $C_1$-$C_2$ dialkyl secondary amines are commonly used. Amides of the compounds of the present invention may be prepared according to methods well known to those skilled in the art.

The term "prodrug" refers to compounds that are rapidly transformed in vivo to yield the parent compound of the above formulae, for example, by hydrolysis in blood. A thorough discussion is provided in T. Higuchi and V. Stella, "Pro-drugs as Novel Delivery Systems," Vol 14 of the A.C.S. Symposium Series, and in Bioreversible Carriers in Drug Design, ed. Edward B. Roche, American Pharmaceutical Association and Pergamon Press, 1987, both of which are incorporated herein by reference.

To illustrate, if the compound of the invention contains a carboxylic acid functional group, a prodrug can comprise an ester formed by the replacement of the hydrogen atom of the acid group with a group such as ($C_1$-$C_8$ alkyl, ($C_2$-$C_{12}$)alkanoyloxymethyl, 1-(alkanoyloxy)ethyl having from 4 to 9 carbon atoms, 1-methyl-1-(alkanoyloxy)ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)aminomethyl having from 4 to 10 carbon atoms, 3-phthalidyl, 4-crotonolactonyl, gamma-butyrolacton-4-yl, di-N, N—($C_1$-$C_2$)alkylamino($C_2$-$C_3$)alkyl (such as β-dimethylaminoethyl), carbamoyl-($C_1$-$C_2$)alkyl, N,N-di ($C_1$-$C_2$)alkylcarbamoyl-($C_1$-$C_2$)alkyl and piperidino-, pyrrolidino- or morpholino($C_2$-$C_3$)alkyl.

Similarly, if a compound of the present invention comprises an alcohol functional group, a prodrug can be formed by the replacement of the hydrogen atom of the alcohol group with a group such as ($C_1$-$C_6$)alkanoyloxymethyl, 1-(($C_1$-$C_6$) alkanoyloxy)ethyl, 1-methyl-1-(($C_1$-$C_6$)alkanoyloxy)ethyl, ($C_1$-$C_6$)alkoxycarbonyloxymethyl, N—($C_1$-$C_6$)alkoxycarbonylaminomethyl, succinoyl, ($C_1$-$C_6$)alkanoyl, α-amino ($C_1$-$C_4$)alkanoyl, arylacyl and α-aminoacyl, or α-aminoacyl-α-aminoacyl, where each α-aminoacyl group is independently selected from the naturally occurring L-amino acids, —P(O)(OH)$_2$, —P(O)(O($C_1$-$C_6$)alkyl)$_2$ or glycosyl (the radical resulting from the removal of a hydroxyl group of the hemiacetal form of a carbohydrate).

Compounds and salts of the present invention may also exist in tautomeric forms, such as an enol and an imine form, and the corresponding keto and enamine forms and geometric isomers and mixtures thereof. Tautomers exist as mixtures of a tautomeric set in solution. In solid form, usually one tautomer predominates. Even though only one tautomer may be described by the formulae above, the present invention includes all tautomers of the present compounds.

The compounds of the present invention may contain asymmetric or chiral centers, and therefore, exist in different stereoisomeric forms. It is contemplated that all stereoisomeric forms of the compounds as well as mixtures thereof, including racemic mixtures, form part of the present invention. In addition, the present invention contemplates all geometric and positional isomers. For example, if the compound contains a double bond, both the cis and trans forms (designated as Z and E, respectively), as well as mixtures, are contemplated.

Mixture of stereoisomers, such as diastereomeric mixtures, can be separated into their individual stereochemical components on the basis of their physical chemical differences by known methods such as chromatography and/or fractional crystallization. Enantiomers can also be separated by converting the enantiomeric mixture into a diasteromeric mixture by reaction with an appropriate optically active compound (e.g., an alcohol), separating the diastereomers and converting (e.g., hydrolyzing) the individual diastereomers to the corresponding pure enantiomers. Also, some compounds may be atropisomers (e.g., substituted biaryls).

The compounds of the present invention may exist in unsolvated as well as solvated forms with pharmaceutically acceptable solvents such as water, ethanol, and the like. The present invention contemplates and encompasses both the solvated and unsolvated forms.

The compounds of the present invention can be administered to a patient either alone or a part of a pharmaceutical composition in a therapeutically effective amount. A variety of non-limiting methods for administering the compounds and related compositions to patients include orally, rectally, parenterally (intravenously, intramuscularly, or subcutaneously), intracisternally, intravaginally, intraperitoneally, intravesically, locally (powders, ointments, or drops), or as a buccal or nasal spray. In addition, the substance or compositions containing the active substances can be administered all at once, as for example, by a bolus injection, multiple times, such as by a series of tablets, or delivered substantially uniformly over a period of time, as for example, using transdermal delivery. It is also noted that the dose of the substances can be varied over time.

The compounds and related compositions of the present invention can be administered alone, or in combination with other pharmaceutically active substances. The other pharmaceutically active substances can be intended to treat the same disease or condition as the substances of the present invention or a different disease or condition. If the patient is to receive, or is receiving multiple pharmaceutically active substances, the substances can be administered simultaneously, or sequentially. For example, in the case of tablets, the active substances may be found in one tablet or in separate tablets, which can be administered at once or sequentially in any order. In addition, it should be recognized that the compositions may be different forms. For example, one or more substance may be delivered via a tablet, while another is administered via injection or orally as a syrup. All combinations, delivery methods and administration sequences are contemplated.

Pharmaceutical compositions to be used comprise a therapeutically effective amount of a compound as described above, or a pharmaceutically acceptable salt or other form thereof together with one or more pharmaceutically acceptable excipients. The phrase "pharmaceutical composition" refers to a composition suitable for administration in medical or veterinary use. It should be appreciated that the determinations of proper dosage forms, dosage amounts, and routes of administration for a particular patient are within the level of ordinary skill in the pharmaceutical and medical arts.

Compositions suitable for parenteral administration conveniently comprise a sterile aqueous preparation of a compound or composition of the invention, which is preferably isotonic with the blood of the recipient. This aqueous preparation may be formulated according to known methods using suitable dispersing or wetting agents, emulsifying and suspending agents. Various antibacterial and antifungal agents, for example, parabens, chlorobutanol, phenol, and sorbic acid also may be included. The sterile injectable preparation also may be a sterile injectable solution or suspension in a non-toxic parenterally-acceptable diluent or solvent, for example, as a solution in 1,3-butane diol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or di-glycerides. In addition, fatty acids such as oleic acid may be used in the preparation of injectables. Prolonged absorption of the injectable pharmaceutical form can be brought about by the use of agents delaying absorption, for example, aluminum monostearate and gelatin. Carrier formulation suitable for subcutaneous, intravenous, intramuscular, etc. administrations can be found in Remington's Pharmaceutical Sciences, Mack Publishing Co., Easton, Pa. which is incorporated herein in its entirety by reference thereto.

Solid dosage forms for oral administration include capsules, tablets, pills, powders, and granules. In such solid dosage forms, the compound is admixed with at least one inert pharmaceutically acceptable excipient such as (a) fillers or extenders, as for example, starches, lactose, sucrose, glucose, mannitol, and silicic acid, (b) binders, as for example, carboxymethylcellulose, alignates, gelatin, polyvinylpyrrolidone, sucrose, and acacia, (c) humectants, as for example, glycerol, (d) disintegrating agents, as for example, agar-agar, calcium carbonate, potato or tapioca starch, alginic acid, certain complex silicates, and sodium carbonate, (e) solution retarders, as for example paraffin, (f) absorption accelerators, as for example, quaternary ammonium compounds, (g) wetting agents, as for example, cetyl alcohol, and glycerol monostearate, (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents. Solid dosage forms such as tablets, dragees, capsules, pills, and granules also can be prepared with coatings and shells, such as enteric coatings and others well known in the art. The solid dosage form also may contain opacifying agents, and can also be of such composition that they release the active compound or compounds in a certain part of the intestinal tract in a delayed manner. Examples of embedding compositions which can be used are polymeric substances and waxes. The active compounds can also be in micro-encapsulated form, if appropriate, with one or more of the above-mentioned excipients. Such solid dosage forms may generally contain from 1% to 95% (w/w) of the active compound. In certain embodiments, the active compound ranges from 5% to 70% (w/w).

Since one aspect of the present invention contemplates the treatment of the disease/conditions with a combination of pharmaceutically active agents that may be administered separately, the invention further relates to combining separate pharmaceutical compositions in kit form. The kit comprises two separate pharmaceutical compositions: a substance of the present invention, and a second pharmaceutical substance. The kit comprises a container for containing the separate compositions such as a divided bottle or a divided foil packet. Additional examples of containers include syringes, boxes and bags. Typically, the kit comprises directions for the use of the separate components. The kit form is particularly advantageous when the separate components are preferably administered in different dosage forms (e.g., oral and parenteral), are administered at different dosage intervals, or when titration of the individual components of the combination is desired by the prescribing physician or veterinarian.

An example of such a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process recesses are formed in the plastic foil. The recesses have the size and shape of the tablets or capsules to be packed. Next, the tablets or capsules are placed in the recesses and the sheet of relatively stiff material is sealed against the plastic foil at the face of the foil which is opposite from the direction in which the recesses were formed. As a result, the tablets or capsules are sealed in the recesses between the plastic foil and the sheet. Preferably the strength of the sheet is such that the tablets or capsules can be removed from the blister pack by manually applying pressure on the recesses whereby an opening is formed in the sheet at the place of the recess. The tablet or capsule can then be removed via said opening.

It may be desirable to provide a memory aid on the kit, e.g., in the form of numbers next to the tablets or capsules whereby the numbers correspond with the days of the regimen which the tablets or capsules so specified should be ingested. Another example of such a memory aid is a calendar printed on the card, e.g., as follows "First Week, Monday, Tuesday, . . . etc. . . . Second Week, Monday, Tuesday, . . . " etc. Other variations of memory aids will be readily apparent. A "daily dose" can be a single tablet or capsule or several pills or capsules to be taken on a given day. Also, a daily dose of a substance of the present invention can consist of one tablet or capsule, while a daily dose of the second substance can consist of several tablets or capsules and vice versa. The memory aid should reflect this and aid in correct administration of the active agents.

In another specific embodiment of the invention, a dispenser designed to dispense the daily doses one at a time in the order of their intended use is provided. Preferably, the dispenser is equipped with a memory-aid, so as to further facilitate compliance with the regimen. An example of such a memory-aid is a mechanical counter which indicates the number of daily doses that has been dispensed. Another example of such a memory-aid is a battery-powered microchip memory coupled with a liquid crystal readout, or audible reminder signal which, for example, reads out the date that the last daily dose has been taken and/or reminds one when the next dose is to be taken.

Liquid dosage forms for oral administration include pharmaceutically acceptable emulsions, solutions, suspensions, syrups, and elixirs. In addition to the compound or composition, the liquid dosage forms may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide, oils, in particular, cottonseed oil, groundnut oil, corn germ oil, olive oil, castor oil and sesame oil, glycerol, tetrahydrofurfuryl alcohol, polyethyleneglycols and fatty acid esters of sorbitan or mixtures of these substances. Besides such inert diluents, the composition can also include adjuvants, such as wetting agents, emulsifying and suspending agents, sweetening, flavoring, and perfuming agents.

Compositions for rectal administrations are preferably suppositories which can be prepared by mixing compounds of the present invention with suitable non-irritating excipients or carriers such as cocoa butter, polyethyleneglycol or a low-melting, suppository wax, which are solid at ordinary temperatures but liquid at body temperature and therefore, melt in the rectum or vaginal cavity and release the active compound.

Dosage forms for topical administration of a compound of this invention include ointments, powders, sprays, and inhalants. The active compound is admixed under sterile conditions with a physiologically acceptable carrier and any preservatives, buffers, or propellants as may be required. Ophthalmic formulations, eye ointments, powders, and solutions are also contemplated as being within the scope of this invention.

The compounds and compositions of the present invention also may benefit from a variety of delivery systems, including time-released, delayed release or sustained release delivery systems. Such option may be particularly beneficial when the compounds and composition are used in conjunction with other treatment protocals as described in more detail below.

Many types of release delivery systems are available and known to those of ordinary skill in the art. They include polymer base systems such as poly(lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109. Delivery systems also include non-polymer systems that are: lipids including sterols such as cholesterol, cholesterol esters and fatty acids or neutral fats such as mono-di- and tri-glycerides; hydrogel release systems; sylastic systems; peptide based systems; wax coatings; compressed tablets using conventional binders and excipients; partially fused implants; and the like. Specific examples include, but are not limited to: (a) erosional systems in which the active compound is contained in a form within a matrix such as those described in U.S. Pat. Nos. 4,452,775, 4,667,014, 4,748,034 and 5,239,660 and (b) diffusional systems in which an active component permeates at a controlled rate from a polymer such as described in U.S. Pat. Nos. 3,832,253, and 3,854,480. In addition, pump-based hardware delivery systems can be used, some of which are adapted for implantation.

Use of a long-term sustained release implant may be desirable. Long-term release, as used herein, means that the implant is constructed and arranged to deliver therapeutic levels of the active compound for at least 30 days, and preferably 60 days. Long-term sustained release implants are well-known to those of ordinary skill in the art and include some of the release systems described above.

In practicing the methods of the present invention, the compounds and compositions of the present invention are administered in a therapeutically effective amount. Generally, doses of active compounds would be from about 0.01 mg/kg per day to 1000 mg/kg per day. It is expected that doses ranging from 50-500 mg/kg will be suitable, preferably intravenously, intramuscularly, or intradermally, and in one or several administrations per day. The compounds of the present invention may also be used in combination with radiation therapy, hormone therapy, surgery and immunotherapy, which therapies are well know to those skilled in the art.

When practicing the conjoint or combination therapy described in more detail below, the administration of the compounds and compositions of the present invention can occur simultaneous with, subsequent to, or prior to chemotherapy or radiation, so long as the chemotherapeutic agent or radiation sensitizes the system to the compounds and compositions of the present invention.

In general, routine experimentation in clinical trials will determine specific ranges for optimal therapeutic effect for a particular compound and composition of the present invention and each administrative protocol, and administration to specific patients will be adjusted to within effective and safe ranges depending on the patient condition and responsiveness to initial administrations. However, the ultimate administration protocol will be regulated according to the judgment of the attending clinician considering such factors as age, condition and size of the patient, the potency of the compound or composition, the duration of the treatment and the severity of the disease being treated. For example, a dosage regimen of the compound or composition can be an oral administration of from 1 mg to 2000 mg/day, preferably 1 to 1000 mg/day, more preferably 50 to 600 mg/day, in two to four (preferably two) divided doses, to reduce tumor growth. Intermittent therapy (e.g., one week out of three weeks or three out of four weeks) may also be used.

In the event that a response in a subject is insufficient at the initial doses applied, higher doses (or effectively higher doses by a different, more localized delivery route) may be employed to the extent that the patient tolerance permits. Multiple doses per day are contemplated to achieve appropriate systemic levels of compounds. Generally, a maximum dose is used, that is, the highest safe dose according to sound medical judgment. Those of ordinary skill in the art will understand, however, that a patient may insist upon a lower dose or tolerable dose for medical reasons, psychological reasons or for virtually any other reason.

The compounds of the present invention and pharmaceutical compositions comprising a compound of the present invention can be administered to a subject suffering from cancer, an autoimmune disease or another disorder where a defect in apoptosis is implicated. In connection with such treatments, the patient can be treated prophylactically, acutely, or chronically using compounds and compositions of the present invention, depending on the nature of the disease. Typically, the host or subject in each of these methods is human, although other mammals may also benefit from the administration of a compound of the present invention.

As described in U.S. Pat. No. 7,244,851, the disclosure of which is incorporated herein by reference, IAP antagonists can be used for the treatment of all cancer types which fail to undergo apoptosis. Thus, compounds of the present invention can be used to provide a therapeutic approach to the treatment of many kinds of solid tumors, including but not limited to carcinomas, sarcomas including Kaposi's sarcoma, erythroblastoma, glioblastoma, meningioma, astrocytoma, melanoma and myoblastoma. Treatment or prevention of non-solid tumor cancers such as leukemia is also contemplated by this invention. Indications may include, but are not limited to brain cancers, skin cancers, bladder cancers, ovarian cancers, breast cancers, gastric cancers, pancreatic cancers, colon cancers, blood cancers, lung cancers and bone cancers. Examples of such cancer types include neuroblastoma, intestine carcinoma such as rectum carcinoma, colon carcinoma, familiary adenomatous polyposis carcinoma and hereditary non-polyposis colorectal cancer, esophageal carcinoma, labial carcinoma, larynx carcinoma, hypopharynx carcinoma, tong carcinoma, salivary gland carcinoma, gastric carcinoma, adenocarcinoma, medullary thyroidea carcinoma, papillary thyroidea carcinoma, renal carcinoma, kidney parenchym carcinoma, ovarian carcinoma, cervix carcinoma, uterine corpus carcinoma, endometrium carcinoma, chorion carcinoma, pancreatic carcinoma, prostate carcinoma, testis carcinoma, breast carcinoma, urinary carcinoma, melanoma, brain tumors such as glioblastoma, astrocytoma, meningioma, medulloblastoma and peripheral neuroectodermal tumors, Hodgkin lymphoma, non-Hodgkin lymphoma, Burkitt lymphoma, acute lymphatic leukemia (ALL), chronic lymphatic leukemia (CLL), acute myeloid leukemia (AML), chronic myeloid leukemia (CML), adult T-cell leukemia lymphoma, hepatocellular carcinoma, gall bladder carcinoma, bronchial carcinoma, small cell lung carcinoma, non-small cell lung carcinoma, multiple myeloma, basalioma, teratoma, retinoblastoma, choroidea melanoma, seminoma, rhabdomyo sarcoma, craniopharyngeoma, osteosarcoma, chondrosarcoma, myosarcoma, liposarcoma, fibrosarcoma, Ewing sarcoma and plasmocytoma.

The inventors believe that the IAP antagonists of the present invention will be particularly active for treating human malignancies where cIAP1 and cIAP2 are over-expressed (e.g., lung cancers, see Dai et al, Hu. Molec. Genetics, 2003 v 12 pp 791-801; leukemias (multiple references), and other cancers (Tamm et al, Clin Cancer Res, 2000, v 6, 1796-1803). The inventors also expect that the IAP antagonists of the present invention will be active in disorders that may be driven by inflammatory cytokines such as TNF playing a pro-survival role (for example, there is a well defined role for TNF acting as a survival factor in ovarian carcinoma, similarly for gastric cancers (see Kulbe, et al, Cancer Res 2007, 67, 585-592).

In addition to apoptosis defects found in tumors, defects in the ability to eliminate self-reactive cells of the immune system due to apoptosis resistance are considered to play a key role in the pathogenesis of autoimmune diseases. Autoimmune diseases are characterized in that the cells of the immune system produce antibodies against its own organs and molecules or directly attack tissues resulting in the destruction of the latter. A failure of those self-reactive cells to undergo apoptosis leads to the manifestation of the disease. Defects in apoptosis regulation have been identified in autoimmune diseases such as systemic lupus erthematosus or rheumatoid arthritis.

Examples of such autoimmune diseases include collagen diseases such as rheumatoid arthritis, systemic lupus erythematosus, Sharp's syndrome, CREST syndrome (calcinosis, Raynaud's syndrome, esophageal dysmotility, telangiectasia), dermatomyositis, vasculitis (Morbus Wegener's) and Sjögren's syndrome, renal diseases such as Goodpasture's syndrome, rapidly-progressing glomerulonephritis and membrano-proliferative glomerulonephritis type II, endocrine diseases such as type-I diabetes, autoimmune polyendocrinopathy-candidiasis-ectodermal dystrophy (APECED), autoimmune parathyroidism, pernicious anemia, gonad insufficiency, idiopathic Morbus Addison's, hyperthyreosis, Hashimoto's thyroiditis and primary myxedema, skin diseases such as pemphigus vulgaris, bullous pemphigoid, herpes gestationis, epidermolysis bullosa and erythema multiforme major, liver diseases such as primary biliary cirrhosis, autoimmune cholangitis, autoimmune hepatitis type-1, autoimmune hepatitis type-2, primary sclerosing cholangitis, neuronal diseases such as multiple sclerosis, myasthenia gravis, myasthenic Lambert-Eaton syndrome, acquired neuromyotony, Guillain-Barré syndrome (Müller-Fischer syndrome), stiff-man syndrome, cerebellar degeneration, ataxia, opsoklonus, sensoric neuropathy and achalasia, blood diseases such as autoimmune hemolytic anemia, idiopathic thrombocytopenic purpura (Morbus Werlhof), infectious diseases with associated autoimmune reactions such as AIDS, Malaria and Chagas disease.

The present invention also is directed to the use of the compounds and compositions as a chemopotentiating agent with other treatment approaches. The term "chemopotentiating agent" refers to an agent that acts to increase the sensitivity of an organism, tissue, or cell to a chemical compound, or treatment namely "chemotherapeutic agents" or "chemo drugs" or to radiation treatment. Thus, compounds and compositions of the present invention can be used for inhibiting tumor growth in vivo by administering them in combination with a biologic or chemotherapeutic agent or by using them in combination with chemoradiation. In these applications, the administration of the compounds and compositions of the present invention may occur prior to, and with sufficient time, to cause sensitization of the site to be treated. Alternatively, the compounds and compositions of the present invention may be used contemporaneously with radiation and/or additional anti-cancer chemical agents (infra). Such systems can avoid repeated administrations of the compounds and compositions of the present invention, increasing convenience to the subject and the physician, and may be particularly suitable for certain compositions of the present invention.

Biological and chemotherapeutics/anti-neoplastic agents and radiation induce apoptosis by activating the extrinsic or intrinsic apoptotic pathways, and, since the compounds and compositions of the present invention relieve antagonists of apoptotic proteins (IAPs) and, thus, remove the block in apoptosis, the combination of chemotherapeutics/anti-neoplastic agents and radiation with the compounds and compositions of the present invention should work synergistically to facilitate apoptosis.

A combination of a compound of the present invention and a chemotherapeutic/anti neoplastic agent and/or radiation therapy of any type that activates the intrinsic pathway may provide a more effective approach to destroying tumor cells. Compounds of the present invention interact with IAP's, such as XIAP, cIAP-1, cIAP-2, ML-IAP, etc., and block the IAP mediated inhibition of apoptosis while chemotherapeutics/anti neoplastic agents and/or radiation therapy kills actively dividing cells by activating the intrinsic apoptotic pathway leading to apoptosis and cell death. As is described in more detail below, embodiments of the invention provide combinations of a compound of the present invention and a chemotherapeutic/anti-neoplastic agent and/or radiation which provide a synergistic action against unwanted cell proliferation. This synergistic action between a compound of the present invention and a chemotherapeutic/anti-neoplastic agent and/or radiation therapy can improve the efficiency of the chemotherapeutic/anti-neoplastic agent and/or radiation therapies. This will allow for an increase in the effectiveness of current chemotherapeutic/anti-neoplastic agents or radiation treatments allowing the dose of the chemotherapeutic/anti-neoplastic agent to be lowered, therein providing both a more effective dosing schedule as well as use of a more tolerable dose of chemotherapeutic/anti-neoplastic agent and/or radiation.

In an embodiment of the present invention, the patient is treated by administering a compound or a pharmaceutical composition of the present invention at a time the patient is subject to concurrent or antecedent radiation or chemotherapy for treatment of a neoproliferative pathology of a tumor such as, but not limited to, bladder cancer, breast cancer, prostate cancer, lung cancer, pancreatic cancer, gastric cancer, colon cancer, ovarian cancer, renal cancer, hepatoma, melanoma, lymphoma, sarcoma, and combinations thereof.

In another embodiment of the present invention, the compound or composition of the present invention can be administered in combination with a chemotherapeutic and/or for use in combination with radiotherapy, immunotherapy, and/or photodynamic therapy, promoting apoptosis and enhance ing the effectiveness of the chemotherapeutic, radiotherapy, immunotherapy, and/or photodynamic therapy.

Embodiments of the invention also include a method of treating a patient afflicted with cancer by the contemporaneous or concurrent administration of a chemotherapeutic agent. Such chemotherapeutic agents include but are not limited to the chemotherapeutic agents described in "Modern Pharmacology with Clinical Applications", Sixth Edition, Craig & Stitzel, Chpt. 56, pg 639-656 (2004), herein incorporated by reference. The chemotherapeutic agent can be, but is not limited to, alkylating agents, antimetabolites, anti-tumor antibiotics, plant-derived products such as taxanes, enzymes, hormonal agents, miscellaneous agents such as cisplatin, monoclonal antibodies, glucocorticoids, mitotic inhibitors, topoisomerase I inhibitors, topoisomerase II inhibitors, immunomodulating agents such as interferons, cellular growth factors, cytokines, and nonsteroidal anti-inflammatory compounds, cellular growth factors and kinase inhibitors. Other suitable classifications for chemotherapeutic agents include mitotic inhibitors and nonsteroidal anti-estrogenic analogs.

Specific examples of suitable biological and chemotherapeutic agents include, but are not limited to, cisplatin, carmustine (BCNU), 5-fluorouracil (5-FU), cytarabine (Ara-C), gemcitabine, methotrexate, daunorubicin, doxorubicin, dexamethasone, topotecan, etoposide, paclitaxel, vincristine, tamoxifen, TNF-alpha, TRAIL, interferon (in both its alpha and beta forms), thalidomide, and melphalan. Other specific examples of suitable chemotherapeutic agents include nitrogen mustards such as cyclophosphamide, alkyl sulfonates, nitrosoureas, ethylenimines, triazenes, folate antagonists, purine analogs, pyrimidine analogs, anthracyclines, bleomycins, mitomycins, dactinomycins, plicamycin, vinca alkaloids, epipodophyllotoxins, taxanes, glucocorticoids, L-asparaginase, estrogens, androgens, progestins, luteinizing hormones, octreotide actetate, hydroxyurea, procarbazine, mitotane, hexamethylmelamine, carboplatin, mitoxantrone, monoclonal antibodies, levamisole, interferons, interleukins, filgrastim and sargramostim. Chemotherapeutic compositions also comprise other members, i.e., other than TRAIL, of the TNF superfamily of compounds.

Another embodiment of the present invention relates to the use of a compound or composition of the present invention in combination with topoismerase inhibitors to potentiate their apoptotic inducing effect. Topoisomerase inhibitors inhibit DNA replication and repair, thereby promoting apoptosis and have been used as chemothemotherapeutic agents. Topoisomerase inhibitors promote DNA damage by inhibiting the enzymes that are required in the DNA repair process. Therefore, export of Smac from the mitochondria into the cell cytosol is provoked by the DNA damage caused by topoisomerase inhibitors. Topoisomerase inhibitors of both the Type I class (camptothecin, topotecan, SN-38 (irinotecan active metabolite)) and the Type II class (etoposide) are expected to show potent synergy with compounds of the present invention. Further examples of topoisomerase inhibiting agents that may be used include, but are not limited to, irinotecan, topotecan, etoposide, amsacrine, exatecan, gimatecan, etc. Other topoisomerase inhibitors include, for example, Aclacinomycin A, camptothecin, daunorubicin, doxorubicin, ellipticine, epirubicin, and mitaxantrone.

In another embodiment of the invention, the chemotherapeutic/anti-neoplastic agent for use in combination with the compounds and compositions of the present invention may be a platinum containing compound. In one embodiment of the invention, the platinum containing compound is cisplatin. Cisplatin can synergize with a compound of the present invention and potentiate the inhibition of an IAP, such as but not limited to XIAP, cIAP-1, c-IAP-2, ML-IAP, etc. In another embodiment a platinum containing compound is carboplatin. Carboplatin can synergize with a compound of the present invention and potentiate the inhibition of an IAP, including, but not limited to, XIAP, cIAP-1, c-IAP-2, ML-IAP, etc. In another embodiment a platinum containing compound is oxaliplatin. The oxaliplatin can synergize with a compound of the present invention and potentiate the inhibition of an IAP, including, but not limited to, XIAP, cIAP-1, c-IAP-2, ML-IAP, etc.

Platinum chemotherapy drugs belong to a general group of DNA modifying agents. DNA modifying agents may be any highly reactive chemical compound that bonds with various nucleophilic groups in nucleic acids and proteins and cause mutagenic, carcinogenic, or cytotoxic effects. DNA modifying agents work by different mechanisms, disruption of DNA function and cell death; DNA damage/the formation of crossbridges or bonds between atoms in the DNA; and induction of mispairing of the nucleotides leading to mutations, to achieve the same end result. Three non-limiting examples of a platinum containing DNA modifying agents are cisplatin, carboplatin and oxaliplatin.

Cisplatin is believed to kill cancer cells by binding to DNA and interfering with its repair mechanism, eventually leading to cell death. Carboplatin and oxaliplatin are cisplatin derivatives that share the same mechanism of action. Highly reactive platinum complexes are formed intracellularly and inhibit DNA synthesis by covalently binding DNA molecules to form intrastrand and interstrand DNA crosslinks.

Non-steroidal anti-inflammatory drugs (NSAIDs) have been shown to induce apoptosis in colorectal cells. NSAIDs appear to induce apoptosis via the release of Smac from the mitochondria (PNAS, Nov. 30, 2004, vol. 101:16897-16902). Therefore, the use of NSAIDs in combination with the compounds and compositions of the present invention would be expected to increase the activity of each drug over the activity of either drug independently.

Many naturally occurring compounds isolated from bacterial, plant, and animals can display potent and selective biological activity in humans including anticancer and antineoplastic activities. In fact, many natural products, or semisynthetic derivatives thereof, which possess anticancer activity, are already commonly used as therapeutic agents; these include paclitaxel, etoposide, vincristine, and camptothecin amongst others. Additionally, there are many other classes of natural products such as the indolocarbazoles and epothilones that are undergoing clinical evaluation as anticancer agents. A reoccurring structural motif in many natural products is the attachment of one or more sugar residues onto an aglycone core structure. In some instances, the sugar portion of the natural product is critical for making discrete protein-ligand interactions at its site of action (i.e., pharmacodynamics) and removal of the sugar residue results in significant reductions in biological activity. In other cases, the sugar moiety or moieties are important for modulating the physical and pharmacokinetic properties of the molecule. Rebeccamycin and staurosporine are representative of the sugar-linked indolocarbazole family of anticancer natural products with demonstrated anti-kinase and anti-topoisomerase activity.

Taxanes are anti-mitotic, mitotic inhibitors or microtubule polymerization agents. Taxanes are characterized as compounds that promote assembly of microtubules by inhibiting tubulin depolymerization, thereby blocking cell cycle progression through centrosomal impairment, induction of abnormal spindles and suppression of spindle microtubule dynamics. Taxanes include but are not limited to, docetaxel and paclitaxel. The unique mechanism of action of taxane is in contrast to other microtubule poisons, such as Vinca alkaloids, colchicine, and cryptophycines, which inhibit tubulin polymerization. Microtubules are highly dynamic cellular polymers made of alpha-beta-tubulin and associated proteins that play key roles during mitosis by participating in the organization and function of the spindle, assuring the integrity of the segregated DNA. Therefore, they represent an effective target for cancer therapy.

Yet another embodiment of the present invention is the therapeutic combination or the therapeutic use in combination of a compound or composition of the present invention with TRAIL or other chemical or biological agents which bind to and activate the TRAIL receptor(s). TRAIL has received considerable attention recently because of the finding that many cancer cell types are sensitive to TRAIL-induced apoptosis, while most normal cells appear to be resistant to this action of TRAIL. TRAIL-resistant cells may arise by a variety of different mechanisms including loss of the receptor, presence of decoy receptors, or overexpression of FLIP which competes for zymogen caspase-8 binding during DISC formation. In TRAIL resistance, a compound or composition of the present invention may increase tumor cell sensitivity to TRAIL leading to enhanced cell death, the clinical correlations of which are expected to be increased apoptotic activity in TRAIL resistant tumors, improved clinical response, increased response duration, and ultimately, enhanced patient survival rate. In support of this, reduction in XIAP levels by in vitro antisense treatment has been shown to cause sensitization of resistant melanoma cells and renal carcinoma cells to TRAIL (Chawla-Sarkar, et al., 2004). The compounds of the present invention bind to IAPs and inhibit their interaction with caspases, therein potentiating TRAIL-induced apoptosis.

Compounds and compositions of the present invention also can be used to augment radiation therapy (or radiotherapy), i.e., the medical use of ionizing radiation as part of cancer treatment to control malignant cells. Although radiotherapy is often used as part of curative therapy, it is occasionally used as a palliative treatment, where cure is not possible and the aim is for symptomatic relief. Radiotherapy is commonly used for the treatment of tumors. It may be used as the primary therapy. It is also common to combine radiotherapy with surgery and/or chemotherapy. The most common tumors treated with radiotherapy are breast cancer, prostate cancer, rectal cancer, head & neck cancers, gynecological tumors, bladder cancer and lymphoma. Radiation therapy is commonly applied just to the localized area involved with the tumor. Often the radiation fields also include the draining lymph nodes. It is possible but uncommon to give radiotherapy to the whole body, or entire skin surface. Radiation therapy is usually given daily for up to 35-38 fractions (a daily dose is a fraction). These small frequent doses allow healthy cells time to grow back, repairing damage inflicted by the radiation. Three main divisions of radiotherapy are external beam radiotherapy or teletherapy, brachytherapy or sealed source radiotherapy and unsealed source radiotherapy, which are all suitable examples of treatment protocol in the present invention. The differences relate to the position of the radiation source; external is outside the body, while sealed and unsealed source radiotherapy has radioactive material delivered internally. Brachytherapy sealed sources are usually extracted later, while unsealed sources are injected into the body.

Administration of the compounds and compositions of the present invention may occur prior to, concurrently with, or subsequent to the combination treatment protocol. A variety of administration routes are available. The particular mode selected will depend, of course, upon the particular chemotherapeutic drug selected, the severity of the condition being treated and the dosage required for therapeutic efficacy. The methods of the invention, generally speaking, may be practiced using any mode of administration that is medically acceptable, meaning any mode that produces effective levels of the active compounds without causing clinically unacceptable adverse effects. Such modes of administration include, but are not limited to, oral, rectal, topical, nasal, intradermal, inhalation, intra-peritoneal, or parenteral routes. The term "parenteral" includes subcutaneous, intravenous, intramuscular, or infusion. Intravenous or intramuscular routes are particularly suitable for purposes of the present invention.

It is understood that the examples and embodiments described herein are for illustrative purposes only and that various modifications or changes in light thereof will be suggested to persons skilled in the art and are to be included within the spirit and purview of this application and the scope of the appended claims.

What is claimed is:
1. A compound of Formula (I):

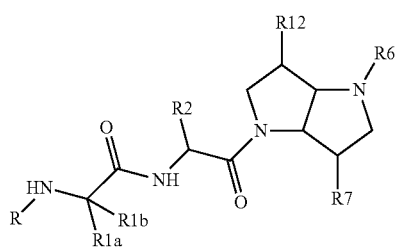

(I)

or a pharmaceutically acceptable salt thereof, wherein:
R is selected from H, alkyl, substituted alkyl, alkenyl, substituted alkenyl, cycloalkyl, substituted cycloalkyl, aryl, substituted aryl, heteroaryl, or substituted heteroaryl;
R1a and R1b are each independently selected from H, alkyl, or substituted alkyl;
R2 is selected from H, alkyl, substituted alkyl, cycloalkyl, heterocycloalkyl, aryl, or heteroaryl;
R6 is selected from H, alkyl, substituted alkyl, alkylsulfonyl, arylsulfonyl, cycloalkyl, substituted cycloalkyl, heterocycloalkyl, substituted heterocycloalkyl, aryl, substituted aryl, heteroaryl, or substituted heteroaryl; or R6 has the following formula (IA):

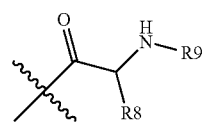

(IA)

where R8 is selected from H, alkyl, substituted alkyl, cycloalkyl, heterocycloalkyl, aryl, or heteroaryl;
and R9 is selected from H, alkyl, substituted alkyl, cycloalkyl, substituted cycloalkyl, aryl, substituted aryl, heterocycloalkyl, substituted heterocycloalkyl, heteroaryl, or substituted heteroaryl; or R9 has the following formula (IB):

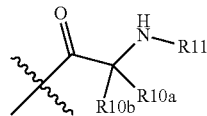

(IB)

where R10a and R10b are independently selected from H, alkyl, or substituted alkyl;
and R11 is selected from H, alkyl, substituted alkyl, alkenyl, substituted alkenyl, cycloalkyl, substituted cycloalkyl, aryl, substituted aryl, heteroaryl, or substituted heteroaryl;
R7 is selected from H, or a 3-indolyl of the formula (IC):

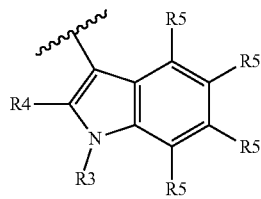

(IC)

where R3 is selected from H, alkyl, or substituted alkyl;
R4 is selected from H, halogen, alkyl, or substituted alkyl; and
each R5 is independently selected from H, halogen, alkyl, or substituted alkyl; and
R12 is selected from H or hydroxy.

2. A compound of claim 1, or a pharmaceutically acceptable salt thereof, wherein:
R is selected from H, alkyl, substituted alkyl, alkenyl, substituted alkenyl, aryl, substituted aryl, cycloalkyl, substituted cycloalkyl, heteroaryl, or substituted heteroaryl; wherein the substitutents are selected from the group consisting of halogen, hydroxy, oxo, mercapto, carboxyl, alkyl, cycloalkyl, aryl, alkoxy, amino, heteroaryl, and nitro;
R1a and R1b are each independently selected from H, alkyl, or substituted alkyl, wherein the substitutents are selected from the group consisting of halogen, hydroxy, oxo, mercapto, carboxyl, cycloalkyl, aryl, alkoxy, amino, heteroaryl, and nitro;
R2 is alkyl, cycloalkyl, aryl, heterocycloalkyl, heteroaryl, or substituted alkyl, wherein the substituents are selected from the group consisting of halogen, hydroxy, oxo, alkoxy, cycloalkyl, aryl, heterocycloalkyl and heteroaryl;
R6 is selected from H; alkylsulfonyl; arylsulfonyl; alkyl; substituted alkyl, wherein the substituents are selected from the group consisting of halogen, hydroxy, oxo, mercapto, carboxyl, alkoxy, amino, nitro, cycloalkyl, aryl, heteroaryl optionally substituted with lower alkyl or halogen, alkylsulfonyl and arylsulfonyl; cycloalkyl; substituted cycloalkyl, wherein the substituents are selected from the group consisting of halogen, hydroxy, oxo, mercapto, carboxyl, alkyl, cycloalkyl, aryl, alkoxy, amino, heteroaryl, and nitro; aryl; substituted aryl, wherein the substituents are selected from the group consisting of alkyl, halogen, hydroxy, mercapto, carboxyl, cycloalkyl, aryl, alkoxy, amino, heteroaryl, nitro, alkylsulfonyl and arylsulfonyl; heterocycloalkyl; substituted heterocycloalkyl, wherein the substituents are selected from the group consisting of halogen, hydroxy, oxo, mercapto, carboxyl, alkyl, cycloalkyl, aryl, alkoxy, amino, heteroaryl, and nitro; heteroaryl; or substituted heteroaryl, wherein the substituents are selected from the group consisting of halogen, hydroxy, mercapto, carboxyl, alkyl, cycloalkyl, aryl, alkoxy, amino, heteroaryl, and nitro; or R6 has the following formula (IA):

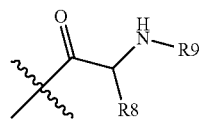
(IA)

where R8 is alkyl, cycloalkyl, aryl, heterocycloalkyl, heteroaryl, or substituted alkyl, wherein the substituents are selected from the group consisting of halogen, hydroxy, oxo, alkoxy, cycloalkyl, aryl, heterocycloalkyl and heteroaryl and R9 is selected from H, alkyl, substituted alkyl, aryl, substituted aryl, cycloalkyl, substituted cycloalkyl, heteroaryl, or substituted heteroaryl; wherein the substitutents are selected from the group consisting of halogen, hydroxy, oxo, mercapto, carboxyl, alkyl, cycloalkyl, aryl, alkoxy, amino, heteroaryl, and nitro; or, R9 has the following formula (IB):

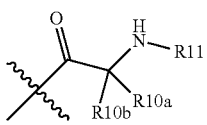
(IB)

where R10a and R10b are independently selected from H, alkyl, or substituted alkyl, wherein the substitutents are selected from the group consisting of halogen, hydroxy, oxo, mercapto, carboxyl, alkyl, cycloalkyl, aryl, alkoxy, amino, heteroaryl, and nitro; and R11 is selected from H, alkyl, substituted alkyl, aryl, substituted aryl, cycloalkyl, substituted cycloalkyl, heteroaryl, or substituted heteroaryl; wherein the substitutents are selected from the group consisting of halogen, hydroxy, oxo, mercapto, carboxyl, alkyl, cycloalkyl, aryl, alkoxy, amino, heteroaryl, and nitro;

R7 is selected from H, or a 3-indolyl of the formula (IC):

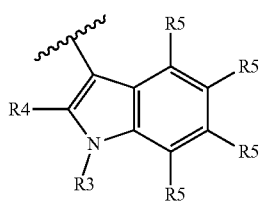
(IC)

where R3 is selected from H, alkyl, or substituted alkyl, where the substituents are selected from the group consisting of halogen, hydroxy, mercapto, carboxyl, alkyl, cycloalkyl, aryl, alkoxy, amino, heteroaryl, and nitro;

R4 is selected from H, halogen, alkyl, or substituted alkyl, where the substituents are selected from the group consisting of halogen, hydroxy, mercapto, carboxyl, alkyl, cycloalkyl, aryl, alkoxy, amino, heteroaryl, and nitro; and each R5 is independently selected from H, halogen, alkyl, or substituted alkyl, where the substituents are selected from the group consisting of halogen, hydroxy, mercapto, carboxyl, alkyl, cycloalkyl, aryl, alkoxy, amino, heteroaryl, and nitro; and R12 is selected from H or hydroxy.

3. A compound of claim 2, or a pharmaceutically acceptable salt thereof, wherein:

R is selected from H, alkyl, substituted alkyl, alkenyl, or substituted alkenyl; wherein the substitutents are selected from the group consisting of halogen, hydroxy, oxo, mercapto, carboxyl, alkyl, cyclopropyl, alkoxy, amino, and nitro; and R1a and R1b are each independently selected from H, alkyl, or substituted alkyl, wherein the substitutents are selected from the group consisting of halogen, hydroxy, oxo, mercapto, carboxyl, alkyl, cyclopropyl, alkoxy, amino, and nitro.

4. A compound of claim 2, or a pharmaceutically acceptable salt thereof, wherein:

R is selected from H, or lower alkyl;

R1a and R1b are each independently selected from H, or lower alkyl;

R2 is selected from H; lower alkyl; cycloalkyl, or substituted lower alkyl wherein the substituents are selected from the group consisting of hydroxy, and alkoxy;

R6 is selected from H; lower alkylsulfonyl; alkyl; substituted alkyl, wherein the alkyl substituents are selected from the group consisting of hydroxy, oxo, halogen, alkoxy, cycloalkyl, aryl, and heteroaryl optionally substituted with lower alkyl or halogen; cycloalkyl; or heteroaryl optionally substituted with lower alkyl or halogen; or R6 has the following formula (IA):

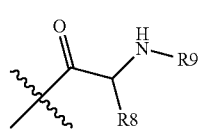
(IA)

wherein R8 is selected from H, lower alkyl, cycloalkyl, or substituted lower alkyl wherein the substituents are selected from the group consisting of hydroxy, and alkoxy; and R9 is selected from H, or lower alkyl; or R9 has the following formula (IB):

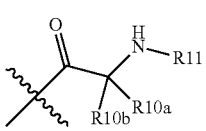
(IB)

where R10a and R10b are independently selected from H, or lower alkyl;

and R11 is selected from H, or lower alkyl;

R7 is selected from H, or a 3-indolyl of the formula (IC):

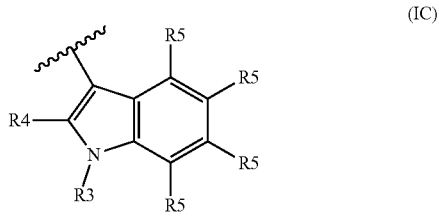
(IC)

where R3 is selected from H, or aralkyl;
R4 is selected from H, or halogen; and
each R5 is independently selected from H, or halogen; and
R12 is H, or hydroxy.

5. A compound of claim 1 having the structure of formula (I-S):

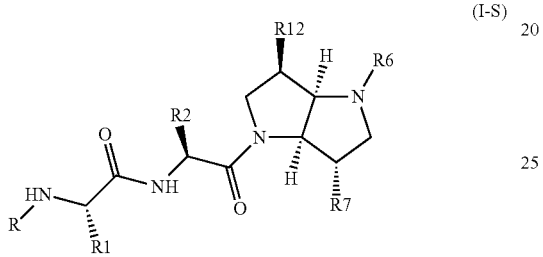
(I-S)

or a pharmaceutically acceptable salt thereof, wherein:
R is selected from H, alkyl, substituted alkyl, alkenyl, substituted alkenyl, cycloalkyl, substituted cycloalkyl, aryl, substituted aryl, heteroaryl, or substituted heteroaryl;
R1 is selected from alkyl, or substituted alkyl;
R2 is selected from alkyl, substituted alkyl, cycloalkyl, heterocycloalkyl, aryl, or heteroaryl;
R6 is selected from H, alkylsulfonyl, arylsulfonyl, alkyl, substituted alkyl, cycloalkyl, substituted cycloalkyl, heterocycloalkyl, substituted heterocycloalkyl, aryl, substituted aryl, heteroaryl, or substituted heteroaryl; or R6 has the following formula (IA*):

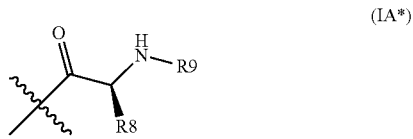
(IA*)

where R8 is selected from H, alkyl, substituted alkyl, cycloalkyl, heterocycloalkyl, aryl, or heteroaryl;
and R9 is selected from H, alkyl, substituted alkyl, cycloalkyl, substituted cycloalkyl, aryl, substituted aryl, heterocycloalkyl, substituted heterocycloalkyl, heteroaryl, or substituted heteroaryl; or R9 has the following formula (IB*):

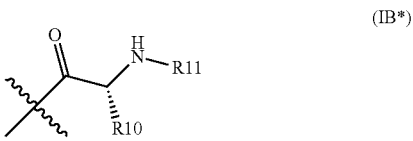
(IB*)

where R10 is selected from alkyl, or substituted alkyl;
and R11 is selected from H, alkyl, substituted alkyl, alkenyl, substituted alkenyl, cycloalkyl, substituted cycloalkyl, aryl, substituted aryl, heteroaryl, or substituted heteroaryl;

R7 is selected from H, or a 3-indolyl of the formula (IC):

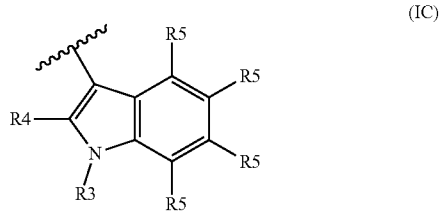
(IC)

where R3 is selected from H, alkyl, or substituted alkyl;
R4 is selected from H, halogen, alkyl, or substituted alkyl; and
each R5 is independently selected from H, halogen, alkyl, or substituted alkyl; and
R12 is selected from H or hydroxy.

6. A compound of claim 5, or a pharmaceutically acceptable salt thereof, wherein:
R is selected from H, alkyl, substituted alkyl, alkenyl, substituted alkenyl, aryl, substituted aryl, cycloalkyl, substituted cycloalkyl, heteroaryl, or substituted heteroaryl; wherein the substitutents are selected from the group consisting of halogen, hydroxy, oxo, mercapto, carboxyl, alkyl, cycloalkyl, aryl, alkoxy, amino, heteroaryl, and nitro;
R1 is alkyl, or substituted alkyl, wherein the substitutents are selected from the group consisting of halogen, hydroxy, oxo, mercapto, carboxyl, alkyl, cycloalkyl, aryl, alkoxy, amino, heteroaryl, and nitro;
R2 is alkyl, cycloalkyl, aryl, heterocycloalkyl, heteroaryl, or substituted alkyl, wherein the substituents are selected from the group consisting of halogen, hydroxy, oxo, alkoxy, cycloalkyl, aryl, heterocycloalkyl and heteroaryl;
R6 is selected from H; alkylsulfonyl; arylsulfonyl; alkyl; substituted alkyl, wherein the substituents are selected from the group consisting of halogen, hydroxy, oxo, mercapto, carboxyl, alkoxy, amino, nitro, cycloalkyl, aryl, heteroaryl optionally substituted with lower alkyl or halogen, alkylsulfonyl and arylsulfonyl; cycloalkyl; substituted cycloalkyl, wherein the substituents are selected from the group consisting of halogen, hydroxy, oxo, mercapto, carboxyl, alkyl, cycloalkyl, aryl, alkoxy, amino, heteroaryl, and nitro; aryl; substituted aryl, wherein the substituents are selected from the group consisting of alkyl, halogen, hydroxy, mercapto, carboxyl, cycloalkyl, aryl, alkoxy, amino, heteroaryl, nitro, alkylsulfonyl and arylsulfonyl; heterocycloalkyl; substituted heterocycloalkyl, wherein the substituents are selected from the group consisting of halogen, hydroxy, oxo, mercapto, carboxyl, alkyl, cycloalkyl, aryl, alkoxy, amino, heteroaryl, and nitro; heteroaryl; or substituted heteroaryl, wherein the substituents are selected from the group consisting of halogen, hydroxy, mercapto, carboxyl, alkyl, cycloalkyl, aryl, alkoxy, amino, heteroaryl, and nitro; or R6 has the following formula (IA*):

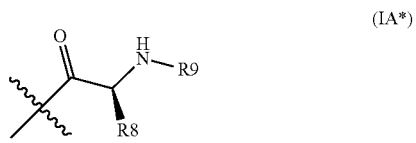
(IA*)

where R8 is alkyl, cycloalkyl, aryl, heterocycloalkyl, heteroaryl, or substituted alkyl, wherein the substituents are selected from the group consisting of halogen, hydroxy, oxo, alkoxy, cycloalkyl, aryl, heterocycloalkyl and heteroaryl;

and R9 is selected from H, alkyl, substituted alkyl, aryl, substituted aryl, cycloalkyl, substituted cycloalkyl, heteroaryl, or substituted heteroaryl; wherein the substitutents are selected from the group consisting of halogen, hydroxy, oxo, mercapto, carboxyl, alkyl, cycloalkyl, aryl, alkoxy, amino, heteroaryl, and nitro; or, R9 has the following formula (IB*):

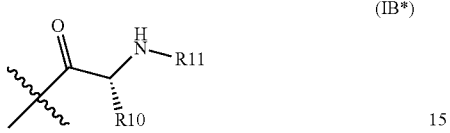

(IB*)

where R10 is selected from alkyl, or substituted alkyl, wherein the substitutents are selected from the group consisting of halogen, hydroxy, oxo, mercapto, carboxyl, alkyl, cycloalkyl, aryl, alkoxy, amino, heteroaryl, and nitro; and R11 is selected from H, alkyl, substituted alkyl, aryl, substituted aryl, cycloalkyl, substituted cycloalkyl, heteroaryl, or substituted heteroaryl; wherein the substitutents are selected from the group consisting of halogen, hydroxy, oxo, mercapto, carboxyl, alkyl, cycloalkyl, aryl, alkoxy, amino, heteroaryl, and nitro;

R7 is selected from H, or a 3-indolyl of the formula (IC):

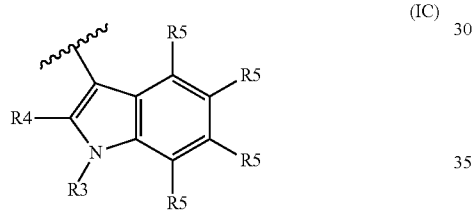

(IC)

where R3 is selected from H, alkyl, or substituted alkyl, where the substituents are selected from the group consisting of halogen, hydroxy, mercapto, carboxyl, alkyl, cycloalkyl, aryl, alkoxy, amino, heteroaryl, and nitro;

R4 is selected from H, halogen, alkyl, or substituted alkyl, where the substituents are selected from the group consisting of halogen, hydroxy, mercapto, carboxyl, alkyl, cycloalkyl, aryl, alkoxy, amino, heteroaryl, and nitro; and each R5 is independently selected from H, halogen, alkyl, or substituted alkyl, where the substituents are selected from the group consisting of halogen, hydroxy, mercapto, carboxyl, alkyl, cycloalkyl, aryl, alkoxy, amino, heteroaryl, and nitro; and R12 is selected from H or hydroxy.

7. A compound of claim 6, or a pharmaceutically acceptable salt thereof, wherein:

R is selected from H, alkyl, substituted alkyl, alkenyl, or substituted alkenyl; wherein the substitutents are selected from the group consisting of halogen, hydroxy, oxo, mercapto, carboxyl, alkyl, cyclopropyl, alkoxy, amino, and nitro; and R1 is selected from alkyl, or substituted alkyl, wherein the substitutents are selected from the group consisting of halogen, hydroxy, oxo, mercapto, carboxyl, alkyl, cyclopropyl, alkoxy, amino, and nitro.

8. A compound of claim 6, or a pharmaceutically acceptable salt thereof, wherein:

R is selected from H, or lower alkyl;
R1 is lower alkyl;

R2 is selected from lower alkyl; cycloalkyl; or substituted lower alkyl, wherein the substituents are selected from the group consisting of hydroxy, and alkoxy;

R6 is selected from H; lower alkylsulfonyl; alkyl; substituted alkyl, wherein the substituents are selected from the group consisting of hydroxy, oxo, halogen, alkoxy, cycloalkyl, aryl, and heteroaryl optionally substituted with lower alkyl or halogen; cycloalkyl; or heteroaryl optionally substituted with lower alkyl or halogen; or R6 has the following formula (IA*):

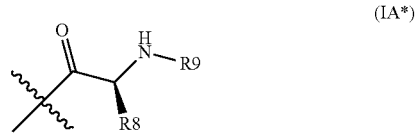

(IA*)

where R8 is selected from lower alkyl, cycloalkyl, or substituted lower alkyl, wherein the substituents are selected from the group consisting of hydroxy, and alkoxy; and R9 is selected from H, or lower alkyl; or R9 has the following formula (IB*):

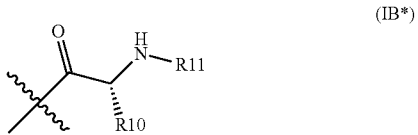

(IB*)

where R10 is lower alkyl; and
R11 is selected from H, or lower alkyl;
R7 is selected from H, or a 3-indolyl of the formula (IC):

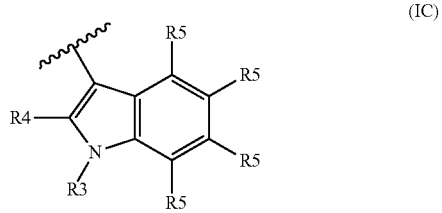

(IC)

where R3 is selected from H, or aralkyl;
R4 is selected from H, or halogen; and
each R5 is independently selected from H, or halogen; and
R12 is H, or hydroxy.

9. A compound of claim 1 having the structure of Formula (II):

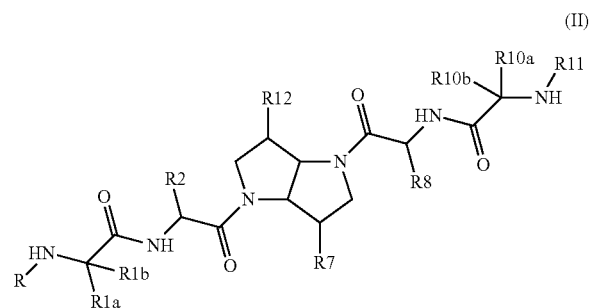

(II)

or a pharmaceutically acceptable salt thereof, wherein:

R and R11 are independently selected from H, alkyl, substituted alkyl, alkenyl, substituted alkenyl, cycloalkyl, substituted cycloalkyl, aryl, substituted aryl, heteroaryl, or substituted heteroaryl;

R1a, R1b, R10a and R10b are independently selected from H, alkyl, or substituted alkyl;
R2 and R8 are independently selected from H, alkyl, substituted alkyl, cycloalkyl, heterocycloalkyl, aryl, or heteroaryl;
R7 is selected from H, or a 3-indolyl of the formula (IIC):

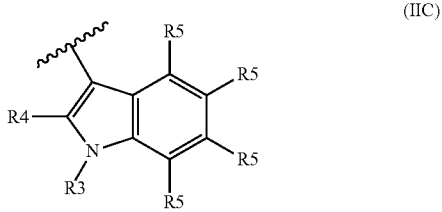

where R3 is selected from H, alkyl, or substituted alkyl;
R4 is selected from H, halogen, alkyl, or substituted alkyl; and
each R5 is independently selected from H, halogen, alkyl, or substituted alkyl; and
R12 is selected from H, or hydroxy.

10. A compound of claim 9, or a pharmaceutically acceptable salt thereof, wherein:
R and R11 are independently selected from H, alkyl, substituted alkyl, alkenyl, substituted alkenyl, aryl, substituted aryl, cycloalkyl, substituted cycloalkyl, heteroaryl, or substituted heteroaryl; wherein the substitutents are selected from the group consisting of halogen, hydroxy, oxo, mercapto, carboxyl, alkyl, cycloalkyl, aryl, alkoxy, amino, heteroaryl, and nitro;
R1a, R1b, R10a and R10b are independently selected from H, alkyl, or substituted alkyl, wherein the substitutents are selected from the group consisting of halogen, hydroxy, oxo, mercapto, carboxyl, alkyl, cycloalkyl, aryl, alkoxy, amino, heteroaryl, and nitro;
R2 and R8 are independently selected from alkyl, cycloalkyl, aryl, heterocycloalkyl, heteroaryl, or substituted alkyl, wherein the substituents are selected from the group consisting of halogen, hydroxy, oxo, alkoxy, cycloalkyl, aryl, heterocycloalkyl and heteroaryl;
R7 is selected from H, or a 3-indolyl of the formula (IIC):

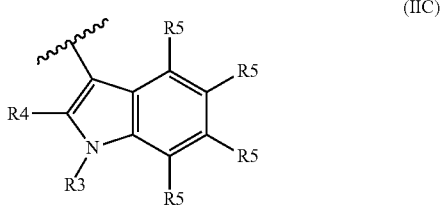

where R3 is selected from H, alkyl, or substituted alkyl, where the substituents are selected from the group consisting of halogen, hydroxy, mercapto, carboxyl, alkyl, cycloalkyl, aryl, alkoxy, amino, heteroaryl, and nitro;
R4 is selected from H, halogen, alkyl, or substituted alkyl, where the substituents are selected from the group consisting of halogen, hydroxy, mercapto, carboxyl, alkyl, cycloalkyl, aryl, alkoxy, amino, heteroaryl, and nitro; and
each R5 is independently selected from H, halogen, alkyl, or substituted alkyl, where the substituents are selected from the group consisting of halogen, hydroxy, mercapto, carboxyl, alkyl, cycloalkyl, aryl, alkoxy, amino, heteroaryl, and nitro; and
R12 is selected from H, or hydroxy.

11. A compound of claim 10, or a pharmaceutically acceptable salt thereof, wherein:
R and R11 are independently selected from H, alkyl, substituted alkyl, alkenyl, or substituted alkenyl; wherein the substitutents are selected from the group consisting of halogen, hydroxy, oxo, mercapto, carboxyl, alkyl, cyclopropyl, alkoxy, amino, and nitro; and
R1a, R1b, R10a and R10b are independently selected from H, alkyl, or substituted alkyl, wherein the substitutents are selected from the group consisting of halogen, hydroxy, oxo, mercapto, carboxyl, alkyl, cyclopropyl, alkoxy, amino, and nitro.

12. A compound of claim 10, or a pharmaceutically acceptable salt thereof, wherein:
R and R11 are independently selected from H, or lower alkyl;
R1a, R1b, R10a and R10b are independently selected from H, or lower alkyl;
R2 and R8 are independently selected from H, lower alkyl, cycloalkyl, or substituted lower alkyl, wherein the substituents are selected from the group consisting of hydroxy, and alkoxy;
R7 is selected from H, or a 3-indolyl of the formula (IIC):

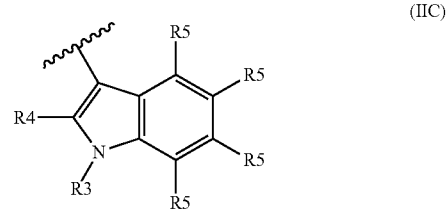

where R3 is selected from H, or aralkyl;
R4 is selected from H, or halogen; and
each R5 is independently selected from H, or halogen; and
R12 is H, or hydroxy.

13. A compound of claim 9 having the structure of Formula (II-S):

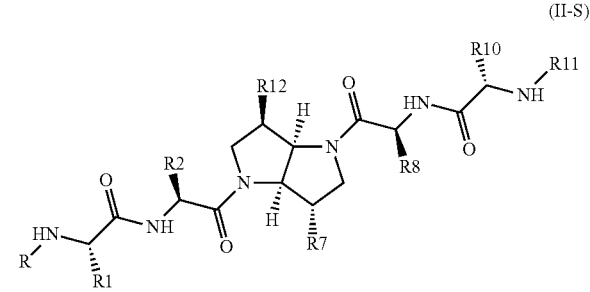

or a pharmaceutically acceptable salt thereof, wherein:
R and R11 are independently selected from H, alkyl, substituted alkyl, alkenyl, substituted alkenyl, cycloalkyl, substituted cycloalkyl, aryl, substituted aryl, heteroaryl, or substituted heteroaryl;
R1 and R10 are independently selected from alkyl, or substituted alkyl;

R2 and R8 are independently selected from alkyl, substituted alkyl, cycloalkyl, heterocycloalkyl, aryl, or heteroaryl;

R7 is selected from H, or a 3-indolyl of the formula (IIC):

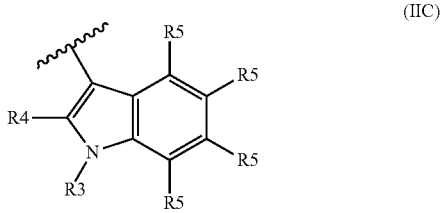

(IIC)

where R3 is selected from H, alkyl, or substituted alkyl;
R4 is selected from H, halogen, alkyl, or substituted alkyl; and
each R5 is independently selected from H, halogen, alkyl, or substituted alkyl; and
R12 is selected from H or hydroxy.

14. A compound of claim 13, or a pharmaceutically acceptable salt thereof, wherein:

R and R11 are independently selected from H, alkyl, substituted alkyl, alkenyl, substituted alkenyl, aryl, substituted aryl, cycloalkyl, substituted cycloalkyl, heteroaryl, or substituted heteroaryl; wherein the substitutents are selected from the group consisting of halogen, hydroxy, oxo, mercapto, carboxyl, alkyl, cycloalkyl, aryl, alkoxy, amino, heteroaryl, and nitro;

R1 and R10 are independently selected from alkyl, or substituted alkyl, wherein the substitutents are selected from the group consisting of halogen, hydroxy, oxo, mercapto, carboxyl, alkyl, cycloalkyl, aryl, alkoxy, amino, heteroaryl, and nitro;

R2 and R8 are independently selected from alkyl, cycloalkyl, aryl, heterocycloalkyl, heteroaryl, or substituted alkyl, wherein the substituents are selected from the group consisting of halogen, hydroxy, oxo, alkoxy, cycloalkyl, aryl, heterocycloalkyl and heteroaryl;

R7 is selected from H, or a 3-indolyl of the formula (IIC):

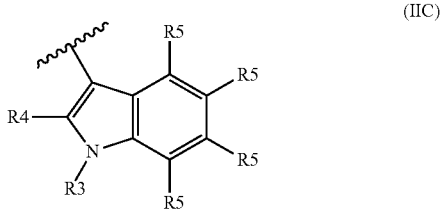

(IIC)

where R3 is selected from H, alkyl, or substituted alkyl, where the substituents are selected from the group consisting of halogen, hydroxy, mercapto, carboxyl, alkyl, cycloalkyl, aryl, alkoxy, amino, heteroaryl, and nitro;

R4 is selected from H, halogen, alkyl, or substituted alkyl, where the substituents are selected from the group consisting of halogen, hydroxy, mercapto, carboxyl, alkyl, cycloalkyl, aryl, alkoxy, amino, heteroaryl, and nitro; and each R5 is independently selected from H, halogen, alkyl, or substituted alkyl, where the substituents are selected from the group consisting of halogen, hydroxy, mercapto, carboxyl, alkyl, cycloalkyl, aryl, alkoxy, amino, heteroaryl, and nitro; and R12 is selected from H or hydroxy.

15. A compound of claim 13, or a pharmaceutically acceptable salt thereof, wherein:

R and R11 are independently selected from H, alkyl, substituted alkyl, alkenyl, or substituted alkenyl; wherein the substitutents are selected from the group consisting of halogen, hydroxy, oxo, mercapto, carboxyl, alkyl, cyclopropyl, alkoxy, amino, and nitro; and R1 and R10 are independently selected from alkyl, or substituted alkyl, wherein the substitutents are selected from the group consisting of halogen, hydroxy, oxo, mercapto, carboxyl, alkyl, cyclopropyl, alkoxy, amino, and nitro.

16. A compound of claim 14, or a pharmaceutically acceptable salt thereof, wherein:

R and R11 are independently selected from H, or lower alkyl;

R1 and R10 are independently selected from lower alkyl;

R2 and R8 are independently selected from lower alkyl; cycloalkyl; or substituted lower alkyl, wherein the substituents are selected from the group consisting of hydroxy, and alkoxy;

R7 is selected from H, or a 3-indolyl of the formula (IIC):

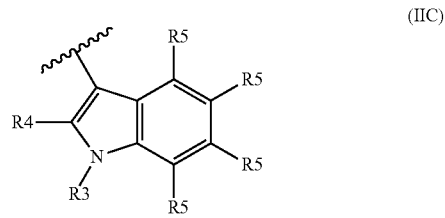

(IIC)

where R3 is selected from H, or aralkyl;
R4 is selected from H, or halogen; and
each R5 is independently selected from H, or halogen; and
R12 is H, or hydroxy.

17. A compound of claim 1 having the structure of Formula (III):

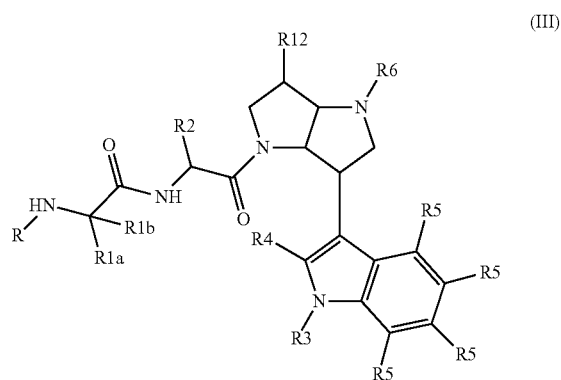

(III)

or a pharmaceutically acceptable salt thereof, wherein:

R is selected from H, alkyl, substituted alkyl, alkenyl, substituted alkenyl, cycloalkyl, substituted cycloalkyl, aryl, substituted aryl, heteroaryl, or substituted heteroaryl;

R1a and R1b are each independently selected from H, alkyl, or substituted alkyl;

R2 is selected from H, alkyl, substituted alkyl, cycloalkyl, heterocycloalkyl, aryl, or heteroaryl;

R6 is selected from H, alkylsulfonyl, arylsulfonyl, alkyl, substituted alkyl, cycloalkyl, substituted cycloalkyl, heterocycloalkyl, substituted heterocycloalkyl, aryl, substituted aryl, heteroaryl, or substituted heteroaryl; or R6 has the following formula (IIIA):

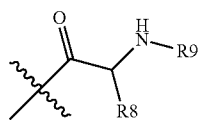

(IIIA)

where R8 is selected from H, alkyl, substituted alkyl, cycloalkyl, heterocycloalkyl, aryl, or heteroaryl;

and R9 is selected from H, alkyl, substituted alkyl, cycloalkyl, substituted cycloalkyl, aryl, substituted aryl, heterocycloalkyl, substituted heterocycloalkyl, heteroaryl, or substituted heteroaryl; or R9 has the following formula (IIIB):

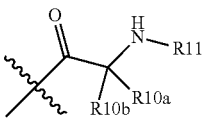

(IIIB)

where R10a and R10b are independently selected from H, alkyl, or substituted alkyl;

and R11 is selected from H, alkyl, substituted alkyl, alkenyl, substituted alkenyl, cycloalkyl, substituted cycloalkyl, aryl, substituted aryl, heteroaryl, or substituted heteroaryl;

R3 is selected from H, alkyl, or substituted alkyl;

R4 is selected from H, halogen, alkyl, or substituted alkyl; and each R5 is independently selected from H, halogen, alkyl, or substituted alkyl; and R12 is selected from H or hydroxy.

18. A compound of claim 17, or a pharmaceutically acceptable salt thereof, wherein:

R is selected from H, alkyl, substituted alkyl, alkenyl, substituted alkenyl, aryl, substituted aryl, cycloalkyl, substituted cycloalkyl, heteroaryl, or substituted heteroaryl; wherein the substitutents are selected from the group consisting of halogen, hydroxy, oxo, mercapto, carboxyl, alkyl, cycloalkyl, aryl, alkoxy, amino, heteroaryl, and nitro;

R1a and R1b are each independently selected from H, alkyl, or substituted alkyl, wherein the substitutents are selected from the group consisting of halogen, hydroxy, oxo, mercapto, carboxyl, alkyl, cycloalkyl, aryl, alkoxy, amino, heteroaryl, and nitro;

R2 is selected from H, alkyl, cycloalkyl, aryl, heterocycloalkyl, heteroaryl, or substituted alkyl, wherein the substituents are selected from the group consisting of halogen, hydroxy, oxo, alkoxy, cycloalkyl, aryl, heterocycloalkyl and heteroaryl;

R6 is selected from H; alkylsulfonyl; arylsulfonyl; alkyl; substituted alkyl, wherein the substituents are selected from the group consisting of halogen, hydroxy, oxo, mercapto, carboxyl, alkoxy, amino, nitro, cycloalkyl, aryl, heteroaryl optionally substituted with lower alkyl or halogen, alkylsulfonyl and arylsulfonyl; cycloalkyl; substituted cycloalkyl, wherein the substituents are selected from the group consisting of halogen, hydroxy, oxo, mercapto, carboxyl, alkyl, cycloalkyl, aryl, alkoxy, amino, heteroaryl, and nitro; aryl; substituted aryl, wherein the substituents are selected from the group consisting of alkyl, halogen, hydroxy, mercapto, carboxyl, cycloalkyl, aryl, alkoxy, amino, heteroaryl, nitro, alkylsulfonyl and arylsulfonyl; heterocycloalkyl; substituted heterocycloalkyl, wherein the substituents are selected from the group consisting of halogen, hydroxy, oxo, mercapto, carboxyl, alkyl, cycloalkyl, aryl, alkoxy, amino, heteroaryl, and nitro; heteroaryl; or substituted heteroaryl, wherein the substituents are selected from the group consisting of halogen, hydroxy, mercapto, carboxyl, alkyl, cycloalkyl, aryl, alkoxy, amino, heteroaryl, and nitro; or R6 has the following formula (MA):

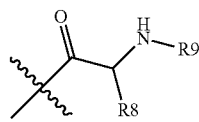

(IIIA)

where R8 is selected from alkyl, cycloalkyl, aryl, heterocycloalkyl, heteroaryl, or substituted alkyl, wherein the substituents are selected from the group consisting of halogen, hydroxy, oxo, alkoxy, cycloalkyl, aryl, heterocycloalkyl and heteroaryl;

and R9 is selected from H, alkyl, substituted alkyl, aryl, substituted aryl, cycloalkyl, substituted cycloalkyl, heteroaryl, or substituted heteroaryl; wherein the substitutents are selected from the group consisting of halogen, hydroxy, oxo, mercapto, carboxyl, alkyl, cycloalkyl, aryl, alkoxy, amino, heteroaryl, and nitro; or, R9 has the following formula (IIIB):

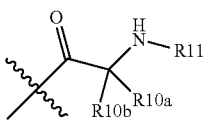

(IIIB)

where R10a and R10b are independently selected from H, alkyl, or substituted alkyl, wherein the substitutents are selected from the group consisting of halogen, hydroxy, oxo, mercapto, carboxyl, alkyl, cycloalkyl, aryl, alkoxy, amino, heteroaryl, and nitro; and R11 is selected from H, alkyl, substituted alkyl, aryl, substituted aryl, cycloalkyl, substituted cycloalkyl, heteroaryl, or substituted heteroaryl; wherein the substitutents are selected from the group consisting of halogen, hydroxy, oxo, mercapto, carboxyl, alkyl, cycloalkyl, aryl, alkoxy, amino, heteroaryl, and nitro;

R3 is selected from H, alkyl, or substituted alkyl, where the substituents are selected from the group consisting of halogen, hydroxy, oxo, mercapto, carboxyl, alkyl, cycloalkyl, aryl, alkoxy, amino, heteroaryl, and nitro;

R4 is selected from H, halogen, alkyl, or substituted alkyl, where the substituents are selected from the group consisting of halogen, hydroxy, mercapto, carboxyl, alkyl, cycloalkyl, aryl, alkoxy, amino, heteroaryl, and nitro; and each R5 is independently selected from H, halogen, alkyl, or substituted alkyl, where the substituents are selected from the group consisting of halogen, hydroxy, mercapto, carboxyl, alkyl, cycloalkyl, aryl, alkoxy, amino, heteroaryl, and nitro; and R12 is selected from H, or hydroxy.

19. A compound of claim 18, or a pharmaceutically acceptable salt thereof, wherein:
R is selected from H, alkyl, substituted alkyl, alkenyl, or substituted alkenyl; wherein the substitutents are selected from the group consisting of halogen, hydroxy, oxo, mercapto, carboxyl, alkyl, cyclopropyl, alkoxy, amino, and nitro; and
R1a and R1b are each independently selected from H, alkyl, or substituted alkyl, wherein the substitutents are selected from the group consisting of halogen, hydroxy, oxo, mercapto, carboxyl, alkyl, cyclopropyl, alkoxy, amino, and nitro.

20. A compound of claim 18, or a pharmaceutically acceptable salt thereof, wherein:
R is selected from H, or lower alkyl;
R1a and R1b are each independently selected from H, or lower alkyl;
R2 is selected from H; lower alkyl; cycloalkyl; or substituted lower alkyl wherein the substituents are selected from the group consisting of hydroxy, and alkoxy;
R6 is selected from H; lower alkylsulfonyl; lower alkyl; substituted lower alkyl, wherein the alkyl substituents are selected from the group consisting of hydroxy, oxo, halogen, alkoxy, cycloalkyl, aryl, and heteroaryl optionally substituted with lower alkyl or halogen; cycloalkyl; or heteroaryl optionally substituted with lower alkyl or halogen; or R6 has the following formula (IIIA):

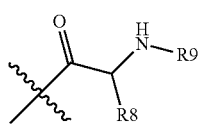

(IIIA)

wherein R8 is selected from H; lower alkyl; cycloalkyl; or substituted lower alkyl wherein the substituents are selected from the group consisting of hydroxy, and alkoxy; and
R9 is selected from H, or lower alkyl; or R9 has the following formula (IIIB):

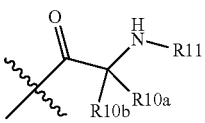

(IIIB)

where R10a and R10b are independently selected from H, or lower alkyl;
and R11 is selected from H, or lower alkyl;
R3 is selected from H, or aralkyl;
R4 is selected from H, or halogen; and
each R5 is independently selected from H, or halogen; and
R12 is H, or hydroxy.

21. A compound of claim 17 having the structure of formula (III-S):

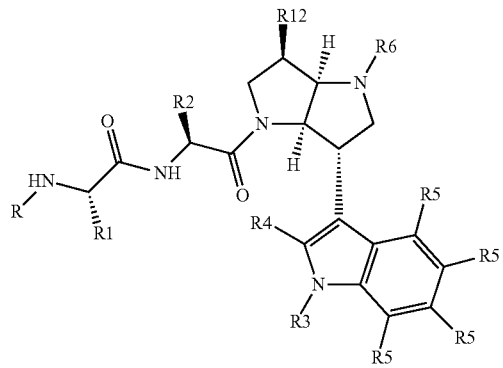

(III-S)

or a pharmaceutically acceptable salt thereof, wherein:
R is selected from H, alkyl, substituted alkyl, alkenyl, substituted alkenyl, cycloalkyl, substituted cycloalkyl, aryl, substituted aryl, heteroaryl, or substituted heteroaryl;
R1 is selected from alkyl, or substituted alkyl;
R2 is selected from alkyl, substituted alkyl, cycloalkyl, heterocycloalkyl, aryl, or heteroaryl;
R6 is selected from H, alkylsulfonyl, arylsulfonyl, alkyl, substituted alkyl, cycloalkyl, substituted cycloalkyl, heterocycloalkyl, substituted heterocycloalkyl, aryl, substituted aryl, heteroaryl, or substituted heteroaryl; or R6 has the following formula (IIIA*):

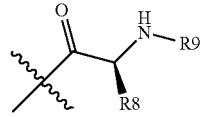

(IIIA*)

where R8 is selected from H, alkyl, substituted alkyl, cycloalkyl, heterocycloalkyl, aryl, or heteroaryl;
and R9 is selected from H, alkyl, substituted alkyl, cycloalkyl, substituted cycloalkyl, aryl, substituted aryl, heterocycloalkyl, substituted heterocycloalkyl, heteroaryl, or substituted heteroaryl; or R9 has the following formula (IIIB*):

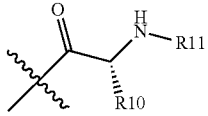

(IIIB*)

where R10 is selected from alkyl, or substituted alkyl;
and R11 is selected from H, alkyl, substituted alkyl, alkenyl, substituted alkenyl, cycloalkyl, substituted cycloalkyl, aryl, substituted aryl, heteroaryl, or substituted heteroaryl;
R3 is selected from H, alkyl, or substituted alkyl;
R4 is selected from H, halogen, alkyl, or substituted alkyl; and
each R5 is independently selected from H, halogen, alkyl, or substituted alkyl; and
R12 is selected from H, or hydroxy.

22. A compound of claim 21, or a pharmaceutically acceptable salt thereof, wherein:

R is selected from H, alkyl, substituted alkyl, alkenyl, substituted alkenyl, aryl, substituted aryl, cycloalkyl, substituted cycloalkyl, heteroaryl, or substituted heteroaryl; wherein the substitutents are selected from the group consisting of halogen, hydroxy, oxo, mercapto, carboxyl, alkyl, cycloalkyl, aryl, alkoxy, amino, heteroaryl, and nitro;

R1 is selected from alkyl, or substituted alkyl, wherein the substitutents are selected from the group consisting of halogen, hydroxy, oxo, mercapto, carboxyl, alkyl, cycloalkyl, aryl, alkoxy, amino, heteroaryl, and nitro;

R2 is selected from alkyl, cycloalkyl, aryl, heterocycloalkyl, heteroaryl, or substituted alkyl, wherein the substituents are selected from the group consisting of halogen, hydroxy, oxo, alkoxy, cycloalkyl, aryl, heterocycloalkyl and heteroaryl;

R6 is selected from H; alkylsulfonyl; arylsulfonyl; alkyl; substituted alkyl, wherein the substituents are selected from the group consisting of halogen, hydroxy, oxo, mercapto, carboxyl, alkoxy, amino, nitro, cycloalkyl, aryl, heteroaryl optionally substituted with lower alkyl or halogen, alkylsulfonyl and arylsulfonyl; cycloalkyl; substituted cycloalkyl, wherein the substituents are selected from the group consisting of halogen, hydroxy, oxo, mercapto, carboxyl, alkyl, cycloalkyl, aryl, alkoxy, amino, heteroaryl, and nitro; aryl; substituted aryl, wherein the substituents are selected from the group consisting of alkyl, halogen, hydroxy, mercapto, carboxyl, cycloalkyl, aryl, alkoxy, amino, heteroaryl, nitro, alkylsulfonyl and arylsulfonyl; heterocycloalkyl; substituted heterocycloalkyl, wherein the substituents are selected from the group consisting of halogen, hydroxy, oxo, mercapto, carboxyl, alkyl, cycloalkyl, aryl, alkoxy, amino, heteroaryl, and nitro; heteroaryl; or substituted heteroaryl, wherein the substituents are selected from the group consisting of halogen, hydroxy, mercapto, carboxyl, alkyl, cycloalkyl, aryl, alkoxy, amino, heteroaryl, and nitro; or R6 has the following formula (IIIA*):

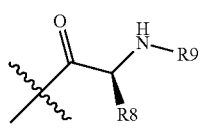

(IIIA*)

where R8 is selected from alkyl, cycloalkyl, aryl, heterocycloalkyl, heteroaryl, or substituted alkyl, wherein the substituents are selected from the group consisting of halogen, hydroxy, oxo, alkoxy, cycloalkyl, aryl, heterocycloalkyl and heteroaryl;

and R9 is selected from H, alkyl, substituted alkyl, aryl, substituted aryl, cycloalkyl, substituted cycloalkyl, heteroaryl, or substituted heteroaryl; wherein the substitutents are selected from the group consisting of halogen, hydroxy, oxo, mercapto, carboxyl, alkyl, cycloalkyl, aryl, alkoxy, amino, heteroaryl, and nitro; or, R9 has the following formula (IIIB*):

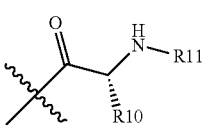

(IIIB*)

where R10 is selected from alkyl, or substituted alkyl, wherein the substitutents are selected from the group consisting of halogen, hydroxy, oxo, mercapto, carboxyl, alkyl, cycloalkyl, aryl, alkoxy, amino, heteroaryl, and nitro; and R11 is selected from H, alkyl, substituted alkyl, aryl, substituted aryl, cycloalkyl, substituted cycloalkyl, heteroaryl, or substituted heteroaryl; wherein the substitutents are selected from the group consisting of halogen, hydroxy, oxo, mercapto, carboxyl, alkyl, cycloalkyl, aryl, alkoxy, amino, heteroaryl, and nitro;

R3 is selected from H, alkyl, or substituted alkyl, where the substituents are selected from the group consisting of halogen, hydroxy, mercapto, carboxyl, alkyl, cycloalkyl, aryl, alkoxy, amino, heteroaryl, and nitro;

R4 is selected from H, halogen, alkyl, or substituted alkyl, where the substituents are selected from the group consisting of halogen, hydroxy, mercapto, carboxyl, alkyl, cycloalkyl, aryl, alkoxy, amino, heteroaryl, and nitro; and each R5 is independently selected from H, halogen, alkyl, or substituted alkyl, where the substituents are selected from the group consisting of halogen, hydroxy, mercapto, carboxyl, alkyl, cycloalkyl, aryl, alkoxy, amino, heteroaryl, and nitro; and R12 is selected from H, or hydroxy.

23. A compound of claim 22, or a pharmaceutically acceptable salt thereof, wherein:
R is selected from H, alkyl, substituted alkyl, alkenyl, or substituted alkenyl; wherein the substitutents are selected from the group consisting of halogen, hydroxy, oxo, mercapto, carboxyl, alkyl, cyclopropyl, alkoxy, amino, and nitro; and
R1 is selected from alkyl, or substituted alkyl, wherein the substitutents are selected from the group consisting of halogen, hydroxy, oxo, mercapto, carboxyl, alkyl, cyclopropyl, alkoxy, amino, and nitro.

24. A compound of claim 22, or a pharmaceutically acceptable salt thereof, wherein:
R is selected from H, or lower alkyl;
R1 is lower alkyl;
R2 is selected from lower alkyl, cycloalkyl, or substituted lower alkyl, wherein the substituents are selected from the group consisting of hydroxy, and alkoxy;
R6 is selected from H; lower alkylsulfonyl; alkyl; substituted alkyl, wherein the alkyl substituents are selected from the group consisting of hydroxy, oxo, halogen, alkoxy, cycloalkyl, aryl, and heteroaryl optionally substituted with lower alkyl or halogen; cycloalkyl; or heteroaryl optionally substituted with lower alkyl or halogen; or R6 has the following formula (IIIA*):

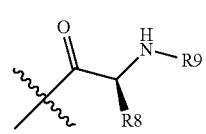

(IIIA*)

where R8 is selected from lower alkyl; cycloalkyl, or substituted lower alkyl wherein the substituents are selected from the group consisting of hydroxy, and alkoxy; and R9 is selected from H, or lower alkyl; or R9 has the following formula (IIIB*):

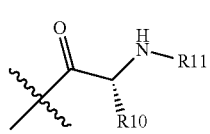

(IIIB*)

where R10 is lower alkyl; and
R11 is selected from H, or lower alkyl;
R3 is selected from H, or aralkyl;
R4 is selected from H, or halogen; and
each R5 is independently selected from H, or halogen; and
R12 is H, or hydroxy.
25. A compound of claim 1, selected from the group consisting of:
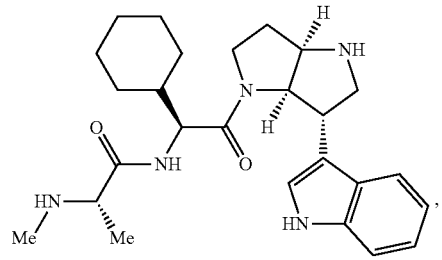
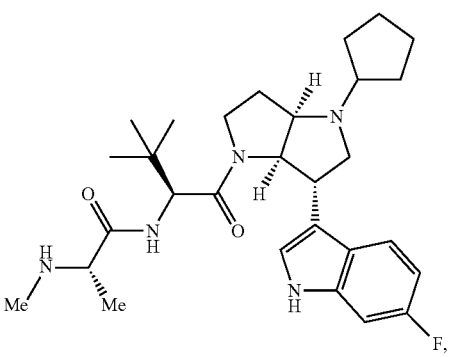
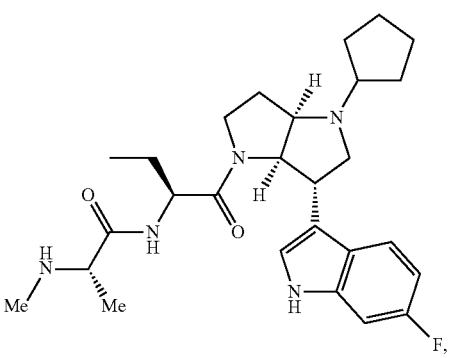
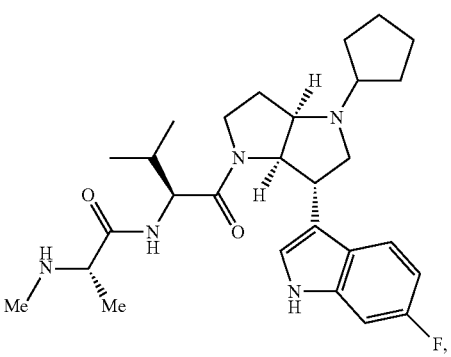
-continued
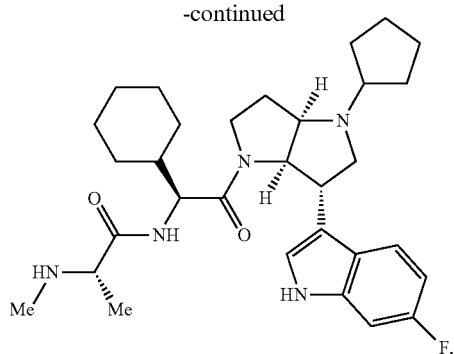
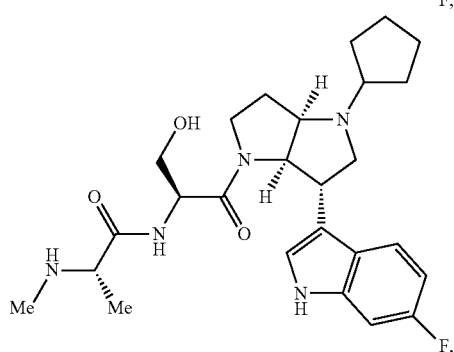
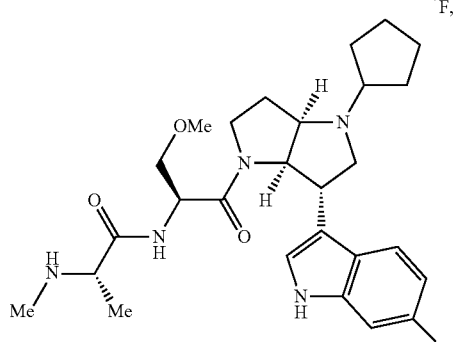
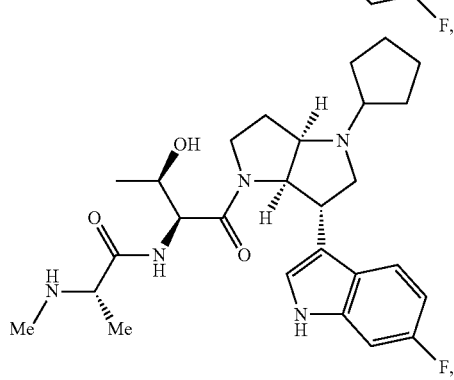
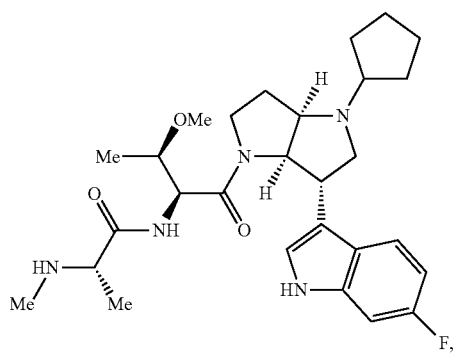

255
-continued
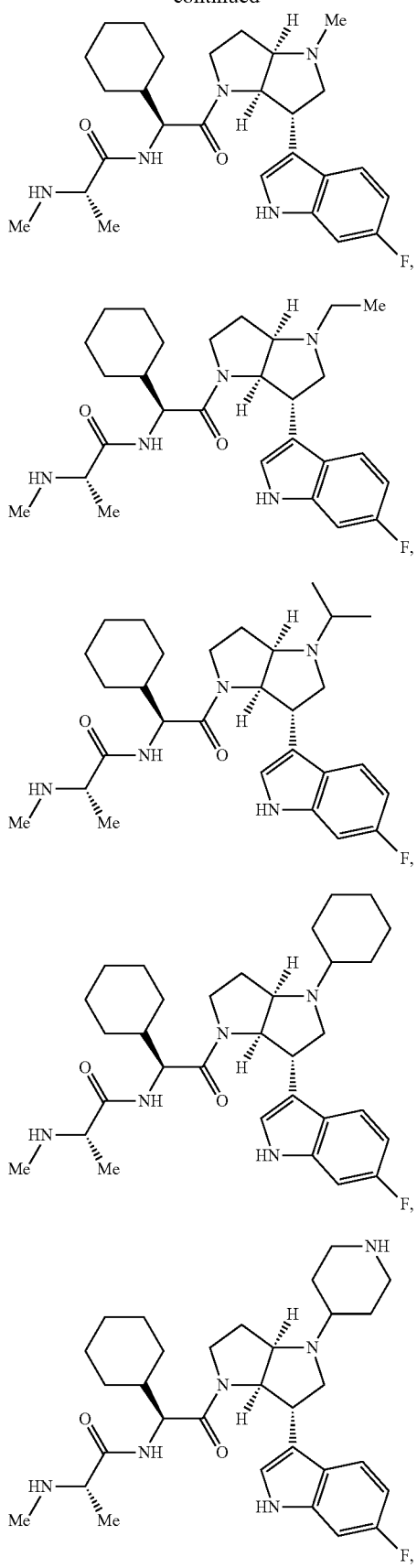
256
-continued
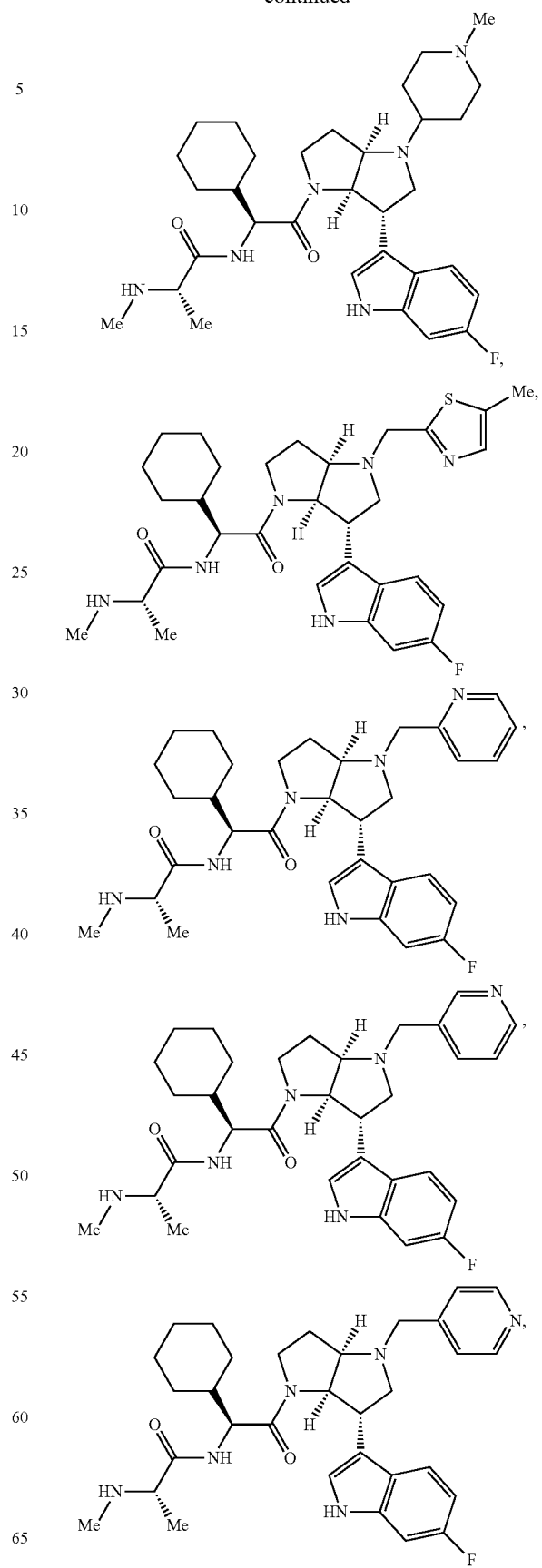

257
-continued
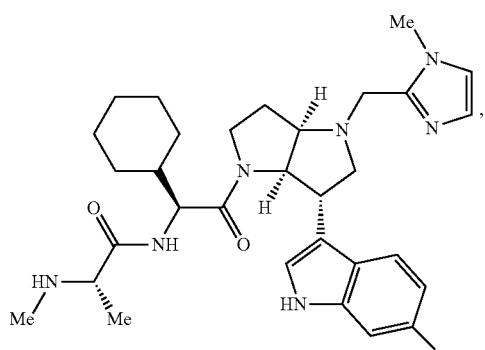
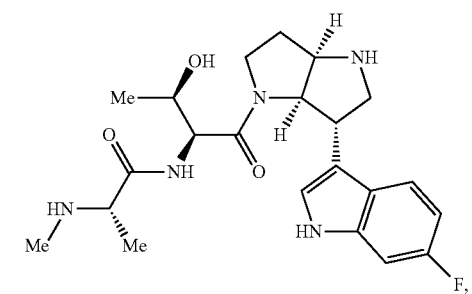
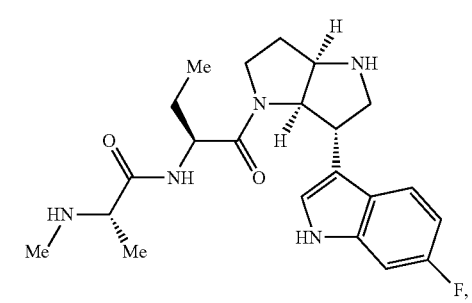
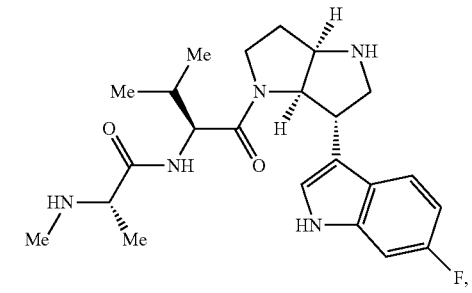
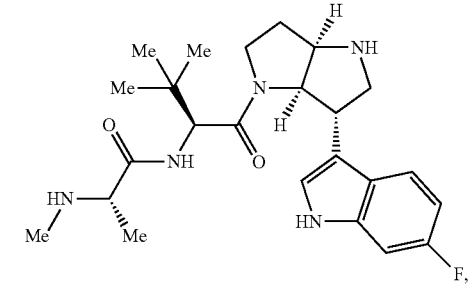
258
-continued
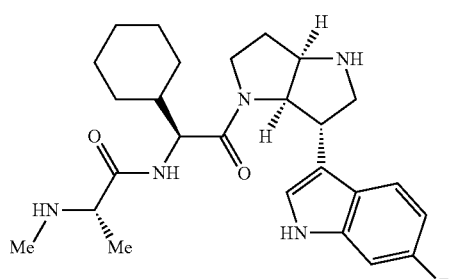
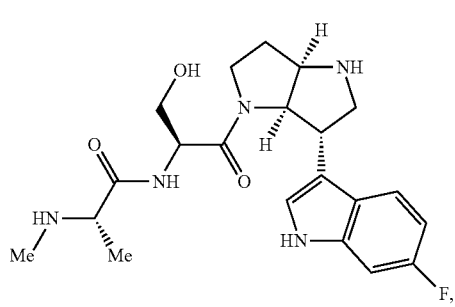
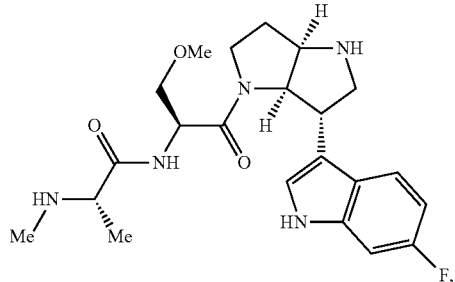
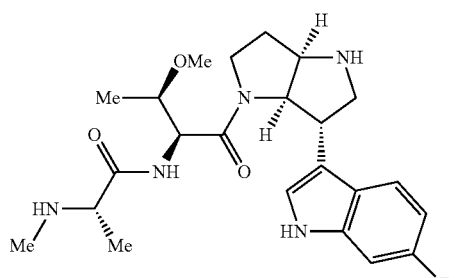
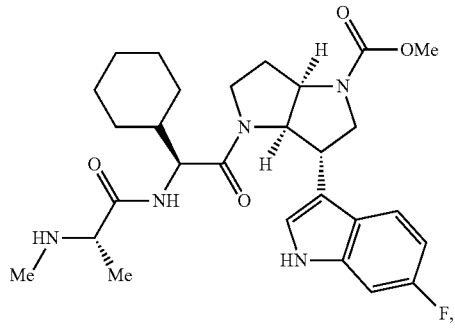

259
-continued
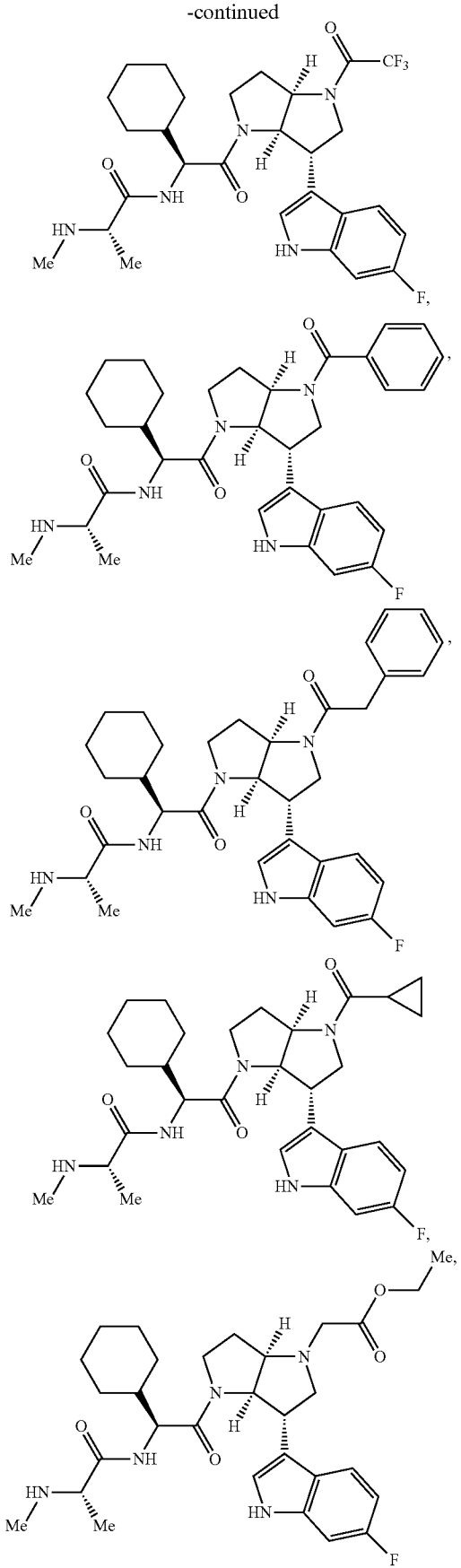
260
-continued
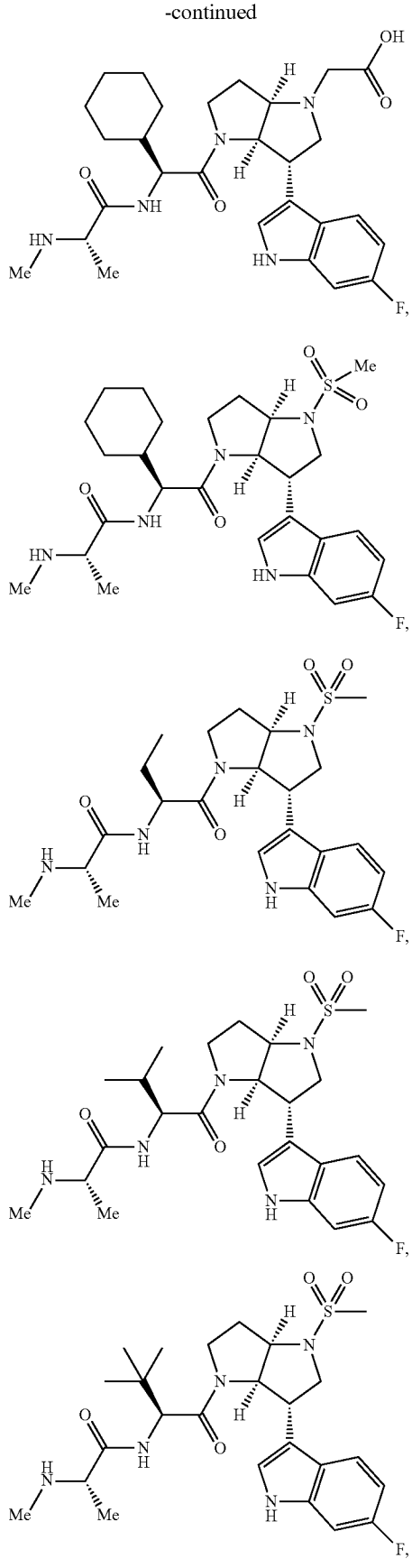

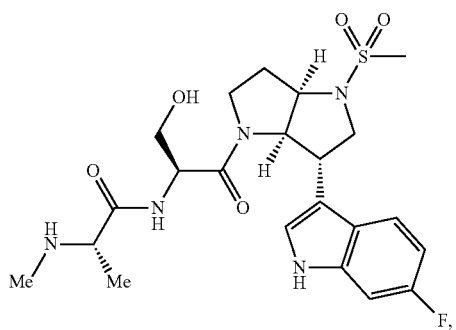
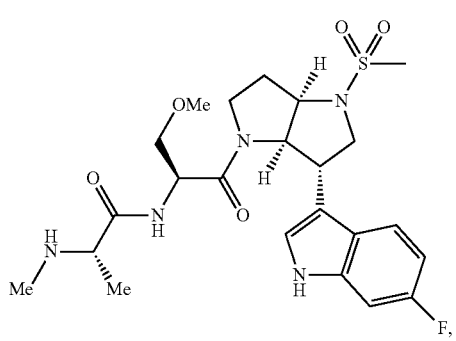
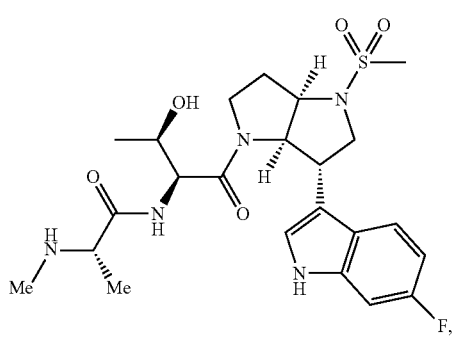
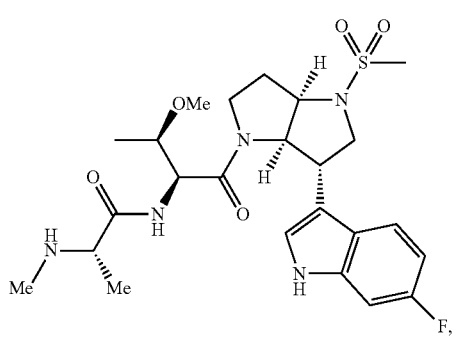
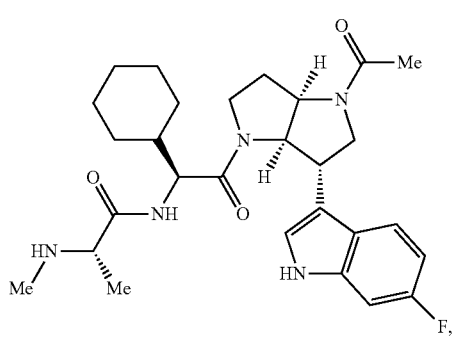
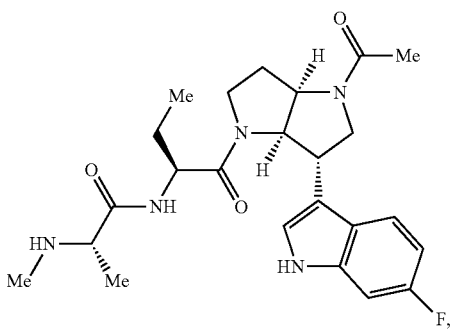
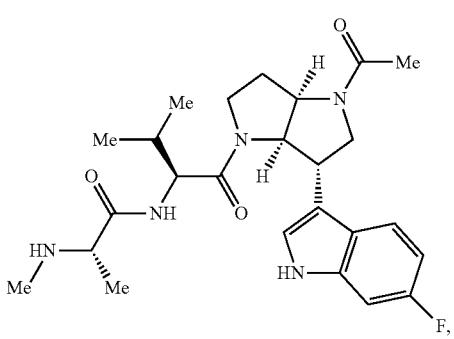
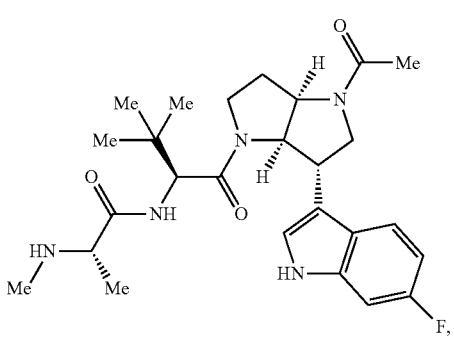
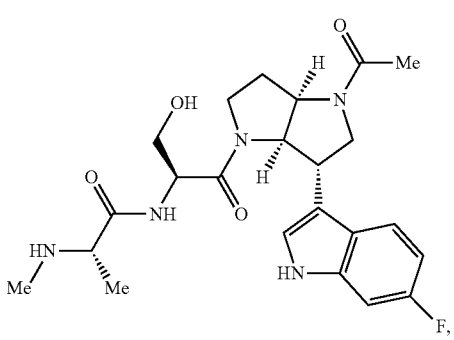
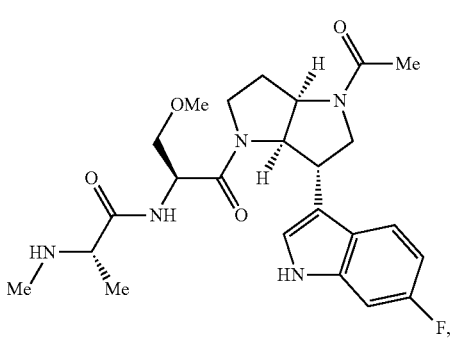

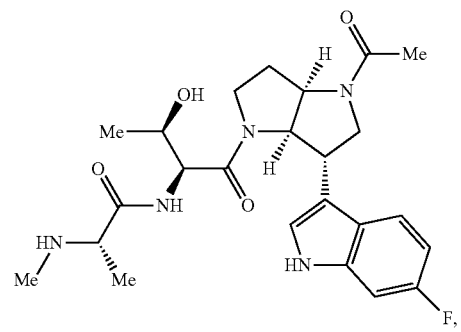
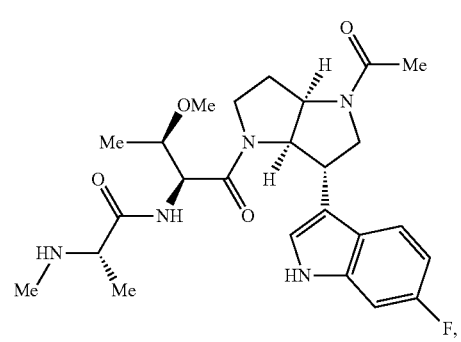
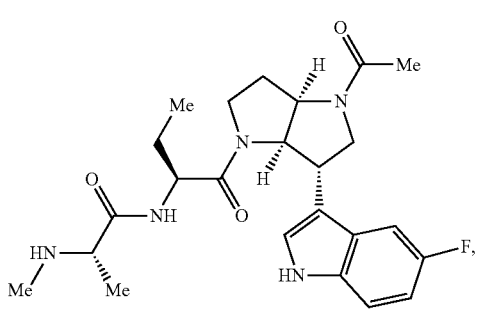
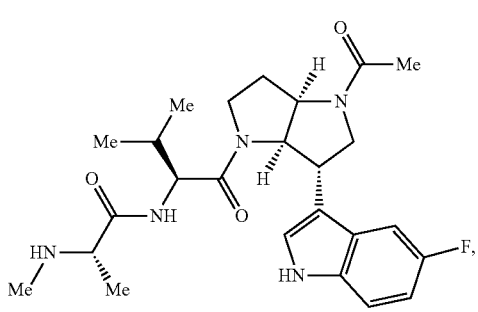
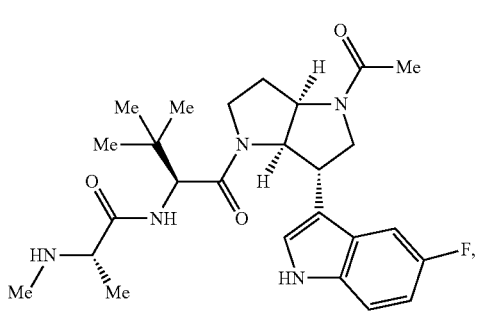
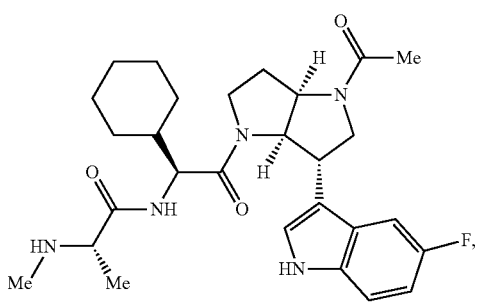
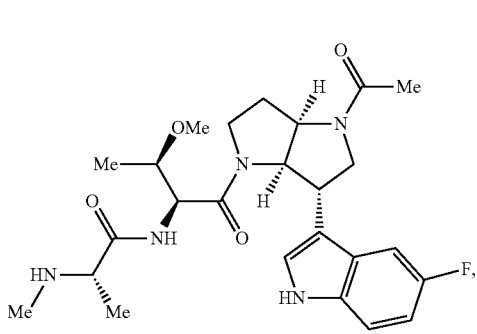
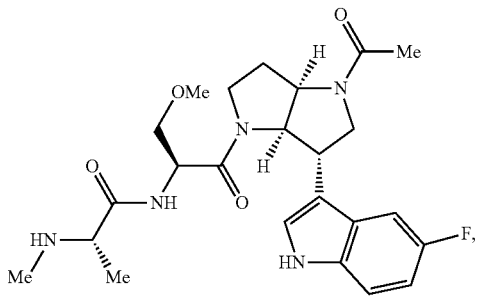
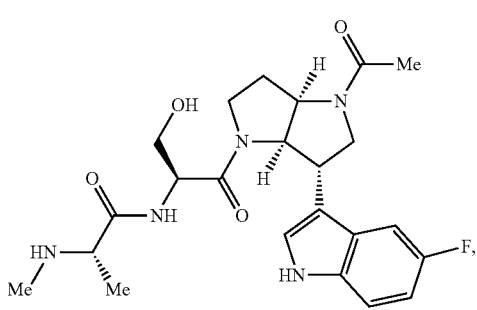
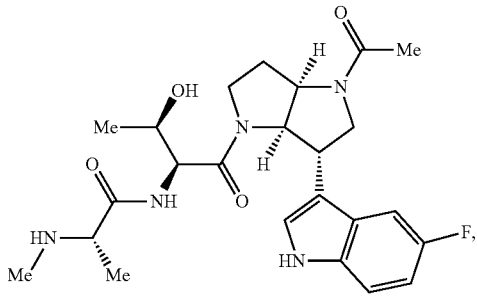

265
-continued
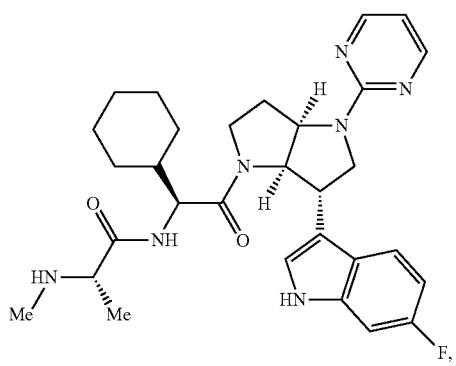
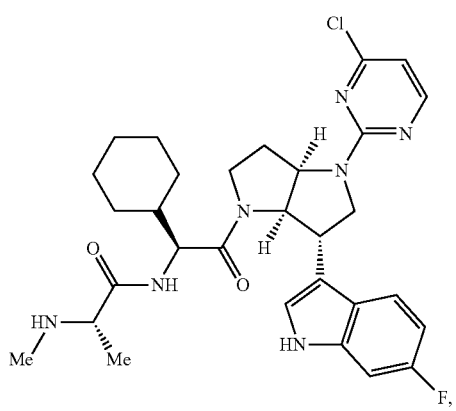
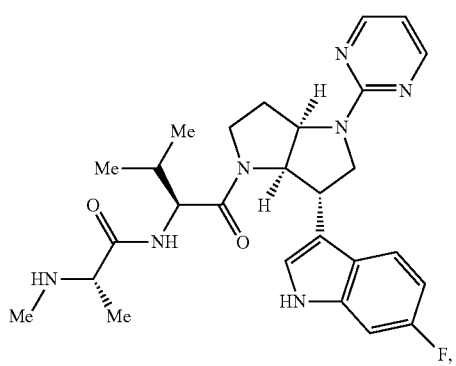
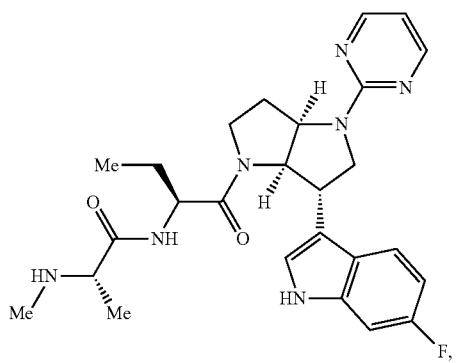
266
-continued
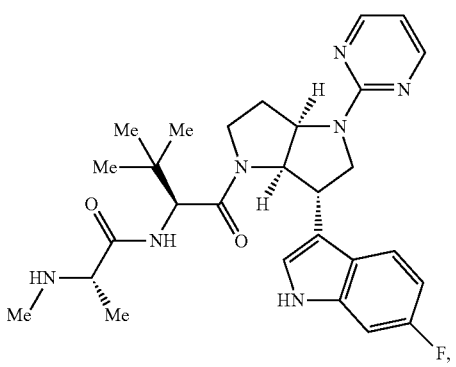
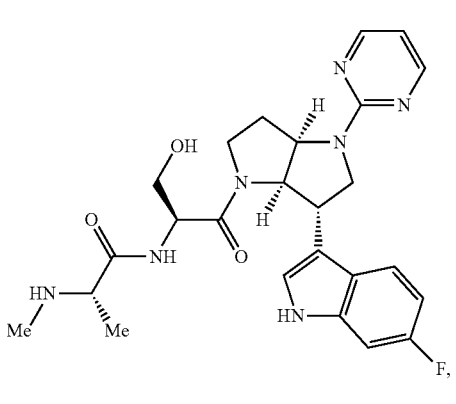
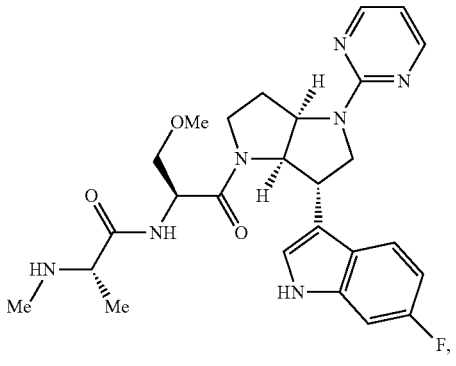 [SMILES: CN[C@@H](C)C(=O)N[C@@H](COC)C(=O)N1CC[C@@H]2[C@H]1[C@@H](c1c[nH]c3cc(F)ccc13)CN2c1ncccn1]
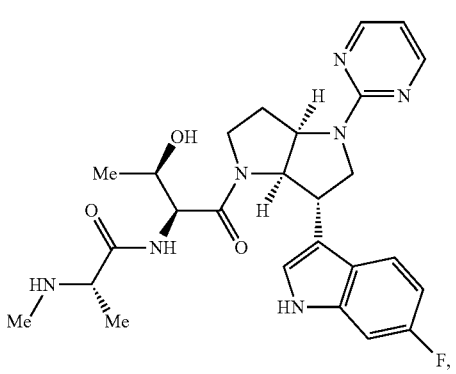

267
-continued
268
-continued
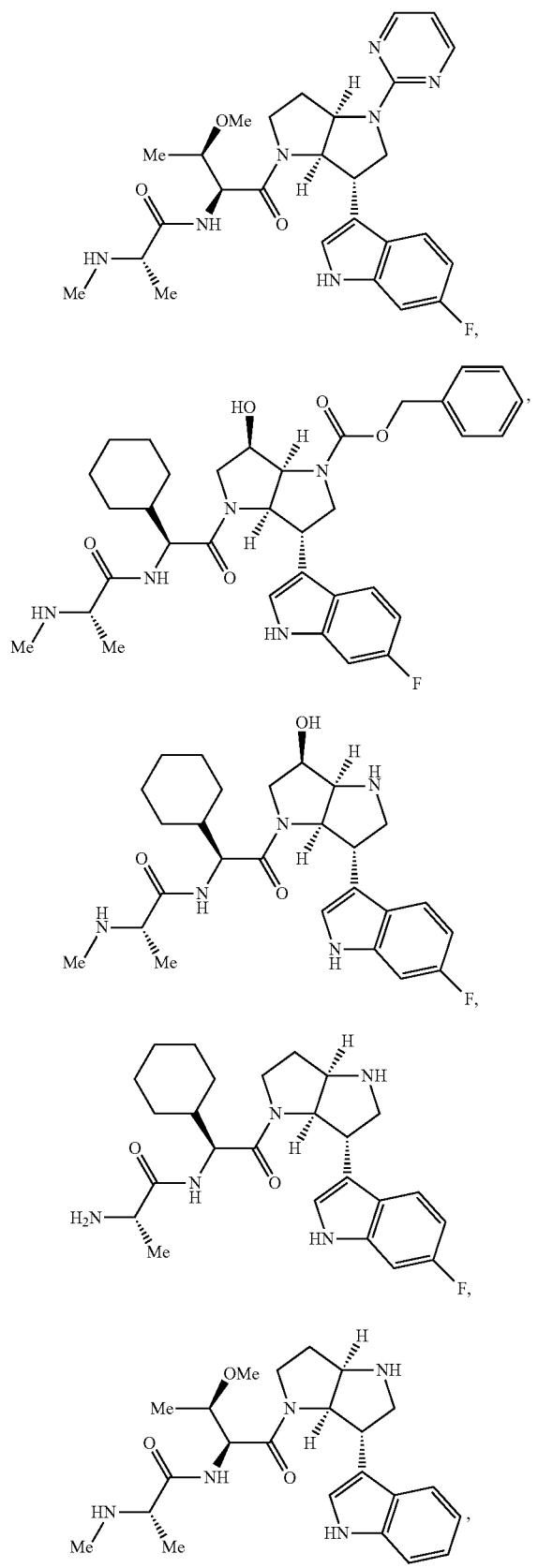
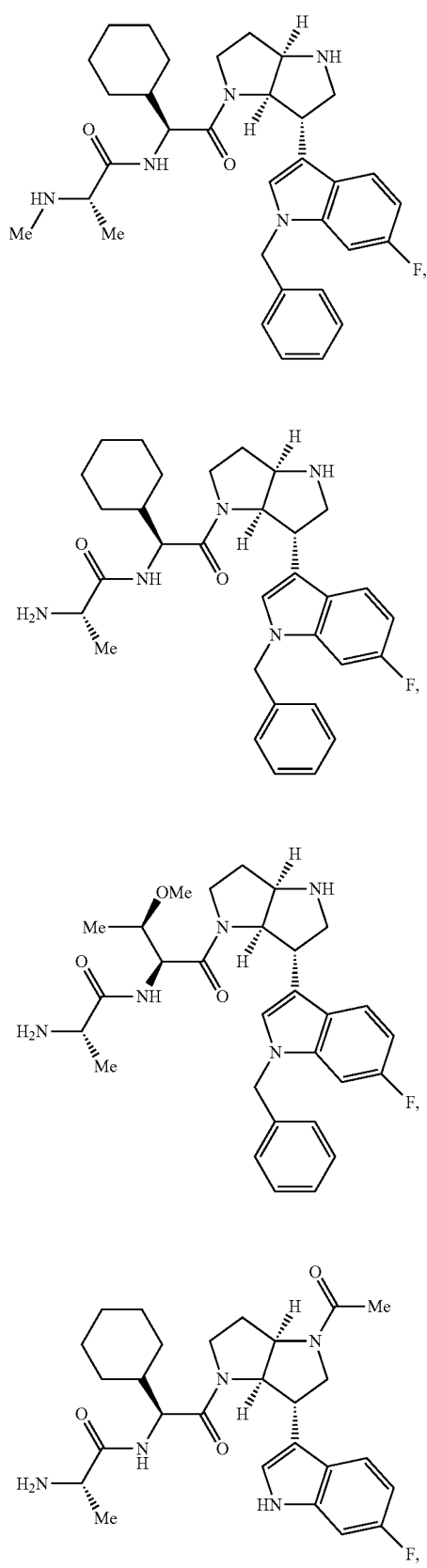

-continued
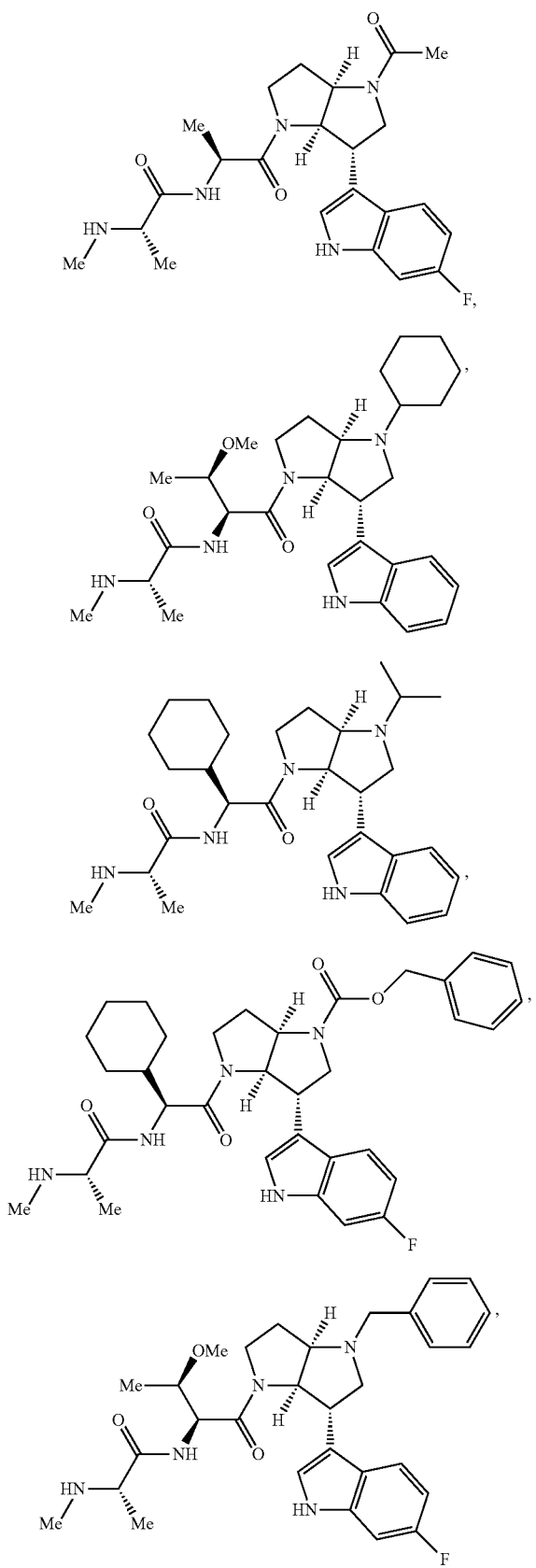
-continued
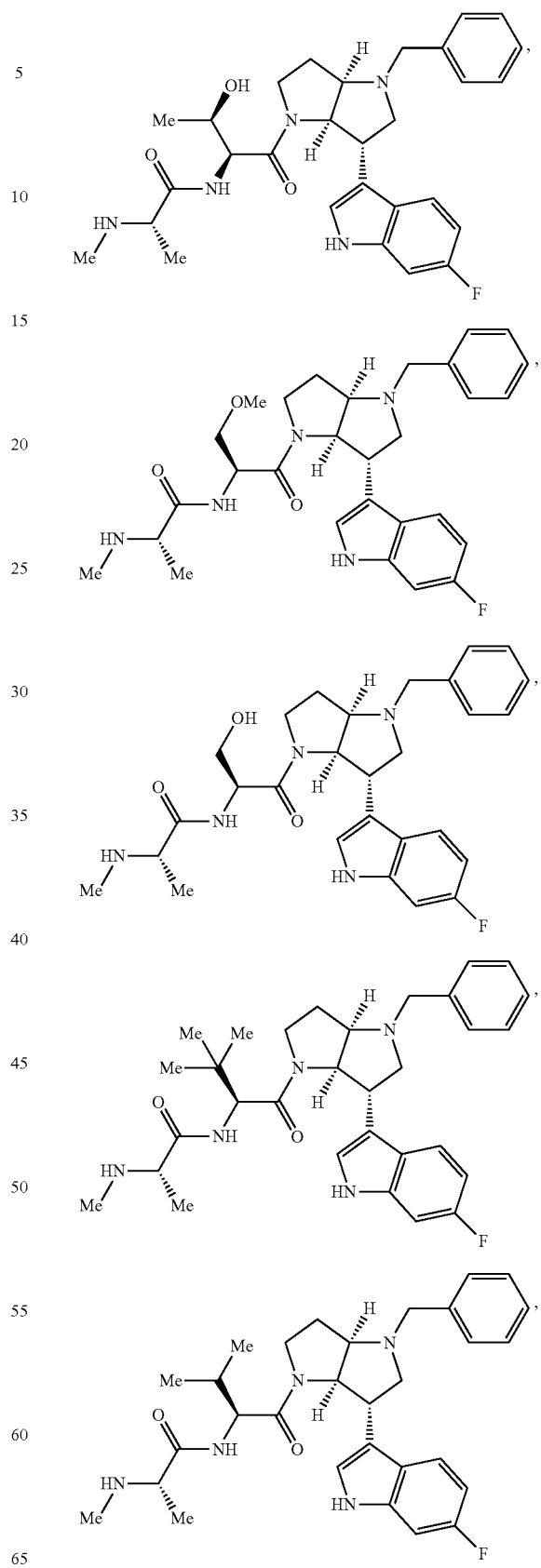

271
-continued

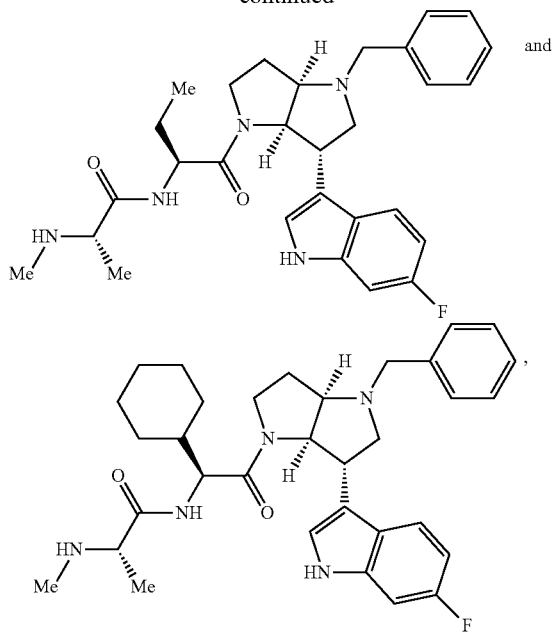

or a pharmaceutically acceptable salt thereof.

26. A compound of claim 1, selected from the group consisting of:

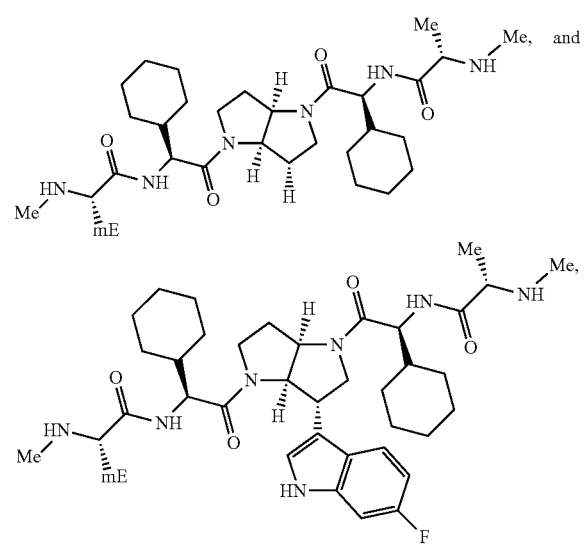

or a pharmaceutically acceptable salt thereof.

27. A compound of claim 1, selected from the group consisting of:

272

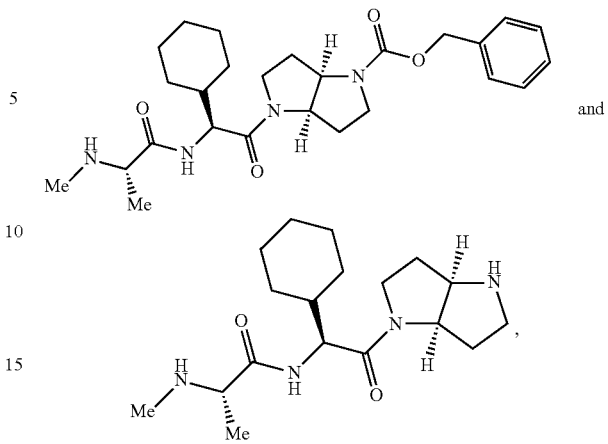

or a pharmaceutically acceptable salt thereof.

28. A pharmaceutical composition comprising a compound, or a pharmaceutically acceptable salt thereof, of claim 1 and a pharmaceutically acceptable excipient.

29. A method for inducing apoptosis in a cell comprising contacting the cell with a compound, or a pharmaceutically acceptable salt thereof, of claim 1, in an amount sufficient to induce apoptosis in the cell.

30. The method of claim 29 wherein the cell is a cancer cell.

31. A method of treating a patient having cancer selected from the group consisting of: sarcomas, bladder cancers, ovarian cancers, breast cancers, brain cancers, pancreatic cancers, colon cancers, blood cancers, skin cancers, lung cancers and bone cancers, the method comprising administering a therapeutically effective amount of a compound, or a pharmaceutically acceptable salt thereof sufficient for inducing apoptosis, of claim 1, to a patient in need thereof.

32. The method of claim 31 wherein the cancers are selected from the group consisting of: colorectal cancer, renal carcinoma, ovarian carcinoma, pancreatic carcinoma, prostate carcinoma, breast carcinoma, melanoma, glioblastoma, acute myeloid leukemia (AML), small cell lung carcinoma, non-small cell lung carcinoma, rhabdomyosarcoma, and basal cell carcinoma.

33. The method of claim 31 further comprising administering a second therapy selected from radiation, chemotherapy, immunotherapy, photodynamic therapy, or combinations thereof.

34. A method of treating a patient having an autoimmune disease selected from the group consisting of: systemic lupus erythematosus, psoriasis and idiopathic thrombocytopenic purpura (Morbus Werlhof); the method comprising administering a therapeutically effective amount of a compound, or a pharmaceutically acceptable salt thereof sufficient for inducing apoptosis, of claim 1, to a patient in need thereof.

* * * * *

UNITED STATES PATENT AND TRADEMARK OFFICE
CERTIFICATE OF CORRECTION

| | |
|---|---|
| PATENT NO. | : 8,399,683 B2 |
| APPLICATION NO. | : 13/063219 |
| DATED | : March 19, 2013 |
| INVENTOR(S) | : Stephen M. Condon |

It is certified that error appears in the above-identified patent and that said Letters Patent is hereby corrected as shown below:

In the Claims

Column 248, Claim 18, Line 20:
Please delete "(MA):" and insert --(IIIA):--

Signed and Sealed this
First Day of July, 2014

Michelle K. Lee
*Deputy Director of the United States Patent and Trademark Office*

UNITED STATES PATENT AND TRADEMARK OFFICE
CERTIFICATE OF CORRECTION

PATENT NO.        : 8,399,683 B2
APPLICATION NO. : 13/063219
DATED             : March 19, 2013
INVENTOR(S)       : Condon et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 90 days.

Signed and Sealed this
First Day of September, 2015

Michelle K. Lee
*Director of the United States Patent and Trademark Office*